(12) United States Patent
Seko et al.

(10) Patent No.: US 6,605,608 B1
(45) Date of Patent: Aug. 12, 2003

(54) AMINO ACID DERIVATIVES AND DRUGS CONTAINING THE SAME AS THE ACTIVE INGREDIENT

(75) Inventors: Takuya Seko, Osaka (JP); Masashi Kato, Osaka (JP)

(73) Assignee: Ono Pharmaceutical Co., Ltd, Osaka (JP)

( * ) Notice: Subject to any disclaimer, the term of this patent is extended or adjusted under 35 U.S.C. 154(b) by 0 days.

(21) Appl. No.: 09/720,433

(22) PCT Filed: Jun. 25, 1999

(86) PCT No.: PCT/JP99/03409

§ 371 (c)(1),
(2), (4) Date: Dec. 22, 2000

(87) PCT Pub. No.: WO00/00470

PCT Pub. Date: Jan. 6, 2000

(30) Foreign Application Priority Data

Jun. 26, 1998 (JP) ............................................. 10-195125

(51) Int. Cl.$^7$ ..................... A61K 31/445; C07D 417/12
(52) U.S. Cl. ................. 514/226.8; 514/227.8; 514/237.7; 514/254.01; 514/254.02; 514/316; 514/317; 514/318; 514/326; 514/327; 544/54; 544/55; 544/56.4; 544/58.6; 544/367; 544/373; 546/189; 546/194; 546/201; 546/208; 546/209; 546/210; 546/213; 548/200; 548/201; 548/204; 548/236; 548/334.1; 548/340.1; 549/76; 549/494
(58) Field of Search .................. 546/209, 194, 546/189, 130, 213; 514/326, 227.8, 226.8, 318, 316, 237.2, 327; 544/60, 53

(56) References Cited

U.S. PATENT DOCUMENTS 4,780,469 A   10/1988   Toda et al. .................. 514/387

4,962,225 A   10/1990   Okada et al. ................ 560/163

FOREIGN PATENT DOCUMENTS

| EP | 0 194 464 | 9/1986 | ......... C07C/103/50 |
| EP | 0 805 147 | 11/1997 | ......... C07C/237/04 |
| JP | 8-217671 | 8/1996 | ......... A61K/31/195 |
| WO | 98/54123 | 12/1998 | ......... C07C/237/12 |
| WO | WO 9902146 A1 * | 1/1999 | |
| WO | WO 9925686 A1 * | 5/1999 | |

OTHER PUBLICATIONS

Sreitwieser e al. Introduction to Organic Chemistry, 2$^{nd}$ Edn., 1981 (see pp. 935–937), ISBN 0–02–418050–5; Macmilan Publishing Co., New York.*

International Search Report, PCT/JP99/03409, 1999.

* cited by examiner

*Primary Examiner*—Richard L. Raymond
(74) *Attorney, Agent, or Firm*—Sughrue Mion, PLLC

(57) ABSTRACT

The present invention relates to the compounds of the formula (I) and salts thereof (all the symbols are the same meanings as described in the specification).

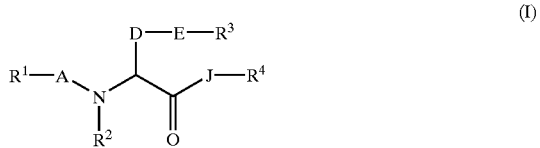

(I)

The compounds of the formula (I) possess inhibitory activity of N-type calcium channel, so they are useful as drug for prevention and/or treatment of cerebral infarct, transient ischemic attack, encephalomyelopathy after cardiac operation, spinal angiopathy, hypertension with stress, neurosis, epilepsy, asthma and pollakiuria etc. or agent for the treatment of pain.

14 Claims, No Drawings

AMINO ACID DERIVATIVES AND DRUGS CONTAINING THE SAME AS THE ACTIVE INGREDIENT

This application is a 371 of PCT/JP99/03409, filed Jun. 25, 1999

THE FIELD OF THE ART

The present invention relates to amino acid derivatives of the formula (I), process for the preparation thereof and pharmaceutical composition, as active ingredients, them.

More particularly, it relates to amino acid derivatives of the formula (I)

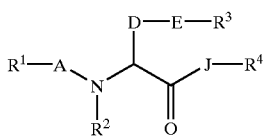

(I)

(wherein all the symbols are the same meanings as hereinafter described), non-toxic salts thereof and the hydrates thereof, processes for the preparation thereof, and N-type calcium channel blocker comprising them as active ingredients.

BACKGROUND OF THE RELATED ARTS

Calcium ion has been known as an intracellular messenger for signal transduction, and it is suggested that various physiological events are triggered by the elevation of intracellular calcium concentration. Calcium influx from extracellular fluid is one of the mechanisms for the elevation of intracellular calcium concentration. The gate of calcium influx is the voltage-dependent calcium channels. The voltage-dependent calcium channel is opened by the polarization of plasma membrane, and calcium ion influxes from extracellular fluid into the cell selectively through the channel according to the electrochemical gradient. The voltage-dependent calcium channels are classified into N-, L-, P-, Q- and T-type at present. It is known that L- and T-type calcium channels are distributed in the various tissues ubiquitously, and especially, L-type calcium channel is enriched in the smooth muscle cells or the cardiac muscle cells. On the other hand, N- and P-type calcium channels are mainly located in the nervous system and related to the neurotransmitter release. This neurotransmitter is stored in synaptic vesicles of nerve terminals at resting state. When action potential by signal transmission on nerve is conducted in pre-synaptic fiber and reaches to the nerve terminal, the voltage-dependent calcium channels are activated and then, calcium ion influxes into the nerve terminals. By these mechanisms, synaptic vesicles are fused with pre-synaptic membrane, and neurotransmitters in the vesicles are released. The released neurotransmitters are related to signal transmission in synapse due to binding to their receptors in post-synaptic membrane. From the above, an N-type calcium channel blocker is thought to be effective on various diseases induced by an excessive release of neurotransmitter. For example, it may be useful as agent for the prevention and/or treatment of cerebral infarct (J. Cereb. Blood Flow Metab., Vol. 17, 421–429, 1997), transient ischemic attack, encephalomyelopathy after cardiac operation, spinal angiopathy, hypertension with stress (Science., 239, 57–61, 1988), neurosis, epilepsy, asthma or pollakiuria etc. or agent for the treatment of pain (Pain, 60, 83–90, 1995).

The venoms isolated from the genus Conus, ω-conotoxin GVIA, MVIIA, are well known as N-type calcium channel blockers.

But, these ω-conotoxins are peptide compounds, so it is expected that they have various problems (for example, they are not absorbed into the living body easily). Therefore, there is a demand for arrangement of these blockers to non-peptide compounds namely to small-molecule. There are some reports relate to small-molecule as follows:

For example, it is described in the specification of Japanese Patent Kokai Hei 8-217671 that glycine derivatives of the formula (A)

$$R^{1A}CH(OCOR^{2A})CH_2CONHCH_2CO_2H \quad (A)$$

(wherein $R^{1A}$ and $R^{2A}$ are, same or different, C1–19 straight or branched alkyl or C2–19 straight or branched alkenyl) and salts thereof are N-type calcium channel blocker.

It is described in the specification of EP 805147 that the compounds of the formula (B)

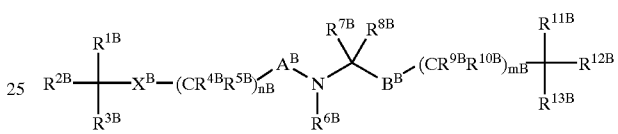

(B)

(wherein $R^{1B}$ is alkyl, $R^{2B}$ is hydrogen, optionally substituted alkyl, optionally substituted aryl or optionally substituted heteroaryl, $R^{3B}$ is hydrogen, CN, $X^B$ is bond or $SO_2$, $R^{4B}$, $R^{5B}$, $R^{6B}$, $R^{8B}$, $R^{9B}$ and $R^{10B}$ are each hydrogen or alkyl, $A^B$ is $CH_2$ or $Y^BCO$ (in which $Y^B$ is bond), $R^{7B}$ is C α-substituent of amino acid or ester thereof, $R^{6B}$ and $R^{7B}$ together form C3–5 alkylene chain optionally substituted by C1–4 alkyl or hydroxy or $CH_2-Z^B-CH_2$ (in which $Z^B$ is CO, S, SO, $SO_2$), $R^{7B}$ and $R^{8B}$ together form C3–5 alkylene chain optionally substituted by C1–4 alkyl or hydroxy, $B^B$ is $CON(R^{21B})$, mB is 0~2, $R^{11B}$ is hydrogen or alkyl, $R^{12B}$ is hydrogen, alkyl, optionally substituted aryl or optionally substituted heteroaryl, $R^{13B}$ is alkyl, optionally substituted aryl or optionally substituted heteroaryl, $R^{12B}$ and $R^{13B}$ together form C3–8 cycloalkyl), the salts thereof or the ester thereof are calcium channel modulator (necessary part is extracted in the explanation of the group).

Also, it is described in the specification of Japanese Patent Kokai Sho 61-200950 that the compound of the formula (C)

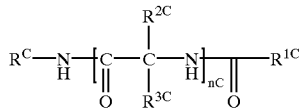

(C)

(wherein $R^C$ and $R^{1C}$ each independently, is lower alkyl, aryl-lower alkyl or phenyl optionally substituted by one or more electron-withdrawing or electron-donating group, $R^{2C}$ and $R^{3C}$ each independently, is hydrogen, lower alkyl, aryl-lower alkyl or phenyl optionally substituted with one or more electron-withdrawing or electron-donating group, and nC is 1~4) and pharmaceutically acceptable salts thereof are anti-convulsant agent.

In addition, the present inventors (applicant(s)) have filed an international application relating to an N-type calcium channel inhibitor (WO99/02146).

Further, as for an application relating to an N-type calcium channel inhibitor, WO 98/54123 is listed.

Besides the above applications, WO 99/25686 (cyclic amine derivatives possessing inhibitory action on chemokine) is listed.

DISCLOSURE OF THE INVENTION

As the result of energetic investigations in order to find compounds possessing inhibitory action on N-type calcium channel, the present inventors have found that the purpose has been accomplished by the compound of the formula (I).

The present invention relates to, (1) an amino acid derivative of the formula (I)

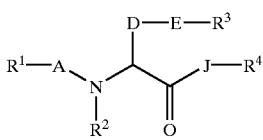

(I)

wherein, $R^1$ is,
1) C1–15 alkyl
2) C1–8 alkoxy,
3) phenyl,
4) C3–8 cycloalkyl,
5) heterocyclic ring,
6) C1–4 alkyl substituted with phenyl, C3–8 cycloalkyl or heterocyclic ring,
7) C1–4 alkoxy substituted with phenyl, C3–8 cycloalkyl or heterocyclic ring or
8) C2–4 alkenyl substituted with phenyl, C3–8 cycloalkyl or heterocyclic ring, wherein all the said phenyl, C3–8 cycloalkyl and heterocyclic ring in $R^1$ may be substituted with 1~3 of substituent(s) selected from the group consisting of the following (i)–(xi):
(i) C1–4 alkyl,
(ii) C1–4 alkoxy,
(iii) phenyl,
(iv) phenoxy,
(v) benzyloxy,
(vi) —$SR^5$ (in which $R^5$ is hydrogen or C1–4 alkyl),
(vii) C2–5 acyl,
(viii) halogen,
(ix) C1–4 alkoxycarbonyl,
(x) nitro and
(xi) —$NR^6R^7$ (in which $R^6$ and $R^7$ are independently, hydrogen, C1–4 alkyl or C1–4 alkoxycarbonyl, or $R^6$ and $R^7$ taken together with nitrogen atom to which they are attached represents 5~7-membered saturated heterocyclic ring necessarily containing one nitrogen atom and optionally further containing one nitrogen atom or one oxygen atom), A is single bond, —CO— or —$SO_2$—, $R^2$ is hydrogen or C1–4 alkyl which may be substituted with one phenyl, D is C1–4 alkylene or C2–4 alkenylene, E is
1) —COO—,
2) —OCO—,
3) —$CONR^8$— (in which $R^8$ is hydrogen or C1–4 alkyl),
4) —$NR^9CO$— (in which $R^9$ is hydrogen or C1–4 alkyl),
5) —O—,
6) —S—,
7) —SO—,
8) —$SO_2$—,
9) —$NR^{10}$— (in which $R^{10}$ is hydrogen or C1–4 alkyl),
10) —CO—,
11) —$SO_2NR^{11}$— (in which $R^{11}$ is hydrogen or C1–4 alkyl) or
12) —$NR^{12}SO_2$— (in which $R^{12}$ is hydrogen or C1–4 alkyl), $R^3$ is
1) carbocyclic ring,
2) heterocyclic ring or
3) C1–4 alkyl substituted with carbocyclic ring or heterocyclic ring, wherein all the said carbocyclic ring and heterocyclic ring in $R^3$ may be substituted with 1~3 of substituent(s) selected from the group consisting of the following (i)–(xi):
(i) C1–4 alkyl,
(ii) C1–4 alkoxy,
(iii) phenyl,
(iv) phenoxy,
(v) benzyloxy,
(vi) —$SR^{13}$ (in which $R^{13}$ is hydrogen or C1–4 alkyl),
(vii) C2–5 acyl,
(viii) halogen,
(ix) C1–4 alkoxycarbonyl,
(x) nitro and
(xi) —$NR^{14}R^{15}$ (in which $R^{14}$ and $R^{15}$ are independently, hydrogen, C1–4 alkyl or C1–4 alkoxycarbonyl, or $R^{14}$ and $R^{15}$ taken together with nitrogen atom to which they are attached represents 5~7-membered saturated heterocyclic ring necessarily containing one nitrogen atom and optionally further containing one nitrogen atom or one oxygen atom), J is $J^1$ or $J^2$, $J^1$ is
1) —O— or
2) —$NR^{16}$— (in which $R^{16}$ is hydrogen or C1–4 alkyl), $J^2$ is
1) —$NR^{17}$— (in which $R^{17}$ is C1–4 alkyl substituted with one phenyl, $NR^{18}R^{19}$ (in which $R^{18}$ and $R^{19}$ are independently, hydrogen or C1–4 alkyl), hydroxy, C1–4 alkoxy, —(C1–4 alkylene)-OH, —(C1–4 alkylene)-O—(C1–4 alkyl) or —(C1–4 alkylene)-O—(C2–5 acyl)),
2) —$NR^{20}$—$NR^{21}$— (in which $R^{20}$ and $R^{21}$ are independently, hydrogen or C1–4 alkyl which may be substituted with one phenyl),
3) —$NR^{22}$—(C1–4 alkylene)-$NR^{21}$— (in which $R^{22}$ and $R^{23}$ are independently, hydrogen or C1–4 alkyl which may be substituted with one phenyl),
4) —$NR^{24}$—(C1–4 alkylene)-O— (in which $R^{24}$ is hydrogen or C1–4 alkyl which may be substituted with one phenyl) or
5) —$NR^{25}$—(C1–4 alkylene)-S— (in which $R^{25}$ is hydrogen or C1–4 alkyl which may be substituted with one phenyl), $R^4$ is $R^{4-1}$, $R^{4-2}$ or $R^{4-3}$, $R^{4-1}$ is
1) C1–8 alkyl,
2) carbocyclic ring,
3) heterocyclic ring or
4) C1–8 alkyl substituted with 1~3 of substituent(s) selected from the group consisting of the following (i)–(v);

(i) carbocyclic ring,
(ii) heterocyclic ring,
(iii) COOR$^{26}$ (in which R$^{26}$ is hydrogen or C1–4 alkyl substituted with one phenyl (in which the said phenyl may be substituted with C1–4 alkoxy),
(iv) SR$^{27}$ (in which R$^{27}$ is hydrogen or C1–4 alkyl) and
(v) OR$^{28}$ (in which R$^{28}$ is hydrogen or C1–4 alkyl), provided that when J is —NR$^{17}$—, —NR$^{20}$—NR$^{21}$— or —NR$^{22}$—(C1–4 alkylene)-NR$^{23}$—, each R$^{4-1}$ and R$^{17}$, R$^{4-1}$ and R$^{21}$, and R$^{4-1}$ and R$^{23}$ taken together with nitrogen atom to which they are attached may represent heterocyclic ring, wherein all the said carbocyclic ring and heterocyclic ring in R$^{4-1}$ and the said heterocyclic ring represented by each R$^{4-1}$ and R$^{17}$, R$^{4-1}$ and R$^{21}$, and R$^{4-1}$ and R$^{23}$ taken together with nitrogen atom to which they are attached may be substituted with 1~3 of the substituent(s) selected from the group consisting of the following (i)–(xi):
(i) C1–4 alkyl,
(ii) C1–4 alkoxy,
(iii) phenyl,
(iv) phenoxy,
(v) benzyloxy,
(vi) —SR$^{29}$ (in which R$^{29}$ is hydrogen or C1–4 alkyl),
(vii) C2–5 acyl,
(viii) halogen,
(ix) C1–4 alkoxycarbonyl,
(x) nitro and
(xi) —NR$^{30}$R$^{31}$ (in which R$^{30}$ and R$^{31}$ are independently, hydrogen, C1–4 alkyl or C1–4 alkoxycarbonyl, or R$^{30}$ and R$^{31}$ taken together with nitrogen atom to which they are attached represents 5~7-membered saturated heterocyclic ring necessarily containing one nitrogen atom and optionally further containing one nitrogen atom or one oxygen atom), R$^{4-2}$ is
1) carbocyclic ring,
2) heterocyclic ring or
3) C1–8 alkyl substituted with 1~3 of substituent(s) selected from the group consisting of the following (i)–(v);
(i) carbocyclic ring,
(ii) heterocyclic ring,
(iii) COOR$^{32}$ (in which R$^{32}$ is hydrogen or C1–4 alkyl substituted with one phenyl (in which the said phenyl may be substituted with C1–4 alkoxy),
(iv) SR$^{33}$ (in which R$^{33}$ is hydrogen or C1–4 alkyl) and
(v) OR$^{34}$ (in which R$^{34}$ is hydrogen or C1–4 alkyl), provided that when J is —NR$^{16}$—, —NR$^{17}$—, —NR$^{20}$—NR$^{21}$— or —NR$^{22}$—(C1–4 alkylene)-NR$^{23}$—, each R$^{4-2}$ and R$^{16}$, R$^{4-2}$ and R$^{17}$, R$^{4-2}$ and R$^{21}$, and R$^{4-2}$ and R$^{23}$ taken together with nitrogen atom to which they are attached may represent heterocyclic ring, wherein at least one ring of all the said carbocyclic ring and heterocyclic ring in R$^{4-2}$ and the said heterocyclic ring represented by each R$^{4-2}$ and R$^{16}$, R$^{4-2}$ and R$^{17}$, R$^{4-2}$ and R$^{21}$, and R$^{4-2}$ and R$^{23}$ taken together with nitrogen atom to which they are attached is substituted with one hydroxy or one —O—(C1–4 alkylene)-O—(C1–4 alkyl) and may be substituted with further 1~2 of substituent(s) selected from the group consisting of the following (i)–(xiii):

(i) C1–4 alkyl,
(ii) C1–4 alkoxy,
(iii) phenyl,
(iv) phenoxy,
(v) benzyloxy,
(vi) —SR$^{35}$ (in which R$^{35}$ is hydrogen or C1–4 alkyl),
(vii) C2–5 acyl,
(viii) halogen,
(ix) C1–4 alkoxycarbonyl,
(x) nitro,
(xi) —NR$^{36}$R$^{37}$ (in which R$^{36}$ and R$^{37}$ are independently, hydrogen, C1–4 alkyl or C1–4 alkoxycarbonyl, or R$^{36}$ and R$^{37}$ taken together with nitrogen atom to which they are attached represents 5~7-membered saturated heterocyclic ring necessarily containing one nitrogen atom and optionally further containing one nitrogen atom or one oxygen atom),
(xii) hydroxy and
(xiii) —O—C1–4 alkylene)-O—(C1–4 alkyl), R$^{4-3}$ is —L—M,
—L— is
1)—(carbocyclic ring which may be substituted with 1~3 of substituent(s))—,
2)—(heterocyclic ring which may be substituted with 1~3 of substituent(s))—or
3)—(C1–4 alkylene)-(carbocyclic ring or heterocyclic ring which may be substituted with 1~3 of substituent(s))—, provided that when J is —NR$^{16}$—, —NR$^{17}$—, —NR$^{20}$—NR$^{21}$— or —NR$^{22}$—(C1–4 alkylene)-NR$^{23}$—, each L and R$^{16}$, L and R$^{17}$, L and R$^{21}$, and L and R$^{23}$ taken together with nitrogen atom to which they are attached may represent—(heterocyclic ring which may be substituted with 1~3 of substituent(s))—, M is
1) carbocyclic ring or heterocyclic ring which may be substituted with 1~3 of substituent(s) (with the proviso that when the said carbocyclic ring is phenyl, such a ring is substituted with at least one substituent (s), and that when the said heterocyclic ring is 5~7-membered saturated heterocyclic ring in which the nitrogen atom in the said heterocyclic ring is bonded to group L shown as

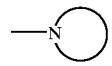

and which may contain further one nitrogen atom or one oxygen atom, then such a ring is substituted with at least one substituent(s)),
2) C1–4 alkyl substituted with 1~2 of substituent(s) selected from the group consisting of the following (i)–(ii);
(i) carbocyclic ring which may be substituted with 1~3 of substituent(s),
(ii) heterocyclic ring which may be substituted with 1~3 of substituent(s),
3) —O-(carbocyclic ring or heterocyclic ring which may be substituted with 1~3 of substituent(s)) (with the proviso that when the said carbocyclic ring is phenyl, such a ring is substituted with at least one substituent(s)),
4) —S-(carbocyclic ring or heterocyclic ring which may be substituted with 1~3 of substituent(s)),
5) —NR$^{38}$-(carbocyclic ring or heterocyclic ring which may be substituted with 1~3 of substituent(s)) (in which $R^{38}$ is hydrogen or C1–4 alkyl which may be substituted with one phenyl), 6) —O—CH$_2$-(carbocyclic ring which may be substituted with 1~3 of substituent(s)) (with the proviso that when the said carbocyclic ring is phenyl, such a ring is substituted with at least one substituent(s)), 7) —O—(C2–4 alkylene)-(carbocyclic ring which may be substituted with 1~3 of substituent(s)), 8) —O—(C1–4 alkylene)-(heterocyclic ring which may be substituted with 1~3 of substituent(s)), 9) —S—(C1–4 alkylene)-(carbocyclic ring or heterocyclic ring which may be substituted with 1–3 of substituent(s)), 10) —NR$^{39}$—(C1–4 alkylene)-(carbocyclic ring or heterocyclic ring which may be substituted with 1~3 of substituent(s)) (in which $R^{39}$ is hydrogen, C1–4 alkyl which may be substituted with one phenyl or C2–5 acyl which may be substituted with 1~3 of halogen) or 11) —CO-(carbocyclic ring or heterocyclic ring which may be substituted with 1~3 of substituent(s)), wherein the substituent(s) of the said carbocyclic ring and heterocyclic ring in L and M and the said heterocyclic ring represented by each L and $R^{16}$, L and $R^{17}$, L and $R^{21}$, and L and $R^{23}$ taken together with nitrogen atom to which they are attached is selected from the following (i)–(xiv);

(i) C1–4 alkyl,
(ii) C2–4 alkenyl,
(iii) hydroxy,
(iv) C1–4 alkoxy,
(v) —(C1–4 alkylene)-OH,
(vi) —O—(C1–4 alkylene)-O—(C1–4 alkyl),
(vii) halogen,
(viii) NR$^{40}$R$^{41}$ (in which $R^{40}$ and $R^{41}$ are independently, hydrogen, C1–4 alkyl or C1–4 alkoxycarbonyl, or $R^{40}$ and $R^{41}$ taken together with nitrogen atom to which they are attached represents 5~7-membered saturated heterocyclic ring necessarily containing one nitrogen atom and optionally further containing one nitrogen atom or one oxygen atom),
(ix) SR$^{42}$ (in which $R^{42}$ is hydrogen or C1–4 alkyl),
(x) nitro,
(xi) trifluoromethyl,
(xii) C1–4 alkoxycarbonyl,
(xiii) oxo and
(xiv) C2–5 acyl, with the proviso that when J is $J^1$, $R^4$ does not represent $R^{4-1}$] or non-toxic salts thereof, or hydrates thereof, (2) N-type calcium channel inhibitor comprising, as active ingredient, amino acid derivatives of the formula (I) or non-toxic salts thereof, or hydrates thereof and (3) process for preparation of amino acid derivatives of the formula (I) or non-toxic salts thereof, or hydrates thereof.

DETAILED EXPLANATION OF THE INVENTION

Unless otherwise specified, all isomers are included in the present invention. For example, alkyl, alkenyl, alkynyl and alkylene group includes straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

In the formula (I), C1–15 alkyl represented by $R^1$ means methyl, ethyl, propyl, butyl, pentyl, hexyl, heptyl, octyl, nonyl, decyl, undecyl, dodecyl, tridecyl, tetradecyl, pentadecyl and isomers thereof.

In the formula (I), C1–4 alkoxy represented by $R^{17}$ means methoxy, ethoxy, propoxy, butoxy and isomers thereof.

In the formula (I), C1–8 alkoxy represented by $R^1$ means methoxy, ethoxy, propoxy, butoxy, pentyloxy, hexyloxy, heptyloxy, octyloxy and isomers thereof.

In the formula (I), C3–8 cycloalkyl represented by $R^1$, C3–8 cycloalkyl as a substituent of C1–4 alkyl, C1–4 alkoxy and C2–4 alkenyl in $R^1$ means cyclopropyl, cyclobutyl, cyclopentyl, cyclohexyl, cycloheptyl and cyclooctyl.

In the formula (I), C1–4 alkyl represented by $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{27}$, $R^{28}$, $R^{29}$, $R^{30}$, $R^{31}$, $R^{33}$, $R^{34}$, $R^{35}$, $R^{36}$, $R^{37}$, $R^{40}$, $R^{41}$ and $R^{42}$ means methyl, ethyl, propyl, butyl and isomers thereof.

In the formula (I), C1–4 alkyl as a substituent of phenyl, C3–8 cycloalkyl and heterocyclic ring in $R^1$, carbocyclic ring and heterocyclic ring in $R^3$, $R^4$, L and M and heterocyclic ring represented by each $R^{4-1}$ and $R^{17}$, $R^{4-1}$ and $R^{21}$, $R^{4-1}$ and $R^{23}$, $R^{4-2}$ and $R^{16}$, $R^{4-2}$ and $R^{17}$, $R^{4-2}$ and $R^{21}$, $R^{4-2}$ and $R^{23}$; L and $R^{16}$, L and $R^{17}$, L and $R^{21}$, and L and $R^{23}$ taken together with nitrogen atom to which they are attached means methyl, ethyl, propyl, butyl and isomers thereof.

In the formula (I), C1–4 alkyl substituted with phenyl, C3–8 cycloalkyl or heterocyclic ring represented by $R^1$ means methyl, ethyl, propyl, butyl substituted with phenyl, C3–8 cycloalkyl or heterocyclic ring and isomers thereof.

In the formula (I), C1–4 alkyl which may be substituted with one phenyl represented by $R^2$, $R^{20}$, $R^{21}$, $R^{22}$, $R^{23}$, $R^{24}$, $R^{25}$, $R^{38}$ and $R^{39}$ means methyl, ethyl, propyl, butyl which may be substituted with one phenyl and isomers thereof.

In the formula (I), C1–4 alkyl substituted with one phenyl represented by $R^{17}$, $R^{26}$ and $R^{32}$ means methyl, ethyl, propyl, butyl substituted with one phenyl and isomers thereof.

In the formula (I), C1–4 alkyl substituted with carbocyclic ring or heterocyclic ring represented by $R^3$ means methyl, ethyl, propyl, butyl substituted with carbocyclic ring or heterocyclic ring and isomers thereof.

In the formula (I), C1–4 alkyl in —(C1–4 alkylene)-O—(C1–4 alkyl) represented by $R^{17}$ and C1–4 alkyl in —O—(C1–4 alkylene)-O—(C1–4 alkyl) as a substituent of carbocyclic ring or heterocyclic ring in $R^{4-2}$, L and M and heterocyclic ring represented by each $R^{4-2}$ and $R^{16}$, $R^{4-2}$ and $R^{17}$, $R^{4-2}$ and $R^{21}$, $R^{4-2}$ and $R^{23}$, L and $R^{16}$, L and $R^{17}$, L and $R^{21}$, and L and $R^{23}$ taken together with nitrogen atom to which they are attached means methyl, ethyl, propyl, butyl and isomers thereof.

In the formula (I), C1–4 alkyl substituted with 1~2 of substituent(s) selected from the group consisting of group (i)–(ii) represented by M means methyl, ethyl, propyl, butyl substituted with 1~2 of substituent(s) selected from the group consisting of group (i)–(ii) and isomers thereof.

In the formula (I), C1–8 alkyl represented by $R^{4-1}$ means methyl, ethyl, propyl, butyl, pentyl, hexyl, heptyl, octyl and isomers thereof.

In the formula (I), C1–8 alkyl substituted with 1~3 of substituent(s) selected from the group consisting of group (i)–(v) represented by $R^{4-1}$ and $R^{4-2}$ means methyl, ethyl, propyl, butyl, propyl, pentyl, hexyl, heptyl, octyl substituted with 1~3 of substituent(s) selected from the group consisting of group (i)–(v) and isomers thereof.

In the formula (I), C1–4 alkoxy substituted with phenyl, C3–8 cycloalkyl or heterocyclic ring represented by $R^1$ means methoxy, ethoxy, propoxy, butoxy substituted with phenyl, C3–8 cycloalkyl or heterocyclic ring and isomers thereof.

In the formula (I), C1–4 alkoxy as a substituent of phenyl, C3–8 cycloalkyl and heterocyclic ring in $R^1$, C1–4 alkoxy as a substituent of carbocyclic ring and heterocyclic ring in $R^3$, $R^4$, L and M, and C1–4 alkoxy as a substituent of heterocyclic ring represented by each $R^{4-1}$ and $R^{17}$, $R^{4-1}$ and $R^{21}$, $R^{4-1}$ and $R^{23}$, $R^{4-2}$ and $R^{16}$, $R^{4-2}$ and $R^{17}$, $R^{4-2}$ and $R^{21}$, $R^{4-2}$ and $R^{23}$, L and $R^{16}$, L and $R^{17}$, L and $R^{21}$, and L and $R^{23}$ taken together with nitrogen atom to which they are attached mean methoxy, ethoxy, propoxy, butoxy and isomers thereof.

In the formula (I), C1–4 alkoxy as a substituent of phenyl in C1–4 alkyl substituted with one phenyl in $R^{26}$ and $R^{32}$ means methoxy, ethoxy, propoxy, butoxy and isomers thereof.

In the formula (I), C2–4 alkenyl substituted with phenyl, cycloalkyl or heterocyclic ring represented by $R^1$ means ethenyl, propenyl, butenyl substituted with phenyl, cycloalkyl or heterocyclic ring and isomers thereof.

In the formula (I), C2–4 alkenyl as a substituent of carbocyclic ring, heterocyclic ring in L and M, and C2–4 alkenyl as a substituent of heterocyclic ring represented by each L and $R^{16}$, L and $R^{17}$, L and $R^{21}$, and L and $R^{23}$ taken together with nitrogen atom to which they are attached means ethenyl, propenyl, butenyl and isomers thereof.

In the formula (I), C2–5 acyl in —(C1–4 alkylene)-O—(C2–5 acyl) represented by $R^{17}$ means acetyl, propionyl, butyryl, valeryl and isomers thereof.

In the formula (I), C2–5 acyl may be substituted with 1~3 of halogen represented by $R^{39}$ means acetyl, propionyl, butyryl, valeryl may be substituted with 1~3 of halogen and isomers thereof.

In the formula (I), C2–5 acyl as a substituent of phenyl, C3–8 cycloalkyl and heterocyclic ring in $R^1$, C2–5 acyl as a substituent of carbocyclic ring, heterocyclic ring in $R^3$, $R^4$, L and M, and C2–5 acyl as a substituent of heterocyclic ring represented by each $R^{4-1}$ and $R^{17}$, $R^{4-1}$ and $R^{21}$, $R^{4-1}$ and $R^{23}$, $R^{4-2}$ and $R^{16}$, $R^{4-2}$ and $R^{17}$, $R^{4-2}$ and $R^{21}$, $R^{4-2}$ and $R^{23}$, L and $R^{16}$, L and $R^{17}$, L and $R^{21}$, and L and $R^{23}$ taken together with nitrogen atom to which they are attached means acetyl, propionyl, butyryl, valeryl and isomers thereof.

In the formula (I), halogen as a substituent of C2–5 acyl represented by $R^{39}$, halogen as a substituent of phenyl, C3–8 cycloalkyl and heterocyclic ring in $R^1$, halogen as a substituent of carbocyclic ring and heterocyclic ring in $R^3$, $R^4$, L and M, halogen as a substituent of heterocyclic ring represented by each $R^{4-1}$ and $R^{17}$, $R^{4-1}$ and $R^{21}$, $R^{4-1}$ and $R^{23}$, $R^{4-2}$ and $R^{16}$, $R^{4-2}$ and $R^{17}$, $R^{4-2}$ and $R^{23}$, L and $R^{16}$, L and $R^{17}$, L and $R^{21}$, and L and $R^{23}$ taken together with nitrogen atom to which they are attached mean fluoride, chloride, bromide and iodide.

In the formula (I), C1–4 alkoxycarbonyl represented by $R^6$, $R^7$, $R^{14}$, $R^{15}$, $R^{30}$, $R^{31}$, $R^{36}$, $R^{37}$, $R^{40}$, and $R^{41}$ means methoxycarbonyl, ethoxycarbonyl, propoxycarbonyl, butoxycarbonyl and isomers thereof.

In the formula (I), C1–4 alkoxycarbonyl as a substituent of phenyl, C3–8 cycloalkyl and heterocyclic ring in $R^1$, C1–4 alkoxycarbonyl as a substituent of carbocyclic ring and heterocyclic ring in $R^3$, $R^4$, L and M, and C1–4 alkoxycarbonyl as a substituent of heterocyclic ring represented by each $R^{4-1}$ and $R^{17}$, $R^{4-1}$ and $R^{21}$, $R^{4-1}$ and $R^{23}$, $R^{4-2}$ and $R^{16}$, $R^{4-2}$ and $R^{17}$, $R^{4-2}$ and $R^{21}$, $R^{4-2}$ and $R^{23}$, L and $R^{16}$, L and $R^{17}$, L and $R^{21}$, and L and $R^{23}$ taken together with nitrogen atom to which they are attached means methoxycarbonyl, ethoxycarbonyl, propoxycarbonyl, butoxycarbonyl and isomers thereof.

In the formula (I), C1–4 alkylene represented by D means methylene, ethylene, propylene, butylene and isomers thereof.

In the formula (I), C1–4 alkylene in —$NR^{22}$—(C1–4 alkylene)-$NR^{23}$—, —$NR^{24}$— (C1–4 alkylene)-O— and —$NR^{25}$—((C1–4 alkylene)-S— represented by $J^2$, C1–4 alkylene in —(C1–4 alkylene)-OH, —(C1–4 alkylene)-O—(C1–4 alkyl) and —(C1–4 alkylene)-O—(C2–5 acyl) represented by $R^{17}$, C1–4 alkylene in —(C1–4 alkylene)-(carbocyclic ring or heterocyclic ring which may be substituted with 1~3 of substituent(s))—represented by L, or C1–4 alkylene in —O—(C1–4 alkylene)-(heterocyclic ring which may be substituted with 1~3 of substituent(s)), —S—(C1–4 alkylene)-(carbocyclic ring or heterocyclic ring which may be substituted with 1~3 of substituent(s)) and —$NR^{39}$—(C1–4 alkylene)-(carbocyclic ring or heterocyclic ring which may be substituted with 1~3 of substituent(s)) represented by M means methylene, ethylene, propylene, butylene and isomers thereof.

In the formula (I), C2–4 alkylene in —O—(C2–4 alkylene)-(carbocyclic ring which may be substituted with 1~3 of substituent(s)) represented by M means ethylene, propylene, butylene and isomers thereof.

In the formula (I), C1–4 alkylene in —O—(C1–4 alkylene)-O—(C1–4 alkyl) as a substituent of carbocyclic ring or heterocyclic ring in $R^4$, L and M and heterocyclic ring represented by each $R^{4-2}$ and $R^{16}$, $R^{4-2}$ and $R^{17}$, $R^{4-2}$ and $R^{21}$, $R^{4-2}$ and $R^{23}$, L and $R^{16}$, L and $R^{17}$, L and $R^{21}$, and L and $R^{23}$ taken together with nitrogen atom to which they are attached mean methylene, ethylene, propylene, butylene and isomers thereof.

In the formula (I), C1–4 alkylene in —(C1–4 alkylene)-OH as a substituent of carbocyclic ring or heterocyclic ring in L and M and heterocyclic ring represented by each L and $R^{16}$, L and $R^{17}$, L and $R^{21}$, and L and $R^{23}$ taken together with nitrogen atom to which they are attached means methylene, ethylene, propylene, butylene and isomers thereof.

In the formula (I), C2–4 alkenylene represented by D means ethenylene, propenylene, butenylene and isomers thereof.

In the formula (I), 5~7-membered saturated heterocyclic ring necessarily containing one nitrogen atom and optionally further containing one nitrogen atom or one oxygen atom represented by each $R^6$ and $R^7$, $R^{14}$ and $R^{15}$, $R^{30}$ and $R^{31}$, $R^{36}$ and $R^{37}$, and $R^{40}$ and $R^{41}$ taken together with nitrogen atom to which they are attached means, for example, pyrrolidine, piperidine, piperazine, morpholine, perhydroazepine.

In the formula (I), carbocyclic ring in $R^3$, $R^4$, L and M means C3–10 mono-, bi-carbocyclic ring and fused carbocyclic ring. The said C3–10 mono-, bi-carbocyclic ring and fused carbocyclic ring means, for example, cyclopropane, cyclobutane, cyclopentane, cyclohexane, cycloheptane, cyclooctane, cyclononane, cyclodecane, cyclopenten, cyclohexen, cyclopentadien, cyclohexadien, benzene, pentalene, indene, naphathalene, azulene, dihydronaphathalene, tetrahydronaphathalene, perhydronaphathalene, indane (dihydroindene), perhydroindene, bicyclopentane, bicyclohexane, bicycloheptane (bicyclo[2.2.1]heptane), bicyclohepten (bicyclo[2.2.1]hept-2-en), bicyclooctane, bicyclononane, bicyclodecane, adamantane etc.

In the formula (I), heterocyclic ring in $R^1$, $R^3$, $R^4$, L and M means 5~15-membered mono- or bi-heterocyclic ring containing 1~2 nitrogen atom(s), 1~2 oxygen atom(s) and/or one sulfur atom which is unsaturated or saturated partially or fully (abbreviated as heterocyclic ring (A)). The said 5~15-membered mono- or bi-heterocyclic ring containing 1~2 nitrogen atom(s), 1~2 oxygen atom(s) and/or one sulfur atom which is unsaturated or saturated partially or fully means, for example, pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, dihydrofran, tetrahydrofran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisooxazole, tetrahydroisooxazole, dihydrothiazole, tetrahydrothiazole (thiazolidine), dihydroisothiazole, tetraisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzooxazole, perhydrobenzooxazole, dihydrobenzothiazole, perhydrobenzothiazole, dihydrobenzoimidazole, perhydrobenzoimidazole, dihydrobenzooxazine, dioxaindane, benzodioxane, quinuclidine, pyrrole, imidazole, pyrazole, pyridine, pyrazine, pyrimidine, pyridazine, pyridazine, azepine, diazepine, fran, pyran, oxepine, oxazepine, thiophene, thiain (thiopyran), thiepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofran, isobenzofran, benzothiophene, isobenzothiophene, indazole, quinoline, isoquinoline, phthalazine, naphthylidine, quinoxaline, quinazoline, cinnoline, benzooxazole, benzothiazole, benzoimidazole, oxatetrahydrofran etc.

In the formula (I), heterocyclic ring represented by each $R^{4-1}$ and $R^{17}$, $R^{4-1}$ and $R^{21}$, $R^{4-1}$ and $R^{23}$, $R^{4-2}$ and $R^{16}$, $R^{4-2}$ and $R^{17}$, $R^{4-2}$ and $R^{23}$, L and $R^{16}$, L and $R^{17}$, L and $R^{21}$, and L and $R^{23}$ taken together with nitrogen atom to which they are attached means 5~15-membered mono- or bi-heterocyclic ring containing one nitrogen atom as an essential and optionally further containing one nitrogen atom, one oxygen atom and/or one sulfur atom which is unsaturated or saturated partially or fully. The said 5~15-membered mono- or bi-heterocyclic ring containing one nitrogen atom as an essential and optionally further containing one nitrogen atom, 1~2 oxygen atom and/or one sulfur atom which is unsaturated or saturated partially or fully means, for example, pyrroline, pyrrolidine, imidazoline, imidazolidine, pyrazoline, pyrazolidine, piperidine, piperazine, tetrahydropyrim idine, hexahydropyrimidine, tetrahydropyridazine, hexahydropyridazine, hexahydroazepine, tetrahydrooxazole, tetrahydroisooxazole, tetrahydrothiazole, tetrahydroisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzooxazole, perhydrobenzooxazole, dihydrobenzothiazole, perhydrobenzothiazole, dihydrobenzoimidazole, perhydrobenzoimidazole, pyrrole, imidazole, pyrazole, indole, isoindole, indazole, benzoimidazole etc.

$R^1$ is preferably C1–8 alkoxy, phenyl, C3–8 cycloalkyl, heterocyclic ring or C1–4 alkyl substituted with phenyl, C3–8 cycloalkyl or heterocyclic ring, and more preferably heterocyclic ring (provided that all the said phenyl, cycloalkyl and heterocyclic ring may be substituted). The said heterocyclic ring (A) is listed as for such a heterocyclic ring. More preferablly, such a ring is 5~15-membered mono- or bi-heterocyclic ring containing 1~2 nitrogen atom(s), 1~2 oxygen atom(s) and/or one sulfur atom which is unsaturated or saturated partially or fully (for example, dihydrooxazole, tetrahydrooxazole, dihydroisooxazole, tetrahydroisooxazole, dihydrothiazole, tetrahydrothiazole (thiazolidine), dihydroisothiazole, tetraisothiazole, morpholine, thiomorpholine, dihydrobenzooxazole, perhydrobenzooxazole, dihydrobenzothiazole, perhydrobenzothiazole, dihydrobenzooxazine, oxazepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, benzooxazole, benzothiazole etc.), and more preferably, 5~7-membered mono-heterocyclic ring containing one nitrogen atom and one oxygen atom or one sulfur atom which is unsaturated or saturated partially or fully (for example, dihydrooxazole, tetrahydrooxazole, dihydroisooxazole, tetrahydroisooxazole, dihydrothiazole, tetrahydrothiazole (thiazolidine), dihydroisothiazole, tetraisothiazole, morpholine, thiomorpholine, oxazepine, oxazole, isooxazole, thiazole, isothiazole, oxazine, oxazepine, thiazine, thiazepine etc.) and most preferably, tetrahydrothiazole (thiazolidine).

A is preferably single bond or —CO—, and more preferably —CO—.

D is preferably each group, more preferably C1–4 alkylene, and most preferably methylene.

$R^2$ is preferably each group, more preferably hydrogen or methyl substituted with one phenyl, and most preferably hydrogen.

E is preferably —COO—, —O—, —S—, —SO— or —SO$_2$—, more preferably —O— or —S—, and most preferably —S—.

$R^3$ is preferably carbocyclic ring or C1–4 alkyl substituted with carbocyclic ring (all the said carbocyclic ring may be substituted), more preferably C3–10 cycloalkyl such as cyclopropane, cyclobutane, cyclopentane, cyclohexane, cycloheptane, cyclooctane, cyclononane, cyclodecane or C1–4 alkyl substituted with C3–10 cycloalkyl (all the said cycloalkyl may be substituted), much more preferably cyclopentyl or cyclohexyl or methyl substituted with cyclopentyl or cyclohexyl, and most preferably methyl substituted with cyclohexyl.

J is preferably —$NR^{16}$— (in which $R^{16}$ is the same meaning as defined hereinbefore) or —$NR^{22}$—(C1–4 alkylene)-$NR^{23}$— (in which $R^{22}$ and $R^{23}$ are the same meanings as defined hereinbefore), and more preferably —$NR^{16}$—.

$R^4$ is preferably (—L—M) represented by $R^{4-3}$.

In the above symbol, L is preferably each group, and more preferably heterocyclic ring which may be substituted with 1~3 of substituent(s). The said heterocyclic ring (A) is listed as such a heterocyclic ring. More preferably, such a ring is 5~15-membered mono- or bi-heterocyclic ring containing 1~2 nitrogen atom(s) which is unsaturated or saturated partially or fully (for example, pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthylidine, tetrahydronaphthylidine, perhydronaphthylidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoimidazole, perhydrobenzoimidazole, quinuclidine, pyrrole, imidazole, pyrazole, pyridine, pyrazine, pyrimidine, pyridazine, pyridazine, azepine, diazepine, indole, isoindole, indazole, quinoline, isoquinoline, phthalazine, naphthylidine, quinoxaline, quinazoline, cinnoline, benzoimidazole etc.), and more preferably, 5~7-membered mono-heterocyclic ring containing 1~2 nitrogen atom(s) which is unsaturated or saturated partially or fully (for example, pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, pyrrole, imidazole, pyrazole, pyridine, pyrazine, pyrimidine, pyridazine, pyridazine, azepine, diazepine etc.) and most preferably piperidine.

M is preferably each group, more preferably C1–4 alkyl substituted with 1~2 of substituent(s) selected from the group consisting of carbocyclic ring or heterocyclic ring which may be substituted with 1~3 of substituent(s), and more preferably C1–4 alkyl substituted with 1~2 of substituent(s) selected from the group consisting of phenyl and C3–10 cycloalkyl which may be substituted with 1~3 of substituent(s), and most preferably methyl substituted with one phenyl.

Each ring in $R^1$ is preferably ring which is unsubstituted or substituted, more preferably ring which is unsubstituted or substituted with C1–4 alkyl, halogen, C1–4 alkoxycarbonyl, and most preferably ring substituted with C1–4 alkoxycarbonyl.

The substituent of ring in $R^4$ or substituent of heterocyclic ring represented by J and $R^4$ is preferably each group (in case of unsubstituted ring, such an unsubstituted ring is also preferable).

In $R^4$, preferably at least one of carbocyclic ring and heterocyclic ring in $R^{4-2}$ and heterocyclic ring represented by each $R^{4-2}$ and $R^{16}$, $R^{4-2}$ and $R^{17}$, $R^{4-2}$ and $R^{21}$, and $R^{4-2}$ and $R^{23}$ taken together with nitrogen atom to which they are attached is substituted with one hydroxy and heterocyclic ring which may be substituted with 1~2 of substituent(s) selected from the group consisting of the following (i)–(xii):

(i) C1–4 alkyl,
(ii) C1–4 alkoxy,
(iii) phenyl,
(iv) phenoxy,
(v) benzyloxy,
(vi) —$SR^{35}$ (in which $R^{35}$ is hydrogen or C1–4 alkyl),
(vii) C2–5 acyl,
(viii) halogen,
(ix) C1–4 alkoxycarbonyl,
(x) nitro,
(xi) —$NR^{36}R^{37}$ (in which $R^{36}$ and $R^{37}$ are independently, hydrogen, C1–4 alkyl or C1–4 alkoxycarbonyl, or $R^{36}$ and $R^{37}$ taken together with nitrogen atom to which they are attached represents 5~7-membered saturated heterocyclic ring necessarily containing one nitrogen atom and optionally further containing one nitrogen atom or one oxygen atom) and
(xii) hydroxy
is preferable.

In addition, in $R^4$, the substituent of carbocyclic ring and heterocyclic ring in L and M, and the substituent of heterocyclic ring represented by each L and $R^{16}$, L and $R^{17}$, L and $R^{21}$, and L and $R^{23}$ taken together with nitrogen atom to which they are attached is preferably group selected from the following (i)–(v) and (vii)–(xiv):

(i) C1–4 alkyl,
(ii) C2–4 alkenyl,
(iii) hydroxy,
(iv) C1–4 alkoxy,
(v) —(C1–4 alkylene)-OH,
(vii) halogen,
(viii) $NR^{40}R^{41}$ (in which $R^{40}$ and $R^{41}$ are independently, hydrogen, C1–4 alkyl or C1–4 alkoxycarbonyl, or $R^{40}$ and $R^{41}$ taken together with nitrogen atom to which they are attached, represents 5~7-membered saturated heterocyclic ring necessarily containing one nitrogen atom and optionally further containing one nitrogen atom or one oxygen atom),
(ix) $SR^{42}$ (in which $R^{42}$ is hydrogen or C1–4 alkyl),
(x) nitro,
(xi) trifluoromethyl,
(xii) C1–4 alkoxycarbonyl,
(xiii) oxo and
(xiv) C2–5 acyl.

[Salts]

All the non-toxic salts are also included in the present invention. For example, the compounds of the formula (I) of the present invention may be converted into the corresponding salts by known methods. Non-toxic and water-soluble salts are preferable. Suitable salts, for example, are follows: salts of alkaline metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, dicyclohexylamine, benzylamine, phenethylamine, piperidine, monoethanolamine, diethanolamine, tris(hydroxymethyl) amine, lysine, arginine, N-methyl-D-glucamine etc.).

The compounds of the formula (I) of the present invention may be converted into the corresponding acid additional salts by methods known per se. Non-toxic and water-soluble acid addition salts are preferable. Suitable acid addition salts, for example, are salts of inorganic acids, e.g., hydrochloride, hydrobromide, sulphate, phosphate, nitrate etc., or salts of organic acids, e.g., acetate, trifluoroacetate, lactate, tartarate, oxalate, fumarate, maleate, citrate, benzoate, methanesulphonate, ethanesulphonate, benzenesulphonate, toluenesulphonate, isethioate, glucuronate, gluconate etc.

The compounds of the formula (I) of the present invention or salts thereof may be converted into hydrate thereof by methods known per se.

In the compounds of the formula (I), the compounds of the formula (Ia)

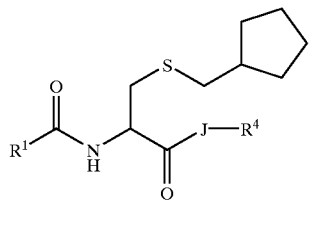

(Ia)

(wherein all the symbols are the same meanings as defined hereinbefore), the compounds of the formula (Ib)

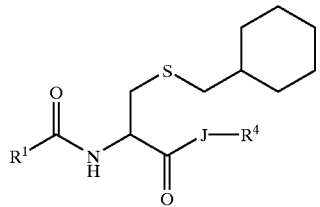

(Ib)

(wherein all the symbols are the same meanings as defined hereinbefore), the compounds of the formula (Ic)

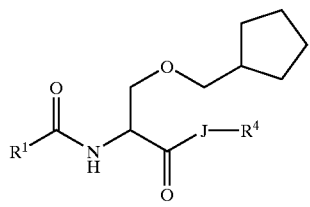

(Ic)

(wherein all the symbols are the same meanings as defined hereinbefore), the compounds of the formula (Id)

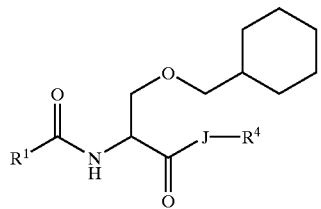

(Id)

(wherein all the symbols are the same meanings as defined hereinbefore), the compounds of the formula (Ie)

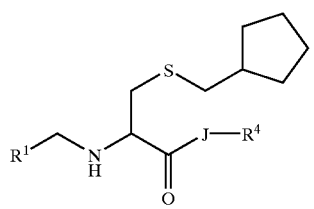

(Ie)

(wherein all the symbols are the same meanings as defined hereinbefore), the compounds of the formula (If)

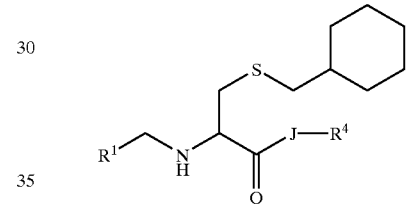

(If)

(wherein all the symbols are the same meanings as defined hereinbefore), the compounds of the formula (Ig)

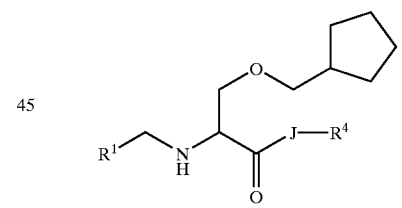

(Ig)

(wherein all the symbols are the same meanings as defined hereinbefore), and the compounds of the formula (Ih)

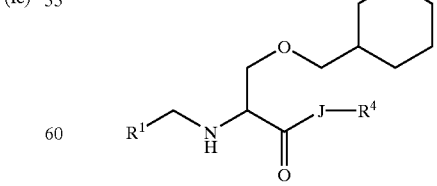

(Ih)

(wherein all the symbols are the same meanings as defined hereinbefore), non-toxic salts thereof or hydrates thereof are prefereable. The compounds of the formula (Ia) or (Ib) (wherein all the symbols are the same meanings as defined hereinbefore), non-toxic salts thereof or hydrates thereof are more preferable.

The concrete compounds are ones shown in the following Tables 1–40, non-toxic salts thereof and the hydrates thereof and ones described in Examples. Also, the following concrete compounds include the isomers generated by asymmetric carbon atom(s), i.e., R, S and RS form. In the following each Table, Me is methyl, Boc is t-butoxycarbonyl, i-Bu is isobutyl and Ac is acetyl.

TABLE 1

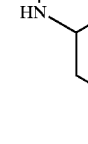

(Ia-1)

| No. | R¹ |
|---|---|
| 1 |  |
| 2 |  |
| 3 |  |
| 4 |  |
| 5 |  |
| 6 |  |
| 7 |  |

TABLE 1-continued

(Ia-1)

| No. | R¹ |
|---|---|
| 8 | Boc-thiazolidine-methyl |
| 9 | H-thiazolidine-methyl |
| 10 | Boc-thiomorpholine-methyl |
| 11 | thiomorpholine-methyl |
| 12 | Boc-thiazinane-methyl |
| 13 | H-thiazinane-methyl |
| 14 | thiophene-methyl |
| 15 | thiazole-methyl |
| 16 | H₂N-thiazole-methyl |

TABLE 1-continued (Ia-1)

| No. | R¹ |
|---|---|
| 17 | 4-methyl-1H-imidazol-yl |
| 18 | 1-Boc-4-methylimidazol-yl |
| 19 | 2-furyl-methyl |
| 20 | 2,5-dimethyloxazol-yl |
| 21 | cyclohexyl-methyl |
| 22 | 4-(MeO₂C)-cyclohexyl-methyl |
| 23 | 4-methylphenyl |
| 24 | 2-methyl-1H-indol-yl |

TABLE 2

(Ia-2)

| No. | R¹ |
|---|---|
| 1 | N-Boc-4-methylthiazolidin-yl |
| 2 | 4-methylthiazolidin-yl (NH) |
| 3 | N-(CO₂Me)-4-methylthiazolidin-yl |
| 4 | N-(iBuOC(O))-4-methylthiazolidin-yl |
| 5 | N-Ac-4-methylthiazolidin-yl |
| 6 | N-(i-Bu-C(O))-4-methylthiazolidin-yl |
| 7 | 2-oxo-4-methylthiazolidin-yl |
| 8 | N-Boc-2-methylthiazolidin-yl |

TABLE 2-continued (Ia-2)

| No. | R¹ |
|---|---|
| 9 | 2-methyl-thiazolidin-2-yl (NH) |
| 10 | N-Boc-3-methyl-thiomorpholine (SH) |
| 11 | 3-methyl-thiomorpholine |
| 12 | N-Boc-4-methyl-1,3-thiazinane |
| 13 | 4-methyl-1,3-thiazinane (NH) |
| 14 | 2-methyl-thiophene |
| 15 | 4-methyl-thiazole |
| 16 | 2-amino-4-methyl-thiazole |
| 17 | 4-methyl-imidazole (NH) |
| 18 | N-Boc-4-methyl-imidazole |
| 19 | 2-methyl-furan |
| 20 | 2,5-dimethyl-oxazole |
| 21 | cyclohexyl |
| 22 | 4-methyl-cyclohexyl-CO₂Me |
| 23 | phenyl (p-methyl) |
| 24 | 2-methyl-indole |

TABLE 3
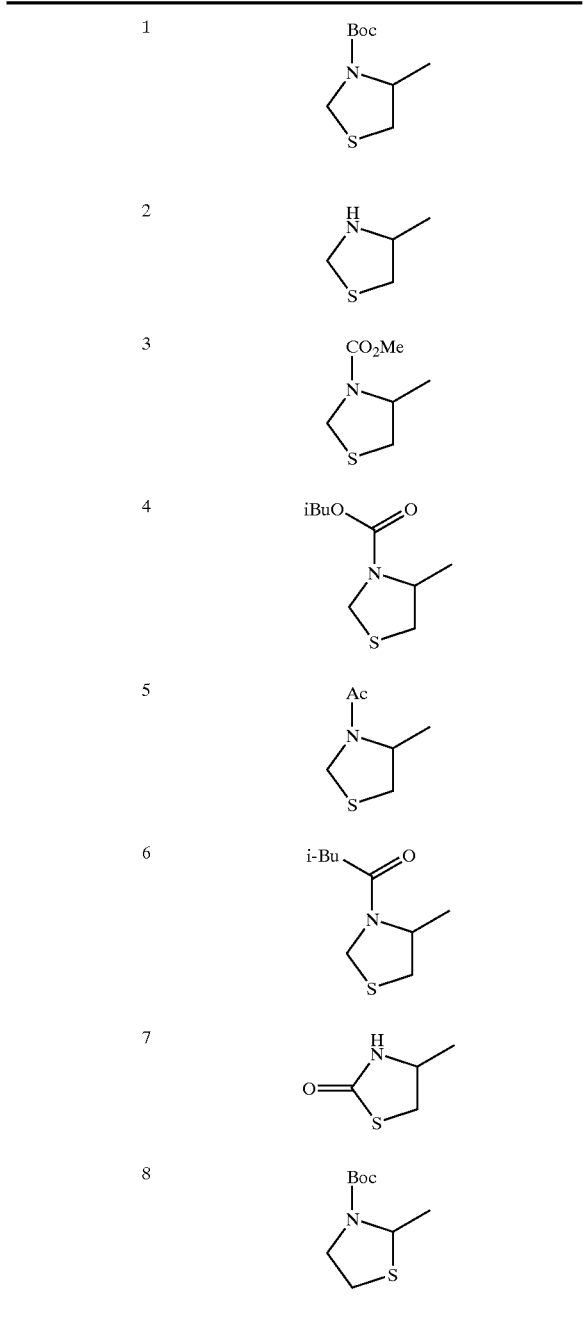
TABLE 3-continued
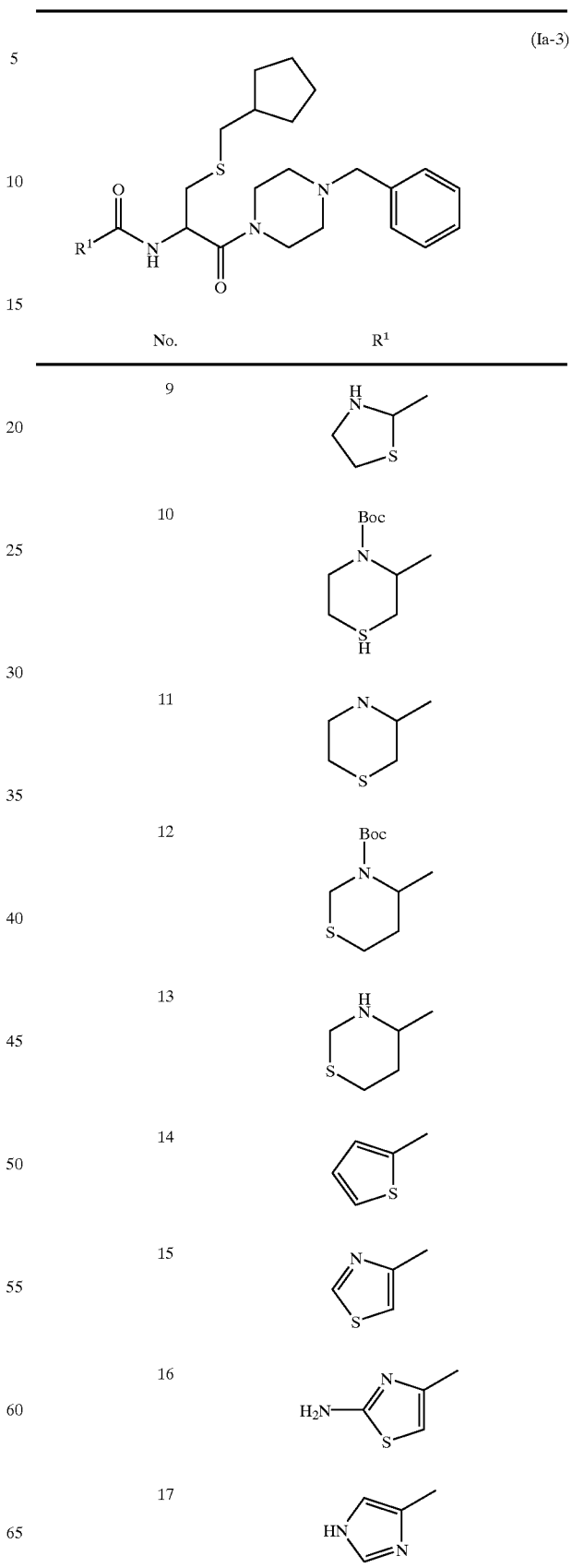

TABLE 3-continued
(Ia-3)
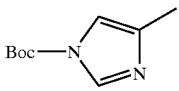
| No. | R¹ |
|---|---|
| 18 | 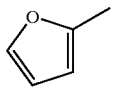 |
| 19 | 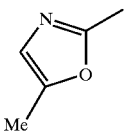 |
| 20 | 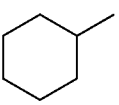 |
| 21 | 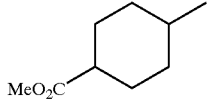 |
| 22 | 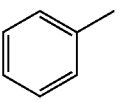 |
| 23 | 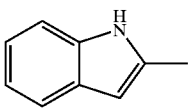 |
| 24 | 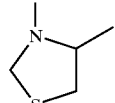 |
TABLE 4
(Ia-4)
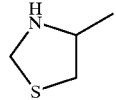
| No. | R¹ |
|---|---|
| 1 | 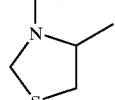 |
| 2 | 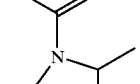 |
| 3 | 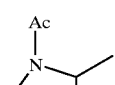 |
| 4 | 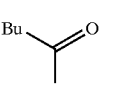 |
| 5 | 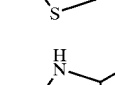 |
| 6 | 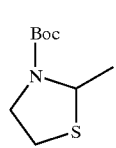 |
| 7 | |
| 8 | |

TABLE 4-continued
(Ia-4)
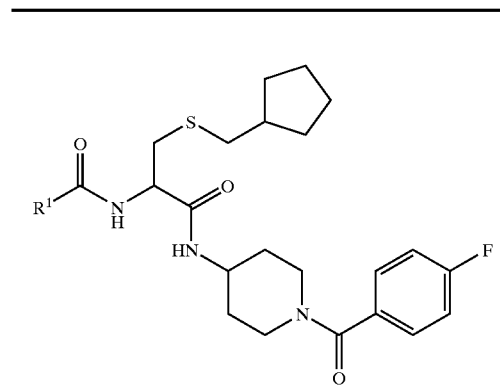
| No. | R¹ |
|---|---|
| 9 |  |
| 10 | 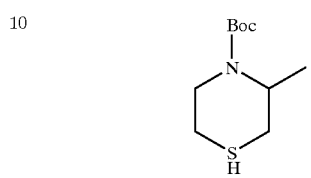 |
| 11 | 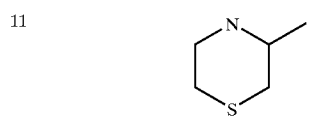 |
| 12 | 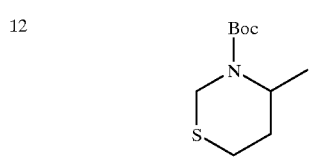 |
| 13 |  |
| 14 | 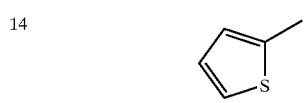 |
| 15 |  |
| 16 | 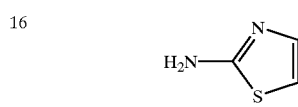 |
TABLE 4-continued
(Ia-4)
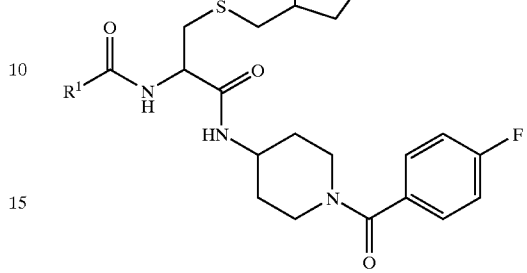
| No. | R¹ |
|---|---|
| 17 | 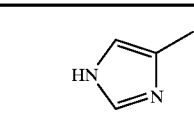 |
| 18 | 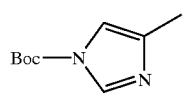 |
| 19 | 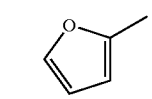 |
| 20 | 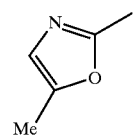 |
| 21 | 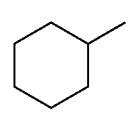 |
| 22 | 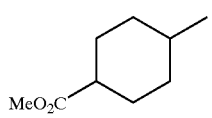 |
| 23 | 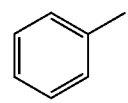 |
| 24 | 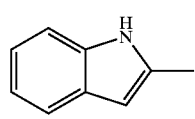 |

TABLE 5
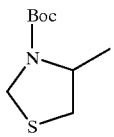
(Ia-5)
| No. | R¹ |
|---|---|
| 1 | 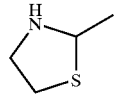 |
| 2 | 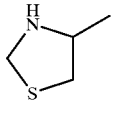 |
| 3 | 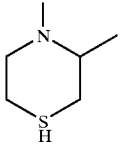 |
| 4 | 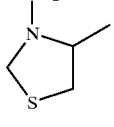 |
| 5 | 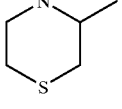 |
| 6 | 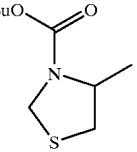 |
| 7 | 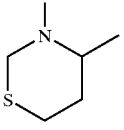 |
| 8 | 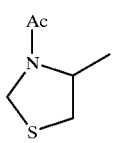 |
TABLE 5-continued
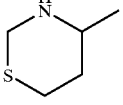
(Ia-5)
| No. | R¹ |
|---|---|
| 9 | 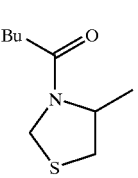 |
| 10 | 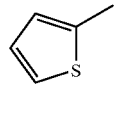 |
| 11 | 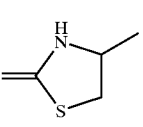 |
| 12 | 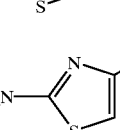 |
| 13 | 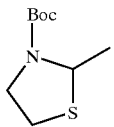 |
| 14 | 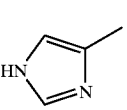 |
| 15 | 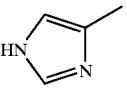 |
| 16 | |
| 17 | |

TABLE 5-continued
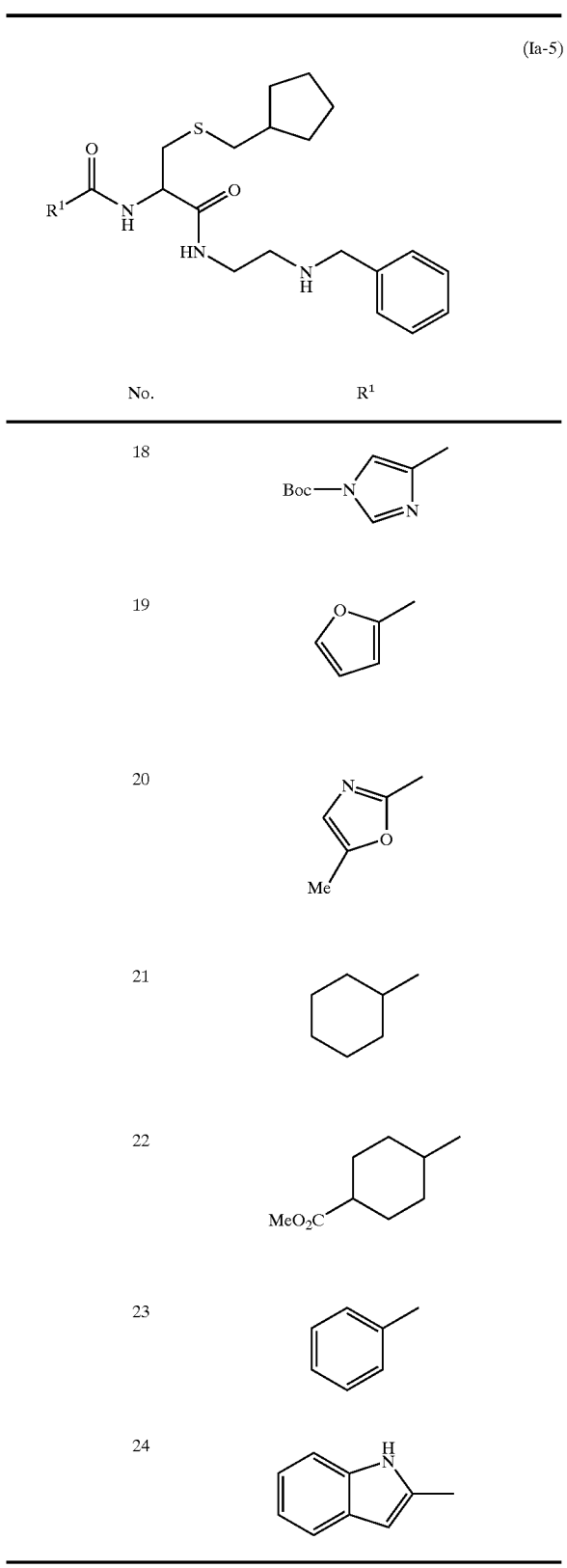
TABLE 6
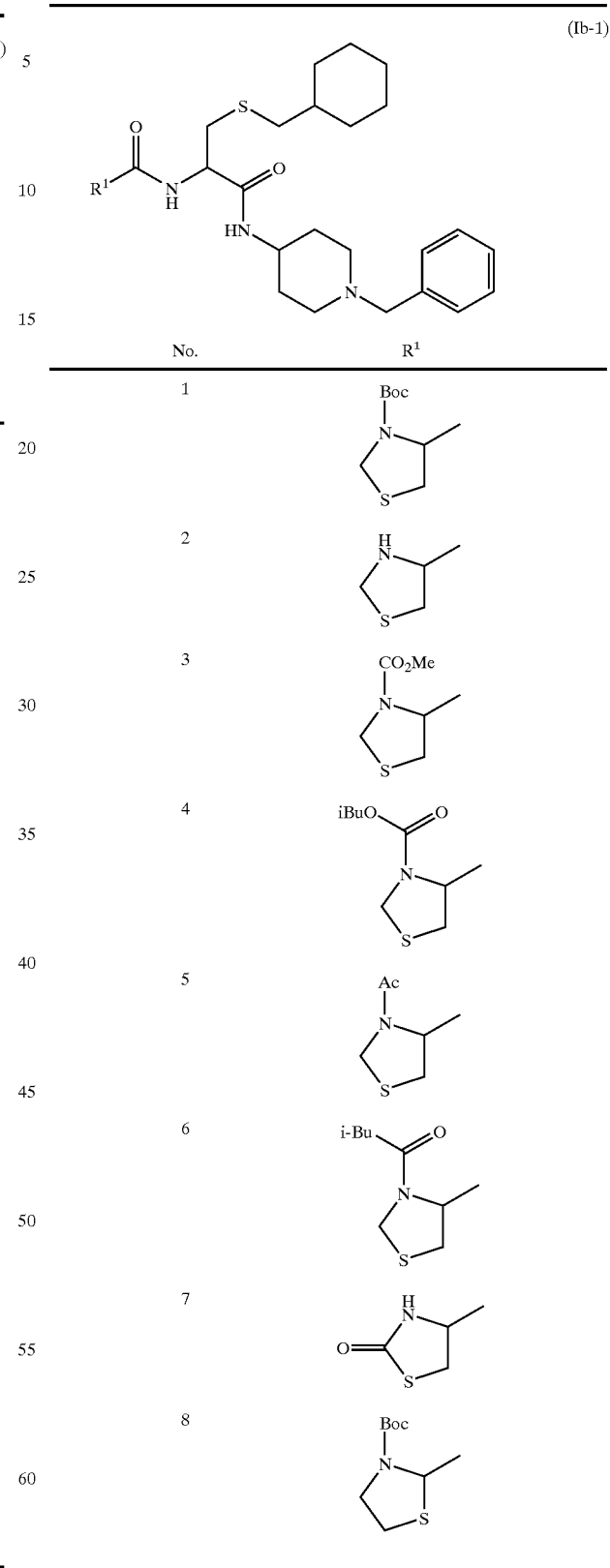

TABLE 6-continued
(Ib-1)
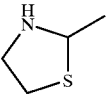
| No. | R¹ |
|---|---|
| 9 | 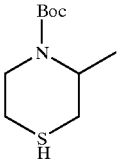 |
| 10 | 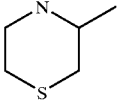 |
| 11 | 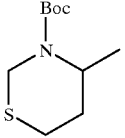 |
| 12 | 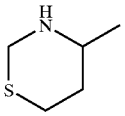 |
| 13 | 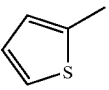 |
| 14 | 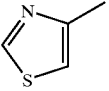 |
| 15 | 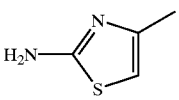 |
| 16 | 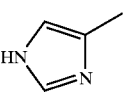 |
TABLE 6-continued
(Ib-1)
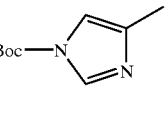
| No. | R¹ |
|---|---|
| 17 | 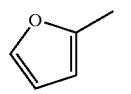 |
| 18 | 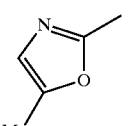 |
| 19 | 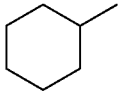 |
| 20 | 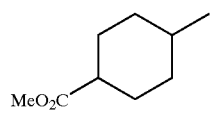 |
| 21 | 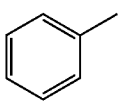 |
| 22 | 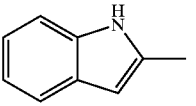 |
| 23 | 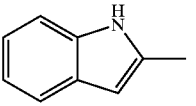 |
| 24 | 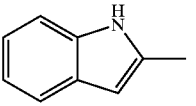 |

TABLE 7

(Ib-2)

[Structure: R¹-C(=O)-NH-CH(CH₂-S-CH₂-cyclohexyl)-C(=O)-NH-(4-piperidinyl)-N-CH₂-(4-fluorophenyl)]

| No. | R¹ |
|---|---|
| 1 | N-Boc-4-methylthiazolidin-3-yl |
| 2 | 4-methylthiazolidin-3-yl (NH) |
| 3 | N-CO₂Me-4-methylthiazolidin-3-yl |
| 4 | N-(iBuO-C(=O))-4-methylthiazolidin-3-yl |
| 5 | N-Ac-4-methylthiazolidin-3-yl |
| 6 | N-(i-Bu-C(=O))-4-methylthiazolidin-3-yl |
| 7 | 2-oxo-4-methylthiazolidin-3-yl |
| 8 | N-Boc-2-methylthiazolidin-3-yl |
| 9 | 2-methylthiazolidin-3-yl (NH) |
| 10 | N-Boc-3-methylthiomorpholin-4-yl (SH) |
| 11 | 3-methylthiomorpholin-4-yl |
| 12 | N-Boc-4-methyl-1,3-thiazinan-3-yl |
| 13 | 4-methyl-1,3-thiazinan-3-yl (NH) |
| 14 | 2-methylthiophen-yl |
| 15 | 4-methylthiazol-yl |
| 16 | 2-amino-4-methylthiazol-yl |
| 17 | 4-methylimidazol-yl |

TABLE 7-continued (Ib-2)

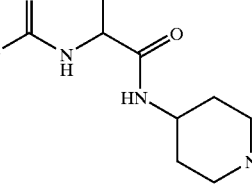

| No. | R¹ |
|---|---|
| 18 | Boc-imidazole-methyl |
| 19 | 2-methylfuran |
| 20 | 2,5-dimethyloxazole |
| 21 | cyclohexyl |
| 22 | 4-(MeO₂C)cyclohexyl |
| 23 | tolyl |
| 24 | 2-methylindole |

TABLE 8

(Ib-3)

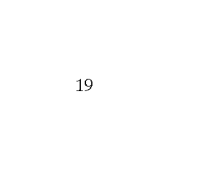

| No. | R¹ |
|---|---|
| 1 | N-Boc-4-methylthiazolidine |
| 2 | 4-methylthiazolidine (NH) |
| 3 | N-CO₂Me-4-methylthiazolidine |
| 4 | N-(iBuO-C(O))-4-methylthiazolidine |
| 5 | N-Ac-4-methylthiazolidine |
| 6 | N-(i-Bu-C(O))-4-methylthiazolidine |
| 7 | 2-oxo-4-methylthiazolidine |
| 8 | N-Boc-2-methylthiazolidine |
| 9 | 2-methylthiazolidine (NH) |

TABLE 8-continued
(Ib-3)
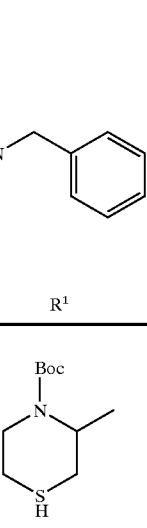
| No. | R¹ |
|---|---|
| 10 | 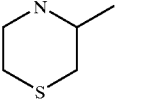 |
| 11 | 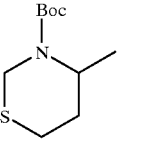 |
| 12 | 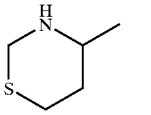 |
| 13 | 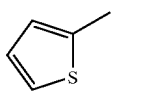 |
| 14 | 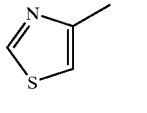 |
| 15 | 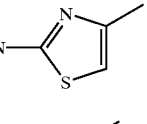 |
| 16 | 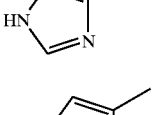 |
| 17 | 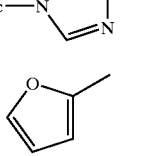 |
| 18 |  |
| 19 | 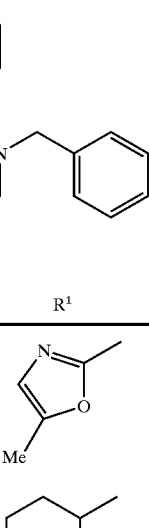 |
TABLE 8-continued
(Ib-3)
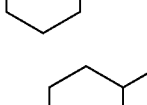
| No. | R¹ |
|---|---|
| 20 | 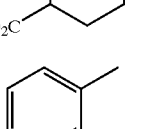 |
| 21 | 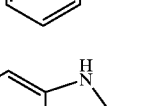 |
| 22 | 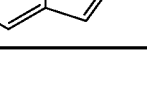 |
| 23 | 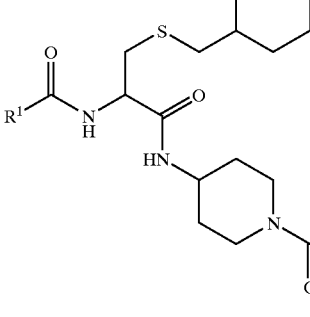 |
| 24 | 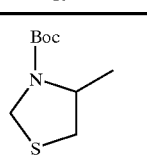 |
TABLE 9
(Ib-4)
| No. | R¹ |
|---|---|
| 1 |  |

TABLE 9-continued
(Ib-4)
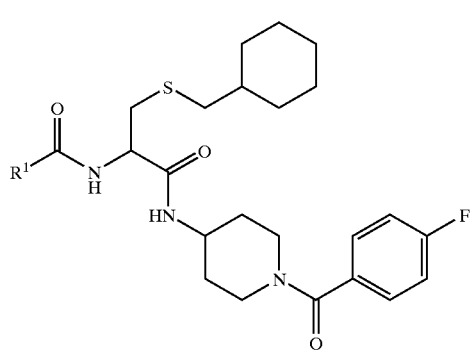
| No. | R¹ |
|---|---|
| 2 | 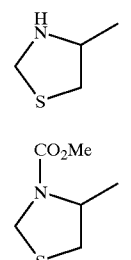 |
| 3 | 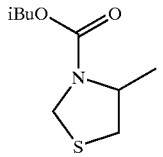 |
| 4 | 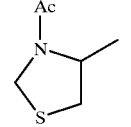 |
| 5 | 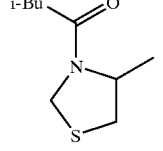 |
| 6 | 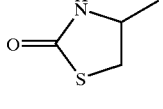 |
| 7 | 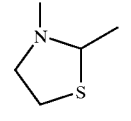 |
| 8 | 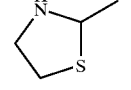 |
| 9 | 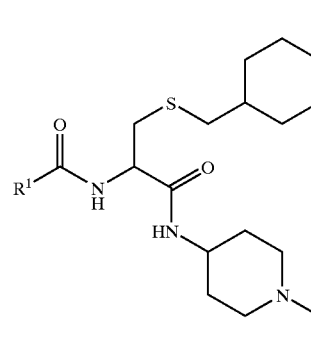 |
TABLE 9-continued
(Ib-4)
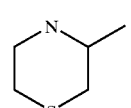
| No. | R¹ |
|---|---|
| 10 | 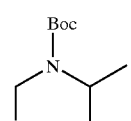 |
| 11 | 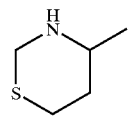 |
| 12 | 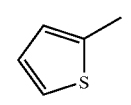 |
| 13 | 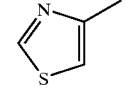 |
| 14 | 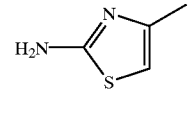 |
| 15 | 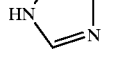 |
| 16 |  |
| 17 |  |

TABLE 9-continued (Ib-4)

| No. | R¹ |
|---|---|
| 18 | Boc-N(imidazole)-Me |
| 19 | 2-methylfuran |
| 20 | 2,5-dimethyloxazole |
| 21 | cyclohexyl |
| 22 | 4-(MeO₂C)-cyclohexyl |
| 23 | p-tolyl |
| 24 | 2-methylindole |

TABLE 10

(Ib-5)

| No. | R¹ |
|---|---|
| 1 | Boc-4-methylthiazolidine |
| 2 | 4-methylthiazolidine (NH) |
| 3 | N-CO₂Me-4-methylthiazolidine |
| 4 | iBuO-C(O)-4-methylthiazolidine |
| 5 | Ac-4-methylthiazolidine |
| 6 | i-Bu-C(O)-4-methylthiazolidine |
| 7 | 4-methyl-2-oxothiazolidine |
| 8 | Boc-2-methylthiazolidine |

TABLE 10-continued
(Ib-5)
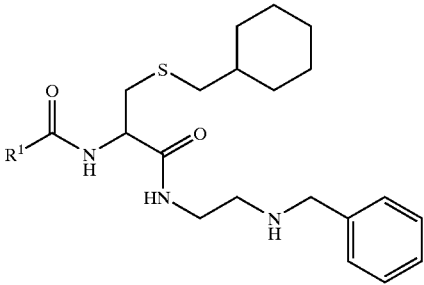
| No. | R¹ |
|---|---|
| 9 | 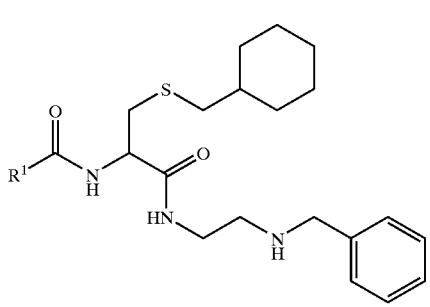 |
| 10 | 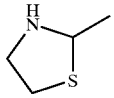 |
| 11 | 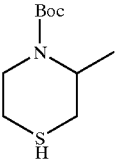 |
| 12 | 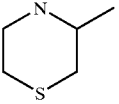 |
| 13 | 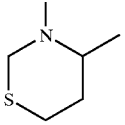 |
| 14 | 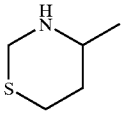 |
| 15 | 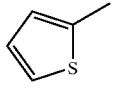 |
| 16 | 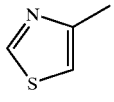 |
TABLE 10-continued
(Ib-5)
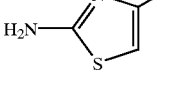
| No. | R¹ |
|---|---|
| 17 | 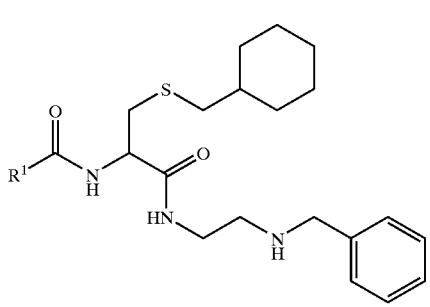 |
| 18 | 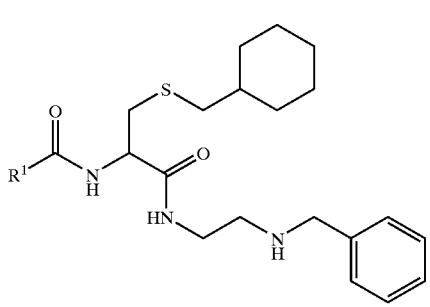 |
| 19 | 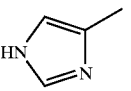 |
| 20 | 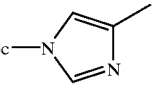 |
| 21 |  |
| 22 | 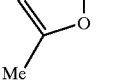 |
| 23 | 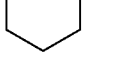 |
| 24 | 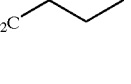 |

TABLE 11
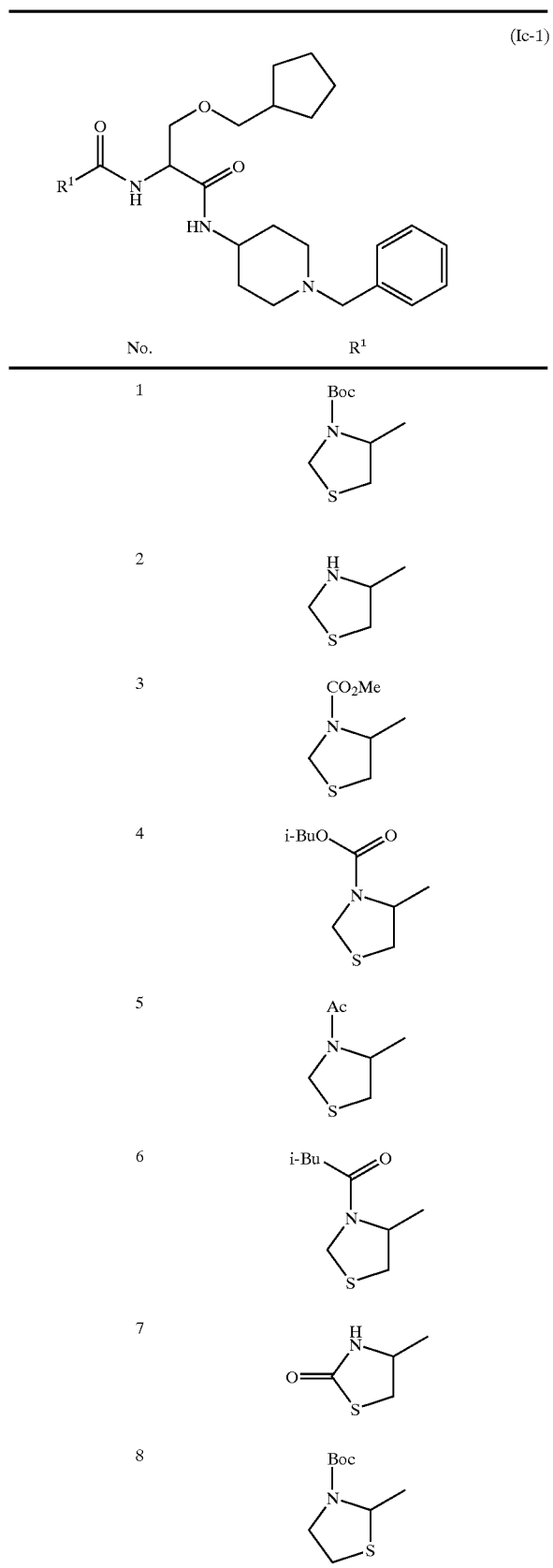
TABLE 11-continued
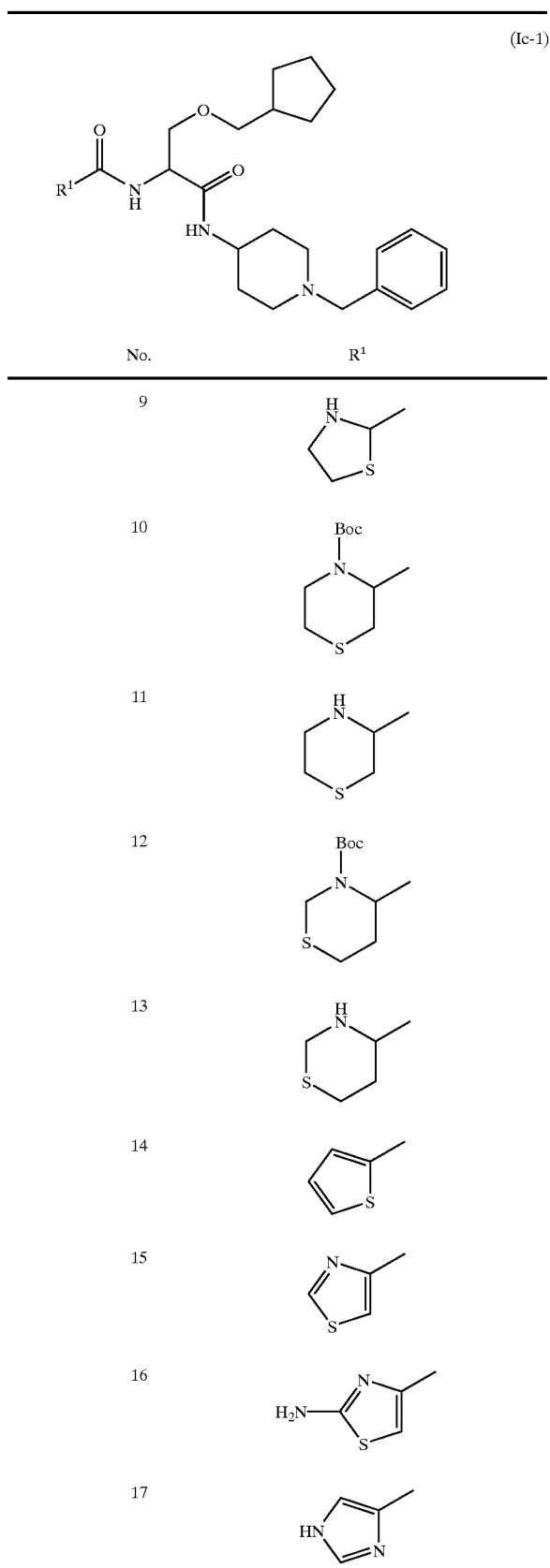

TABLE 11-continued
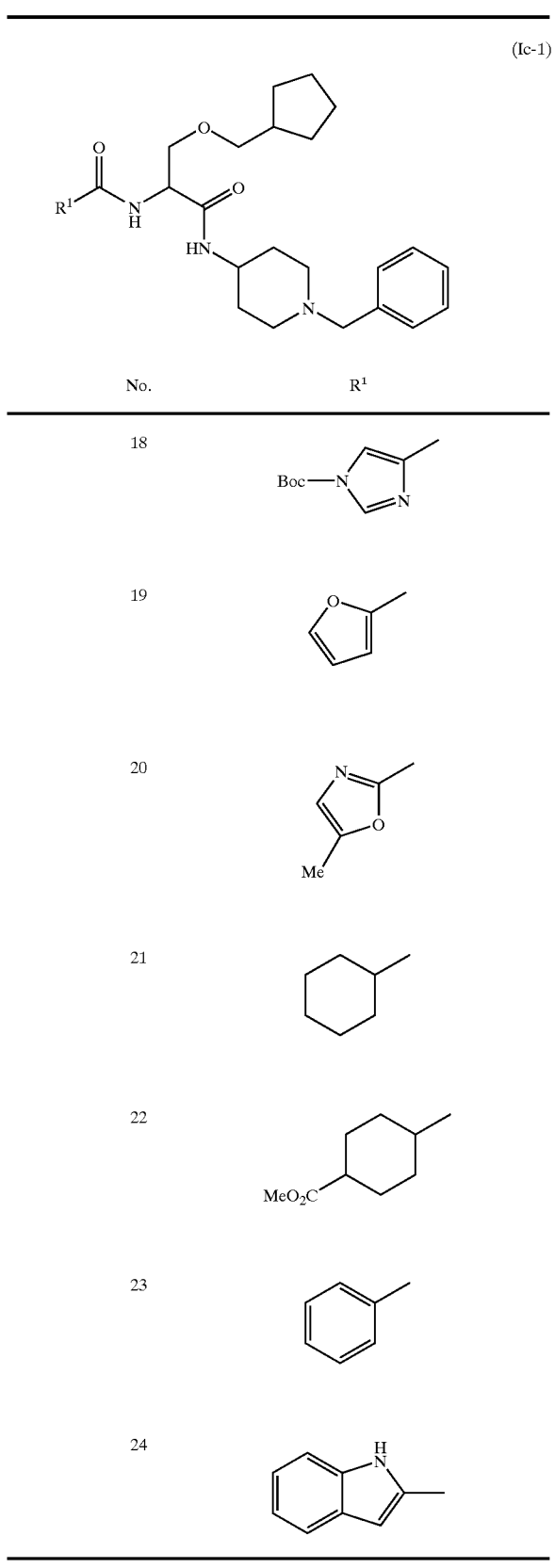
TABLE 12
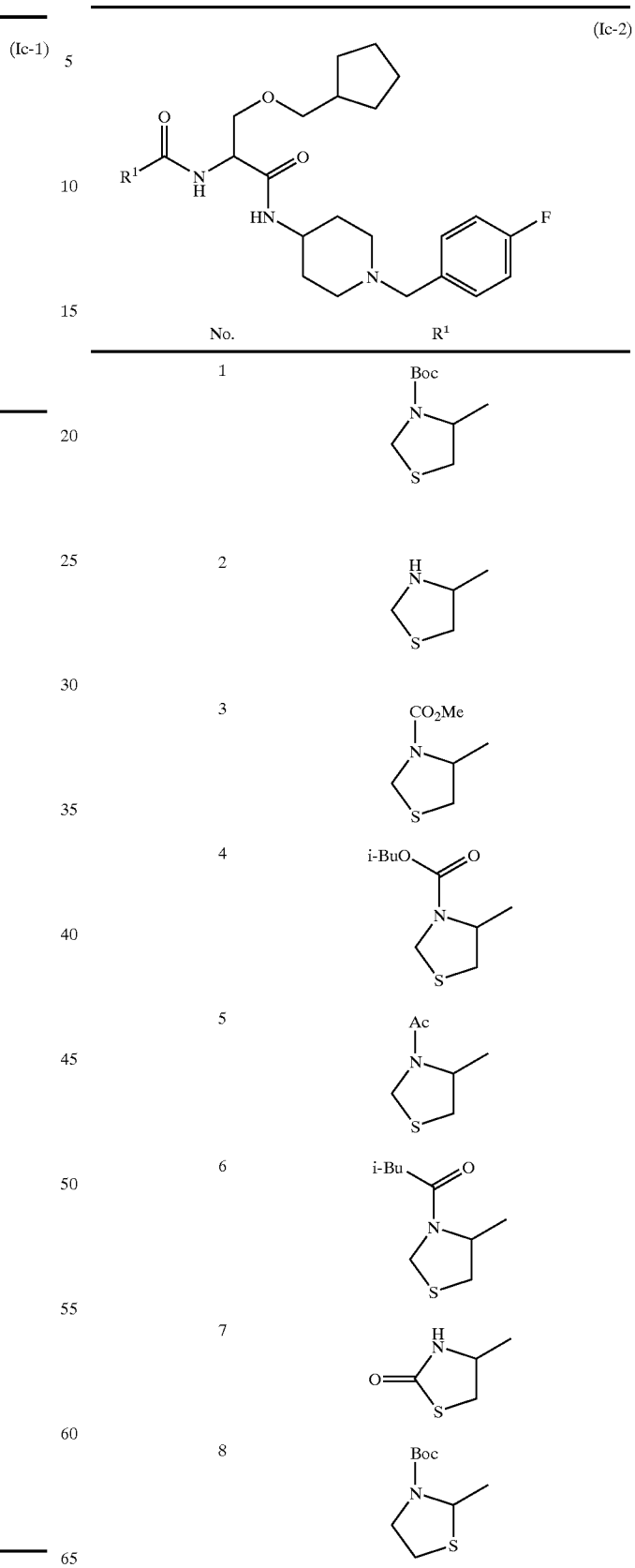

TABLE 12-continued

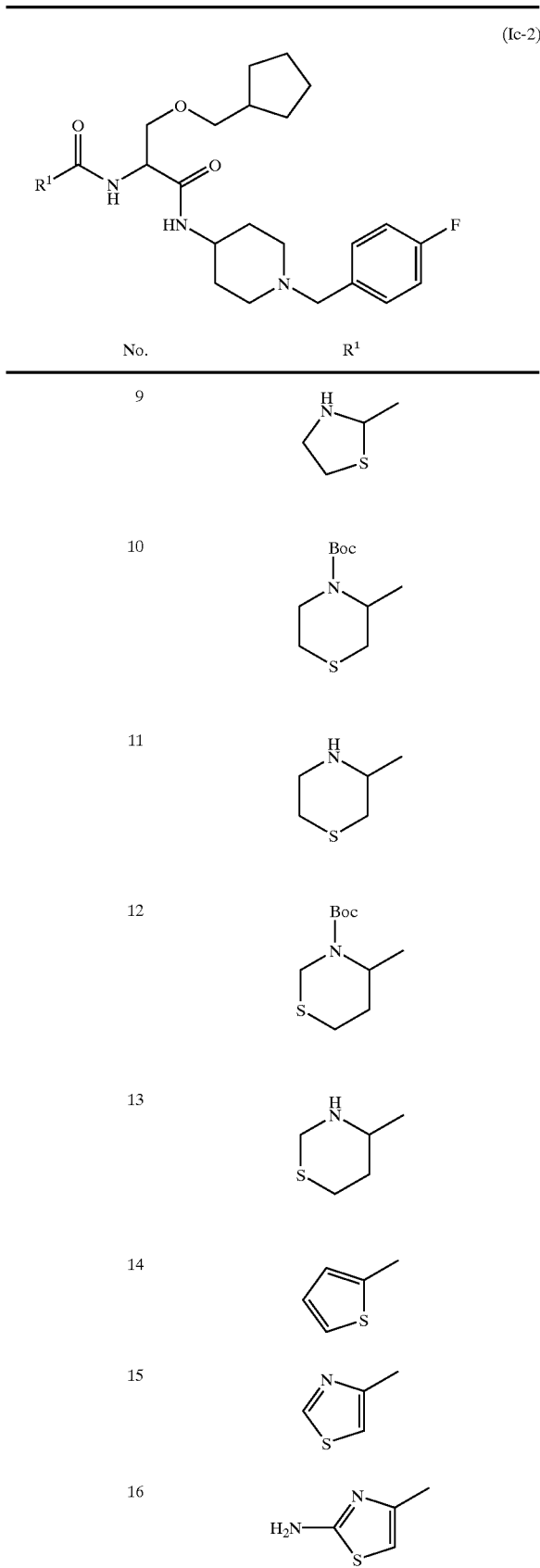

| No. | R¹ |
|---|---|
| 9 | 2-methyl-thiazolidine |
| 10 | N-Boc-3-methyl-thiomorpholine |
| 11 | 3-methyl-thiomorpholine |
| 12 | N-Boc-4-methyl-1,3-thiazinane |
| 13 | 4-methyl-1,3-thiazinane |
| 14 | 2-methyl-thiophene |
| 15 | 4-methyl-thiazole |
| 16 | 2-amino-4-methyl-thiazole |

TABLE 12-continued

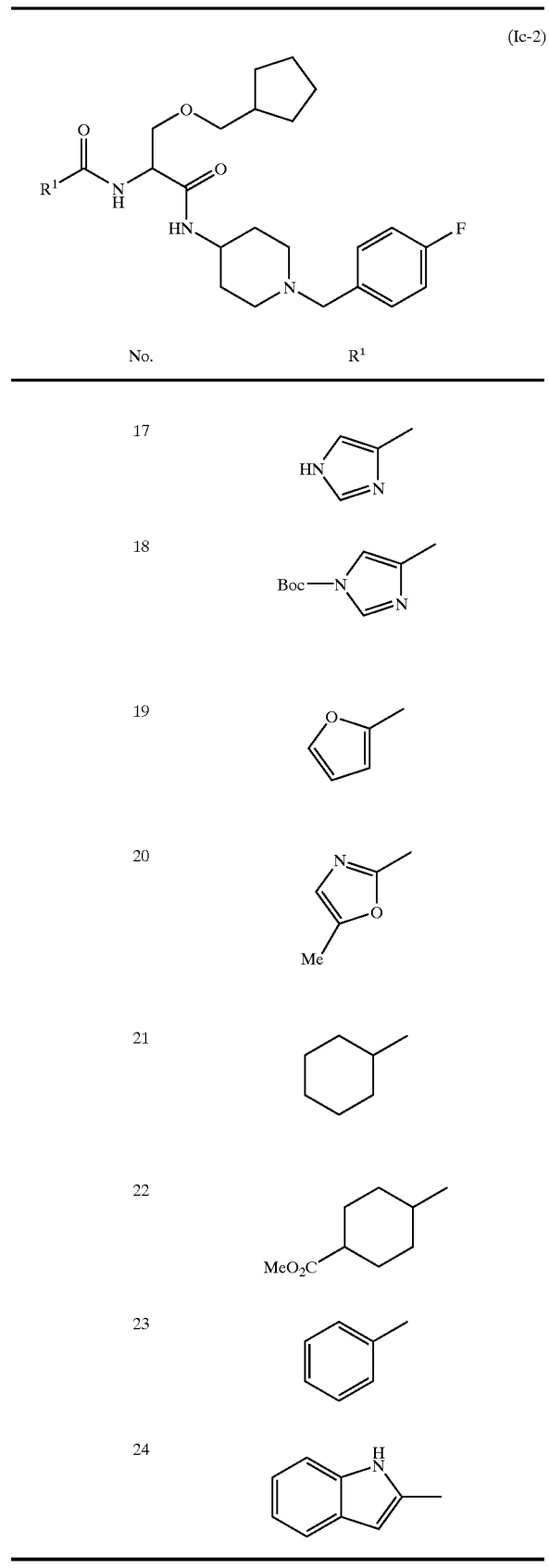

| No. | R¹ |
|---|---|
| 17 | 4-methyl-1H-imidazole |
| 18 | N-Boc-4-methyl-imidazole |
| 19 | 2-methyl-furan |
| 20 | 2,5-dimethyl-oxazole |
| 21 | methyl-cyclohexane |
| 22 | 4-(methoxycarbonyl)-methylcyclohexane |
| 23 | methyl-benzene |
| 24 | 2-methyl-1H-indole |

TABLE 13

(Ic-3)

| No. | R¹ |
|---|---|
| 1 | N-Boc, 4-methyl thiazolidine |
| 2 | NH, 4-methyl thiazolidine |
| 3 | N-CO₂Me, 4-methyl thiazolidine |
| 4 | N-C(O)O-i-Bu, 4-methyl thiazolidine |
| 5 | N-Ac, 4-methyl thiazolidine |
| 6 | N-C(O)-i-Bu, 4-methyl thiazolidine |
| 7 | 2-oxo, 4-methyl thiazolidine (NH) |
| 8 | N-Boc, 2-methyl thiazolidine |

TABLE 13-continued (Ic-3)

| No. | R¹ |
|---|---|
| 9 | NH, 2-methyl thiazolidine |
| 10 | N-Boc, 3-methyl thiomorpholine |
| 11 | NH, 3-methyl thiomorpholine |
| 12 | N-Boc, 4-methyl thiazinane |
| 13 | NH, 4-methyl thiazinane |
| 14 | 2-methyl thiophene |
| 15 | 4-methyl thiazole |
| 16 | 2-amino-4-methyl thiazole |
| 17 | 4-methyl imidazole |

TABLE 13-continued
(Ic-3)
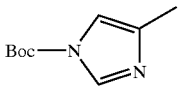
| No. | R¹ |
|---|---|
| 18 | 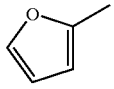 |
| 19 | 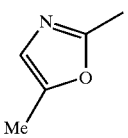 |
| 20 | 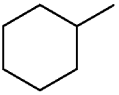 |
| 21 | 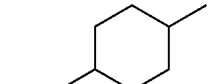 |
| 22 | 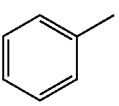 |
| 23 | 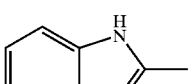 |
| 24 | 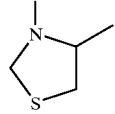 |
TABLE 14
(Ic-4)
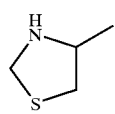
| No. | R¹ |
|---|---|
| 1 | 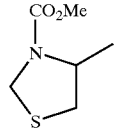 |
| 2 | 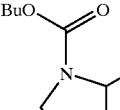 |
| 3 | 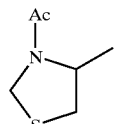 |
| 4 | 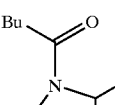 |
| 5 | 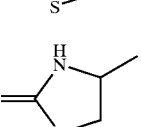 |
| 6 | 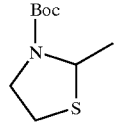 |
| 7 | |
| 8 | |

TABLE 14-continued (Ic-4)

| No. | R¹ |
|---|---|
| 9 | 2-methyl-thiazolidine |
| 10 | N-Boc-3-methyl-thiomorpholine |
| 11 | 3-methyl-thiomorpholine (NH) |
| 12 | N-Boc-4-methyl-1,3-thiazinane |
| 13 | 4-methyl-1,3-thiazinane (NH) |
| 14 | 2-methyl-thiophene |
| 15 | 4-methyl-thiazole |
| 16 | 2-amino-4-methyl-thiazole |
| 17 | 4-methyl-1H-imidazole |
| 18 | N-Boc-4-methyl-imidazole |
| 19 | 2-methyl-furan |
| 20 | 2,5-dimethyl-oxazole |
| 21 | methyl-cyclohexane |
| 22 | 4-methyl-cyclohexanecarboxylic acid methyl ester |
| 23 | methyl-benzene |
| 24 | 2-methyl-1H-indole |

TABLE 15
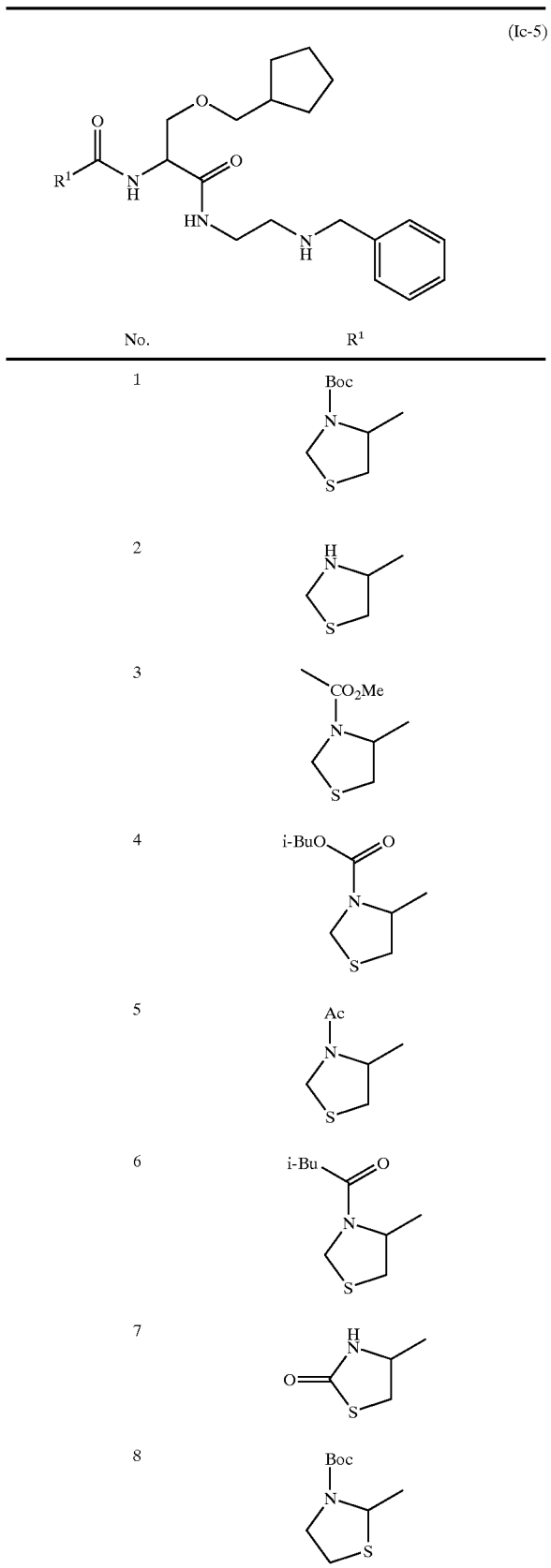
TABLE 15-continued
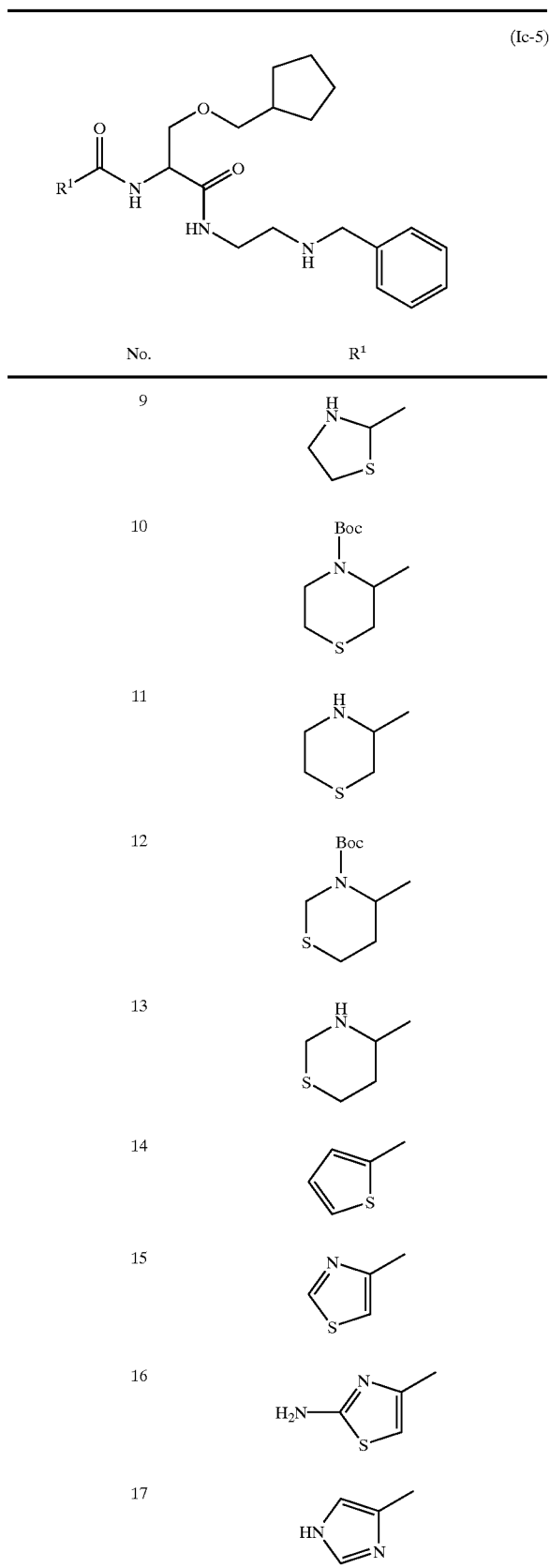

TABLE 15-continued (Ic-5)

| No. | R¹ |
|---|---|
| 18 | Boc-N(4-methylimidazole) |
| 19 | 2-methylfuran |
| 20 | 2,5-dimethyloxazole |
| 21 | methylcyclohexane |
| 22 | methyl 4-methylcyclohexanecarboxylate |
| 23 | toluene |
| 24 | 2-methylindole |

TABLE 16

(Id-1)

| No. | R¹ |
|---|---|
| 1 | Boc-4-methylthiazolidine |
| 2 | 4-methylthiazolidine (NH) |
| 3 | $CO_2Me$-4-methylthiazolidine |
| 4 | i-BuO-C(O)-4-methylthiazolidine |
| 5 | Ac-4-methylthiazolidine |
| 6 | i-Bu-C(O)-4-methylthiazolidine |
| 7 | 2-oxo-4-methylthiazolidine |
| 8 | Boc-2-methylthiazolidine |

TABLE 16-continued
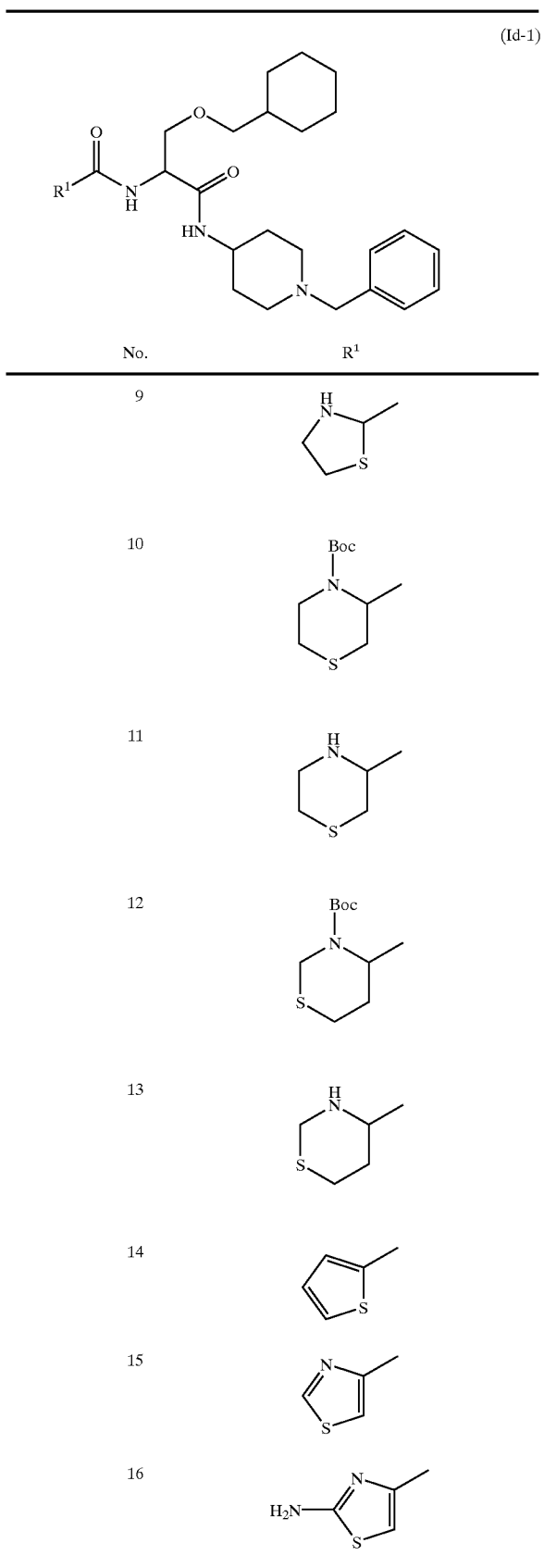
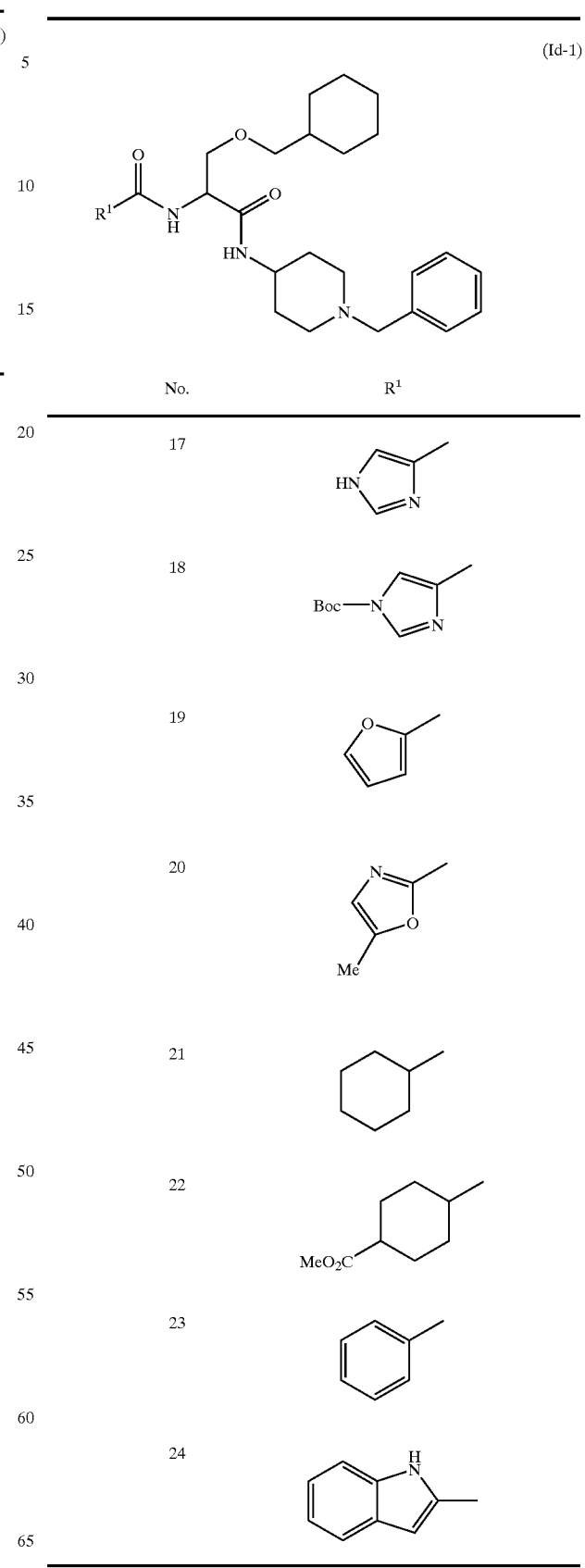

TABLE 17
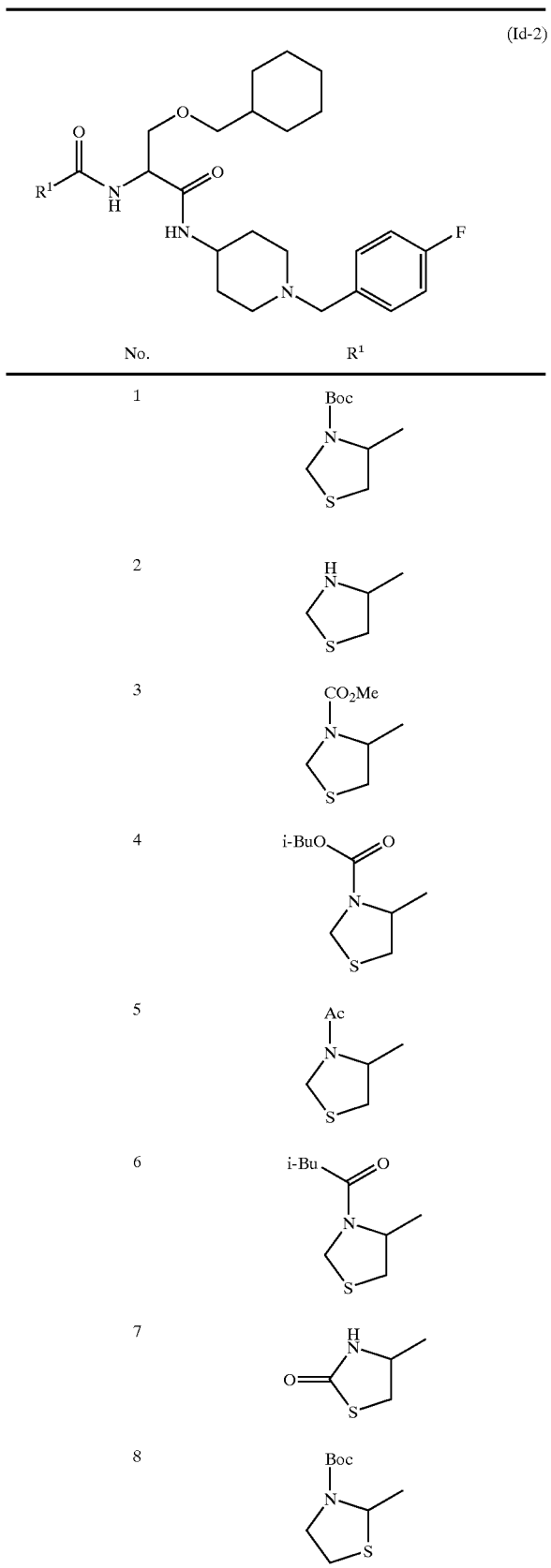
TABLE 17-continued
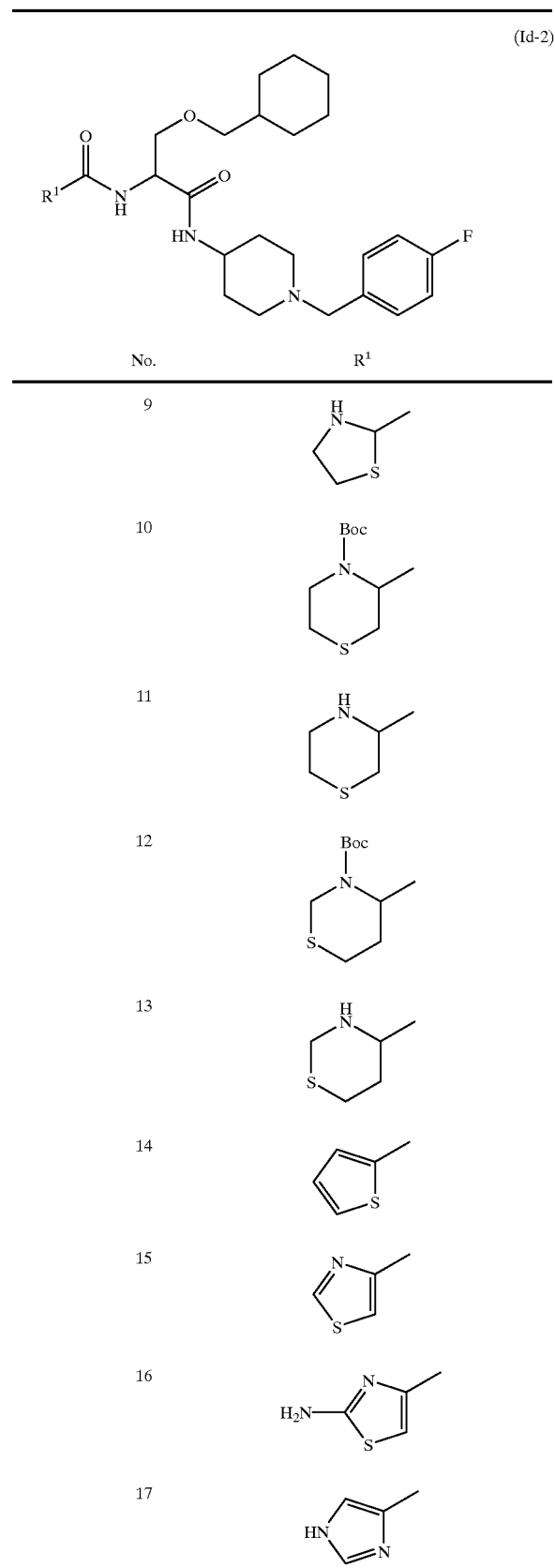

TABLE 17-continued (Id-2)

| No. | R¹ |
|---|---|
| 18 | Boc-N(imidazole)-Me |
| 19 | 2-methylfuran |
| 20 | 2,5-dimethyloxazole |
| 21 | cyclohexyl |
| 22 | 4-methylcyclohexyl-CO₂Me |
| 23 | p-tolyl |
| 24 | 2-methylindole |

TABLE 18

(Id-3)

| No. | R¹ |
|---|---|
| 1 | Boc-4-methylthiazolidine |
| 2 | 4-methylthiazolidine (NH) |
| 3 | MeO₂C-4-methylthiazolidine |
| 4 | i-BuO-C(O)-4-methylthiazolidine |
| 5 | Ac-4-methylthiazolidine |
| 6 | i-Bu-C(O)-4-methylthiazolidine |
| 7 | 4-methyl-2-oxothiazolidine |
| 8 | Boc-2-methylthiazolidine |

TABLE 18-continued (Id-3)

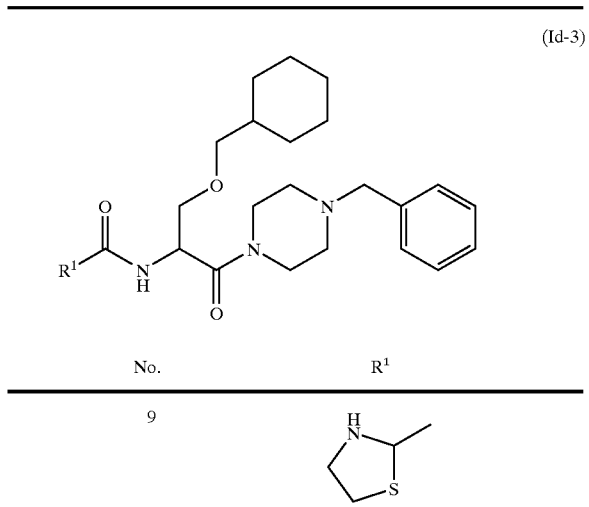

| No. | R¹ |
|---|---|
| 9 | 2-methylthiazolidin-2-yl (NH, S ring) |
| 10 | N-Boc-3-methylthiomorpholine |
| 11 | 3-methylthiomorpholine (NH) |
| 12 | N-Boc-4-methyl-1,3-thiazinane |
| 13 | 4-methyl-1,3-thiazinane (NH) |
| 14 | 2-methylthiophene |
| 15 | 4-methylthiazole |
| 16 | 2-amino-4-methylthiazole |
| 17 | 4-methyl-1H-imidazole |
| 18 | 1-Boc-4-methylimidazole |
| 19 | 2-methylfuran |
| 20 | 2,5-dimethyloxazole |
| 21 | cyclohexyl-methyl |
| 22 | 4-(methoxycarbonyl)cyclohexyl-methyl |
| 23 | 4-methylphenyl |
| 24 | 2-methyl-1H-indole |

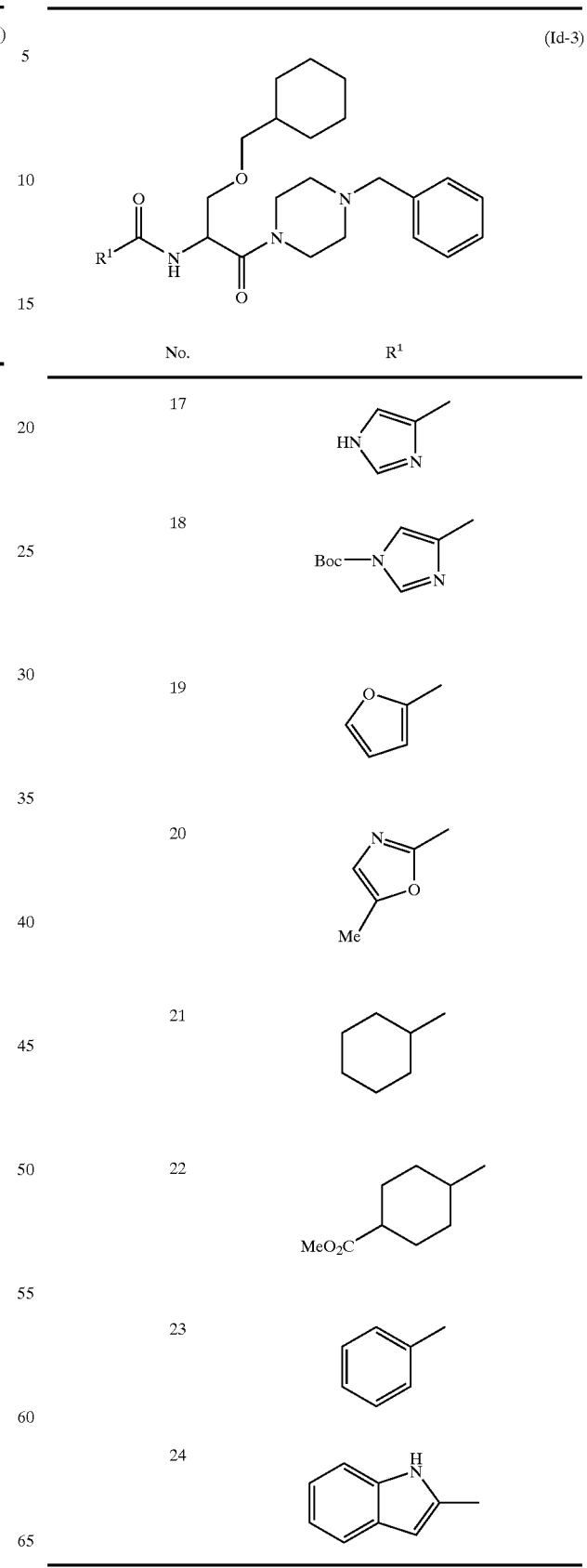

TABLE 19

(Id-4)

| No. | R¹ |
|---|---|
| 1 | 3-methyl-N-Boc-thiazolidine |
| 2 | 4-methyl-thiazolidine (NH) |
| 3 | 4-methyl-N-CO₂Me-thiazolidine |
| 4 | 4-methyl-N-(i-BuO-C(O))-thiazolidine |
| 5 | 4-methyl-N-Ac-thiazolidine |
| 6 | 4-methyl-N-(i-Bu-C(O))-thiazolidine |
| 7 | 4-methyl-2-oxo-thiazolidine |
| 8 | 2-methyl-N-Boc-thiazolidine |

TABLE 19-continued (Id-4)

| No. | R¹ |
|---|---|
| 9 | 2-methyl-thiazolidine (NH) |
| 10 | 3-methyl-N-Boc-thiomorpholine |
| 11 | 3-methyl-thiomorpholine (NH) |
| 12 | 4-methyl-N-Boc-thiazinane |
| 13 | 4-methyl-thiazinane (NH) |
| 14 | 2-methyl-thiophene |
| 15 | 4-methyl-thiazole |
| 16 | 2-amino-4-methyl-thiazole |

TABLE 19-continued (Id-4)

| No. | R¹ |
|---|---|
| 17 | 4-methyl-1H-imidazol-5-yl |
| 18 | 1-Boc-4-methyl-imidazol-5-yl |
| 19 | 2-furyl |
| 20 | 2,5-dimethyl-oxazol-4-yl |
| 21 | cyclohexyl |
| 22 | 4-(methoxycarbonyl)cyclohexyl |
| 23 | 4-methylphenyl |
| 24 | 2-methyl-1H-indol-3-yl |

TABLE 20

(Id-5)

| No. | R¹ |
|---|---|
| 1 | N-Boc-4-methyl-thiazolidin-3-yl |
| 2 | 4-methyl-thiazolidin-3-yl |
| 3 | N-(CO₂Me)-4-methyl-thiazolidin-3-yl |
| 4 | N-(i-BuOCO)-4-methyl-thiazolidin-3-yl |
| 5 | N-Ac-4-methyl-thiazolidin-3-yl |
| 6 | N-(i-BuCO)-4-methyl-thiazolidin-3-yl |
| 7 | 2-oxo-4-methyl-thiazolidin-3-yl |
| 8 | N-Boc-2-methyl-thiazolidin-3-yl |

TABLE 20-continued
(Id-5)
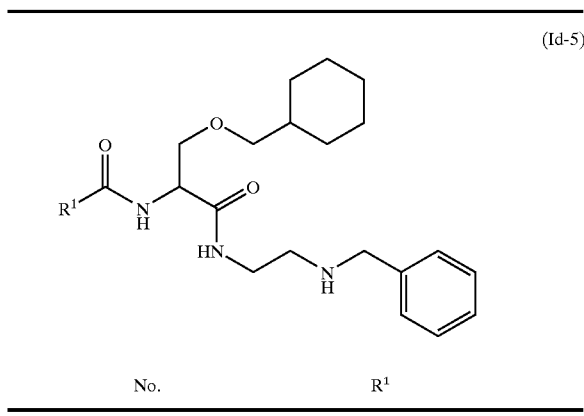
| No. | R¹ |
|---|---|
| 9 | 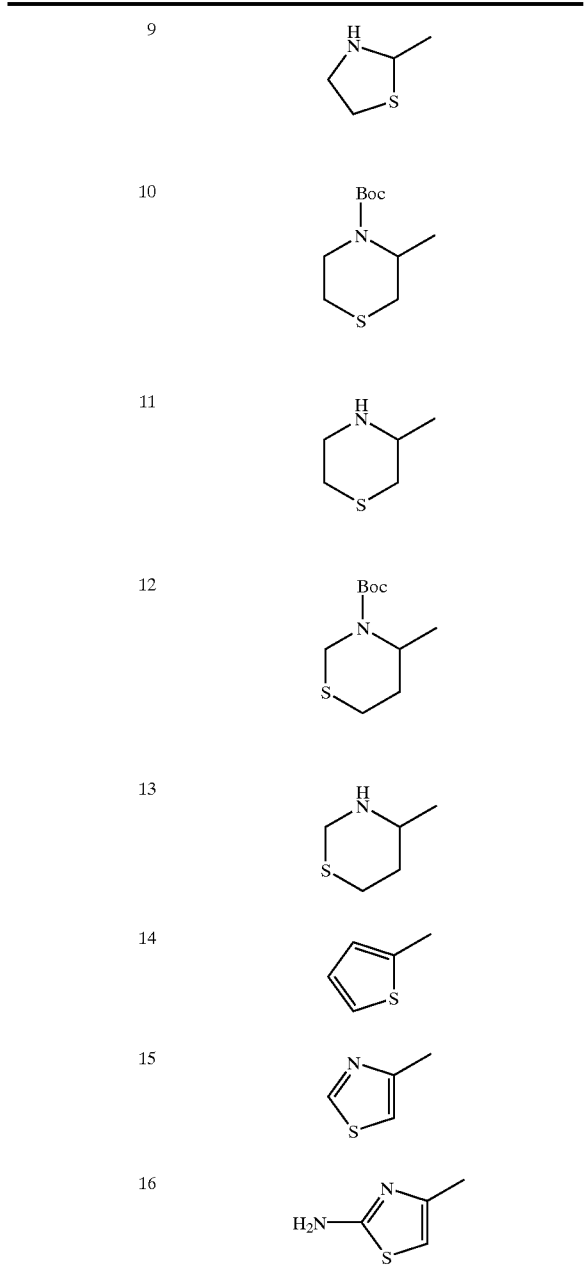 |
| 10 | |
| 11 | |
| 12 | |
| 13 | |
| 14 | |
| 15 | |
| 16 | |
TABLE 20-continued
(Id-5)
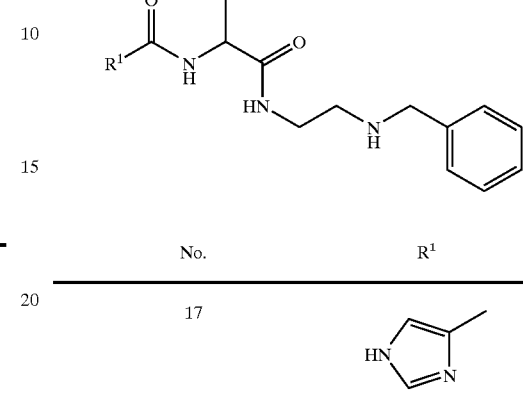
| No. | R¹ |
|---|---|
| 17 | 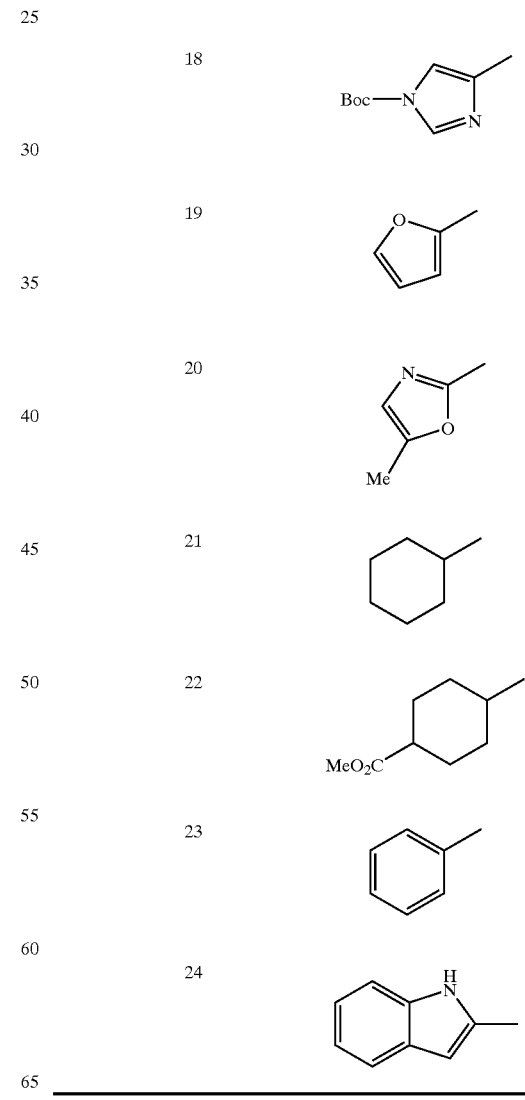 |
| 18 | |
| 19 | |
| 20 | |
| 21 | |
| 22 | |
| 23 | |
| 24 | |

TABLE 21
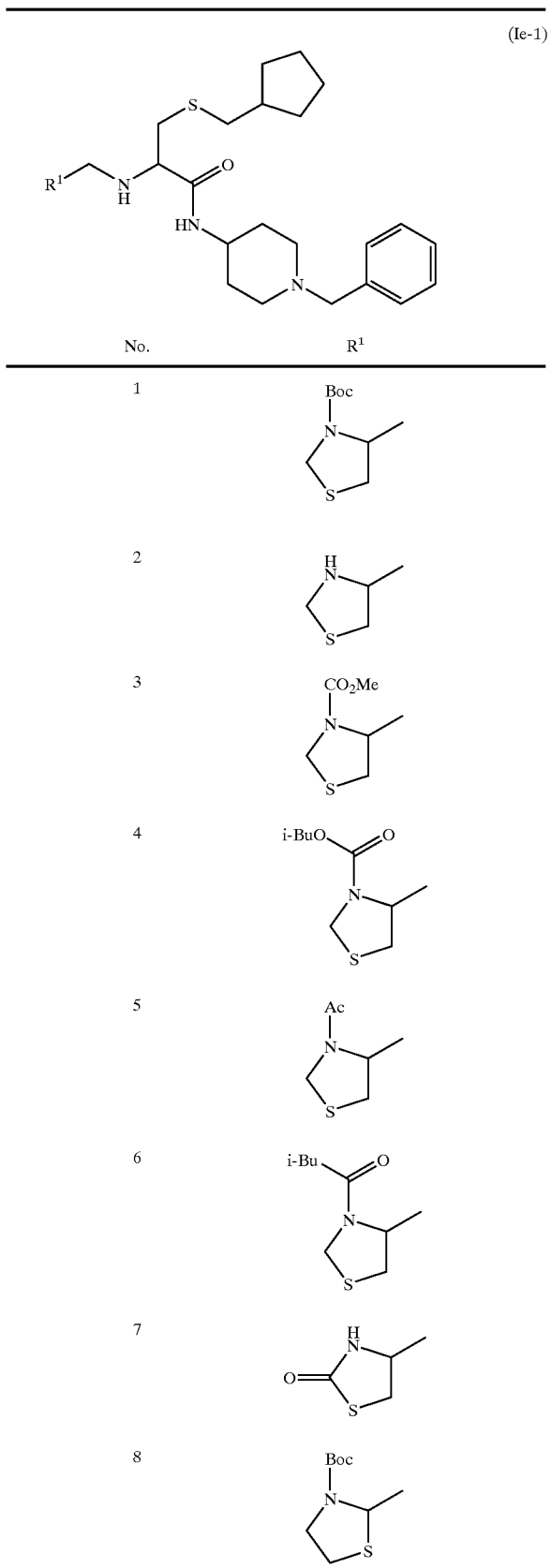
TABLE 21-continued
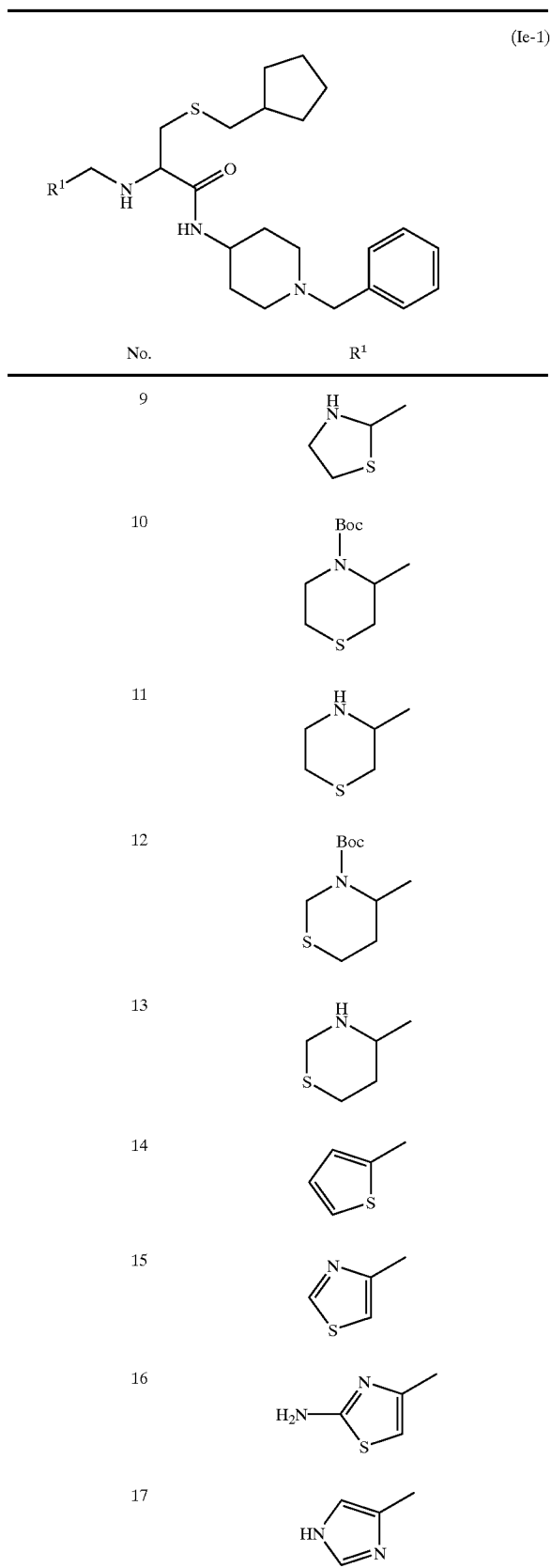

TABLE 21-continued
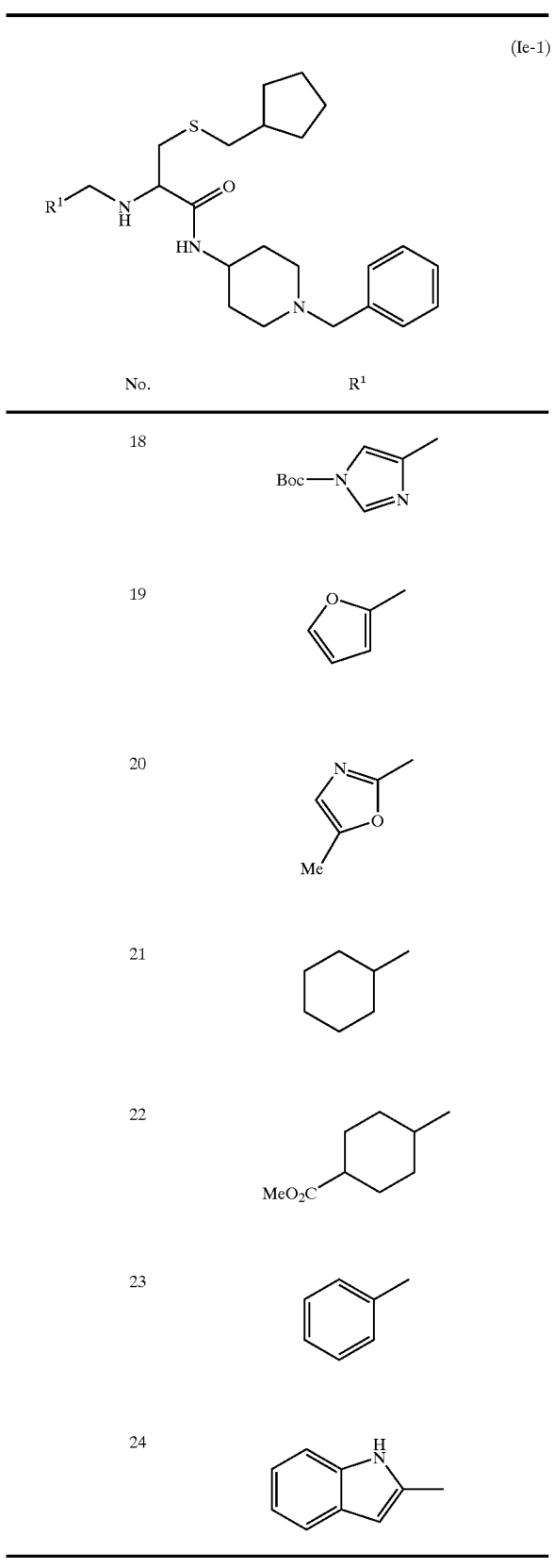
(Ie-1)
TABLE 22
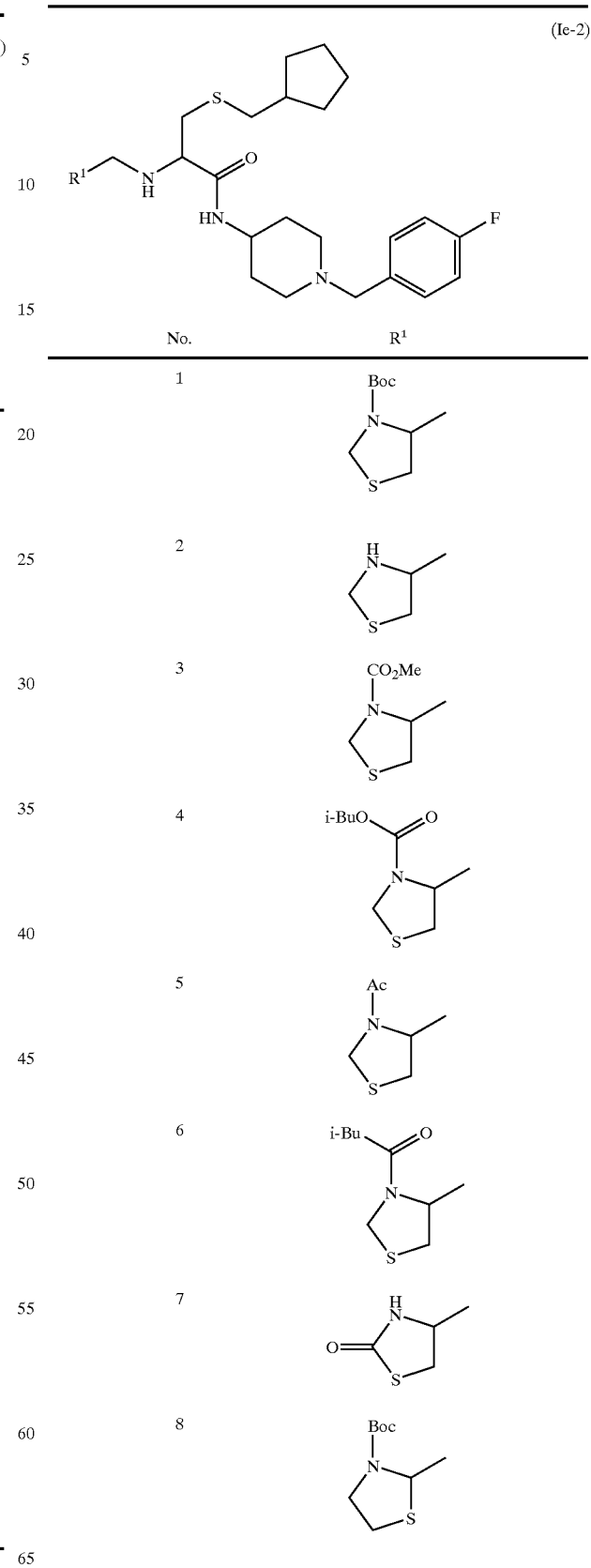
(Ie-2)

TABLE 22-continued
(Ie-2)
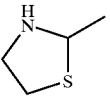
| No. | R¹ |
|---|---|
| 9 | 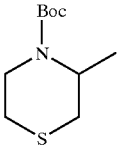 |
| 10 | 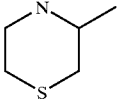 |
| 11 | 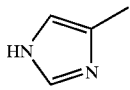 |
| 12 | 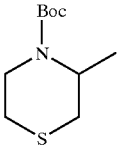 |
| 13 | 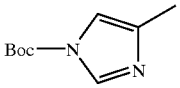 |
| 14 | 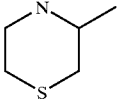 |
| 15 | 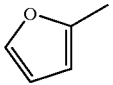 |
| 16 | 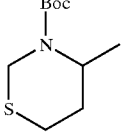 |
| 17 | 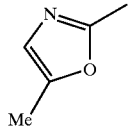 |
| 18 | 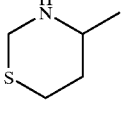 |
| 19 | 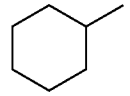 |
| 20 | 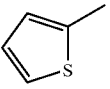 |
| 21 | 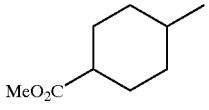 |
| 22 | 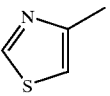 |
| 23 | 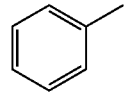 |
| 24 | 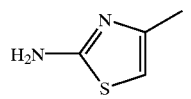 |

TABLE 23
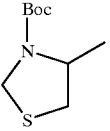
(Ie-3)
| No. | R¹ |
|---|---|
| 1 | 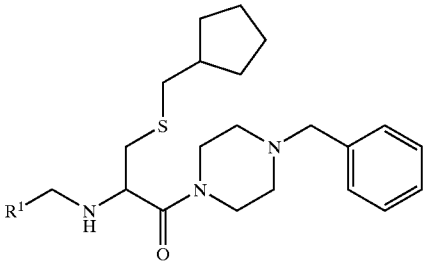 |
| 2 | 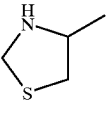 |
| 3 | 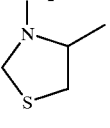 |
| 4 | 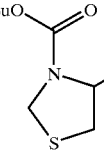 |
| 5 | 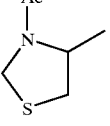 |
| 6 | 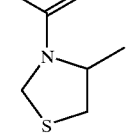 |
| 7 | 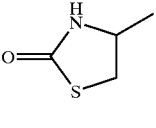 |
| 8 | 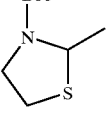 |
TABLE 23-continued
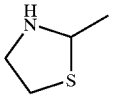
(Ie-3)
| No. | R¹ |
|---|---|
| 9 | 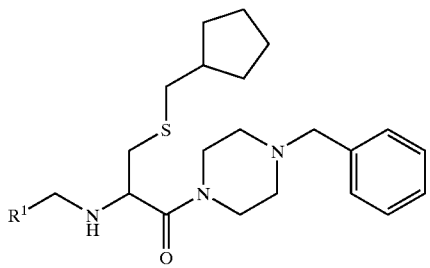 |
| 10 | 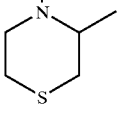 |
| 11 | 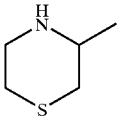 |
| 12 | 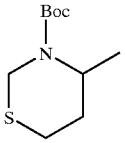 |
| 13 | 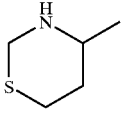 |
| 14 | 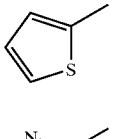 |
| 15 | 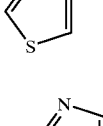 |
| 16 | 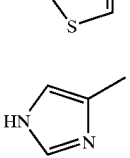 |
| 17 |  |

TABLE 23-continued
(Ie-3)
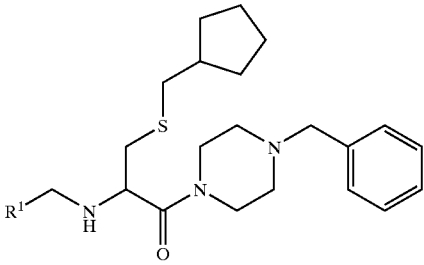
| No. | R¹ |
|---|---|
| 18 | 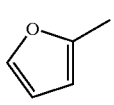 |
| 19 | 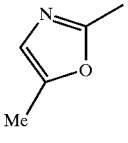 |
| 20 | 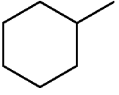 |
| 21 | 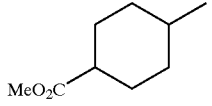 |
| 22 | 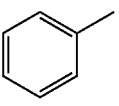 |
| 23 | 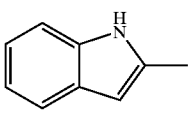 |
| 24 | 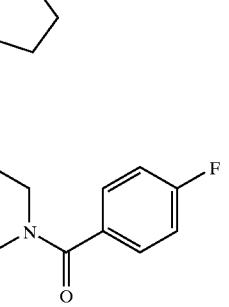 |
TABLE 24
(Ie-4)
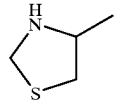
| No. | R¹ |
|---|---|
| 1 | 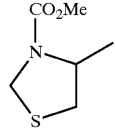 |
| 2 | 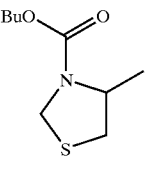 |
| 3 | 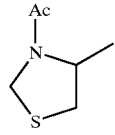 |
| 4 | 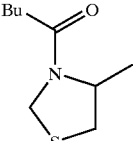 |
| 5 | 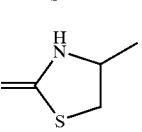 |
| 6 | 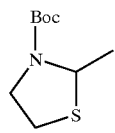 |
| 7 |  |
| 8 |  |

TABLE 24-continued

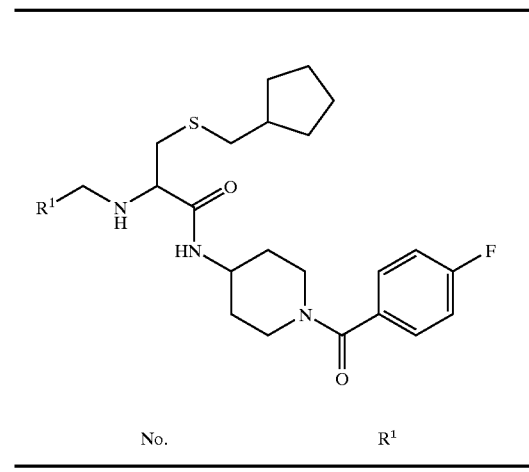

(Ie-4)

| No. | R¹ |
|---|---|
| 9 | 2-methyl-thiazolidine |
| 10 | N-Boc-3-methyl-thiomorpholine |
| 11 | 3-methyl-thiomorpholine |
| 12 | N-Boc-4-methyl-1,3-thiazinane |
| 13 | 4-methyl-1,3-thiazinane |
| 14 | 2-methyl-thiophene |
| 15 | 4-methyl-thiazole |
| 16 | 2-amino-4-methyl-thiazole |

TABLE 24-continued

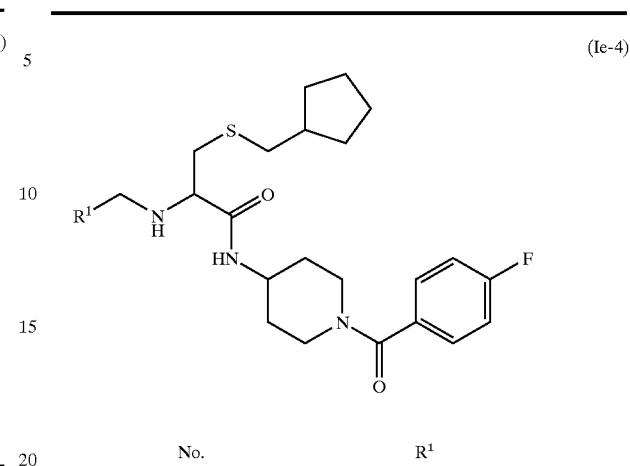

(Ie-4)

| No. | R¹ |
|---|---|
| 17 | 4-methyl-1H-imidazole |
| 18 | N-Boc-4-methyl-imidazole |
| 19 | 2-methyl-furan |
| 20 | 2,5-dimethyl-oxazole |
| 21 | methyl-cyclohexane |
| 22 | 4-methyl-cyclohexane-1-carboxylic acid methyl ester |
| 23 | methyl-benzene |
| 24 | 2-methyl-1H-indole |

TABLE 25

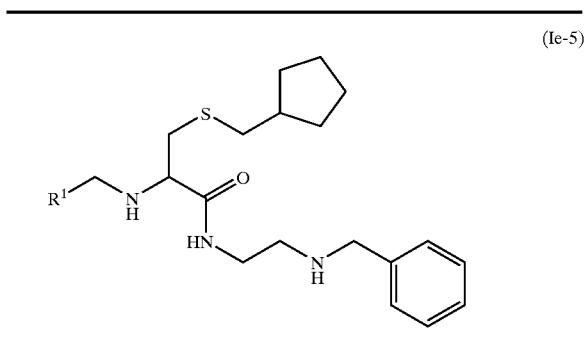

(Ie-5)

| No. | R¹ |
|---|---|
| 1 | Boc-N-thiazolidine-4-methyl |
| 2 | HN-thiazolidine-4-methyl |
| 3 | CO₂Me-N-thiazolidine-4-methyl |
| 4 | i-BuO-C(O)-N-thiazolidine-4-methyl |
| 5 | Ac-N-thiazolidine-4-methyl |
| 6 | i-Bu-C(O)-N-thiazolidine-4-methyl |
| 7 | O=C(NH)-thiazolidine-4-methyl |
| 8 | Boc-N-thiazolidine-2-methyl |

TABLE 25-continued

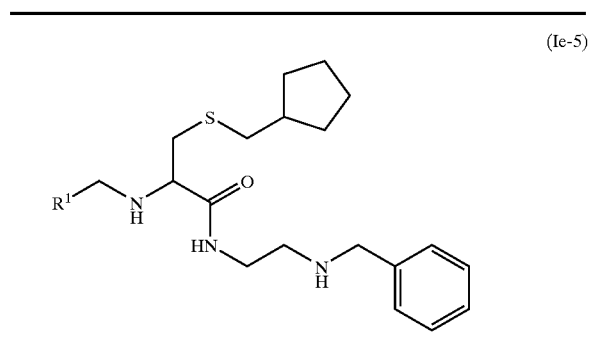

(Ie-5)

| No. | R¹ |
|---|---|
| 9 | HN-thiazolidine-2-methyl |
| 10 | Boc-N-thiomorpholine-3-methyl |
| 11 | HN-thiomorpholine-3-methyl |
| 12 | Boc-N-1,3-thiazinane-4-methyl |
| 13 | HN-1,3-thiazinane-4-methyl |
| 14 | 2-methylthiophene |
| 15 | 4-methylthiazole |
| 16 | 2-amino-4-methylthiazole |
| 17 | 4-methylimidazole |

TABLE 25-continued
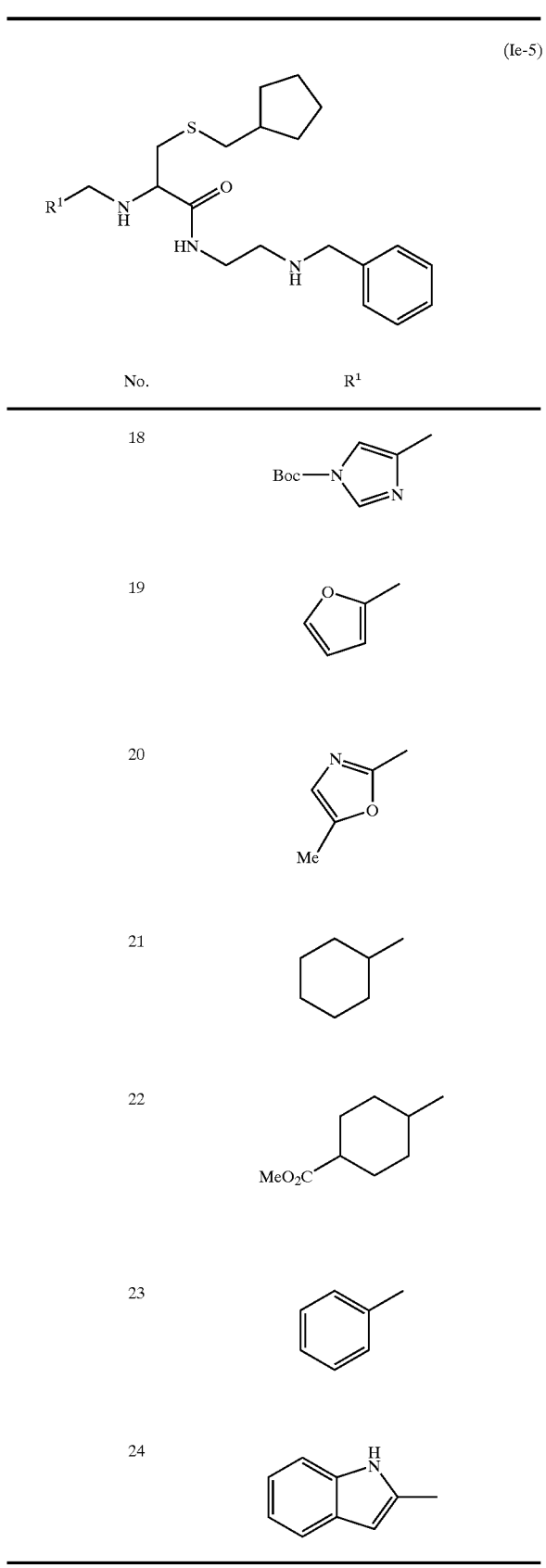
TABLE 26
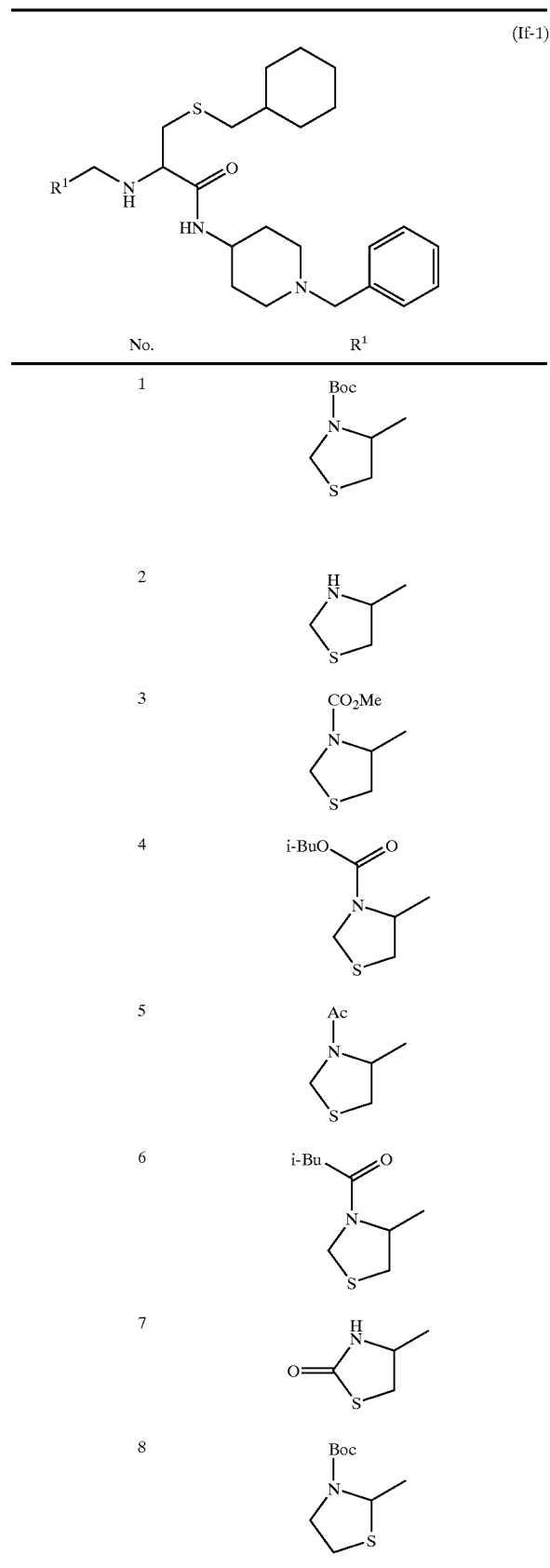

TABLE 26-continued
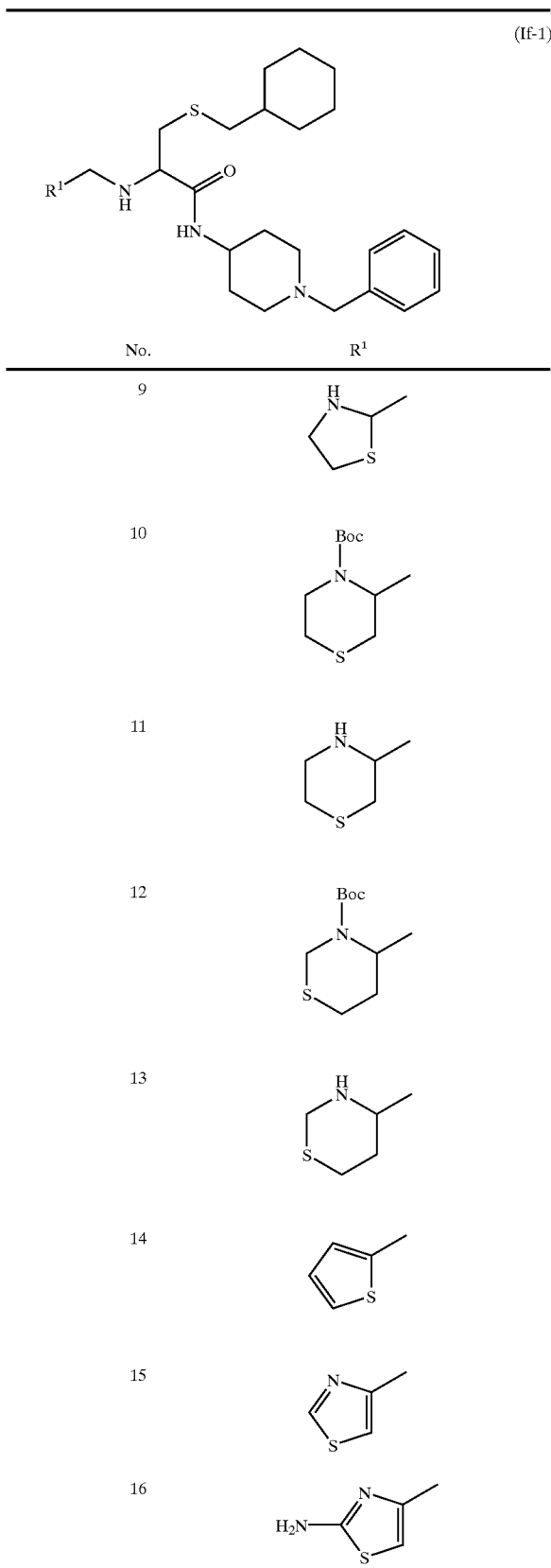
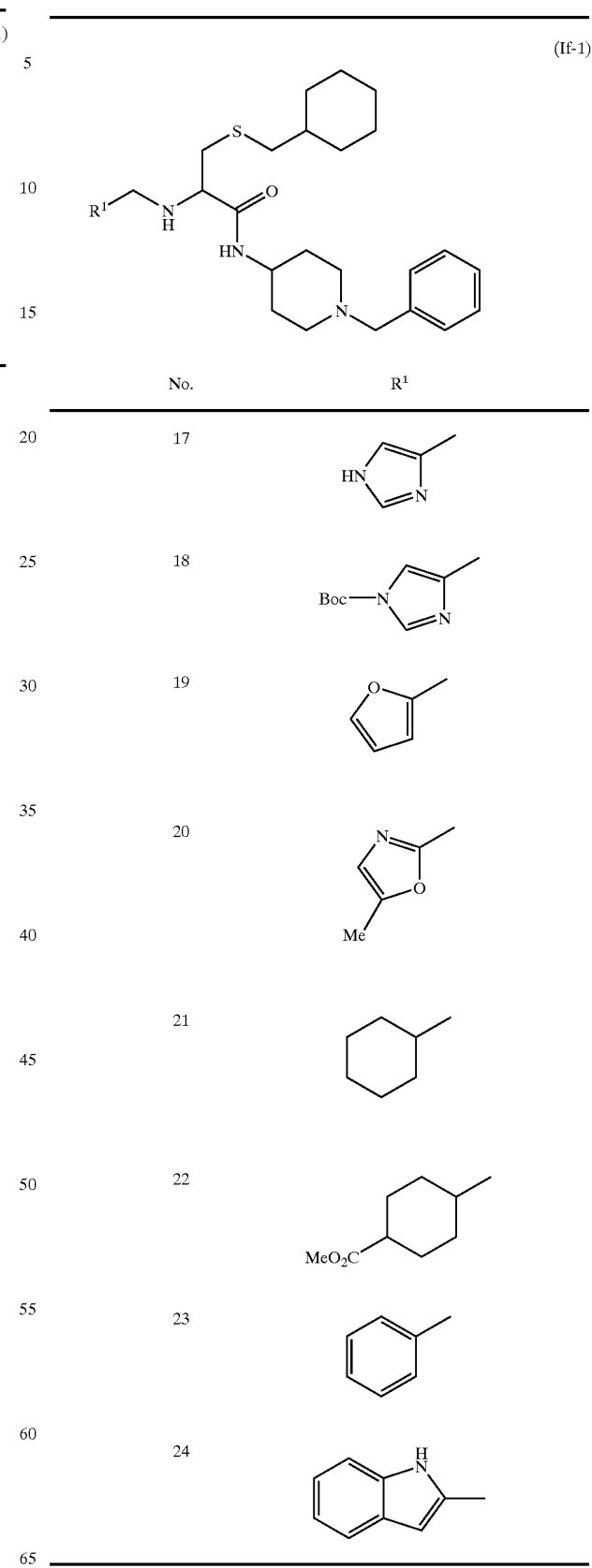

TABLE 27
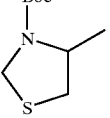
(If-2)
| No. | R¹ |
|---|---|
| 1 | 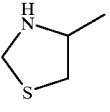 |
| 2 | 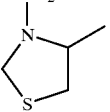 |
| 3 | 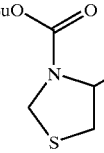 |
| 4 | 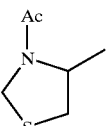 |
| 5 | 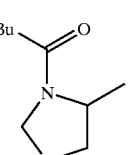 |
| 6 | 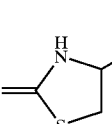 |
| 7 | 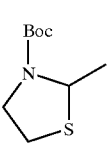 |
| 8 | 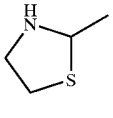 |
TABLE 27-continued
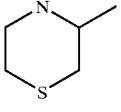
(If-2)
| No. | R¹ |
|---|---|
| 9 | 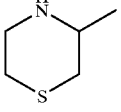 |
| 10 | 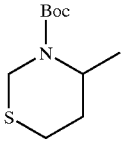 |
| 11 | 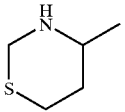 |
| 12 | 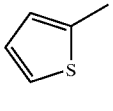 |
| 13 | 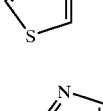 |
| 14 | 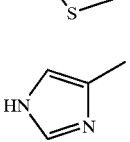 |
| 15 | 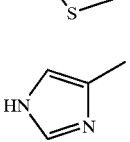 |
| 16 | |
| 17 | |

TABLE 27-continued
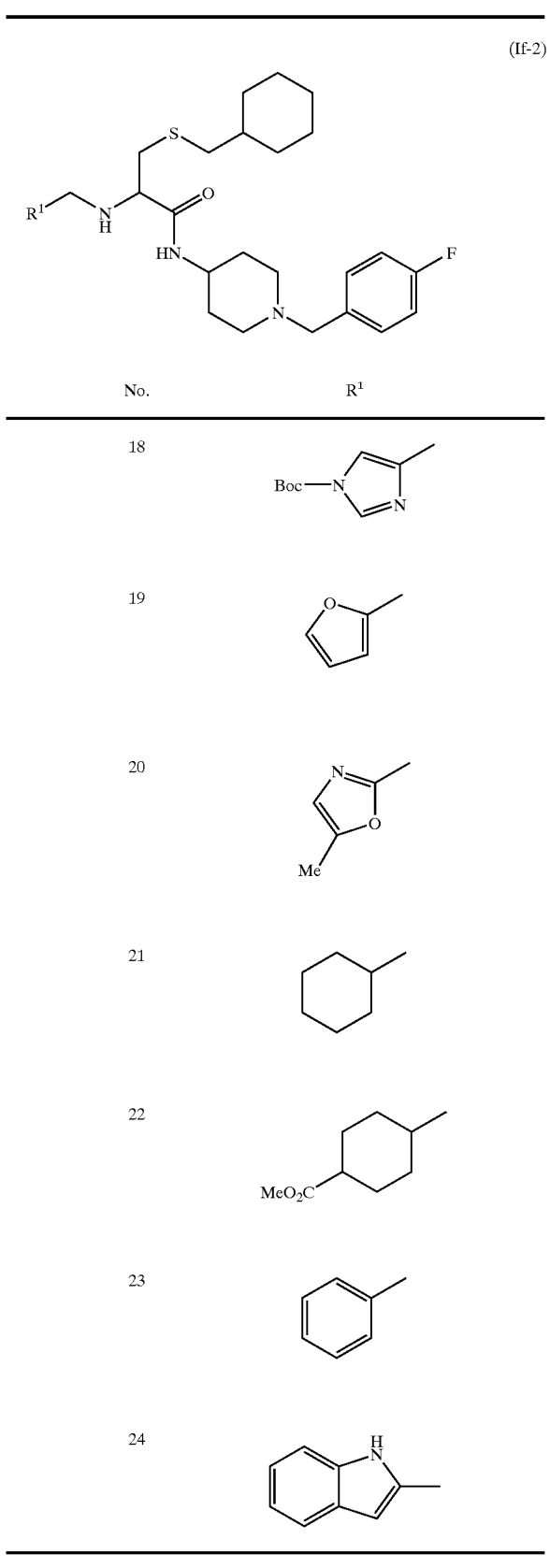
TABLE 28
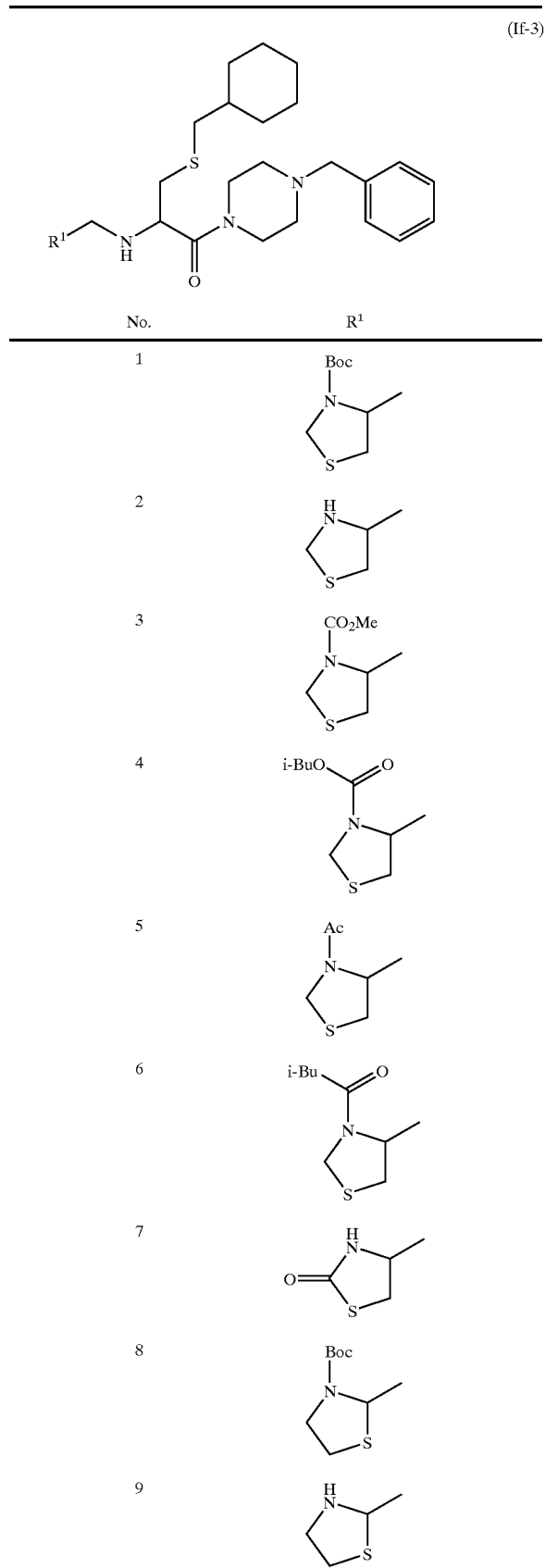

TABLE 28-continued
(If-3)
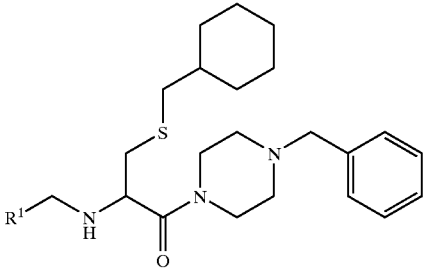
| No. | R¹ |
|---|---|
| 10 | 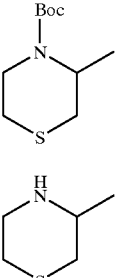 |
| 11 | 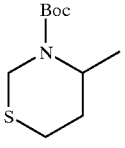 |
| 12 | 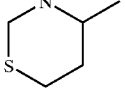 |
| 13 | 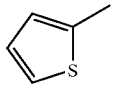 |
| 14 | 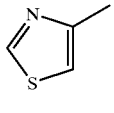 |
| 15 | 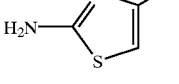 |
| 16 | 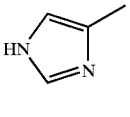 |
| 17 | 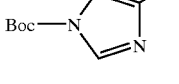 |
| 18 | 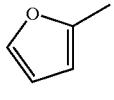 |
| 19 | 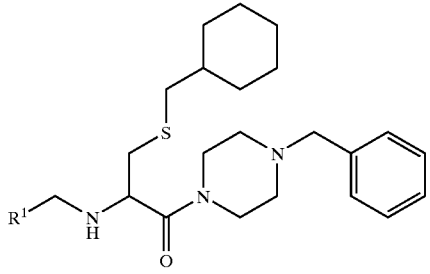 |
| 20 | 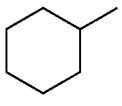 |
| 21 | 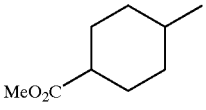 |
| 22 | 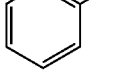 |
| 23 | 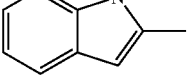 |
| 24 | 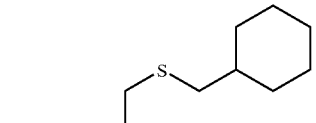 |
TABLE 29
(If-4)
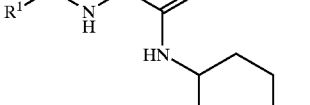
| No. | R¹ |
|---|---|
| 1 | 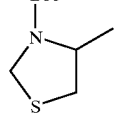 |

TABLE 29-continued (If-4)

| No. | R¹ |
|---|---|
| 2 | 4-methylthiazolidine |
| 3 | N-CO₂Me 4-methylthiazolidine |
| 4 | N-C(O)O-i-Bu 4-methylthiazolidine |
| 5 | N-Ac 4-methylthiazolidine |
| 6 | N-C(O)-i-Bu 4-methylthiazolidine |
| 7 | 2-oxo-4-methylthiazolidine |
| 8 | N-Boc 2-methylthiazolidine |
| 9 | 2-methylthiazolidine |
| 10 | N-Boc 3-methylthiomorpholine |
| 11 | 3-methylthiomorpholine |
| 12 | N-Boc 4-methyl-1,3-thiazinane |
| 13 | 4-methyl-1,3-thiazinane |
| 14 | 2-methylthiophene |
| 15 | 4-methylthiazole |
| 16 | 2-amino-4-methylthiazole |
| 17 | 4-methyl-1H-imidazole |

TABLE 29-continued (If-4)

| No. | R¹ |
|-----|-----|
| 18 | Boc-N(imidazole)-4-methyl |
| 19 | 2-methylfuran |
| 20 | 2,5-dimethyloxazole |
| 21 | 4-methylcyclohexyl |
| 22 | 4-methyl-MeO₂C-cyclohexyl |
| 23 | 4-methylphenyl |
| 24 | 2-methyl-1H-indole |

TABLE 30

(If-5)

| No. | R¹ |
|-----|-----|
| 1 | Boc-N-(4-methylthiazolidine) |
| 2 | HN-(4-methylthiazolidine) |
| 3 | CO₂Me-N-(4-methylthiazolidine) |
| 4 | i-BuO-C(=O)-N-(4-methylthiazolidine) |
| 5 | Ac-N-(4-methylthiazolidine) |
| 6 | i-Bu-C(=O)-N-(4-methylthiazolidine) |
| 7 | 4-methyl-2-oxo-thiazolidine |
| 8 | Boc-N-(2-methylthiazolidine) |

TABLE 30-continued (If-5)

| No. | R¹ |
|---|---|
| 9 | 2-methyl-thiazolidine |
| 10 | N-Boc-3-methyl-thiomorpholine |
| 11 | 3-methyl-thiomorpholine |
| 12 | N-Boc-4-methyl-1,3-thiazinane |
| 13 | 4-methyl-1,3-thiazinane |
| 14 | 2-methyl-thiophene |
| 15 | 4-methyl-thiazole |
| 16 | 2-amino-4-methyl-thiazole |
| 17 | 4-methyl-1H-imidazole |
| 18 | N-Boc-4-methyl-imidazole |
| 19 | 2-methyl-furan |
| 20 | 2,5-dimethyl-oxazole |
| 21 | methyl-cyclohexane |
| 22 | methyl 4-methyl-cyclohexanecarboxylate |
| 23 | methyl-benzene |
| 24 | 2-methyl-1H-indole |

TABLE 31
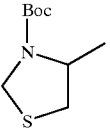
(Ig-1)
| No. | R¹ |
|---|---|
| 1 | 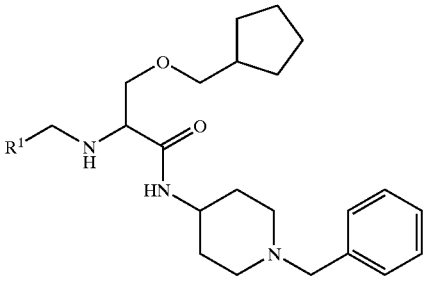 |
| 2 | 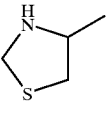 |
| 3 | 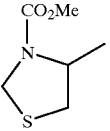 |
| 4 | 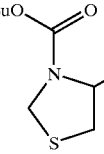 |
| 5 | 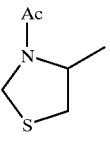 |
| 6 | 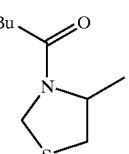 |
| 7 | 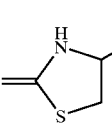 |
| 8 | 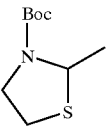 |
TABLE 31-continued
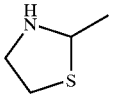
(Ig-1)
| No. | R¹ |
|---|---|
| 9 | 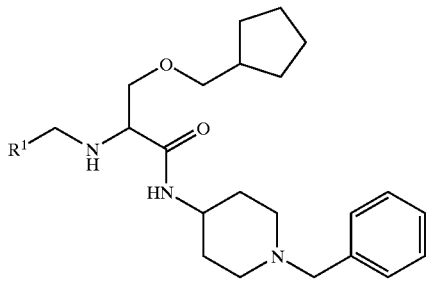 |
| 10 | 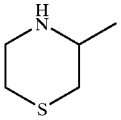 |
| 11 | 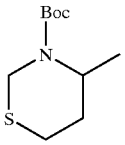 |
| 12 | 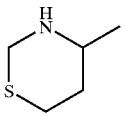 |
| 13 | 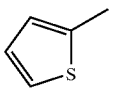 |
| 14 | 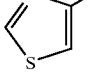 |
| 15 | 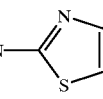 |
| 16 | 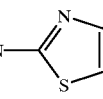 |

TABLE 31-continued (Ig-1)

| No. | R¹ |
|---|---|
| 17 | 4-methyl-1H-imidazole |
| 18 | 1-Boc-4-methyl-imidazole |
| 19 | 2-methylfuran |
| 20 | 2,5-dimethyloxazole |
| 21 | cyclohexyl |
| 22 | 4-(methoxycarbonyl)cyclohexyl |
| 23 | 4-methylphenyl |
| 24 | 2-methyl-1H-indole |

TABLE 32

(Ig-2)

| No. | R¹ |
|---|---|
| 1 | 3-Boc-4-methylthiazolidine |
| 2 | 4-methylthiazolidine |
| 3 | 3-(methoxycarbonyl)-4-methylthiazolidine |
| 4 | 3-(isobutoxycarbonyl)-4-methylthiazolidine |
| 5 | 3-acetyl-4-methylthiazolidine |
| 6 | 3-(isobutylcarbonyl)-4-methylthiazolidine |
| 7 | 4-methyl-2-oxothiazolidine |
| 8 | 3-Boc-2-methylthiazolidine |

TABLE 32-continued (Ig-2)

[Structure: R¹-NH-CH₂-CH(NH-)-C(=O)-NH-(piperidine-N-CH₂-(4-fluorophenyl)), with CH₂-O-CH₂-cyclopentyl side chain]

| No. | R¹ |
|---|---|
| 9 | 2-methylthiazolidin-2-yl (NH) |
| 10 | N-Boc-3-methylthiomorpholine |
| 11 | 3-methylthiomorpholine (NH) |
| 12 | N-Boc-4-methyl-1,3-thiazinane |
| 13 | 4-methyl-1,3-thiazinane (NH) |
| 14 | 2-thienyl |
| 15 | 4-methylthiazol-5-yl |
| 16 | 4-methylthiazol-2-yl |
| 17 | 2-amino-4-methylthiazol-5-yl |
| 18 | 4-methyl-1H-imidazol-5-yl |
| 19 | N-Boc-4-methylimidazol-1-yl |
| 20 | 5-methylfuran-2-yl |
| 21 | 2,5-dimethyloxazol-4-yl |
| 22 | cyclohexyl |
| 23 | 4-(methoxycarbonyl)cyclohexyl |
| 24 | phenyl |

TABLE 33

(Ig-3)

[Structure: R¹-NH-CH₂-CH(NH-)-C(=O)-N(piperazine-N-benzyl), with CH₂-O-CH₂-cyclopentyl side chain]

| No. | R¹ |
|---|---|
| 1 | N-Boc-4-methylthiazolidin-3-yl |

TABLE 33-continued
(Ig-3)
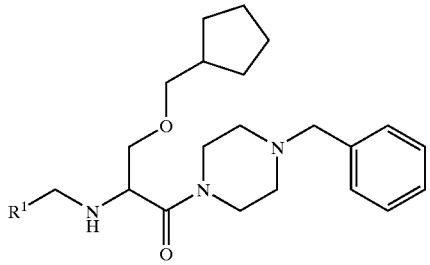
| No. | R¹ |
|---|---|
| 2 | 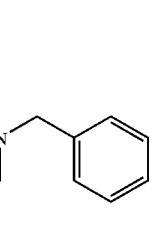 |
| 3 | 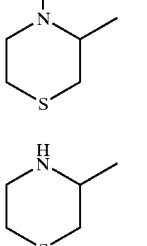 |
| 4 | 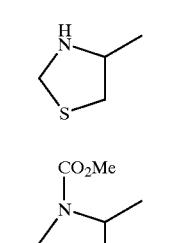 |
| 5 | 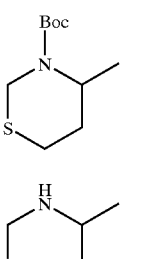 |
| 6 | 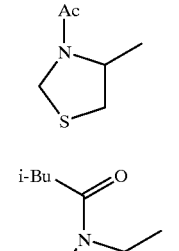 |
| 7 | 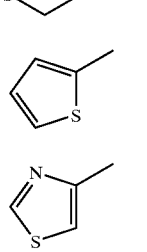 |
| 8 | 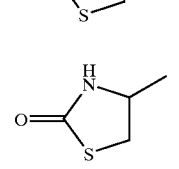 |
| 9 | 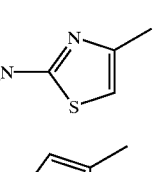 |
| 10 | 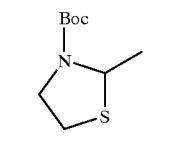 |
| 11 | 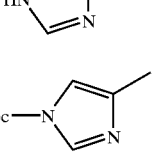 |
| 12 | 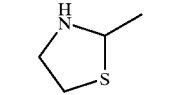 |
| 13 | 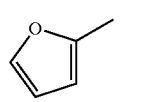 |
| 14 | 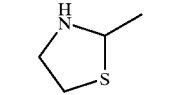 |
| 15 | 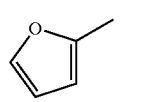 |
| 16 | 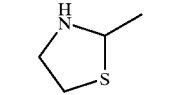 |
| 17 | 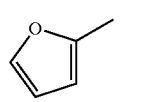 |
| 18 | Boc—<image placeholder> |
| 19 | <image placeholder> |

TABLE 33-continued (Ig-3)

| No. | R¹ |
|---|---|
| 20 | 2,5-dimethyloxazol-4-yl |
| 21 | cyclohexylmethyl |
| 22 | 4-(methoxycarbonyl)cyclohexyl |
| 23 | 4-methylphenyl |
| 24 | 2-methyl-1H-indol-3-yl |

TABLE 34

(Ig-4)

| No. | R¹ |
|---|---|
| 1 | N-Boc-4-methylthiazolidin-3-yl |

TABLE 34-continued (Ig-4)

| No. | R¹ |
|---|---|
| 2 | 4-methylthiazolidin-3-yl (NH) |
| 3 | N-CO₂Me-4-methylthiazolidin-3-yl |
| 4 | N-(i-BuOC(O))-4-methylthiazolidin-3-yl |
| 5 | N-Ac-4-methylthiazolidin-3-yl |
| 6 | N-(i-BuC(O))-4-methylthiazolidin-3-yl |
| 7 | 4-methyl-2-oxothiazolidin-3-yl |
| 8 | N-Boc-2-methylthiazolidin-3-yl |
| 9 | 2-methylthiazolidin-3-yl (NH) |

TABLE 34-continued

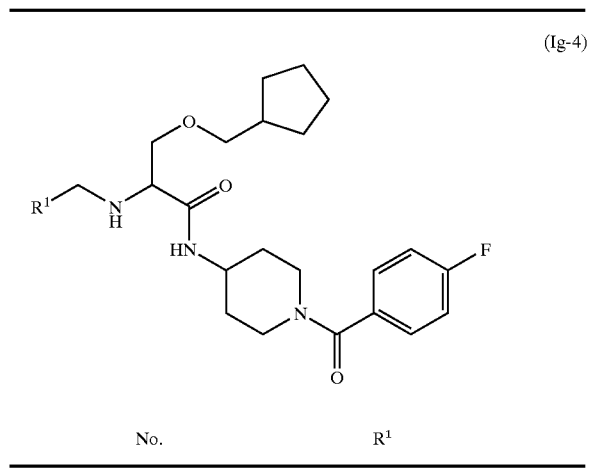

(Ig-4)

| No. | R¹ |
|-----|-----|
| 10 | Boc-N, 3-methyl thiomorpholine |
| 11 | 3-methyl thiomorpholine (NH) |
| 12 | Boc-N, 4-methyl thiomorpholine |
| 13 | 4-methyl thiomorpholine (NH) |
| 14 | 2-methyl thiophene |
| 15 | 4-methyl thiazole |
| 16 | 2-amino-4-methyl thiazole |

TABLE 34-continued

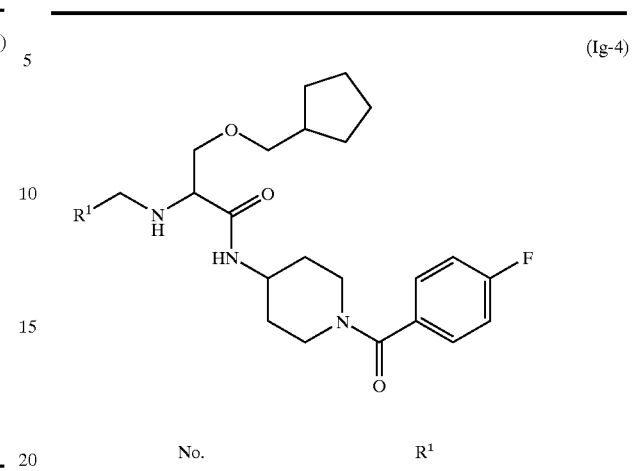

(Ig-4)

| No. | R¹ |
|-----|-----|
| 17 | 4-methyl-1H-imidazole |
| 18 | 1-Boc-4-methyl imidazole |
| 19 | 2-methyl furan |
| 20 | 2,5-dimethyl oxazole |
| 21 | cyclohexyl-methyl |
| 22 | 4-(MeO₂C)-cyclohexyl-methyl |
| 23 | 4-methyl phenyl |
| 24 | 2-methyl-1H-indole |

TABLE 35

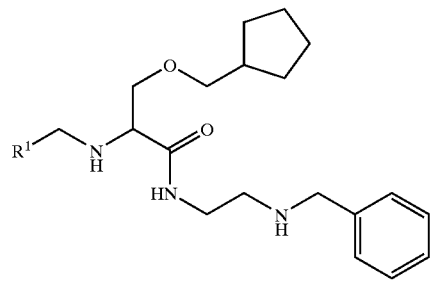

(Ig-5)

| No. | R¹ |
|---|---|
| 1 | Boc-N(thiazolidine)-4-methyl |
| 2 | HN(thiazolidine)-4-methyl |
| 3 | CO₂Me-N(thiazolidine)-4-methyl |
| 4 | i-BuOC(O)-N(thiazolidine)-4-methyl |
| 5 | Ac-N(thiazolidine)-4-methyl |
| 6 | i-Bu-C(O)-N(thiazolidine)-4-methyl |
| 7 | 2-oxo-thiazolidine-4-methyl |
| 8 | Boc-N(thiazolidine)-2-methyl |

TABLE 35-continued

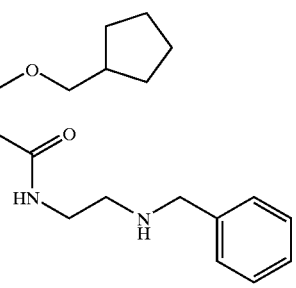

(Ig-5)

| No. | R¹ |
|---|---|
| 9 | HN(thiazolidine)-2-methyl |
| 10 | Boc-N(thiomorpholine)-3-methyl |
| 11 | HN(thiomorpholine)-3-methyl |
| 12 | Boc-N(thiazinane)-4-methyl |
| 13 | HN(thiazinane)-4-methyl |
| 14 | 2-methylthiophene |
| 15 | 4-methylthiazole |
| 16 | 2-amino-4-methylthiazole |
| 17 | 4-methylimidazole |

TABLE 35-continued
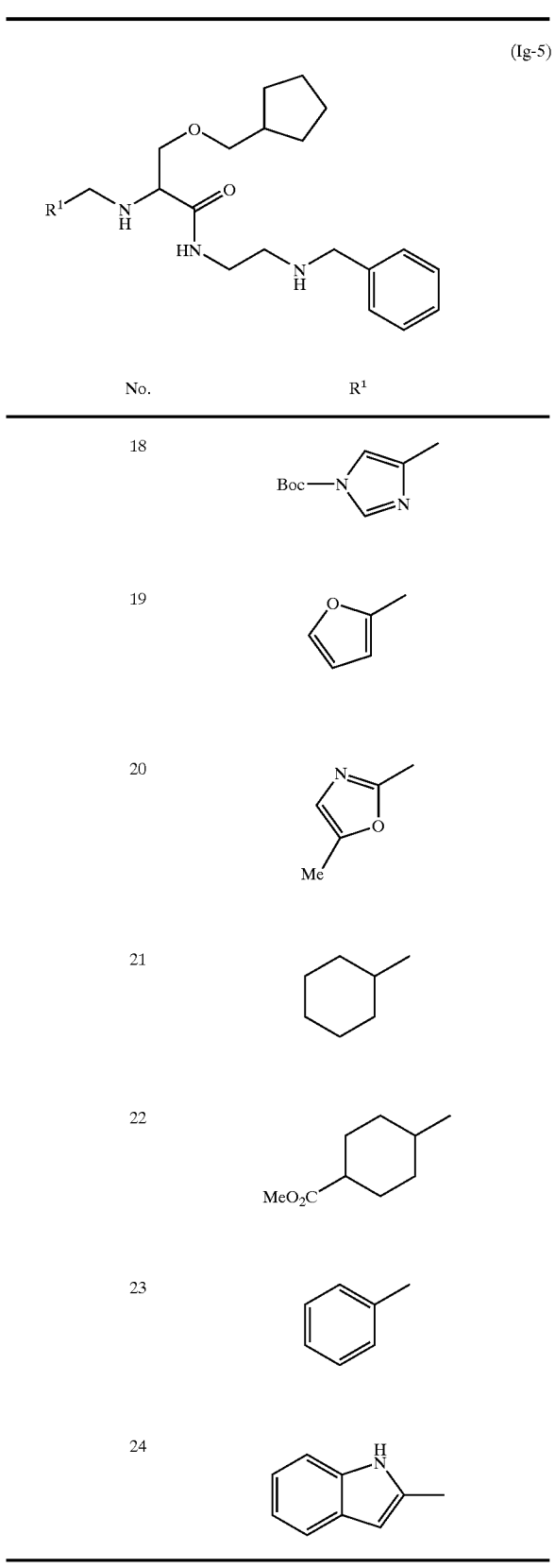
TABLE 36
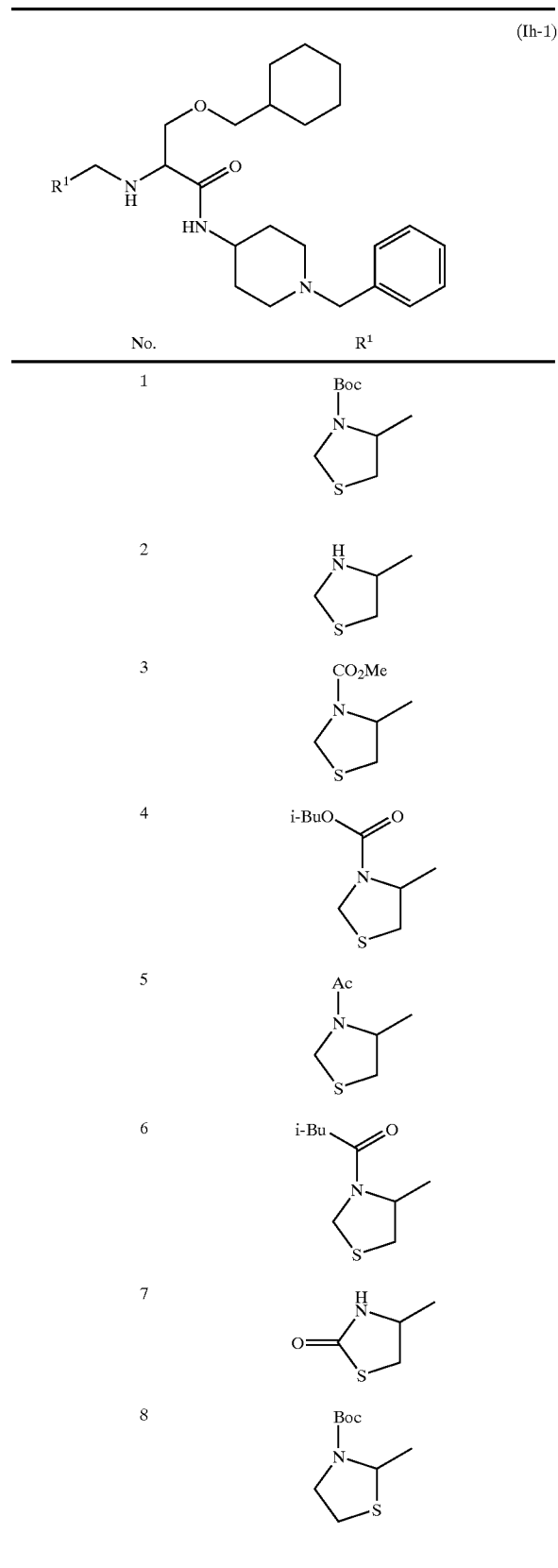

TABLE 36-continued (Ih-1)

| No. | R¹ |
|---|---|
| 9 | 2-methyl-thiazolidine |
| 10 | N-Boc-3-methyl-thiomorpholine |
| 11 | 3-methyl-thiomorpholine |
| 12 | N-Boc-4-methyl-1,3-thiazinane |
| 13 | 4-methyl-1,3-thiazinane |
| 14 | 2-methyl-thiophene |
| 15 | 4-methyl-thiazole |
| 16 | 2-amino-4-methyl-thiazole |
| 17 | 4-methyl-1H-imidazole |
| 18 | N-Boc-4-methyl-imidazole |
| 19 | 2-methyl-furan |
| 20 | 2,5-dimethyl-oxazole |
| 21 | methyl-cyclohexane |
| 22 | methyl 4-methyl-cyclohexanecarboxylate |
| 23 | methyl-benzene |
| 24 | 2-methyl-1H-indole |

TABLE 37
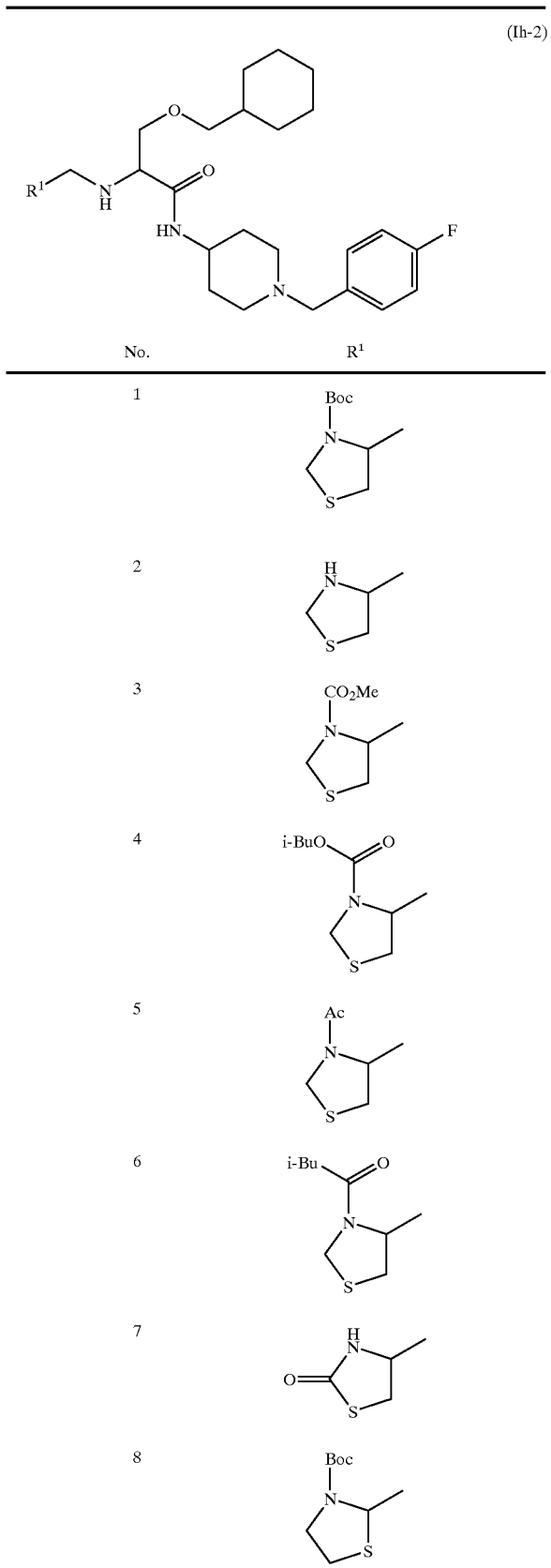
TABLE 37-continued
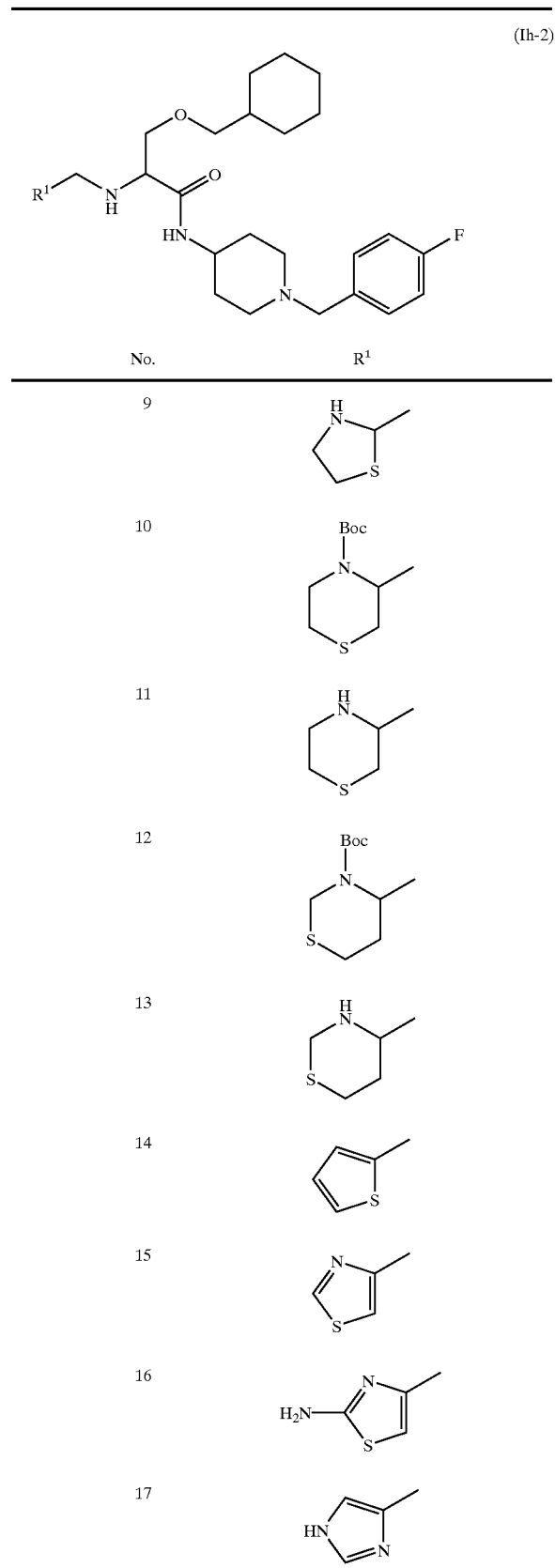

TABLE 37-continued
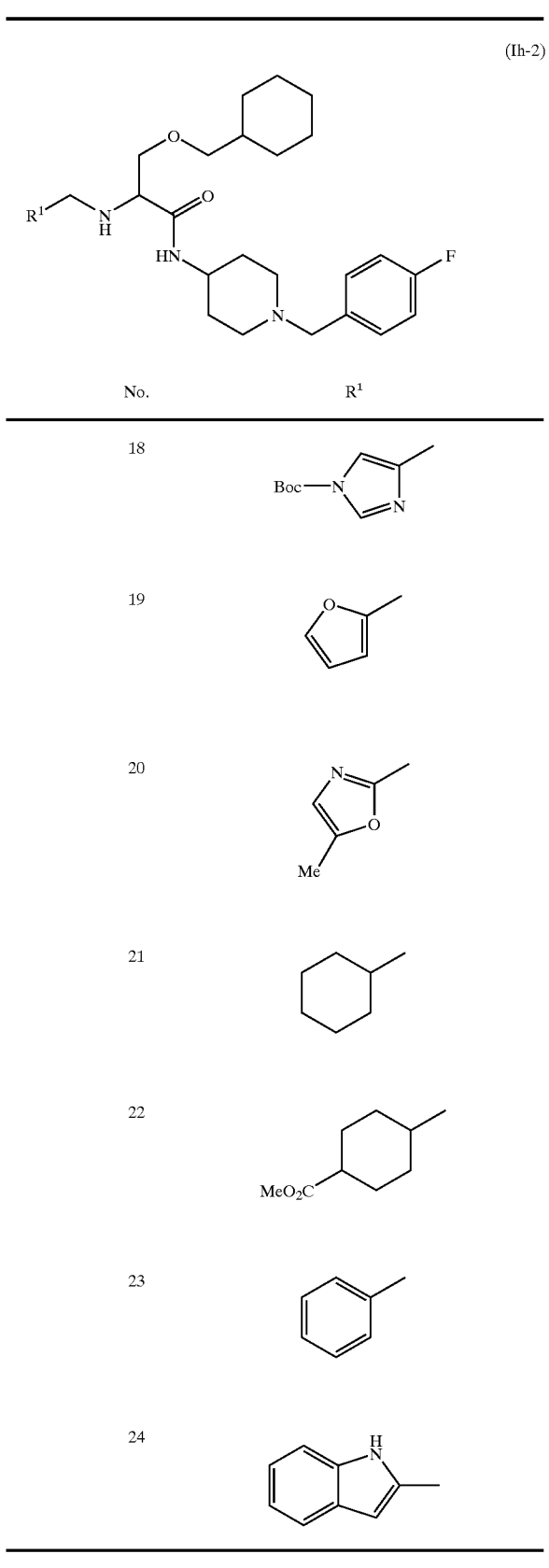
TABLE 38
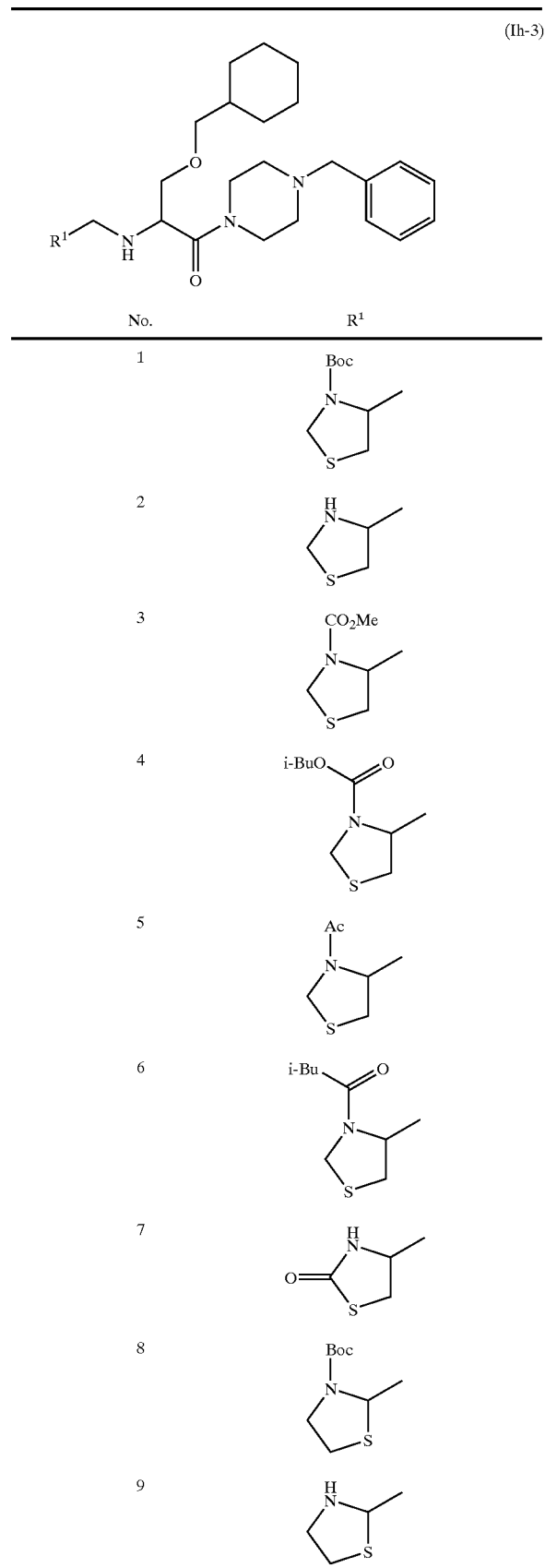

TABLE 38-continued
(Ih-3)
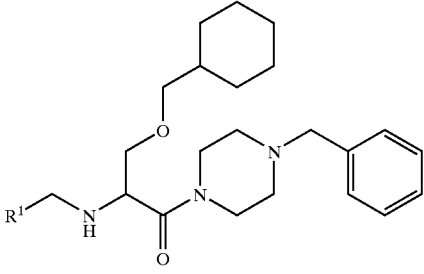
| No. | R¹ |
|---|---|
| 10 | 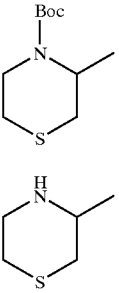 |
| 11 | 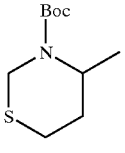 |
| 12 | 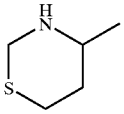 |
| 13 | 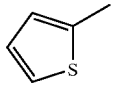 |
| 14 | 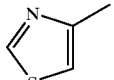 |
| 15 | 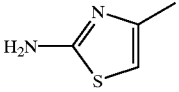 |
| 16 | 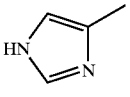 |
| 17 | 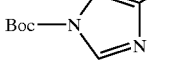 |
| 18 | 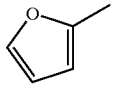 |
| 19 | 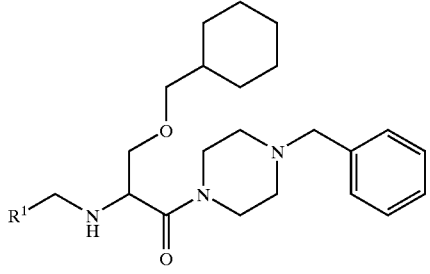 |
TABLE 38-continued
(Ih-3)
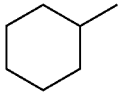
| No. | R¹ |
|---|---|
| 20 | 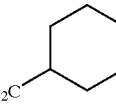 |
| 21 | 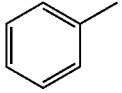 |
| 22 | 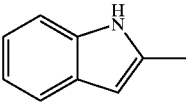 |
| 23 | 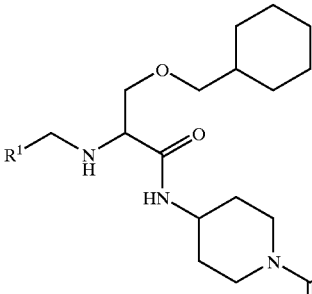 |
| 24 | 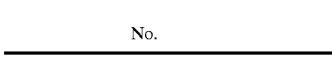 |
TABLE 39
(Ih-4)
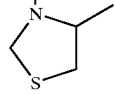
| No. | R¹ |
|---|---|
| 1 | 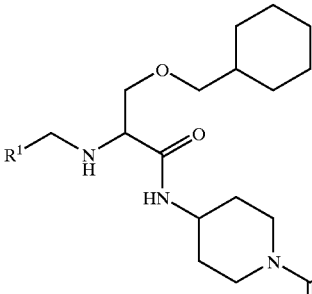 |

TABLE 39-continued
(Ih-4)
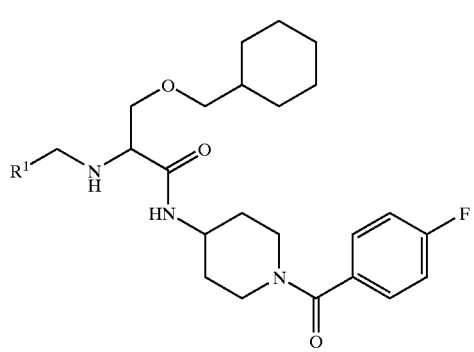
| No. | R¹ |
|---|---|
| 2 | 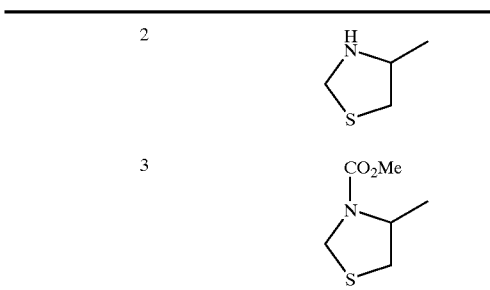 |
| 3 | 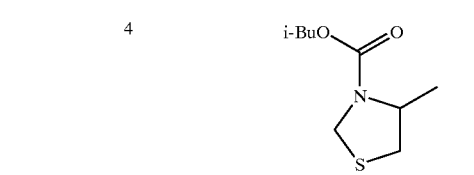 |
| 4 |  |
| 5 | 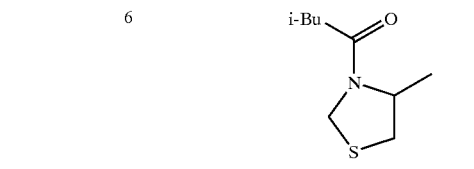 |
| 6 | 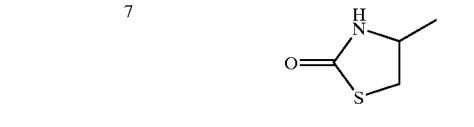 |
| 7 |  |
| 8 |  |
| 9 | 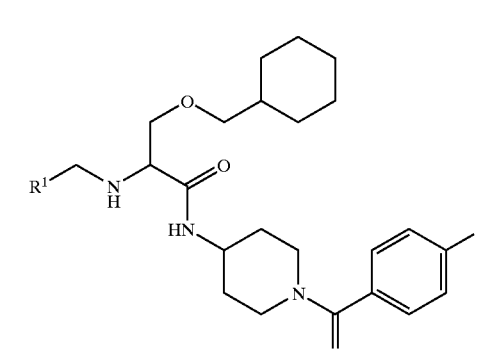 |
TABLE 39-continued
(Ih-4)
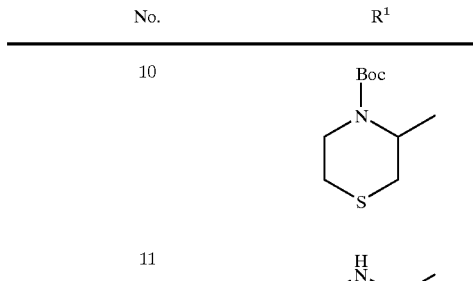
| No. | R¹ |
|---|---|
| 10 | 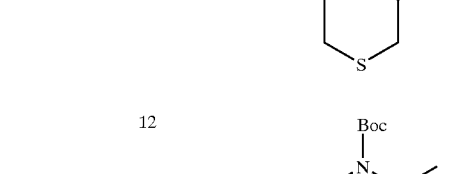 |
| 11 |  |
| 12 | 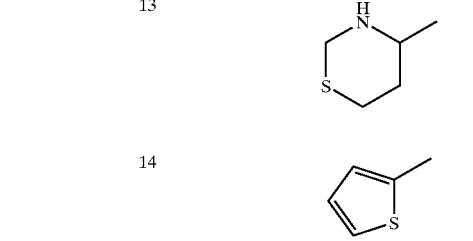 |
| 13 |  |
| 14 | 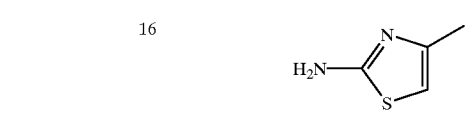 |
| 15 |  |
| 16 |  |
| 17 |  |

TABLE 39-continued
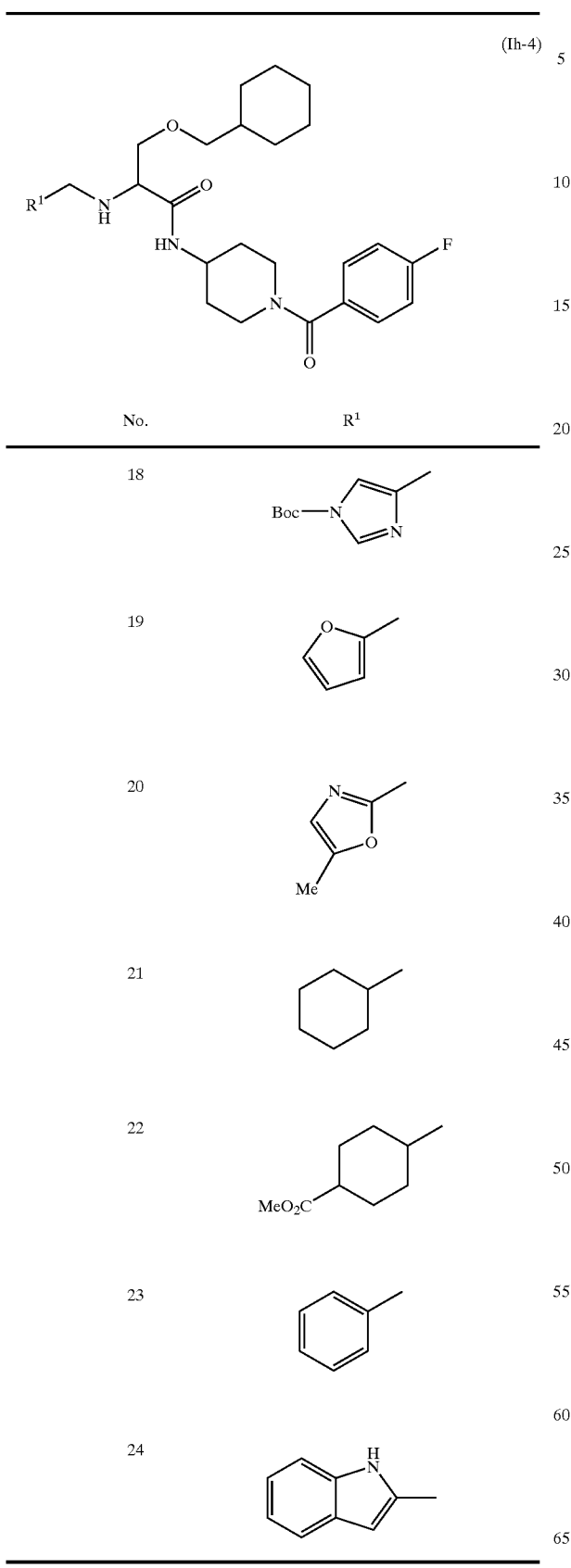
TABLE 40
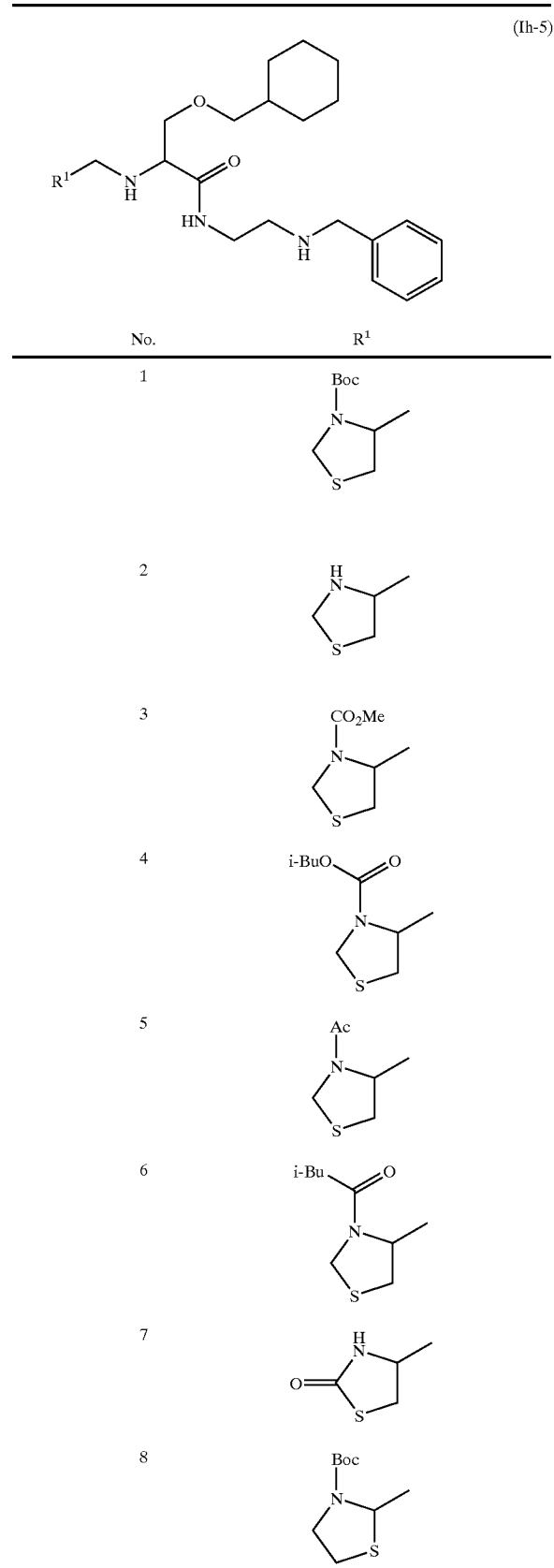

[Process for Preparation of the Compounds of the Present Invention]

(a) The compounds of the formula (I), wherein E is —COO—, —OCO—, —CONR⁸—, —NR⁹CO—, —O—, —S— or —CO—, i.e., the compounds of the present invention of the formula (I-A)

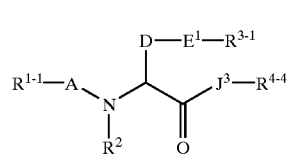

(I-A)

(wherein, $R^{1-1}$ is the same meaning as hereinbefore described for $R^1$, provided that amino group in $^{1-1}$ is protected with protecting group, if necessary, $R^{3-1}$ is the same meaning as hereinbefore described for $R^3$, provided that amino group in $R^{3-1}$ is protected with protecting group, if necessary, $R^{4-4}$ is the same meaning as hereinbefore described for $R^4$, provided that —COOH, hydroxy or amino group in $R^{4-4}$ is protected with protecting group, if necessary, $J^3$ is the same meaning as hereinbefore described for J, provided that amino or hydroxy group in $J^3$ is protected with protecting group, if necessary, $E^1$ is —COO—, —OCO—, —$CONR^8$—, —$NR^9CO$—, —O—, —S— or —CO— and the other symbols are the same meanings as defined hereinbefore) may be prepared by amidation or esterification of the compounds of the formula (II)

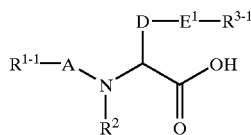

(II)

(wherein all the symbols are the same meanings as defined hereinbefore) with the compounds of the formula (III)

$$J^4—R^{4-4}$$ (III)

(wherein, $J^4$ is —OH, —$NHR^{16}$, —$NHR^{17}$, —$NR^{21}$—$NHR^{20}$, —$NR^{23}$—(C1–4 alkylene)-$NHR^{22}$, —O—(C1–4 alkylene)-$NHR^{24}$, —S—(C1–4 alkylene)-$NHR^{25}$ or heterocyclic ring possessing NH (this heterocyclic ring is the same meaning as hereinbefore described for the heterocyclic ring represented by each $R^{4-2}$ and $R^{16}$, L and $R^{16}$, $R^{4-1}$ and $R^{17}$, $R^{4-2}$ and $R^{17}$, and L and $R^{17}$ taken together with nitrogen atom to which they are attached) (in which all the symbols are the same meanings as defined hereinbefore), $R^{4-4}$ is the same meaning as defined hereinbefore), or by amidation or esterification of the compounds of the formula (IV)

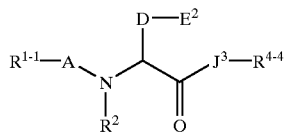

(IV)

(wherein, $E^2$ is —COOH, —$NHR^9$ (in which $R^9$ is the same meaning as defined hereinbefore) or —OH and the other symbols are the same meanings as defined hereinbefore) with the compounds of the formula (V)

$$E^3—R^{3-1}$$ (V)

(wherein, $E^3$ is —OH, —$NHR^8$ (in which $R^8$ is the same meaning as defined hereinbefore) or —COOH and the other symbols are the same meanings as defined hereinbefore).

The amidation is well known. For example, it may be carried out (1) by the method with using acid halide,
(2) by the method with using mixed acid anhydride,
(3) by the method with using conducing agent etc.

Concrete description of these methods are as follows:

(1) Method with using acid halide may be carried out, for example; carboxylic acid is reacted with an acid halide (oxalyl chloride, thionyl chloride or isobutyl chloroformate etc.) in an organic solvent (chloroform, methylene chloride, diethyl ether, tetrahydrofuran or ethyl acetate etc.) or without solvents at from −20° C. to a refluxing temperature to give an acid halide. The obtained acid halide and an amine are reacted in an organic solvent (chloroform, methylene chloride, diethyl ether, tetrahydrofuran etc.) in the presence of tertiary amine (pyridine, triethylamine, dimethylaniline, dimethylaminopyridine or N-methylmorpholine etc.) at 0~40° C.

(2) Method with using mixed acid anhydride may be carried out, for example; carboxylic acid is reacted with an acid halide (pivaloyl chloride, tosyl chloride, mesyl chloride, ethyl chloroformate, isobutyl chloroformate etc.) in an organic solvent (chloroform, methylene chloride, diethyl ether, tetrahydrofuran. etc.) or without solvents, in the presence of tertiary amine (pyridine, triethylamine, dimethylaniline, dimethylaminopyridine or N-methylmorpholine etc.) at −20~40° C. to give mixed acid anhydride. The obtained mixed acid anhydride and corresponding amine are reacted in an organic solvent (chloroform, methylene chloride, diethyl ether, tetrahydrofuran etc.) at 0~40° C.

(3) Method with using condensing agent may be carried out, for example; a carboxylic acid and an amine are reacted in an organic solvent (chloroform, methylene chloride, dimethylformamide, diethyl ether or tetrahydrofuran. etc.) or without solvents in the presence or absence of tertiary amine (pyridine, triethylamine, dimethylaniline or dimethylaminopyridine etc.) using with condensing agent (1,3-dicyclohexylcarbodiimido (DCC), 1-ethyl-3-[3-(dimethylamino)propyl] carbodiimido (EDC), 2-chloro-1-methylpyridinium iodide, 1,1'-carbonydiimidazole (CDI) etc.) using or without 1-hydroxybenztriazole (HoBt) at 0~40° C.

Preferably, the above reactions (1), (2) and (3) described above are carried out under an atmosphere of an inert gas (argon, nitrogen etc.) on anhydrous condition.

The esterification may be carried out by the same procedure as described in the above amidation.

The compounds of the formula (I-A), wherein $E^1$ is —S— i.e., the compounds of the formula (I-A-1)

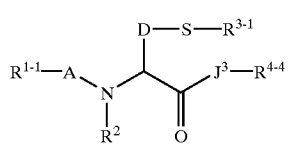

(I-A-1)

(wherein all the symbols are the same meanings as defined hereinbefore) may be prepared by reacting the compounds of the formula (VI)

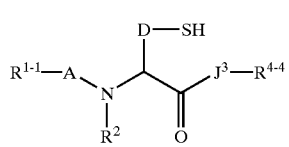

(VI)

(wherein all the symbols are the same meanings as defined hereinbefore) with the compounds of the formula (VII)

$$X—R^{3-1}$$ (VII)

(wherein, X is halogen and the other symbols are the same meanings as defined hereinbefore).

The reaction of the compounds of the formula (VI) and the compounds of the formula (VII) may be carried out by known methods. For example, it may be carried out in an organic solvent (dimethylformamide, aceton etc.) in the presence of base (potassium carbonate etc.) at 0~40° C.

(b) The compounds of the formula (I), wherein E is —SO—, —$SO_2$—, i.e., the compounds of the formula (I-B)

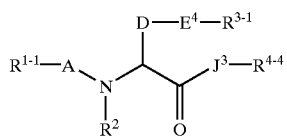
(I-B)

(wherein, $E^4$ is —SO— or —$SO_2$— and the other symbols are the same meanings as defined hereinbefore) may be prepared by oxidadtion of the said compounds of the formula (I-A) wherein $E^1$ is —S—.

The oxidation is known per su. In case of oxidation of sulfide into sulfoxide, it may be carried out, for example, in an organic solvent (methylene chloride, chloroform, benzene, hexane, t-butyl alcohol etc.) in the presence of one equivalent of oxidizing agent (hydrogen peroxide, sodium periodate, acyl nitrite, sodium perborate, peracid (e.g., m-chloroperbenzoic acid, peracetic acid etc.) etc.) for a few minutes at −78~0° C.

In case of oxidation of sulfide into sulfon, it may be carried out, for example, in an organic solvent (methylene chloride, chloroform, benzene, hexane, t-butyl alcohol etc.) in the presence of an excessive amount of oxidizing agent (hydrogen peroxide, sodium periodate, potassium permanganate, sodium perbromate, potassium peroxymonosulfate, peracid (e.g., m-chloroperbenzoic acid, peracetic acid etc.) etc.) for a few hours at −78~40° C.

(c) The compounds of the formula (I), wherein E is —$NR^{10}$—, i.e., the compounds of the formula (I-C)

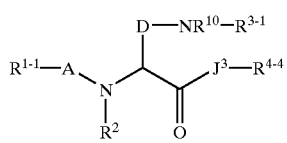
(I-C)

(wherein all the symbols are the same meanings as defined hereinbefore) may be prepared by reacting the compounds of the formula (VIII)

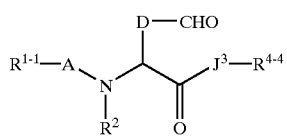
(VIII)

(wherein all the symbols are the same meanings as defined hereinbefore) with the compounds of the formula (IX)

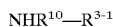   (IX)
$NHR^{10}$—$R^{3-1}$ (wherein all the symbols are the same meanings as defined hereinbefore).

The reaction of the compounds of the formula (VIII) and the compounds of the formula (IX) may be carried out by known methods, for example, by reacting the compounds of the formula (VIII) and the compounds of the formula (IX) in an organic solvent (methanol, ethanol etc.) using reductant (sodium cyanoborohydride, sodium borohydride, etc.) or, using pH adjustifying agent (acetic acid etc.) if necessary, at 0~40° C.

(d) The compounds of the formula (I), wherein E is —$SO_2NR^{11}$—, i.e., the compounds of the formula (I-D)

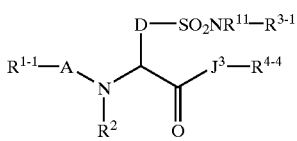
(I-D)

(wherein all the symbols are the same meanings as defined hereinbefore) may be prepared by reacting the compounds of the formula (X)

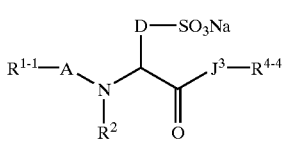
(X)

(wherein all the symbols are the same meanings as defined hereinbefore) with the compounds of the formula (XI)

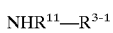   (XI)
$NHR^{11}$—$R^{3-1}$ (wherein all the symbols are the same meanings as defined hereinbefore).

The reaction of the compounds of the formula (X) and the compounds of the formula (XI) may be carried out by known methods, for example, by reacting the compounds of the formula (X) with base (triphenylphosphine etc.) and acid halide (oxazolyl chloride, thionyl chloride etc.) in an organic solvent (chloroform, methylene chloride, diethyl ether, tetrahydrofran etc.), at from −20° C. to refluxing temperature, and then by reacting thus obtained compounds and the compounds of the formula (XI) in the presence of tertiary amine (pyridine, triethylamine, dimethylaniline, dimethylaminopyridine etc.) in an organic solvent (chloroform, methylene chloride, diethyl ether, tetrahydrofran etc.) at 0~40° C.

(e) The compounds of the formula (I), wherein E is —$NR^{12}SO_2$—, i.e., the compounds of the formula (I-E)

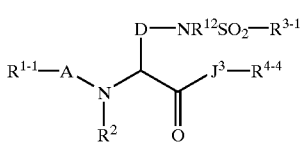
(I-E)

(wherein all the symbols are the same meanings as defined hereinbefore) may be prepared by reacting the compounds of the formula (XII)

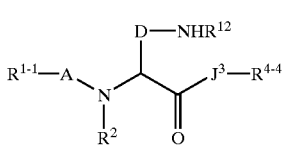
(XII)

(wherein all the symbols are the same meanings as defined hereinbefore) with the compounds of the formula (XIII)

   (XIII)
X—$SO_2$—$R^{3-1}$ (wherein, X is halogen and the other symbols are the same meanings as defined hereinbefore).

The reaction of the compounds of the formula (XII) and the compounds of the formula (XIII) may be carried out, for example, by reacting the compounds of the formula (XII) and the compounds of the formula (XIII) in an organic solvent (chloroform, methylene chloride, diethyl ether, tetrahydrofran etc.) in the presence of tertiary amine (pyridine, triethylamine, dimethylaniline, dimethylaminopyridine etc.) at 0–40° C.

(f) The compounds of the formula (I), wherein A is —CO— or —SO$_2$—, i.e., the compounds of the formula (I-F)

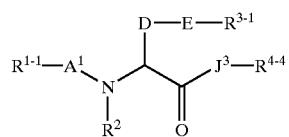

(I-F)

(wherein, $A^1$ is —CO— or —SO$_2$— and the other symbols are the same meanings as defined hereinbefore) may be prepared by amidation or sulfonamidation of the compounds of the formula (XIV)

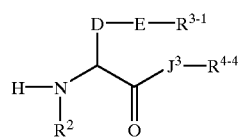

(XIV)

(wherein all the symbols are the same meanings as defined hereinbefore) with the compounds of the formula (XV)

$$R^{1-1}—A^2 \quad (XV)$$

(wherein, $A^2$ is —COOH or —SO$_3$H and the other symbols are the same meanings as defined hereinbefore).

The amidation and sulfonamidation may be carried out by the same procedure as described hereinbefore.

(g) The compounds of the formula (I), wherein A is single bond and $R^1$ is C1–4 alkyl substituted with phenyl, C3–8 cycloalkyl or heterocyclic ring, i.e., the compounds of the formula (I-G)

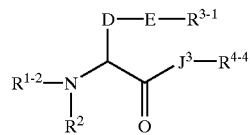

(I-G)

($R^{1-2}$ is C1–4 alkyl substituted with phenyl, C3–8 cycloalkyl or heterocyclic ring (with the proviso that when amino group exists as a substituent of each ring, such an amino group is protected with protecting group, if necessary) and the other symbols are the same meanings as defined hereinbefore) may be prepared by reacting the compounds of the formula (XIV)

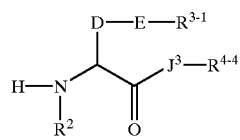

(XIV)

(wherein all the symbols are the same meanings as defined hereinbefore) with the compounds of the formula (XVI)

$$R^{1-3}—CHO \quad (XVI)$$

(wherein, $R^{1-3}$ is phenyl, C3–8 cycloalkyl, heterocyclic ring or C1–3 alkyl substituted with phenyl, C3–8 cycloalkyl or heterocyclic ring (with the proviso that when amino group exists as a substituent of each ring, such an amino group is protected with protecting group, if necessary)).

This reaction may be carried out by the same procedure as described in the reaction of the compounds of the formula (VIII) and the compounds of the formula (IX).

(h) The compounds of the formula (I), wherein $R^1$ is heterocyclic ring containing at least one nitrogen atom or C1–4 alkyl substituted with heterocyclic ring containing at least one nitrogen atom and the said heterocyclic ring is substituted with C2–5 acyl or C1–4 alkoxycarbonyl, i.e., the compounds of the formula (I-H)

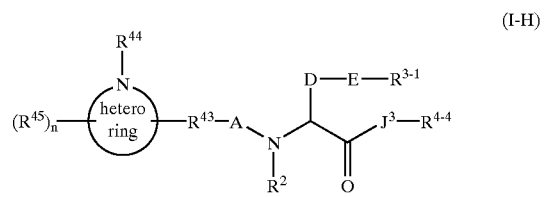

(I-H)

(wherein, $R^{43}$ is single bond or C1–4 alkylene, $R^{44}$ is C1–4 alkoxycarbonyl or C2–5 acyl, $R^{45}$ is C1–4 alkyl, C1–4 alkoxy, phenyl, phenoxy, benzyloxy, —SR$^5$, halogen, nitro or —NR$^6$R$^7$, n is 0–2 and

is the same meaning for heterocyclic ring in $R^1$, provided that such a heterocyclic ring contains at least one nitrogen atom and that when amino group exists as a substituent represented by $R^{45}$, such an amino group is protected with protecting group, if necessary and the other symbols are the same meanings as defined hereinbefore) may be prepared by amidation of the compounds of the formula (XVII)

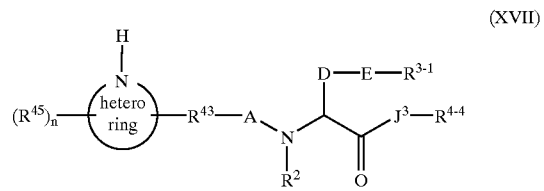

(XVII)

(wherein all the symbols are the same meanings as defined hereinbefore) with the compounds of the formula (XVIII)

$$R^{44}—OH \quad (XVIII)$$

(wherein, $R^{44}$ is the same meaning as defined hereinbefore).

The amidation may be carried out by the same procedure as described hereinbefore.

(i) Among the compounds of the formula (I), the compounds of the formula (I-I)

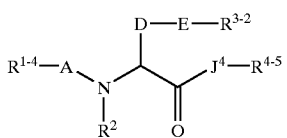

(wherein, $R^{1-4}$, $R^{3-2}$, $R^{4-5}$ and $J^4$ are the same meanings as hereinbefore described for $R^1$, $R^3$, $R^4$ and J respectively, provided that at least one of them is a group containing —COOH, hydroxy or amino and the other symbols are the same meanings as defined hereinbefore) may be prepared by removal of protecting group according to alkaline hydrolysis, by removal of protecting group in an acidic condition and/or by hydrogenolysis of the compounds of the said formulae (I-A), (I-A-1), (I-B), (I-C), (I-D), (I-E), (I-F), (I-G) or (I-H).

The removal of a protecting group according to alkaline hydrolysis is well known. For example, it may be carried out in an organic solvent (methanol tetrahydrofuran, dioxane etc.), using hydroxide of an alkaline metal (sodium hydroxide, potassium hydroxide, lithium hydroxide etc.), hydroxide of an alkaline earth metal (calcium hydroxide etc.) or carbonate (sodium carbonate, potassium carbonate etc.) or an aqueous solution thereof or a mixture thereof at 0~40° C.

The removal of a protecting group in an acidic condition is well known. For example, it may be carried out in an organic solvent (methyhlene chloride, chloroform, dioxane, ethyl acetate, anisole etc.) or without solvent, in the presence of organic acid (trifluoroacetic acid, methanesulfonic acid, trimethylsilyliodide etc.) or inorganic acid (hydrochloric acid etc.) or a mixture thereof (bromohydroacetic acid etc.) at 0~90° C.

The hydrogenolysis is well known. For example, it may be carried out in an organic solvent (tetrahydrofran, dioxane, diethyl ether, ethyl acetate, methanol, ethanol etc.), in the presence of catalyst to hydrogenate (e.g., Pd—C, palladium, palladium hydroxide, palladium acetate, palladium black, platinum black, Ni, Raney nickel etc.), at an ordinary or increased pressure under an atmosphere of hydrogen gas at 0~80° C.

As well known to the person in the art, a protecting group of carboxy or hydroxy includes, for example, t-butyl, benzyl etc. In addition, such a group includes the other protecting group which is removable selectively and easily, for example, one described in T. W. Greene, Protective Groups in Organic Synthesis, Wiley, New York, 1991. A protecting group of amino includes, for example, benzyloxycarbonyl, t-butoxycarbonyl. In addition, such a group includes the other protecting group which is removable selectively and easily. Further, the aimed compounds of the present invention may be prepared easily by choice of these protecting group.

The compounds of the formulae (II), (III), (IV), (V), (VI), (VII), (VIII), (IX), (X), (XI), (XII), (XIII), (XIV), (XV), (XVI), (XVII), (XVIII) may be known per su or may be prepared by known methods or the methods described in Examples. But, the above compounds may be prepared by the other methods.

For example, the compounds of the formula (X) may be prepared by the method described in Liebigs Ann. Chem, 776–783, 1979.

For example, the compounds of the formula (XII) may be prepared by the method described in J. Org. Chem., Vol. 44, No. 10, 1979.

For example, the compounds of the formula (XIV), wherein E is —O—, —S—, —SO—, -SO$_2$—, i.e., the compounds of the formula (XIV') and the compounds of the formula (XVII), wherein E is —O—, —S—, —SO—, —SO$_2$—, i.e., the compounds of the formula (XVII') may be prepared by the method shown in the following Reaction Schemes 1 and 2.

Further, among the compounds of the formula (II), the compounds of the formula (II')

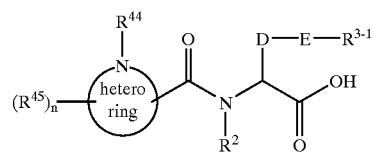

(wherein all the symbols are the same meanings as defined hereinbefore) may be prepared by the method shown in the following Reaction Scheme 3.

Reaction Scheme 1

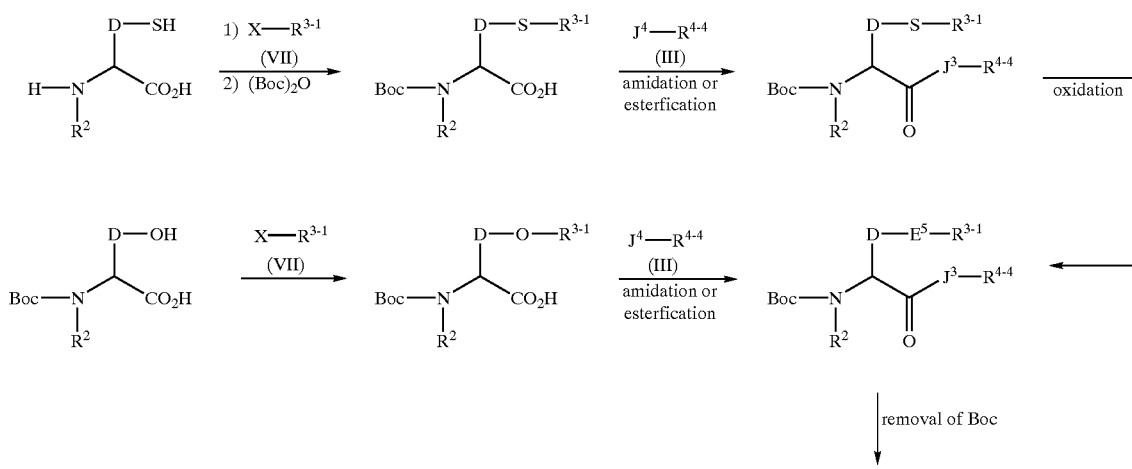

-continued

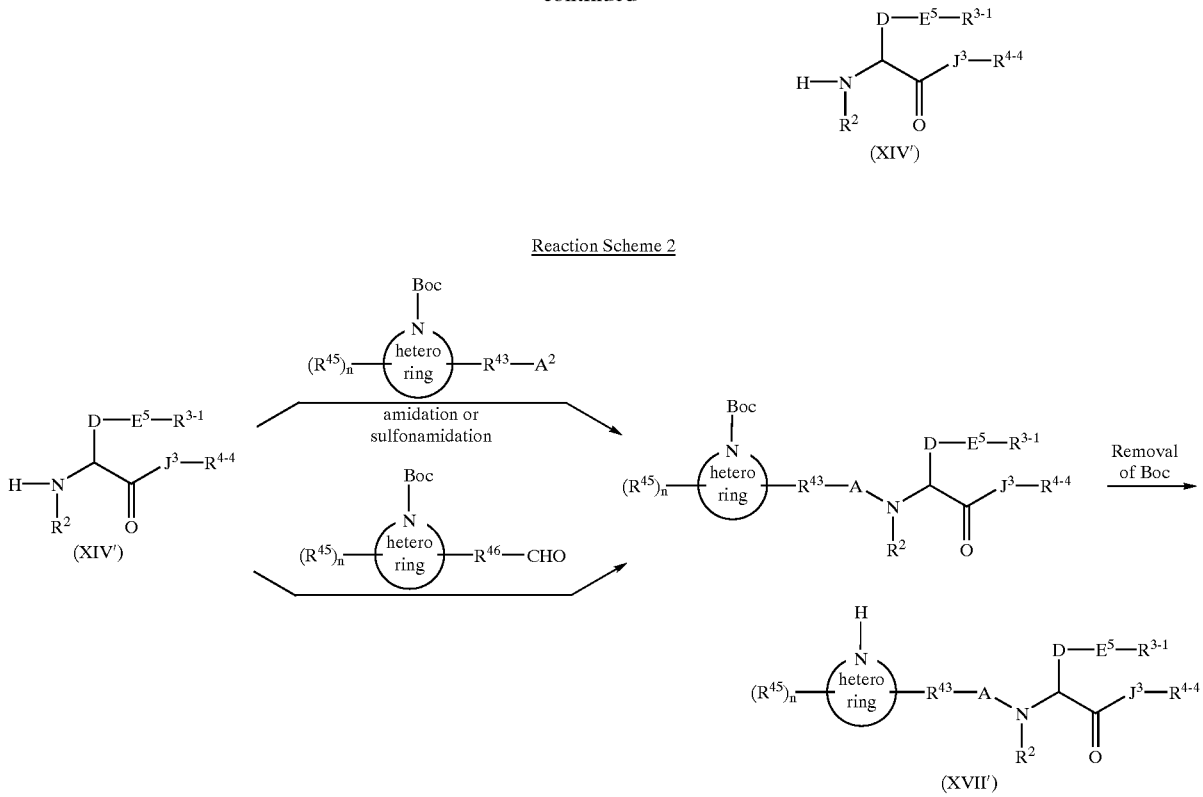

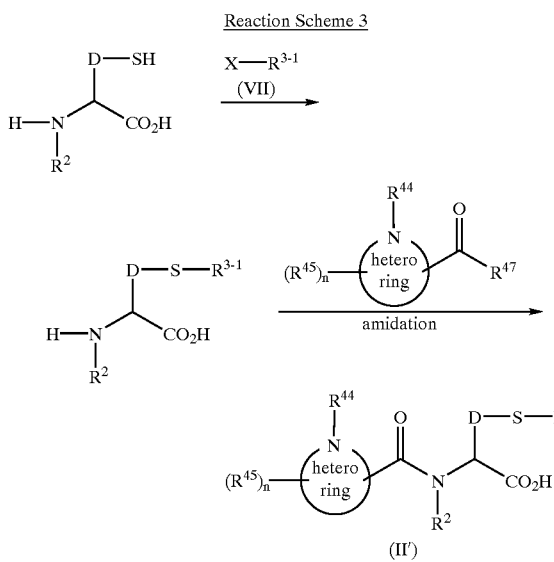

(In each Reaction Scheme, $E^5$ is —O—, —S—, —SO— or $SO_2$—, Boc is t-butoxycarbonyl, (Boc)$_2$O is di-t-butyl dicarbonate, $R^{46}$ is single bond or C1–3 alkylene, $R^{47}$ is hydroxy or 2,5-dioxopyrrolidin-1-yloxy and the other symbols are the same meanings as defined hereinbefore)

The reactions described in the above-mentioned Schemes may be carried out by known methods. In the above-mentioned Schemes, compounds used for starting materials are may be known per se or may be easily prepared by known methods.

In the present invention, the other starting materials and each reagent are known per se or may be prepared by known methods.

In each reaction in the present specification, products may be purified by a conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction or after a series of reactions.

[Pharmacological Activity]

It has been confirmed that the compounds of the present invention of the formula (I) possess an inhibitory action on N-type calcium channel according to the following experiment.

Determination of Inhibitory Activity on N-type Calcium Channel

Cell line was differentiated according to the method described in FEBS Letters, 235, 178–182, 1988. The cell was loaded with fluorescent reagent, Fura-2.AM (at the final concentration of 10 $\mu$M), at 37° C. for 30 minutes and suspended in Krebs-buffer containing HEPES (25 mM) to obtain the cell suspension. The obtained cell suspension was incubated in the presence or absence of the compounds of the present invention with nifedipine for 5 minutes. The cell was depolarized by adding potassium chloride solution (at the final concentration of 80 mM) thereto and then a fluorescence intensity at the emission wavelength of 500 nm excited by the UV of 340 nm and 380 nm alternately was measured using the intracellular calcium analyzer (Nippon Bunko Co., CAF-110). The inhibitory activity of the compound of the present invention (at the final concentration of 3 $\mu$M) on calcium influx into the cell was calculated from the difference in changing the fluorescence intensity at peak ($\Delta R$) according to the following equation.

$$\text{Inhibitory effect (\%) of the compound of the present invention (3 } \mu\text{M) on calcium flow} = \left[1 - \frac{\text{Mean of } \Delta R \text{ in case of a solution containing the compound of the present invention}}{\text{Mean of } \Delta R \text{ in case of a solution not containing the compound of the present invention}}\right] \times 100$$

The results were shown in Table 41.

TABLE 41

| Example No. | Inhibitory effect on calcium flow (%) |
|---|---|
| 2 | 95 |

From the results of an experiment using the patch-clamp technique described in Pflungers Archives, 391, 85–100, 1981, the compounds of the present invention at the concentration of 10 $\mu$M showed clearly an inhibitory action on flux of barium ion (calcium current) passed through an N-type calcium channel. The cells used in this experiment had been incubated according to the method described in FEBS Letters, 23, 178–182, 1988.

[Toxicity]

The toxicity of the compounds of the present invention are very low and therefore, it may be considered that the compounds of the present invention are safe for pharmaceutical use.

INDUSTRIAL APPLICATION

The compounds of the formula (I) possess an inhibitory action on N-type calcium channel, so they are useful as agent for the prevention and/or treatment of cerebral infarct, transient ischemic attack, encephalomyelopathy after cardiac operation, spinal angiopathy, hypertension with stress, neurosis, epilepsy, asthma and pollakiuria etc. or agent for the treatment of pain.

For the purpose above described, the compounds of the present invention of the formula (I), non-toxic salts and acid addition salts thereof and hydrates thereof may be normally administered systematically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Capsules contain hard capsules and soft capsules.

In such inner solid compositions, one or more of the active compound(s) is or are, admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administ ration include pharmaceutically-acceptable water-agents, suspensions, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavouring agents, perfuming agents, preserving agents and buffer agents etc.

Injections for parenteral administration include solutions, suspensions and emulsions and solid injections which are dissolved or suspended in solvent when it is used. One or more active compound(s) is or are dissolved, suspended or emulsified in a solvent when such compositions are used. Aqueous solutions or suspensions include distilled water for injection and physiological salt solution plant oil, propylene glycol, polyethylene glycol and alcohol such as ethanol etc., and mixture thereof. Such compositions may comprise additional diluents such as stabilizing agent, assisting agents for dissolving (glutamic acid, asparaginic acid, POLYSOL-BATE80 (registered trade mark) etc.), suspending agents, emulsifying agents, dispersing agents, buffer agents, preserving agents etc. They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, ointments, endermic liniments, aerosols, spray compositions, suppositories and pessaries for vaginal administration etc. which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or U.S. Pat. No. 3,095,355 may be used.

BEST MODE FOR CARRYING OUT THE INVENTION

The following Reference Examples and Examples are intended to illustrate, but do not limit the present invention.

The solvents in parenthesis show the developing or eluting solvents and the ratios of the solvents used are by volume in chromatographic separations and TLC.

The solvents in parentheses in NMR show the solvents used for measurement.

Reference Example 1

(2R)-2-t-butoxycarbonylamino-3-cyclohexylmethylthiopropanoic acid

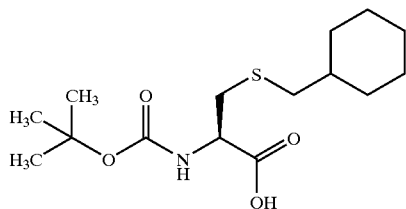

To a solution of L-cystein (133 mg) in ethanol (10 ml), an aqueous solution of 2N—NaOH (1.1 ml), (bromomethyl)cyclohexane (0.17 ml) were added. The mixture was stirred for 2.5 hours at room temperature. To the reaction mixture, an aqueous solution of 2N—NaOH (0.6 ml) and di-t-butyl dicarbonate (0.28 ml) were added. The mixture was stirred for 1 hour. After ethanol was distilled off, the mixture was acidified by addition of 1N—HCl and extracted with ethyl acetate. The extract was washed by saturated solution of sodium chloride, dried over anhydrous magnesium sulfate and concentrated. The residue was purified with column chromatography on silica gel (chloroform:methanol=19:1) to obtain the title compound (135 mg) having the following physical data.

TLC: Rf 0.21 (ethyl acetate:acetic acid:water=9:1:1);

NMR (CDCl$_3$): δ4.42–4.28 (1H, m), 3.01 (1H, dd, J=14.2, 5.2 Hz), 2.92 (1H, dd, J=14.2, 3.4 Hz), 2.45 (2H, d, J=7.0 Hz), 1.91–0.81 (20H, m).

Reference Example 2

(2S)-2-t-butoxycarbonylamino-3-cyclohexylmethoxypropanoic acid

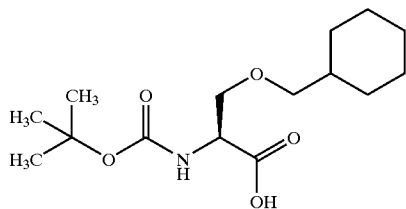

To a solution of (2S)-3-hydroxy-2-t-butoxycarbonylaminopropanoic acid (10.11 g) in dimethylformamide (200 ml, abbreviated as DMF), sodium hydride (60%, 3.95 g) was added under cooling with ice. The mixture was stirred for 30 minutes at 0° C. To the reaction mixture, (bromomethyl)cyclohexane (9.0 ml) was added at a dropwise under cooling with ice. Tetra-n-butylammonium iodide (910 mg) was added thereto. The mixture was stirred for 23 hours at room temperature. In addition, to the reaction mixture, (bromomethyl)cyclohexane (2.1 ml) was added at a dropwise. The mixture was stirred for 4 hours. Again, (bromomethyl)cyclohexane (2.1 ml) was added at a dropwise thereto. The mixture was stirred for 25 hours at room temperature. After the concentration of reaction mixture, the residue was diluted with 1N—HCl and extracted with ethyl acetate. The extract solution was washed by water and saturated solution of sodium chloride successively, dried over anhydrous sodium sulfate and concentrated. The residue was purified with column chromatography on silica gel (chloroform:methanol=97:3) to obtain the title compound (2.52 g) having the following physical data.

TLC: Rf 0.21 (chloroform:methanol=9:1);

NMR (CDCl$_3$): δ5.59–5.40 (1H, m), 4.46–4.27 (1H, m), 3.89–3.76 (1H, m), 3.64 (1H, dd, J=9.4, 4.6 Hz), 3.27 (2H, d, J=6.2 Hz), 1.79–0.79 (20H, m).

EXAMPLE 1

(2R)-N-(1-benzylpiperidin-4-yl)-2-t-butoxycarbonylamino-3-cyclohexylmethylthiopropanamide

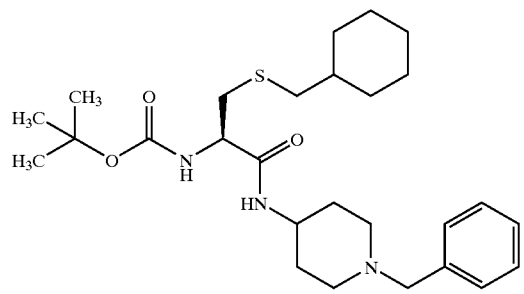

To a solution of the compound prepared in Reference Example 1 (726 mg) and 4-amino-1-benzylpiperidine (0.47 ml) in methylene chloride (12 ml), 1-ethyl-3-(3-dimethylaminopropyl)-carbodiimide.hydrochloride (527 mg) and 1-hydroxybenzotriazole (421 mg) were added under cooling with ice, successively. The mixture was stirred for 3 hours. The reaction mixture was washed by saturated solution of sodium hydrogencarbonate, water and saturated solution of sodium chloride successively, dried over anhydrous sodium sulfate and concentrated. The residue was purified with column chromatography on silica gel (methanol chloroform=3:97) to obtain the compound (1.05 g) of the present invention having the following physical data.

TLC: Rf 0.62 (methanol:chloroform=1:9);

NMR (CDCl$_3$): δ7.34–7.22 (m, 5H), 6.31 (d, J=7.8 Hz, 1H), 5.37 (d, J=6.0 Hz, 1H), 4.17–4.11 (m, 1H), 3.86–3.74 (m, 1H), 3.49 (s, 2H), 2.94 (dd, J=13.5, 5.4 Hz, 1H), 2.80–2.73 (m, 3H), 2.47 (dd, J=12.6, 6.9 Hz, 1H), 2.43 (dd, J=12.6, 6.9 Hz, 1H), 2.19–2.10 (m, 2H), 1.95–1.60 (m, 8H), 1.58–1.38 (m, 13H), 1.30–1.05 (m, 3H), 1.00–0.85 (m, 2H).

EXAMPLE 1 (1)~EXAMPLE 1 (30)

By the same procedure described in Example 1 to react the compounds prepared in Reference Example 1 or Reference Example 2 and 4-amino-1-benzylpiperidine or corresponding amine derivatives in Example 1, the following compounds of the present invention were obtained.

EXAMPLE 1 (1)

(2R)-N-(4-hydroxybenzyl)-2-t-butoxycarbonylamino-3-cyclohexylmethylthiopropanamide

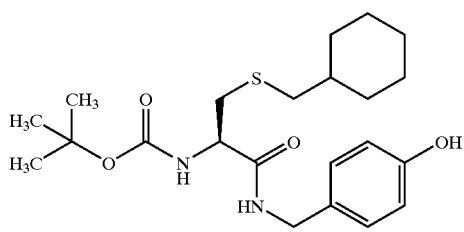

TLC: Rf 0.52 (ethyl acetate:hexane=1:1);

NMR (CDCl$_3$): δ7.13–7.06 (2H, m), 6.78–6.67 (3H, m), 6.20 (1H, s), 5.38 (1H, d, J=7.2 Hz), 4.36 (2H, d, J=6.0 Hz), 4.29–4.19 (1H, m), 2.96 (1H, dd, J=14.0, 6.0 Hz), 2.83 (1H, dd, J=14.0, 6.6 Hz), 2.42 (2H, d, J=6.6 Hz), 1.85–0.78 (20H, m).

EXAMPLE 1 (2)

(2S)-N-(1-benzylpiperidin-4-yl)-2-t-butoxycarbonylamino-3-cyclohexylmethoxypropanamide

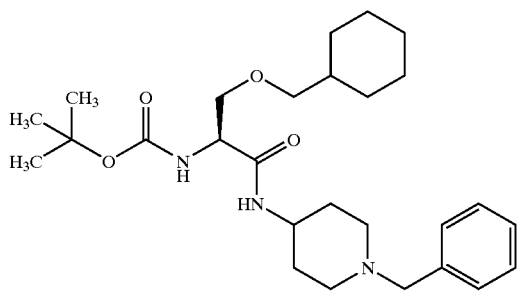

TLC: Rf 0.23 (methanol:methylene chloride=1:19);

NMR (CDCl$_3$): δ7.37–7.23 (m, 5H), 6.47–6.35 (m, 1H), 5.45–5.32 (m, 1H), 4.20–4.10 (m, 1H), 3.88–3.73 (m, 2H), 3.50 (s, 2H), 3.50–3.40 (m, 1H), 3.26 (d, J=6 Hz, 2H), 2.84–2.72 (m, 2H), 2.22–2.10 (m, 2H), 1.95–1.84 (m, 2H), 1.76–1.61 (m, 5H), 1.50–1.37 (m, 12H), 1.31–1.06 (m, 3H), 1.00–0.83 (m, 2H).

EXAMPLE 1 (3)

(2R)-N-(1-benzylpiperidin-4-ylmethyl)-2-t-butoxycarbonylramino-3-cyclohexylmethylthiopropanamide

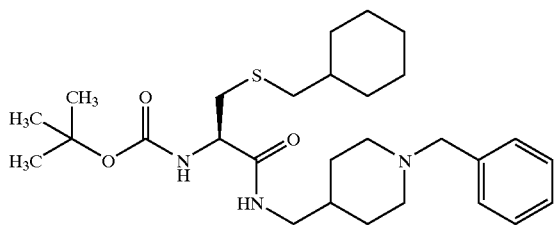

TLC: Rf 0.41 (methanol:chloroform=1:9);

NMR (CDCl$_3$): δ7.31–7.20 (m, 5H), 6.47 (t, J=5.4 Hz, 1H), 5.36 (d, J=7.2 Hz, 1H), 4.16 (dd, J=12.6, 7.5 Hz, 1H), 3.49 (s, 2H), 3.23–3.09 (m, 2H), 2.95 (dd, J=14.1, 5.7 Hz, 1H), 2.90–2.86 (m, 2H), 2.78 (dd, J=14.1, 7.2 Hz, 1H), 2.47 (dd, J=12.6, 6.9 Hz, 1H), 2.42 (dd, J=12.6, 6.6 Hz, 1H), 1.99–1.90 (m, 2H), 1.84–1.65 (m, 7H), 1.55–1.05 (m, 16H), 0.98–0.86 (m, 2H).

EXAMPLE 1 (4)

(2R)-N-(3-methoxymethoxy-4-methoxybenzyl)-2-t-butoxycarbonylamino-3-cyclohexylmethylthiopropanamide

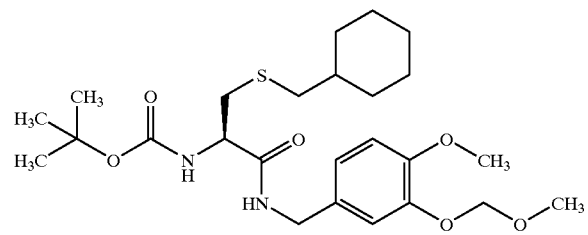

TLC: Rf 0.36 (hexane:ethyl acetate=2:1);

NMR (CDCl$_3$): δ7.07 (d, J=1.8 Hz, 1H), 6.93 (dd, J=8.4, 1.8 Hz, 1H), 6.84 (d, J=8.4 Hz, 1H), 6.65 (t, J=6.0 Hz, 1H), 5.37 (d, J=6.6 Hz, 1H), 5.23 (s, 2H), 4.38 (d, J=6.0 Hz, 2H), 4.29–4.19 (m, 1H), 3.87 (s, 3H), 3.52. (s, 3H), 2.98. (dd, J=13.8, 5.4 Hz, 1H), 2.82 (dd, J=13.8, 7.0 Hz, 1H), 2.52–2.35 (m, 2H), 1.86–1.59 (m, 5H), 1.53–1.36 (m, 10H), 1.34–0.80 (m, 5H).

EXAMPLE 1 (5)

(2R)-N-(1-(4-methoxybenzyl)piperidin-4-ylmethyl)-2-t-butoxycarbonylamino-3-cyclohexylmethylthiopropanamide

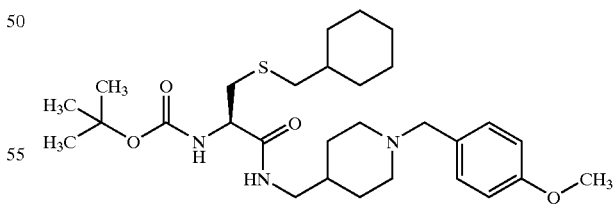

TLC: Rf 0.39 (methanol:chloroform=1:9);

NMR (CDCl$_3$): δ7.25–7.19 (m, 2H), 6.89–6.81 (m, 2H), 6.48 (t, J=5.8 Hz, 1H), 5.35 (d, J=7.4 Hz, 1H), 4.21–4.11 (m, 1H), 3.80 (s, 3H), 3.46 (s, 2H), 3.19–3.11 (m, 2H), 3.00–2.72 (m, 4H), 2.44 (d, J=6.6 Hz, 2H), 2.04–0.79 (m, 27H).

EXAMPLE 1 (6)

(2R)-N-methyl-N-(1-benzylpyrrolidin-3-yl)-2-t-butoxycarbonylamino-3-cyclohexylmethylthiopropanamide

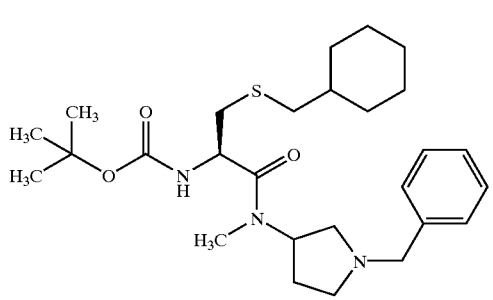

TLC: Rf 0.49 (chloroform:methanol=9:1);

NMR (CD$_3$OD): δ7.33–7.20 (m, 5H), 5.17–4.68 (m, 2H), 3.73–3.49 (m, 2H), 3.16 and 2.91–2.03 (m, 12H), 1.98–1.59 (m, 6H), 1.48–0.80 (m, 15H).

EXAMPLE 1 (7)

(2R)-N-(1-(4-methoxybenzyl)piperidin-4-yl)-2-t-butoxycarbonylamino-3-cyclohexylmethylthiopropanamide

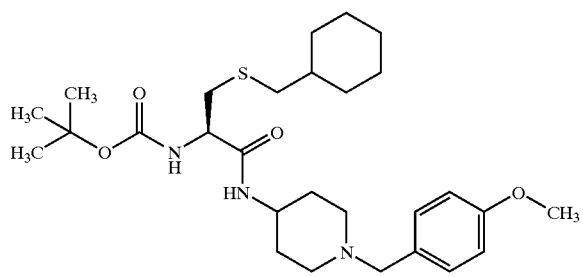

TLC: Rf 0.37 (methanol:chloroform=1:9);

NMR (CDCl$_3$): δ7.25–7.18 (m, 2H), 6.89–6.82 (m, 2H), 6.31 (d, J=8.4 Hz, 1H), 5.36 (d, J=7.4 Hz, 1H), 4.19–4.09 (m, 1H), 3.91–3.70 (m, 4H), 3.43 (s, 2H), 2.94 (dd, J=13.6, 5.2 Hz, 1H), 2.81–2.71 (m, 3H), 2.45 (d, J=6.6 Hz, 2H), 2.19–2.05 (m, 2H), 1.85–0.81 (m, 24H)

EXAMPLE 1 (8)

(2R)-N-(1-(4-methoxybenzoyl)piperidin-4-yl)-2-t-butoxycarbonylamino-3-cyclohexylmethylthiopropanamide

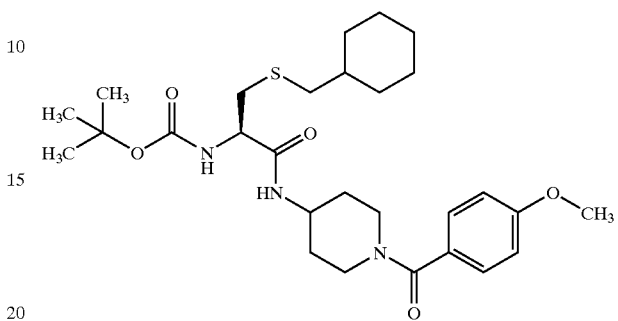

TLC: Rf 0.17 (ethyl acetate:hexane=1:2);

NMR (CDCl$_3$): δ7.40–7.33 (m, 2H), 6.93–6.89 (m, 2H), 6.45 (d, J=7.5 Hz, 1H), 5.35 (d, J=7.5 Hz, 1H), 4.16 (dd, J=12.9, 7.2 Hz), 4.09–3.93 (m, 1H), 3.83 (s, 3H), 3.14–3.04 (m, 2H), 2.95 (dd, J=13.8, 5.4 Hz, 1H), 2.78 (dd, J=13.8, 7.2 Hz, 1H), 2.47 (dd, J=13.8, 7.2 Hz, 1H), 2.43 (dd, J=13.8, 6.9 Hz, 1H), 2.03–1.91 (m, 2H), 1.85–1.78 (m, 2H), 1.75–1.63 (m, 4H), 1.54–1.38 (m, 13H), 1.30–1.06 (m, 3H), 1.00–0.85 (m, 2H).

EXAMPLE 1 (9)

(2R)-N-(1-(4-fluorobenzyl)piperidin-4-ylmethyl)-2-t-butoxycarbonylamino-3-cyclohexylmethylthiopropanamide

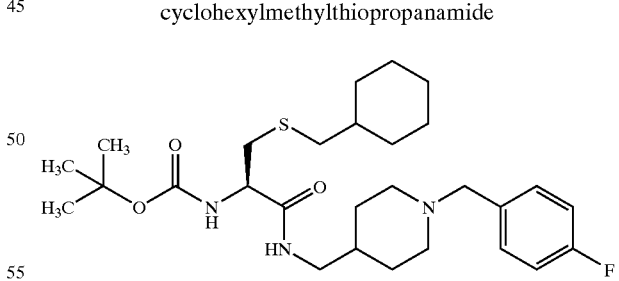

TLC: Rf 0.28 (methanol:chloroform=1:19);

NMR (CDCl$_3$): δ7.31–7.20 (m, 2H), 7.05–6.93 (m, 2H), 6.48 (t, J=5.8 Hz, 1H), 5.36 (d, J=7.2 Hz, 1H), 4.17 (td, J=7.0, 5.4 Hz, 1H), 3.46 (s, 2H), 3.20–3.13 (m, 2H), 3.00–2.73 (m, 4H), 2.45 (d, J=6.6 Hz, 2H), 2.00–0.78 (m, 27H).

EXAMPLE 1 (10)

N-((1R)-2-cyclohexylmethylthio-1-(4-benzylpiperazin-1-ylcarbonyl)ethyl)carbamic acid.t-butyl ester

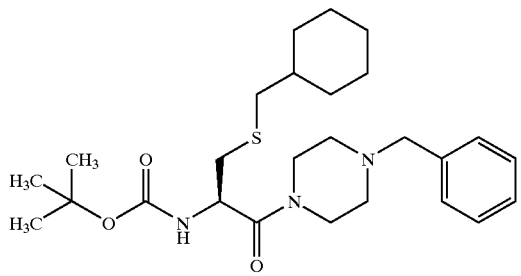

TLC: Rf 0.45 (hexane:ethyl acetate=1:1);

NMR (CD$_3$OD): δ7.34–7.22 (m, 5H), 4.70 (t, J=6.9 Hz, 1H), 3.74–3.44 (m, 6H), 2.83 (dd, J=13.5, 6.9 Hz, 1H), 2.63 (dd, J=13.5, 6.9 Hz, 1H), 2.57–2.41 (m, 6H), 1.86–1.64 (m, 5H), 1.50–1.36 (m, 10H), 1.33–1.09 (m, 3H), 1.01–0.87 (m, 2H),

EXAMPLE 1 (11)

N-((1R)-2-cyclohexylmethylthio-1-(4-diphenylmethylpiperazin-1-ylcarbonyl)ethyl)carbamic acid.t-butyl ester

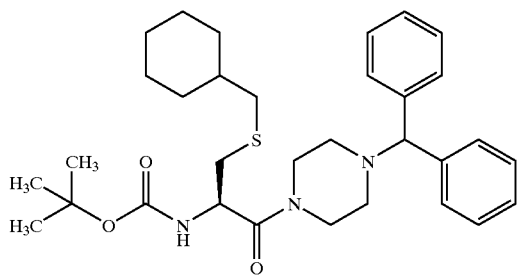

TLC: Rf 0.22 (ethyl acetate:chloroform=1:39);

NMR (CDCl$_3$): δ7.41 (d, J=7.5 Hz, 4H), 7.28 (d, J=7.5 Hz, 4H), 7.21–7.17 (m, 2H), 5.42 (d, J=10.2 Hz, 1H), 4.76–4.68 (m, 2H), 4.23 (s, 2H), 3.69–3.50 (m, 4H), 2.81 (dd, J=14.4, 9.0 Hz, 1H), 2.68 (dd, J=14.4, 6.9 Hz, 1H), 2.46–2.32 (m, 6H), 1.86–1.57 (m, 5H), 1.49–1.34 (m, 10H), 1.30–1.05 (m, 3H), 0.98–0.83 (m, 2H),

EXAMPLE 1 (12)

(2R)-N-(2-benzylaminoethyl)-2-t-butoxycarbonylamino-3-cyclohexylmethylthiopropanamide

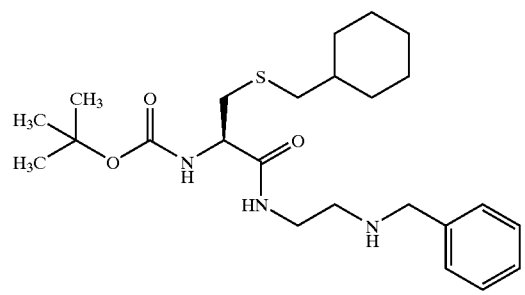

TLC: Rf 0.49 (chloroform:methanol=9:1);

NMR (CDCl$_3$): δ7.34–7.22 (m, 5H), 6.88–6.72 (br, 1H), 4.25–4.15 (m, 1H), 3.79 (s, 2H), 3.42–3.33 (m, 2H), 2.94 (dd, J=13.6, 5.6 Hz, 1H), 2.85–2.75 (m, 3H), 2.43 (d, J=6.6 Hz, 2H), 1.86–1.58 (m, 5H), 1.55–1.35 (m, 10H), 1.33–0.81 (m, 5H).

EXAMPLE 1 (13)

N-((1R)-2-cyclohexylmethylthio-1-(4-(4-methoxyphenyl)piperazin-1-ylcarbonyl)ethyl)carbamic acid.t-butyl ester TLC: Rf 0.33 (ethyl acetate:hexane=1:2);

NMR (CDCl$_3$): δ6.92–6.83 (m, 4H), 5.43 (d, J=9.0 Hz, 1H), 4.82 (dd, J=15.0, 7.5 Hz, 1H), 3.83–3.72 (m, 7H), 3.15–3.04 (m, 4H), 2.87 (dd, J=13.5, 7.2 Hz, 1H), 2.75 (dd, J=13.5, 6.0 Hz, 1H), 2.44 (d, J=6.9 Hz, 2H), 1.88–0.85 (m, 20H).

EXAMPLE 1 (14)

(2R)-N-(1-(4-fluorobenzyl)piperidin-4-yl)-2-t-butoxycarbonylamino-3-cyclohexylmethylthiopropanamide

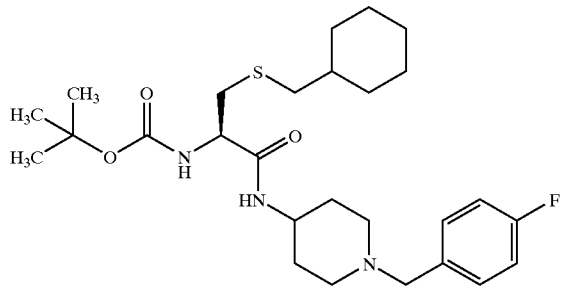

TLC: Rf 0.33 (ethyl acetate:hexane=1:2);

NMR (CDCl₃): δ7.31–7.23 (m, 2H), 7.03–6.95 (m, 2H), 6.32 (d, J=7.8 Hz, 1H), 5.37 (d, J=6.6 Hz, 1H), 4.14 (dd, J=12.9, 6.6 Hz, 1H), 3.86–3.73 (m, 1H), 3.45 (s, 2H), 2.94 (dd, J=13.8, 5.4 Hz, 1H), 2.80–2.73 (m, 3H), 2.47 (dd, J=12.6, 6.9 Hz, 1H), 2.43 (dd, J=12.6, 6.9 Hz, 1H), 2.17–2.08 (m, 2H), 1.95–1.60 (m, 7H), 1.55–1.38 (m, 12H), 1.30–1.05 (m, 3H), 1.00–0.85 (m, 2H).

EXAMPLE 1 (15)

(2R)-N-(1-(4-fluorobenzoyl)piperidin-4-yl)-2-t-butoxycarbonylamino-3-cyclohexylmethylthiopropanamide

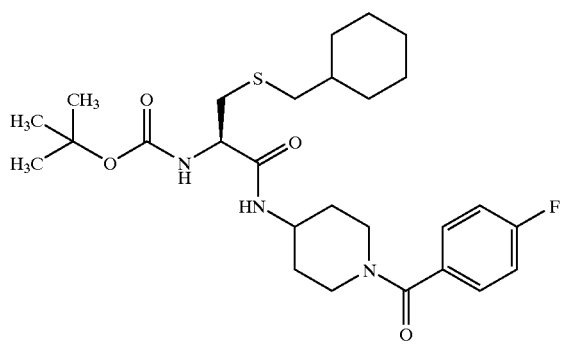

TLC: Rf 0.33 (ethyl acetate:hexane=1:2);

NMR (CDCl₃): δ7.44–7.37 (m, 2H), 7.14–7.06 (m, 2H), 6.46 (d, J=7.5 Hz, 1H), 5.35 (d, J=6.9 Hz, 1H), 4.52 (br.s, 1H), 4.20–4.13 (m, 1H), 4.07–3.96 (m, 1H), 3.75 (br.s, 1H), 3.22–3.00 (m, 2H), 2.95 (dd, J=13.8, 5.4 Hz, 1H), 2.78 (dd, J=13.8, 7.2 Hz, 1H), 2.51–2.39 (m, 2H), 2.08–1.60 (m, 7H), 1.54–1.06 (m, 15H), 1.00–0.84 (m, 2H).

EXAMPLE 1 (16)

N-((1R)-2-cyclohexylmethylthio-1-(4-(pyridin-2-yl)piperazin-1-ylcarbonyl)ethyl)carbamic acid.t-butyl ester

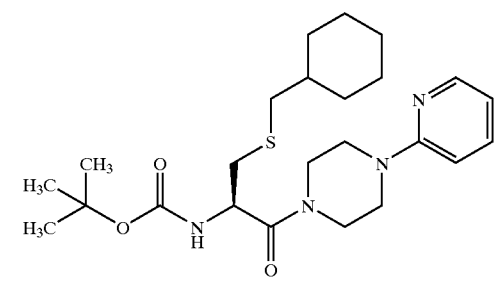

TLC: Rf 0.73 (ethyl acetate:hexane=2:1);

NMR (CDCl₃): δ8.23–8.20 (m, 1H), 7.56–7.47 (m, 1H), 6.71–6.64 (m, 2H), 5.44 (d, J=8.8 Hz, 1H), 4.82 (dd, J=14.6, 6.6 Hz, 1H), 3.83–3.52 (m, 8H), 2.88 (dd, J=13.4, 7.6 Hz, 1H), 2.75 (dd, J=13.4, 5.8 Hz, 1H), 2.44 (d, J=6.8 Hz, 2H), 1.89–0.80 (m, 20H).

EXAMPLE 1 (17)

N-((1R)-2-cyclohexylmethylthio-1-(4-(pyridin-4-yl)piperazin-1-ylcarbonyl)ethyl)carbamic acid.t-butyl ester

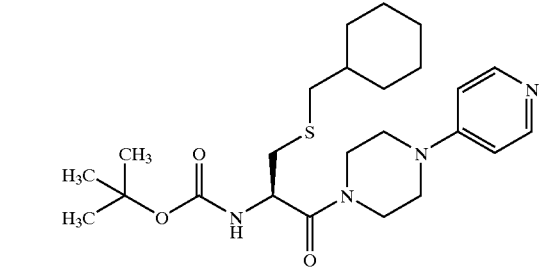

TLC: Rf 0.35 (methanol:chloroform=1:9);

NMR (CDCl₃): δ8.32 (dd, J=4.8, 1.8 Hz, 1H), 6.67 (dd, J=4.8, 1.8 Hz, 1H), 5.40 (d, J=9.2 Hz, 1H), 4.86–4.74 (m, 1H), 3.86–3.75 (m, 4H), 3.50–3.30 (m, 4H), 2.87 (dd, J=13.6, 7.8 Hz, 1H), 2.76 (dd, J=13.6, 5.8 Hz, 1H), 2.44 (d, J=6.6 Hz, 2H), 1.88–0.80 (m, 20H).

EXAMPLE 1 (18)

(2R)-N-(4-(morpholin-4-ylmethyl)phenyl)-2-t-butoxycarbonylamino-3-cyclohexylmethylthiopropanamide

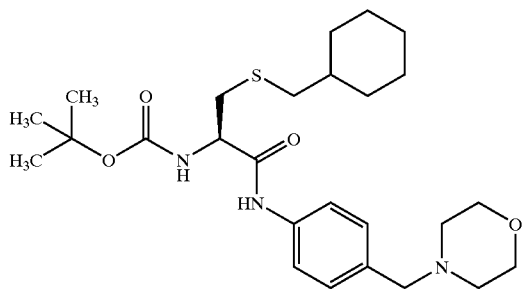

TLC: Rf 0.40 (methanol:chloroform=1:19);

NMR (CDCl$_3$): δ8.40 (s, 1H), 7.47 (d, J=8.4 Hz, 2H), 7.28 (d, J=8.4 Hz, 2H), 5.47 (d, J=6.9 Hz, 1H), 4.37–4.30 (m, 1H), 3.71–3.68 (m, 4H), 3.46 (s, 2H), 3.04 (dd, J=13.8, 5.7 Hz, 1H), 2.88 (dd, J=13.8, 6.9 Hz, 1H), 2.48 (d, J=6.6 Hz, 2H), 2.44–2.39 (m, 4H), 1.86–1.60 (m, 5H), 1.53–1.38 (m, 10H), 1.29–1.04 (m, 3H), 0.99–0.85 (m, 2H).

EXAMPLE 1 (19)

N-((1R)-2-cyclohexylmethylthio-1-(4-phenylaminopiperidin-1-ylcarbonyl)ethyl)carbamic acid.t-butyl ester

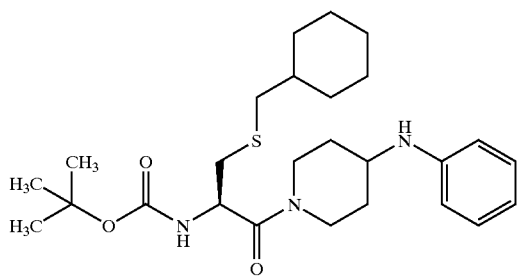

TLC: Rf 0.40 (hexane:ethyl acetate=2:1);

NMR (CDCl$_3$): δ7.19 (t, J=8.4 Hz, 2H), 6.72 (t, J=7.2 Hz, 1H), 6.61 (d, J=8.4 Hz, 2H), 5.43 (d, J=8.4 Hz, 1H), 4.84–4.77 (m, 1H), 4.52–4.42 (br, 1H), 4.07–3.95 (br, 1H), 3.66–3.44 (m, 2H), 3.32–3.23 (m, 1H), 3.00–2.82 (m, 2H), 2.75–2.69 (m, 1H), 2.46–2.42 (m, 2H), 2.21–2.07 (m, 2H), 1.87–1.07 (m, 20H), 0.99–0.86 (m, 2H).

EXAMPLE 1 (20)

(2R)-N-(4-(N'-methyl-N'-phenylamino)benzyl)-2-t-butoxycarbonylamino-3-cyclohexylmethylthiopropanamide

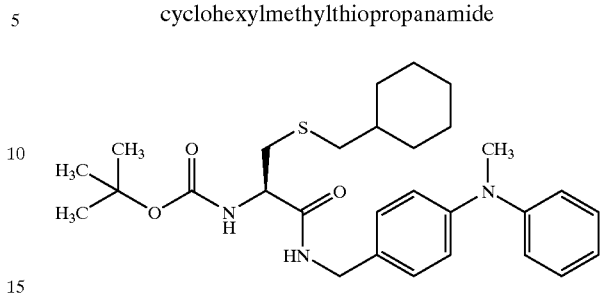

TLC: Rf 0.55 (ethyl acetate:hexane 1:2);

NMR (CDCl$_3$): δ7.31–7.24 (m, 2H), 7.21–7.15 (m, 2H), 7.04–6.93 (m, 5H), 6.64 (t, J=5.1 Hz, 1H), 5.36 (d, J=6.0 Hz, 1H), 4.40 (d, J=5.4 Hz, 2H), 4.24 (dd, J=12.9, 6.6 Hz, 1H), 3.30 (s, 3H), 2.99 (dd, J=14.1, 5.7 Hz, 1H), 2.82 (dd, J=14.1, 6.9 Hz, 1H), 2.46 (dd, J=12.6, 6.9 Hz, 1H), 2.41 (dd, J=12.6, 6.9 Hz, 1H), 1.85–0.83 (m, 20H).

EXAMPLE 1 (21)

(2R)-N-((4-methoxyphenyl)amino)-2-t-butoxycarbonylamino-3-cyclohexylmethylthiopropanamide

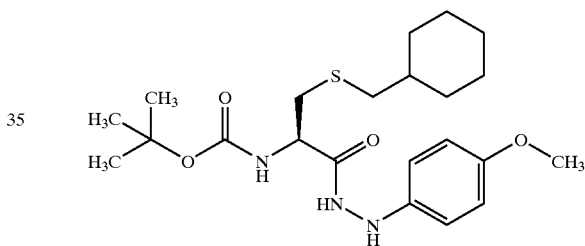

TLC: Rf 0.26 (ethyl acetate:hexane=1:2);

NMR (CDCl$_3$): δ8.22 (s, 1H), 6.86–6.76 (m, 4H), 6.05–5.90 (b, 1H), 5.36 (d, J=8 Hz, 1H), 4.35–4.25 (m, 1H), 3.76 (s, 3H), 2.95 (dd, J=14, 6 Hz, 1H), 2.84 (dd, J=14, 8 Hz, 1H), 2.45 (d, J=8 Hz, 2H), 1.85–1.55 (m, 5H), 1.55–1.35 (m, 10H), 1.32–1.03 (m, 3H), 1.00–0.84 (m, 2H).

EXAMPLE 1 (22)

(2R)-N-amino-N-benzyl-2-t-butoxycarbonylamino-3-cyclohexylmethylthiopropanamide

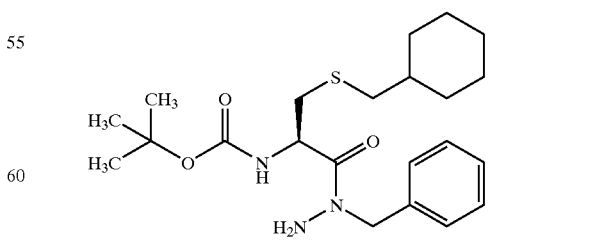

TLC: Rf 0.28 (ethyl acetate:hexane=1:2);

NMR (CDCl$_3$): δ7.77 (s, 1H), 7.42–7.25 (m, 5H), 5.32–5.22 (d, J=8 Hz, 1H), 5.00–4.75 (b, 1H), 4.23–4.13 (m,

1H), 3.98 (s, 2H), 2.91 (dd, J=14, 6 Hz, 1H), 2.78 (dd, J=14, 8 Hz, 1H), 2.50–2.35 (m, 2H), 1.85–1.55 (m, 5H), 1.50–1.35 (m, 10H), 1.35–1.04 (m, 3H), 1.00–0.83 (m, 2H).

EXAMPLE 1 (23)

(2S)-N-(1-benzylpiperidin-4-yl)-2-t-butoxycarbonylamino-3-cyclohexylmethylthiopropanamide

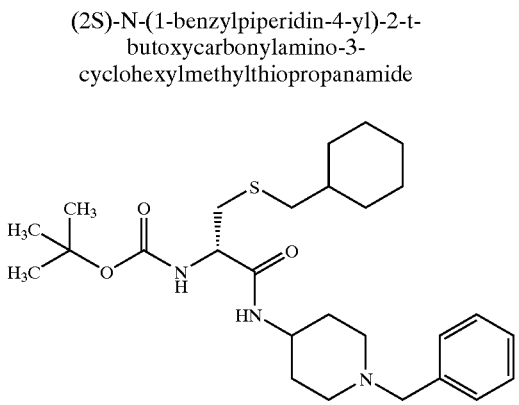

TLC: Rf 0.40 (methanol:chloroform=1:9);

NMR (CDCl$_3$): δ7.34–7.20 (m, 5H), 6.32 (d, J=7.8 Hz, 1H), 5.37 (d, J=7.0 Hz, 1H), 4.19–4.07 (m, 1H), 3.90–3.71 (m, 1H), 3.49 (s, 2H), 2.94 (dd, J=13.6, 5.6 Hz, 1H), 2.84–2.69 (m, 3H), 2.45 (d, J=6.6 Hz, 2H), 2.21–2.08 (m, 2H), 1.95–0.79 (m, 24H).

EXAMPLE 1 (24)

(2R)-N-(1-benzylpiperidin-4-yl)-2-t-butoxycarbonylamino-3-cyclopentylmethylthiopropanamide

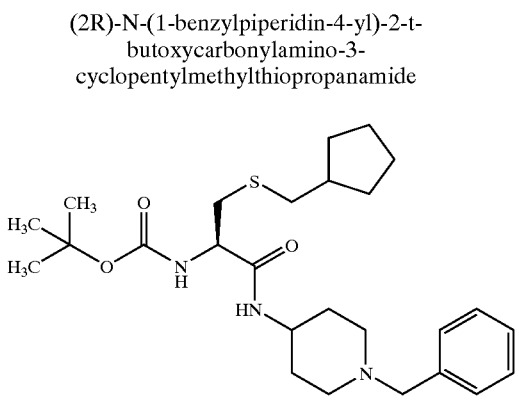

TLC: Rf 0.54 (chloroform:methanol=9:1);

NMR (CDCl$_3$): δ7.32–7.20 (m, 5H), 6.32 (d, J=8.2 Hz, 1H), 5.37 (d, J=7.4 Hz, 1H), 4.20–4.10 (m, 1H), 3.90–3.71. (m, 1H), 3.49 (s, 2H), 2.96 (dd, J=13.8, 5.4 Hz, 1H), 2.83–2.73 (m, 3H), 2.57 (d, J=6.4 Hz, 2H), 2.21–1.68 (m, 7H), 1.66–1.40 (m, 15H), 1.28–1.13 (m, 2H).

EXAMPLE 1 (25)

(2R)-N-(1-benzylpiperidin-4-yl)-2-t-butoxycarbonylamino-3-cycloheptylmethylthiopropanamide

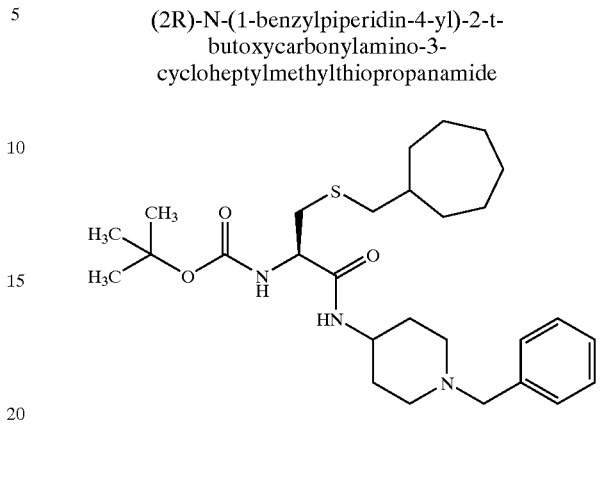

TLC: Rf 0.32 (methylene chloride:methanol=19:1);

NMR (CDCl$_3$): δ7.40–7.20 (m, 5H), 6.31 (d, J=8.0 Hz, 1H), 5.36 (d, J=7.0 Hz, 1H), 4.19–4.09 (m, 1H), 3.89–3.70 (m, 1H), 3.49 (s, 2H), 2.94 (dd, J=13.4, 5.4 Hz, 1H), 2.81–2.71 (m, 3H), 2.48 (d, J=6.6 Hz, 2H), 2.21–2.09 (m, 2H), 1.92–1.13 (m, 26H).

EXAMPLE 1 (26)

(2R)-N-(1-benzylpiperidin-4-yl)-N-methyl-2-t-butoxycarbonylamino-3-cyclohexylmethylthiopropanamide

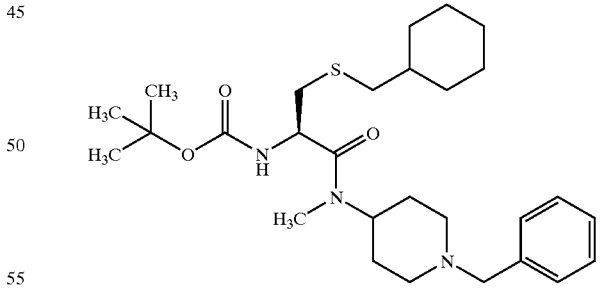

TLC: Rf 0.46 (methanol:chloroform=1:19);

NMR (CDCl$_3$): δ7.36–7.20 (m, 5H), 5.39 (d, J=8.7 Hz, 1 H), 4.83–4.72 (m, 1H), 4.51–4.40 and 3.87–3.73 (m, 1H), 3.52 (s, 2H), 3.04–2.66 (m, 7H), 2.44–2.41 (m, 2H), 2.16–0.84 (m, 26H).

EXAMPLE 1 (27)

(2R)-N-(2-acetoxyethyl)-N-(1-benzylpiperidin-4-yl)-2-t-butoxycarbonylamino-3-cyclohexylmethylthiopropanamide

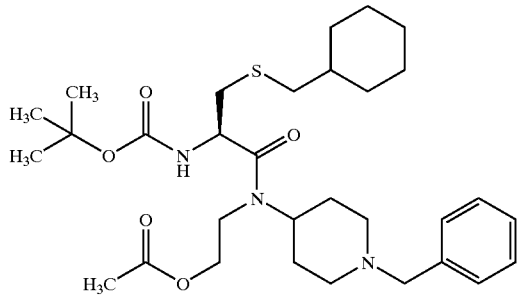

TLC: Rf 0.42 (methanol:chloroform=1:19);

NMR (CDCl$_3$): δ7.38–7.20 (m, 5H), 5.36–5.26 (m, 1H), 4.38–4.09 (m, 2H), 3.87–3.24 (m, 5H), 3.06–2.65 (m, 4H), 2.44–2.38 (m, 2H), 2.16–0.80 (m, 29H).

EXAMPLE 1 (28)

(2R)-N-(-benzylpiperidin-4-yl)-2-t-butoxycarbonylamino-3-cyclohexyl methylthio-3-methylbutanamide

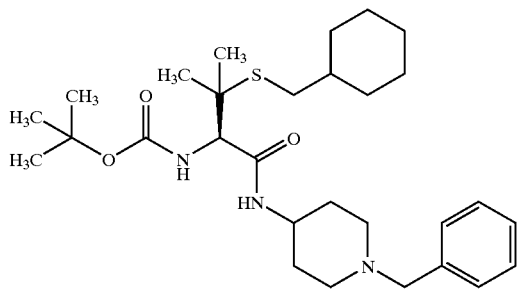

TLC: Rf 0.34 (methanol:methylene chloride=1:19);

NMR (CDCl$_3$): δ7.38–7.20 (m, 5H), 6.65–6.55 (m, 1H), 5.66–5.57 (m, 1H), 4.14–4.04 (m, 1H), 3.89–3.75 (m, 1H), 3.49 (s, 2H), 2.83–2.72 (m, 2H), 2.49 (d, J=7 Hz, 2H), 2.21–2.09 (m, 2H), 1.98–1.60 (m, 7H), 1.60–1.33 (m, 15H), 1.33–1.10 (m, 6H), 1.05–0.88 (m, 2H).

EXAMPLE 1 (29)

N-((1R)-2-cyclohexylmethylthio-1-(4-(N'-benzyl-N'-trifluoroacetylamino)piperidin-1-ylcarbonyl)ethyl)carbamic acid.t-butyl ester

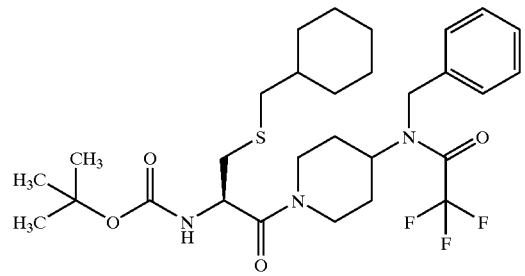

TLC: Rf 0.60 (ethyl acetate:hexane=1:2);
NMR (CDCl$_3$): δ7.41–7.11 (m, 6H), 5.39–5.23 (m, 1H), 4.84–4.48 (m, 4H), 4.34–3.93 (m, 2H), 3.21–2.23 (m, 6H), 1.98–0.75 (m, 23H).

EXAMPLE 1 (30)

N-((1R)-2-cyclohexylmethylthio-1-(4-(N'-benzyl-N'-methylamino)piperidin-1-ylcarbonyl)ethyl)carbamic acid.t-butyl ester

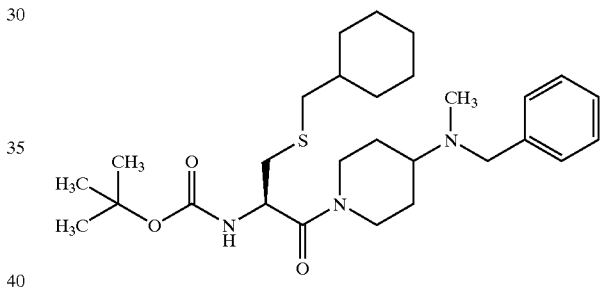

TLC: Rf 0.26 (methanol:chloroform=1:49);
NMR (CDCl$_3$): δ7.40–7.20 (m, 5H), 5.44 (d, J=8.4 Hz, 1H), 4.86–4.56 (m, 2H), 4.16–3.99 (m, 1H), 3.58 (s, 2H), 3.16–2.40 (m, 7H), 2.19 (s, 3H), 2.00–0.80 (m, 24H).

Reference Example 3

(2R)-N-(1-benzylpiperidin-4-yl)-2-amino-3-cyclohexylmethylthiopropanamide.2hydrochloride

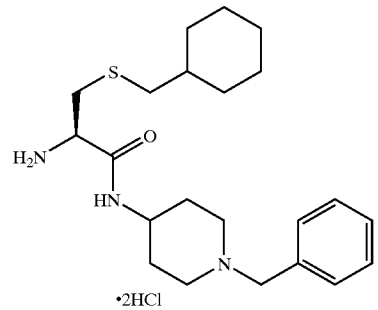

To a soltion of the compound prepared in Example 1 (933 mg) in dioxane (2 ml), 4N-HCl-dioxane (10 ml) was added.

The mixture was stirred for 30 minutes at room temperature. The reaction mixture was concentrated to obtain the crude title compound (916 mg). Thus obtained compound was used in the next reaction without purification.

EXAMPLE 2

(2R)-N-(1-benzylpiperidin-4-yl)-3-cyclohexylmethylthio-2-((4R)-3-t-butoxycarbonylthiazolidin-4-ylcarbonylamino)propanamide

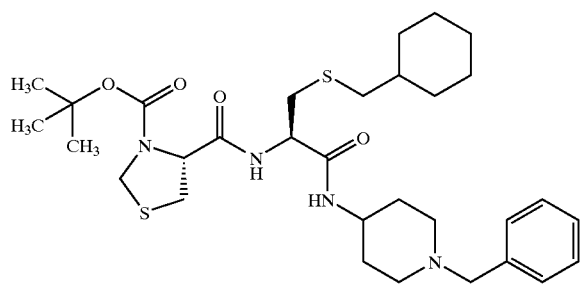

To a soltion of the compound prepared in Reference Example 3 (916 mg) and (4R)-3-t-butoxycarbonylthiazolidin-4-ylcarboxylic acid (0.30 ml) in methylene chloride (11 ml), 1-ethyl-3-(3-dimethylaminopropyl)-carbodiimide hydrochloride (495 mg) and 1-hydroxybenzotriazole (396 mg) were added successively under cooling with ice. The mixture was stirred for 3 hours. The reaction mixture was washed by water, saturated solution of sodium hydrogencarbonate and saturated solution of sodium chloride successively, dried over anhydrous sodium sulfate and concentrated. The residue was purified with column chromatography on silica gel (methanol:chloroform=3:97) to obtain the compound (1.17 g) of the present invention having the following physical data.

TLC: Rf 0.44 (methanol:chloroform=1:9);

NMR (CDCl$_3$): δ7.34–7.21 (5H, m), 7.15 (1H, d, J=6.6 Hz), 6.77 (1H, br.s), 4.67–4.40 (4H, m), 3.81–3.69 (1H, m), 3.49 (2H, s), 3.35–3.12 (3H, m), 2.82–2.69 (3H, m), 2.49–2.37 (2H, m), 2.16–2.09 (2H, m), 1.93–1.3 6 (19H, m), 1.30–1.05 (3H, m), 0.96–0.85 (2H, m).

EXAMPLE 3~EXAMPLE 3 (36)

By the same procedure described in Reference Example 3→Example 2, using the compounds prepared in Example 1~Example 1 (30) (In Example 2, using (4R)-3-t-butoxycarbonylthiazolidin-4-ylcarboxylic acid or the corresponding derivatives), the following compounds of the present invention were obtained, provided that when the compound of Example 3 (36) was prepared, (+)-3-t-butoxycarbonylthiazolidin-2-ylcarboxylic acid was used.

EXAMPLE 3

(2R)-N-(4-hydroxybenzyl)-3-cyclohexylmethylthio-2-((2RS)-3-t-butoxycarbonylthiazolidin-2-ylcarbonylamino)propanamide

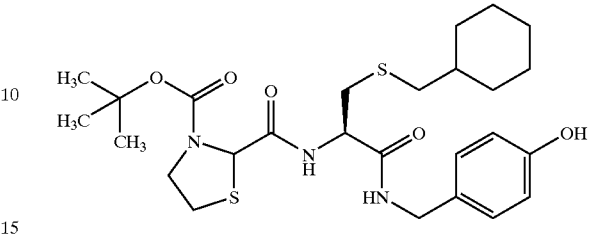

TLC: Rf 0.36 (ethyl acetate:hexane=1:1);

NMR (CD$_3$OD): δ7.12 (2H, d, J=8.4 Hz), 6.71 (2H, d, J=8.4 Hz), 5.22 (1H, br.s), 4.53–4.44 (1H, m), 4.34 (1H, d, J=14.8 Hz), 4.23 (1H, d, J=14.8 Hz), 3.98–3.86 (1H, m), 3.77–3.64 (1H, m), 3.34–2.69 (4H, m), 2.42 (2H, d, J=7.0 Hz), 1.90–0.83 (20H, m).

EXAMPLE 3 (1)

(2R)-N-(4-hydroxybenzyl)-3-cyclohexylmethylthio-2-((4R)-3-t-butoxycarbonylthiazolidin-4-ylcarbonylamino)propanamide

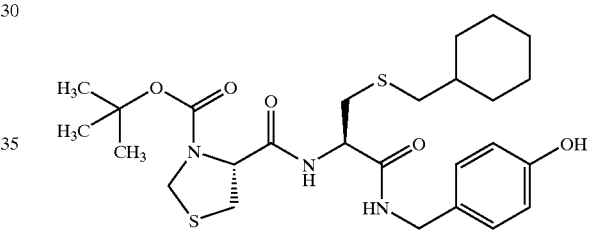

TLC:Rf 0.44 (ethyl acetate:hexane=1:1);

NMR (CD$_3$OD): δ7.12 (2H, d, J=8.4 Hz), 6.74–6.68 (2H, m), 4.65–4.44 (1H, m), 4.31 (1H, d, J=14.8 Hz), 4.23 (1H, d, J=14.8 Hz), 3.35 (1H, dd, J=12.2, 7.4 Hz), 3.12 (1H, dd, J=12.2, 4.8 Hz), 2.99–2.68 (2H, m), 2.41 (2H, d, J=7.0 Hz), 1.88–0.81 (20H, m).

EXAMPLE 3 (2)

(2R)-N-(1-benzylpiperidin-4-ylmethyl)-3-cyclohexylmethylthio-2-((4R)-3-t-butoxycarbonylthiazolidin-4-ylcarbonylamino)propanamide

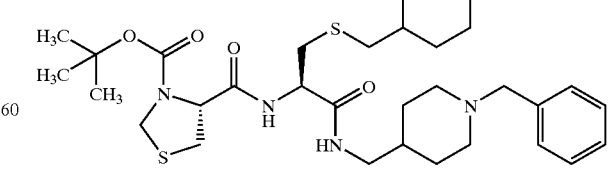

TLC: Rf 0.28 (methanol:chloroform=1:19);

NMR (CDCl$_3$): δ7.32–7.20 (5H, m), 7.11 (1H, d, J=8.1 Hz), 6.96 (1H, br.s), 4.65–4.44 (4H, m), 3.49 (2H, s), 3.30–3.20 (4H, m), 3.08–2.93 (1H, m), 2.91–2.81 (2H, m), 2.74 (1H, dd, J=13.8, 6.6 Hz), 2.49–2.32 (2H, m), 1.98–1.88 (2H, m), 1.84–1.04 (23H, m), 0.98–0.82 (2H, m).

EXAMPLE 3 (3)

(2R)-N-(3-hydroxy-4-methoxybenzyl)-3-cyclohexylmethylthio-2-((4R)-3-t-butoxycarbonylthiazolidin-4-ylcarbonylamino)propanamide

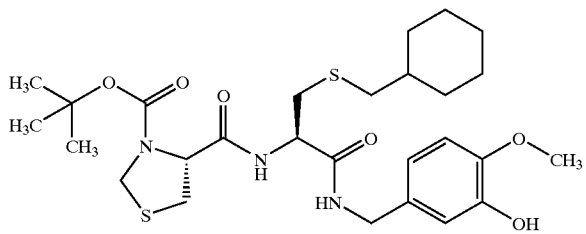

TLC: Rf 0.38 (hexane:ethyl acetate=1:1);

NMR (CD₃OD) δ6.86–6.70 (3H, m), 4.65–4.45 (4H, m), 4.25 (2H, s), 3.81 (3H, s), 3.35 (1 H, dd, J=7.2, 12.0 Hz), 3.12 (1 H, dd, J=4.8, 12.0 Hz), 3.03–2.67 (2H, br), 2.41 (2H, d, J=7.0 Hz), 1.84–1.58 (5H, m), 1.53–1.34 (10H, m), 1.32–0.83 (5H, m).

EXAMPLE 3 (4)

(2R)-N-(-(4-methoxybenzyl)piperidin-4-ylmethyl)-3-cyclohexylmethylthio-2-((4R)-3-t-butoxycarbonylthiazolidin-4-ylcarbonylamino)propanamide

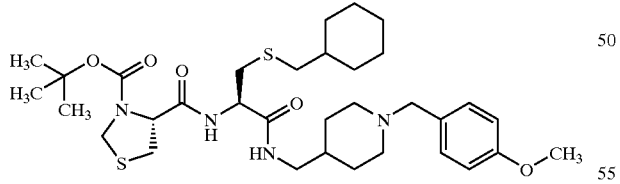

TLC: Rf 0.44 (methanol:chloroform=1:9);

NMR (CDCl₃): δ7.22 (2H, d, J=8.7 Hz), 7.11 (1 H, d, J=8.1 Hz), 6.97 (1H, br.s), 6.87–6.82 (2H, m), 4.65–4.45 (4H, m), 3.80 (3H, s), 3.45 (2H, s), 3.30–3.21 (4H, m), 3.04–2.86 (3H, m), 2.74 (1H, dd, J=13.8, 6.3 Hz), 2.48–2.34 (2H, m), 1.98–0.82 (27H, m).

EXAMPLE 3 (5)

(2R)-N-methyl-N-(1-benzylpyrrolidin-3-yl)-3-cyclohexylmethylthio-2-((4R)-3-t-butoxycarbonylthiazolidin-4-ylcarbonylamino)propanamide

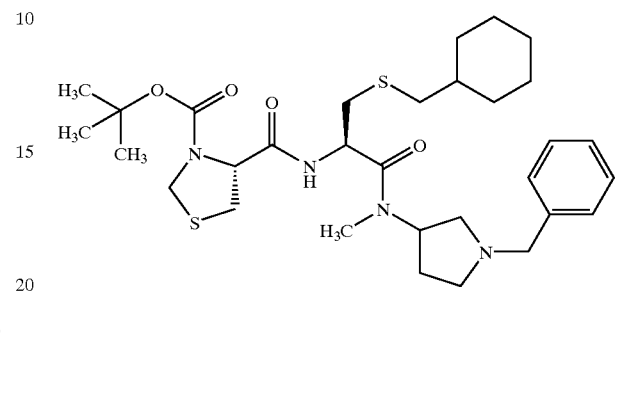

TLC: Rf 0.46 (methylene chloride:methanol=19:1);

NMR (CDCl₃): δ7.33–7.22 (m, 5H), 7.19–6.79 (br, 1H), 5.24–4.97 (br, 1.5H), 4.83–4.52 (br, 2.5H), 4.38 (d, J=9.6 Hz, 1H), 3.71–3.64 (m, 1H), 3.50 (d, J=12.9 Hz, 1H), 3.37–3.16 (m, 3.5H), 2.96–2.11 (m, 10.5H), 1.93–1.64 (m, 6H), 1.48–1.33 (m, 10H), 1.28–0.81 (m, 5H).

EXAMPLE 3 (6)

(2R)-N-(-(4-methoxybenzyl)piperidin-4-yl)-3-cyclohexylmethylthio-2-((4R)-3-t-butoxycarbonylthiazolidin-4-ylcarbonylamino)propanamide

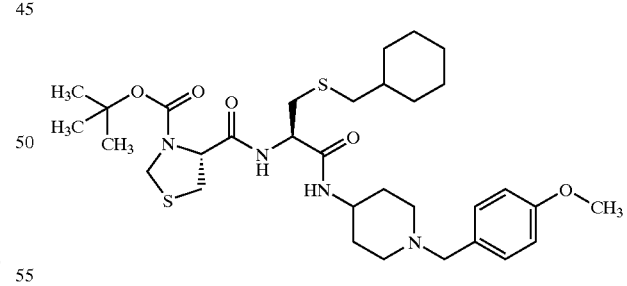

TLC: Rf 0.34 (methanol:chloroform=1:9);

NMR (CDCl₃): δ7.25–7.21 (m, 2H), 7.14 (d, J=6.6 Hz, 1H), 6.87–6.83 (m, 2H), 6.72 (br.s, 1H), 4.66–4.43 (m, 4H), 3.81–3.67 (m, 4H), 3.44 (s, 2H), 3.35–3.14 (m, 3H), 2.81–2.69 (m, 3H), 2.50–2.35 (m, 2H), 2.16–2.05 (m, 2H), 1.94–1.35 (m, 19H), 1.30–1.04 (m, 3H), 0.98–0.83 (m, 2H).

EXAMPLE 3 (7)

(2R)-N-(1-(4-methoxybenzoyl)piperidin-4-yl)-3-cyclohexylmethylthio-2-((4R)-3-t-butoxycarbonylthiazolidin-4-ylcarbonylamino)propanamide

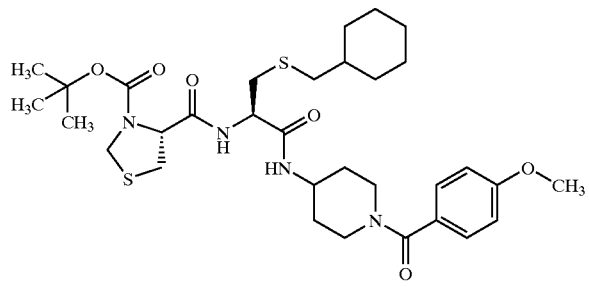

TLC: Rf 0.36 (ethyl acetate);

NMR (CDCl$_3$): δ7.38–7.34 (m, 2H), 7.12 (d, J=6.6 Hz, 1H), 7.04 (br.s, 1H), 6.91–6.87 (m, 2H), 4.64–4.48 (m, 4H), 4.05–3.92 (m, 1H), 3.83 (m, 3H), 3.37–3.25 (m, 3H), 3.16–2.97 (m, 2H), 2.75 (dd, J=13.8, 5.7 Hz, 1H), 2.47–2.34 (m, 2H), 2.06–1.35 (m, 21H), 1.31–1.06 (m, 3H), 0.98–0.83 (m, 2H).

EXAMPLE 3 (8)

(2S)-N-(1-benzylpiperidin-4-yl)-3-cyclohexylmethoxy-2-((4R)-3-t-butoxycarbonylthiazolidin-4-ylcarbonylamino)propanamide

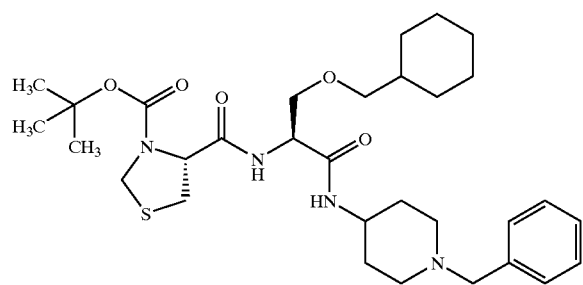

TLC: Rf 0.19 (methanol:methylene chloride=1:19);

NMR (CDCl$_3$): δ7.40–7.20 (m, 5H), 6.99 (d, J=7 Hz, 1H), 6.83–6.65 (m, 1H), 4.67–4.54 (m, 2H), 4.45–4.36 (m, 2H), 4.02–3.87 (m, 1H), 3.85–3.70 (m, 1H), 3.54–3.40 (m, 3H), 3.33–3.15 (m, 4H), 2.87–2.74 (m, 2H), 2.20–2.05 (m, 2H), 1.94–1.80 (m, 2H), 1.78–1.62 (m, 5H), 1.62–1.40 (m, 12H), 1.31–1.06 (m, 3H), 1.00–0.82 (m, 2H).

EXAMPLE 3 (9)

(2R)-N-(2-benzylaminoethyl)-3-cyclohexylmethylthio-2-((4R)-3-t-butoxycarbonylthiazolidin-4-ylcarbonylamino)propanamide

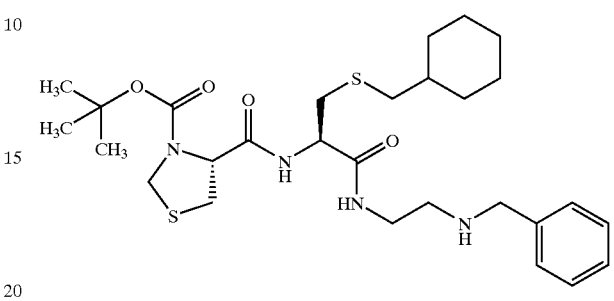

TLC: Rf 0.37 (chloroform:methanol=9:1);

NMR (CD$_3$OD): δ7.36–7.21 (m, 5H), 4.62 (d, J=9.0 Hz, 1H), 4.61–4.54 (br, 1H), 4.45 (d, J=9.0 Hz, 1H), 4.42 (t, J=6.9 Hz, 1H), 3.75 (s, 2H), 3.48–3.27 (m, 3H), 3.13 (dd, J=12.0, 4.8 Hz, 1H), 2.96–2.75 (br, 2H), 2.74 (t, J=6.0 Hz, 2H), 2.42 (d, J=6.9 Hz, 2H), 1.84–1.61 (m, 5H), 1.57–1.34 (m, 10H), 1.32–1.08 (m, 3H), 0.99–0.86 (m, 2H).

EXAMPLE 3 (10)

(4R)-N-((1R)-2-cyclohexylmethylthio-1-(4-benzylpiperazin-1-ylcarbonyl) ethyl)-3-t-butoxycarbonylthiazolidin-4-ylcarboxamide

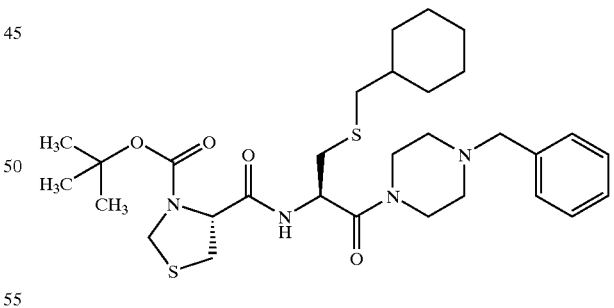

TLC: Rf 0.40 (chloroform:methanol 19:1);

NMR (CD$_3$OD): δ7.33–7.22 (m, 5H), 4.99 (t, J=6.9 Hz, 1 H), 4.64–4.52 (m, 2H), 4.46 (d, J=9.0 Hz, 1H), 3.72–3.43 (m, 6H), 3.41–3.29 (br, 1H), 3.10 (dd, J=12.0, 4.5 Hz, 1 H), 2.92 (dd, J=13.5, 7.5 Hz, 1 H), 2.68 (dd, J=13.5, 6.3 Hz, 1 H), 2.52–2.42 (m, 6H), 1.85–1.63 (m, 5H), 1.52–1.36 (m, 10H), 1.33–1.09 (m, 3H), 1.03–0.87 (m, 2H).

EXAMPLE 3 (11)

(4R)-N-((1R)-2-cyclohexylmethylthio-1-(4-diphenylmethylpiperazin-1-ylcarbonyl)ethyl)-3-t-butoxycarbonylthiazolidin-4-ylcarboxamide

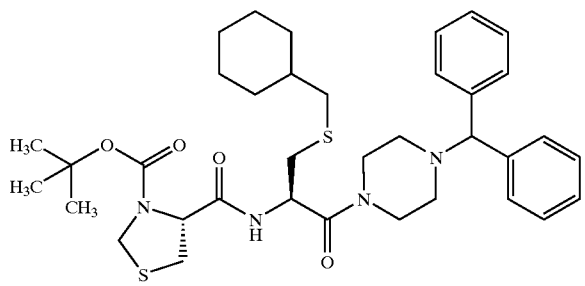

TLC: Rf 0.38 (ethyl acetate:hexane=1:2);

NMR (CDCl$_3$): δ7.48–6.90 (m, 11H), 5.04–4.97 (m, 1H), 4.84–4.55 (m, 2H), 4.38 (d, J=9.3 Hz, 1H), 4.24 (s, 1H), 3.77–3.52 (m, 4H), 3.40–3.34 (m, 1H), 3.26–3.14 (m, 1H), 2.85 (dd, J=13.5, 6.9 Hz, 1H), 2.70 (dd, J=13.5, 5.4 Hz, 1H), 2.45–2.34 (m, 6H), 1.84–1.32 (m, 15H), 1.29–1.04 (m, 3H), 0.98–0.82 (m, 2H).

EXAMPLE 3 (12)

(4R)-N-((1R)-2-cyclohexylmethylthio-1-(4-(4-methoxyphenyl)piperazin-1-ylcarbonyl)ethyl)-3-t-butoxycarbonylthiazolidin-4-ylcarboxamide

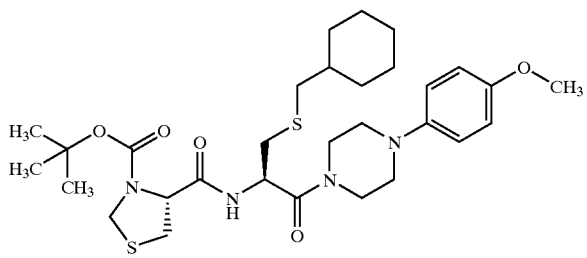

TLC: Rf 0.45 (ethyl acetate:hexane=1:1);

NMR (CDCl$_3$): δ7.15 (br.s, 1H), 6.92–6.83 (m, 4H), 5.13–5.07 (m, 1H), 4.72–4.66 (m, 2H), 4.40 (d, J=9.3 Hz, 1H), 3.85–3.71 (m, 7H), 3.37 (dd, J=11.4, 2.7 Hz, 1H), 3.28–3.17 (m, 1H), 3.12–3.03 (m, 4H), 2.90 (dd, J=13.5, 7.2 Hz, 1H), 2.76 (dd, J=13.5, 6.0 Hz, 1H), 2.44 (d, J=6.6 Hz, 2H), 1.86–1.59 (m, 5H), 1.54–1.36 (m, 10H), 1.29–1.05 (m, 3H), 0.98–0.85 (m, 2H).

EXAMPLE 3 (13)

(2R)-N-(1-(4-fluorobenzyl)piperidin-4-yl)-3-cyclohexylmethylthio-2-((4R)-3-t-butoxycarbonylthiazolidin-4-ylcarbonylamino)propanamide

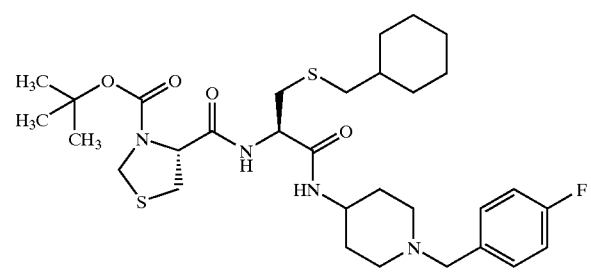

TLC: Rf 0.56 (methanol:chloroform=1:9);

NMR (CDCl$_3$): δ7.32–7.23 (m, 2H), 7.14 (d, J=6.9 Hz, 1H), 7.02–6.95 (m, 2H), 6.79 (br.s, 1H), 4.67–4.40 (m, 4H), 3.82–3.68 (m, 1H), 3.45 (s, 2H), 3.35–3.16 (m 3H), 2.79–2.69 (m, 3H), 2.50–2.34 (m, 2H), 2.16–2.06 (m, 2H), 1.93–1.36 (m, 19H), 1.30–1.04 (m, 3H), 0.98–0.82 (m, 2H).

EXAMPLE 3 (14)

(2R)-N-(1-(4-fluorobenzoyl)piperidin-4-yl)-3-cyclohexylmethylthio-2-((4R)-3-t-butoxycarbonylthiazolidin-4-ylcarbonylamino)propanamide

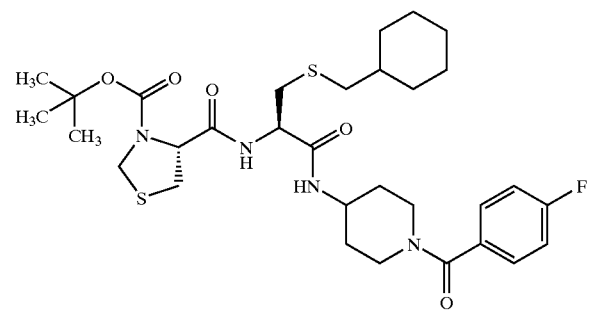

TLC: Rf 0.50 (ethyl acetate);

NMR (CDCl$_3$): δ7.43–7.36 (m, 2H), 7.12–7.05 (m, 4H), 4.63–4.48 (m, 5H), 4.07–3.94 (m, 1H), 3.73 (br.s, 1H), 3.37–3.25 (m, 3H), 3.07 (br.s, 2H), 2.75 (dd, J=14.1, 6.0 Hz, 1H), 2.47–2.34 (m, 2H), 2.05–1.36 (m, 19H), 1.32–1.05 (m, 3H), 0.98–0.82 (m, 2H).

EXAMPLE 3 (15)

(4R)-N-((1R)-2-cyclohexylmethylthio-1-(4-(pyridin-2-yl)piperazin-1-ylcarbonyl)ethyl)-3-t-butoxycarbonylthiazolidin-4-ylcarboxamide

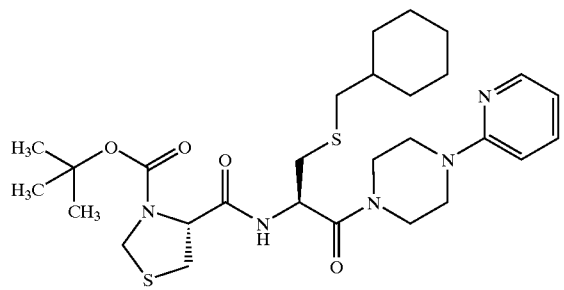

TLC: Rf 0.42 (ethyl acetate:hexane=2:1);

NMR (CDCl$_3$): δ8.22–8.19 (m, 1H), 7.55–7.49 (m, 1H), 7.26 (br.s, 1H), 6.70–6.65 (m, 1H), 5.14–5.07 (m, 1H), 4.86–4.50 (m, 2H), 4.40 (d, J=9.3 Hz, 1H), 3.84–3.54 (m, 8H), 3.38 (dd, J=11.7, 2.7 Hz, 1H), 3.26–3.16 (m, 1H), 2.91 (dd, J=13.5, 7.2 Hz, 1 H), 2.77 (dd, J=13.5, 5.7 Hz, 1 H), 2.44 (d, J=6.9 Hz, 2H), 1.85–1.58 (m, 5H), 1.54–1.35 (m, 10H), 1.28–1.05 (m, 3H), 0.98–0.83 (m, 2H).

EXAMPLE 3 (16)

(4R)-N-((1R)-2-cyclohexylmethylthio-1-(4-(pyridin-4-yl)piperazin-1-ylcarbonyl)ethyl)-3-t-butoxycarbonylthiazolidin-4-ylcarboxamide

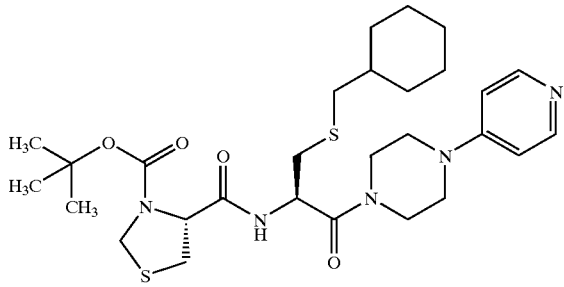

TLC: Rf 0.42 (methanol:chloroform 1:19);

NMR (CDCl$_3$): δ8.33–8.31 (m, 2H), 7.10 (br.s, 1H), 6.68–6.66 (m, 2H), 5.12–5.04 (m, 1H), 4.79–4.50 (m, 2H), 4.39 (d, J=9.3 Hz, 1H), 3.91–3.61 (m, 4H), 3.49–3.19 (m, 6H), 2.90 (dd, J=13.5, 7.8 Hz, 1H), 2.77 (dd, J=13.5, 5.7Hz, 1H), 2.44 (d, J=6.9 Hz, 2H), 1.89–1.60 (m, 5H), 1.53–1.35 (m, 10H), 1.30–1.05 (m, 3H), 0.99–0.83 (m, 2H).

EXAMPLE 3 (17)

(2R)-N-(1-benzylpiperidin-4-yl)-3-cyclohexylmethylthio-2-((3RS)-4-t-butoxycarbonylthiomorpholin-3-ylcarbonylamino)propanamide

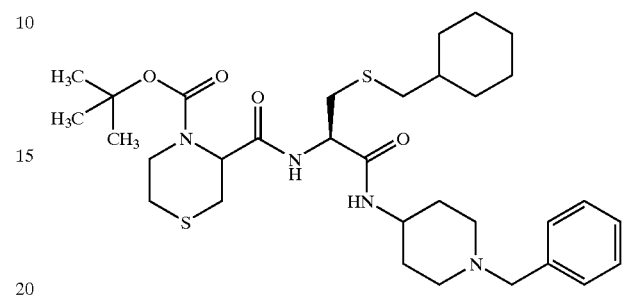

TLC: Rf 0.39 (methylene chloride:methanol 93:7);

NMR (CDCl$_3$): δ7.40–7.20 (m, 5H), 7.12–6.93 (m, 1H), 6.68–6.45 (m, 1H), 5.11–4.93 (m, 1 H), 4.54–4.18 (m, 2H), 3.86–3.70 (m, 1 H), 3.49 (s, 2H), 3.34–2.60 (m, 8H), 2.57–2.37 (m, 3H), 2.21–2.07 (m, 2H), 1.96–1.35 (m, 19H), 1.31–1.05 (m, 3H), 1.03–0.84 (m, 2H).

EXAMPLE 3 (18)

(2R)-N-(4-(morpholin-4-ylmethyl) phenyl)-3-cyclohexylmethylthio-2-((4R)-3-t-butoxycarbonylthiazolidin-4-ylcarbonylamino)propanamide

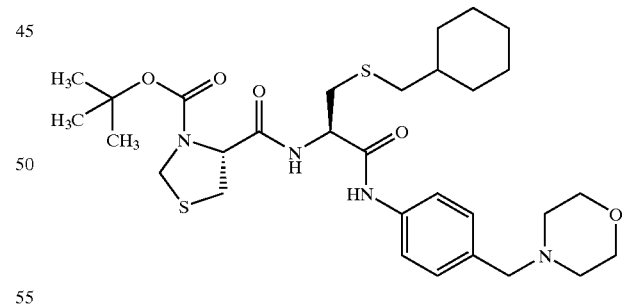

TLC: Rf 0.38 (methanol:chloroform=1:19);

NMR (CD$_3$OD): δ7.57 (d, J=8.1 Hz, 2H), 7.31–7.27 (m, 2H), 4.66–4.56 (m, 3H), 4.50 (d, J=9.3 Hz, 1H), 3.68–3.65 (m, 4H), 3.48 (s, 2H), 3.39 (dd, J=12.0, 8.1 Hz, 1H), 3.22 (dd, J=12.0, 4.8 Hz, 1H), 3.06–2.80 (m, 2H), 2.47–2.42 (m, 6H), 1.86–1.75 (m, 2H), 1.73–1.58 (m, 3H), 1.54–1.36 (m, 10H), 1.30–1.05 (m, 3H), 0.98–0.83 (m, 2H).

EXAMPLE 3 (19)

(4R)-N-((1R)-2-cyclohexylmethylthio-1-(4-phenylaminopiperidin-1-ylcarbonyl)ethyl)-3-t-butoxycarbonylthiazolidin-4-ylcarboxamide

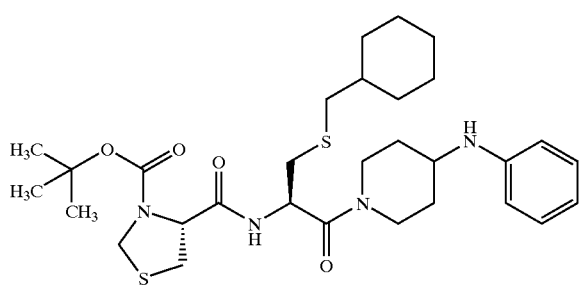

TLC: Rf 0.50 (hexane:ethyl acetate=1:1);

NMR (CDCl$_3$): δ7.22–7.04 (m, 3H), 6.77–6.71 (br, 1H), 6.67–6.59 (br, 2H), 5.12–5.05 (m, 1H), 4.86–4.55 (br, 2H), 4.48–4.37 (m, 2H), 4.09–3.94 (br, 1H), 3.59–3.50 (m, 1H), 3.39–3.19 (m, 3H), 2.95–2.85 (m, 2H), 2.78–2.70 (m, 1H), 2.45–2.41 (m, 2H), 2.22–2.06 (br, 2H), 1.83–1.06 (m, 20H), 0.98–0.85 (m, 2H).

EXAMPLE 3 (20)

(2R)-N-(1-benzylpiperidin-4-yl)-3-cyclohexylmethylthio-2-((4RS)-3-t-butoxycarbonyl-1,3-perhydrothiazin-4-ylcarbonylamino)propanamide

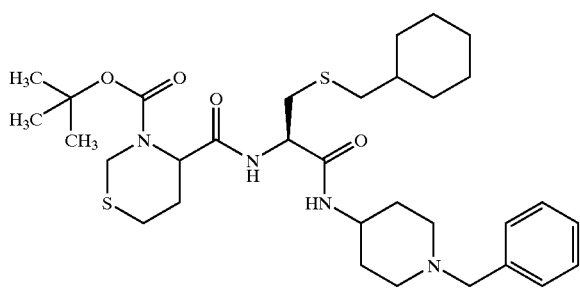

TLC: Rf 0.33 (ethyl acetate:hexane=1:2);

NMR (CD$_3$OD): δ7.40–7.23 (m, 5H), 4.93–4.38 (m, 4H), 3.73–3.57 (m, 1H), 3.53 (s, 2H), 3.05–2.71 (m, 5H), 2.65–2.52 (m, 1H), 2.50–2.34 (m, 3H), 2.23–2.06 (m, 2H), 2.06–1.78 (m, 5H), 1.78–1.35 (m, 15H), 1.31–1.07 (m, 3H), 1.05–0.85 (m, 2H).

EXAMPLE 3 (21)

(2R)-N-(4-(N'-methyl-N'-phenylamino) benzyl)-3-cyclohexylmethylthio-2-((4R)-3-t-butoxycarbonylthiazolidin-4-ylcarbonylamino)propanamide

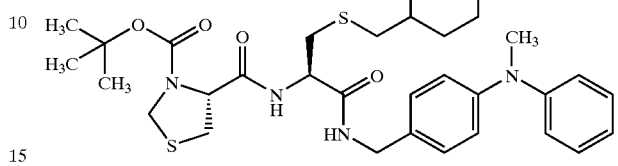

TLC: Rf 0.28 (ethyl acetate:hexane=1:2);

NMR (CDCl$_3$): δ7.32–7.12 (m, 6H), 7.00 (d, J=8.4 Hz, 2H), 6.97–6.92 (m, 3H), 4.65 (dd, J=6.6, 4.2 Hz, 1 H), 0.8 (m, 2H), 4.45 (d, J=9.6 Hz, 1 H), 4.41–4.30 (m, 2H), 3.36–3.12 (m, 6H), 2.79 (dd, J=13.8, 6.3 Hz, 1H), 2.47–2.30 (m, 2H), 1.84–1.56 (m, 5H), 1.47–1.38 (m, 10H), 1.30–1.04 (m, 3H), 0.97–0.78 (m, 2H).

EXAMPLE 3 (22)

(2R)-N-((4-methoxyphenyl)amino)-3-cyclohexylmethylthio-2-((4R)-3-t-butoxycarbonylthiazolidin-4-ylcarbonylamino)propanamide

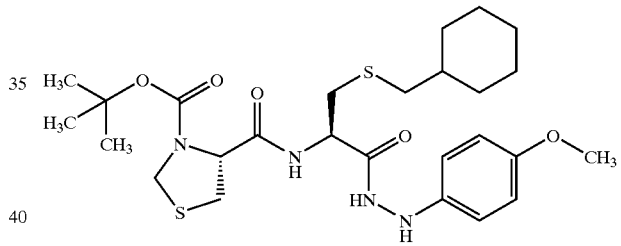

TLC: Rf 0.20 (ethyl acetate:hexane=2:3);

NMR (CDCl$_3$): δ8.85–8.63 (b, 1H), 7.22–7.08 (m, 1H), 6.88–6.75 (m, 4H), 6.07–5.90 (m, 1H), 4.77–4.45 (m, 4H), 3.74 (s, 3H), 3.40–3.10 (m, 3H), 2.82 (dd, J=14, 7 Hz, 1H), 2.50–2.28 (m, 2H), 1.84–1.58 (m, 5H), 1.55–1.36 (m, 10H), 1.31–1.04 (m, 3H), 0.99–0.83 (m, 2H).

EXAMPLE 3 (23)

(2R)-N-amino-N-benzyl-3-cyclohexylmethylthio-2-((4R)-3-t-butoxycarbonylthiazolidin-4-ylcarbonylamino)propanamide

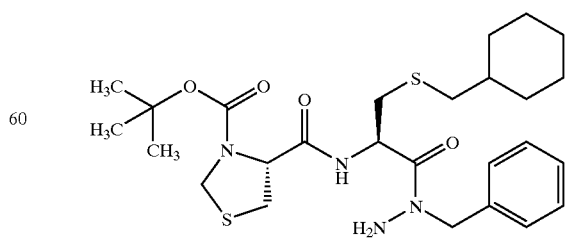

TLC: Rf 0.20 (ethyl acetate:hexane=2:3);

NMR (CDCl$_3$): δ8.40–8.15 (b, 1H), 7.39–7.24 (m, 5H), 7.15–7.00 (m, 1H), 4.64–4.40 (m, 4H), 3.96 (s, 2H), 3.34–3.20 (m, 2H), 3.20–3.00 (b, 1H), 2.76 (dd, J=14, 7 Hz, 1H), 2.43 (dd, J=12, 7 Hz, 1H), 2.40 (dd, J=14, 7 Hz, 1H), 1.86–1.55 (m, 5H), 1.55–1.35 (m, 10H), 1.30–1.03 (m, 3H), 0.98–0.83 (m, 2H).

EXAMPLE 3 (24)

(2R)-N-(1-benzylpiperidin-4-yl)-3-cyclohexylmethylthio-2-((4S)-3-t-butoxycarbonylthiazolidin-4-ylcarbonylamino) propanamide

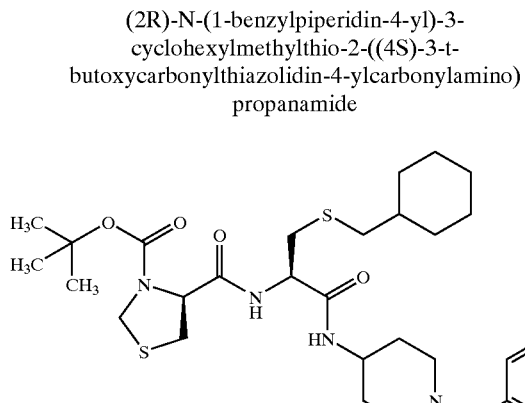

TLC: Rf 0.63 (methanol: chloroform=1:9);

NMR (CDCl$_3$): δ7.34–7.23 (m, 5H), 7.14 (d, J=6.9 Hz, 1H), 6.58 (br.s, 1H), 4.70 (dd, J=6.3, 3.0 Hz, 1 H), 4.63 (d, J=9.3 Hz, 1 H), 4.52–4.43 (m, 2H), 3.84–3.71 (m, 1H), 3.49 (s, 2H), 3.35 (dd, J=11.7, 3.0 Hz, 1H), 3.26–3.04 (m, 2H), 2.84–2.70 (m, 3H), 2.49 (dd, J=12.9, 6.6 Hz, 1H), 2.42 (dd, J=12.9, 6.9 Hz, 1H), 2.17–2.07 (m, 2H), 1.94–1.37 (m, 19H), 1.32–1.04 (m, 3H), 1.00–0.84 (m, 2H).

EXAMPLE 3 (25)

(2S)-N-(1-benzylpiperidin-4-yl)-3-cyclohexylmethylthio-2-((4R)-3-t-butoxycarbonylthiazolidin-4-ylcarbonylamino) propanamide

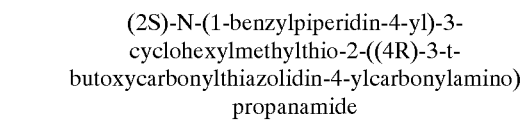

TLC: Rf 0.46 (methanol:chloroform=1:9);

NMR (CDCl$_3$): δ7.36–7.22 (m, 5H), 7.13 (d, J=7.2 Hz, 1H), 6.58 (br.s, 1H), 4.70 (dd, J=6.3, 3.0 Hz, 1 H), 4.63 (d, J=9.3 Hz, 1 H), 4.52–4.43 (m, 2H), 3.83–3.70 (m, 1H), 3.49 (s, 2H), 3.35 (dd, J=11.7, 3.0 Hz, 1H), 3.24–3.06 (m, 2H), 2.81–2.70 (m, 3H), 2.49 (dd, J=12.9, 6.6 Hz, 1H), 2.42 (dd, J=12.9, 6.9 Hz, 1H), 2.17–2.07 (m, 2H), 1.93–1.37 (m, 19H), 1.31–1.04 (m, 3H), 0.99–0.84 (m, 2H).

EXAMPLE 3 (26)

(2S)-N-(1-benzylpiperidin-4-yl)-3-cyclohexylmethylthio-2-((4S)-3-t-butoxycarbonylthiazolidin-4-ylcarbonylamino) propanamide

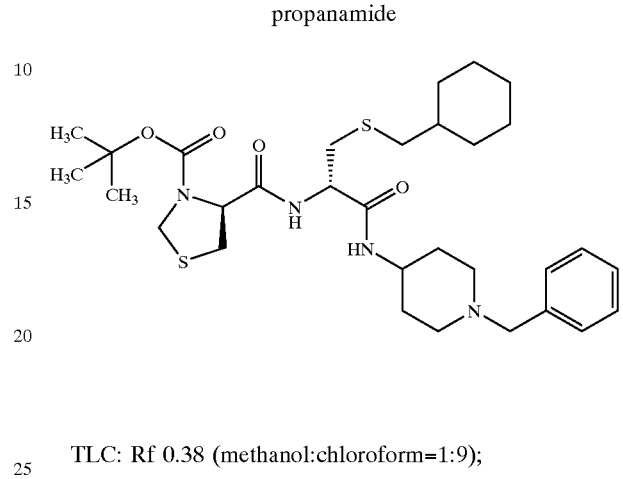

TLC: Rf 0.38 (methanol:chloroform=1:9);

NMR (CDCl$_3$): δ7.34–7.21 (m, 5H), 7.15 (d, J=6.9 Hz, 1H), 6.78 (br.s, 1H), 4.67–4.44 (m, 4H), 3.82–3.68 (m, 1H), 3.50 (s, 2H), 3.32 (dd, J=12.0, 3.9 Hz, 1H), 3.27 (dd, J=12.0, 6.3 Hz, 1H), 3.19 (br.s, 1H), 2.82–2.69 (m, 3H), 2.50–2.34 (m, 2H), 2.17–2.08 (m, 2H), 1.93–1.36 (m, 19H), 1.31–1.04 (m, 3H), 0.99–0.82 (m, 2H).

EXAMPLE 3 (27)

(2R)-N-(1-benzylpiperidin-4-yl)-3-cyclopentylmethylthio-2-((4R)-3-t-butoxycarbonylthiazolidin-4-ylcarbonylamino) propanamide

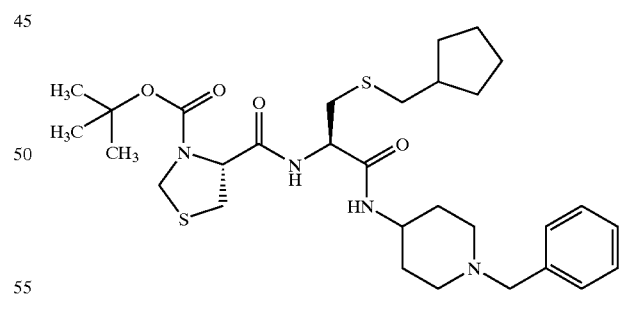

TLC: Rf 0.48 (chloroform:methanol=9:1);

NMR (CD$_3$OD): δ7.32–7.22 (m, 5H), 4.64–4.43 (m, 4H), 3.70–3.58 (m, 1H), 3.52 (s, 2H), 3.39–3.37 (m, 1H), 3.14 (dd, J=12.0, 4.8 Hz, 1H), 2.95–2.69 (br, 4H), 2.56 (d, J=7.2 Hz, 2H), 2.17–1.96 (m, 3H), 1.85–1.75 (m, 4H), 1.68–1.46 (m, 15H), 1.32–1.17 (m, 2H).

EXAMPLE 3 (28)

(2R)-N-(1-benzylpiperidin-4-yl)-3-cycloheptylmethylthio-2-((4R)-3-t-butoxycarbonylthiazolidin-4-ylcarbonylamino)propanamide

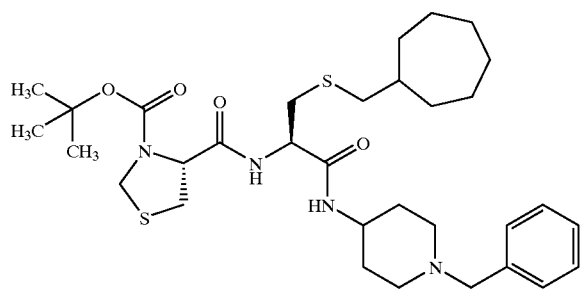

TLC: Rf 0.35 (chloroform:methanol=19:1);

NMR (CD$_3$OD): δ7.33–7.00 (m, 5H), 4.65–4.41 (m, 4H), 3.72–3.58 (m, 1H), 3.52 (s, 2H), 3.37. (dd, J=12.0, 7.6 Hz, 1H), 3.14 (dd, J=12.0, 4.8 Hz, 1H), 2.95–2.67 (br, 4H), 2.46 (d, J=6.6 Hz, 2H), 2.20–2.07 (m, 2H), 1.87–1.16 (m, 26H).

EXAMPLE 3 (29)

(2R)-N-(1-benzylpiperidin-4-yl)-3-cyclohexylmethylthio-2-((4R)-3-t-butoxycarbonyl-5,5-dimethylthiazolidin-4-ylcarbonylamino)propanamide

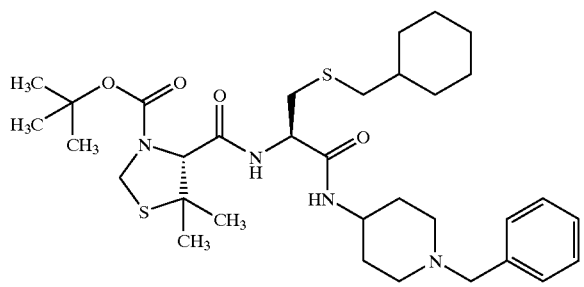

TLC: Rf 0.40 (methylene chloride:methanol=93:7);

NMR (CD$_3$OD): δ7.40–7.20 (m, 5H), 4.69–4.39 (m, 3H), 4.10 (s, 1H), 3.70–3.58 (m, 1 H), 3.52 (s, 2H), 2.96–2.65 (m, 4H), 2.50–2.40 (m, 2H), 2.19–2.04 (m, 2H), 1.91–1.08 (m, 28H), 1.03–0.87 (m, 2H).

EXAMPLE 3 (30)

(2R)-N-(2-acetoxyethyl)-N-(1-benzylpiperidin-4-yl)-3-cyclohexylmethylthio-2-((4R)-3-t-butoxycarbonylthiazolidin-4-ylcarbonylamino)propanamide

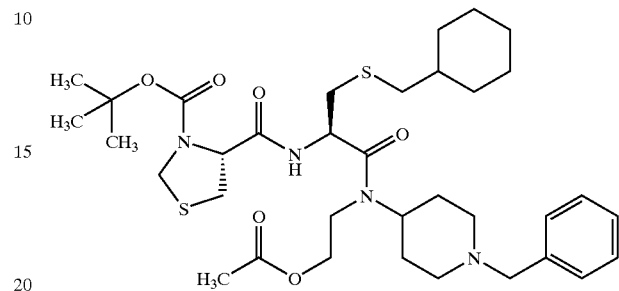

TLC: Rf 0.50 (methanol:chloroform=1:19);

NMR (CDCl$_3$): δ7.36–6.80 (m, 6H), 5.14–5.04 (m, 1H), 4.85–4.53 (m, 2H), 4.40–4.25 (m, 1H), 4.22–4.10 (m, 2H), 3.86–3.11 (m, 7H), 3.04–2.65 (m, 4H), 2.44–2.41 (m, 2H), 2.16–0.82 (m, 29H).

EXAMPLE 3 (31)

(2R)-N-(1-benzylpiperidin-4-yl)-3-cyclohexylmethylthio-3-methyl-2-((4R)-3-t-butoxycarbonylthiazolidin-4-ylcarbonylamino)butanamide

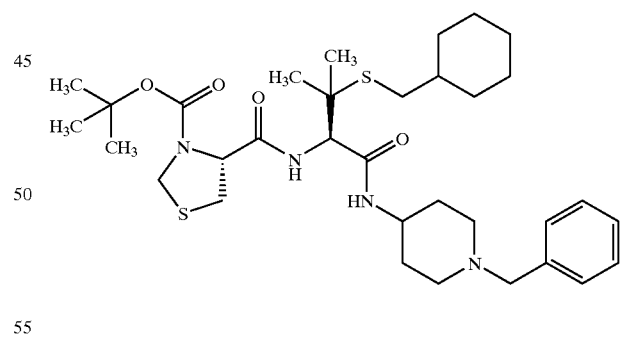

TLC: Rf 0.18 (methylene chloride:methanol=19:1);

NMR (CDCl$_3$): δ7.40–7.20 (m, 6H), 6.80–6.63 (b, 1H), 4.66 (dd, J=8, 3 Hz, 1H), 4.69–4.52 (m, 1H), 4.46 (d, J=10 Hz, 1H), 4.35–4.20 (m, 1H), 3.84–3.69 (m, 1H), 3.49 (s, 2H), 3.33 (dd, J=14,3 Hz, 1H), 3.25 (dd, J=14, 8 Hz, 1H), 2.86–2.73 (m, 2H), 2.55–2.32 (m, 2H), 2.20–2.05 (m, 2H), 1.96–1.60 (m, 9H), 1.60–1.33 (m, 13H), 1.33–1.05 (m, 6H), 1.03–0.85 (m, 2H).

EXAMPLE 3 (32)

(4R)-N-((1R)-2-cyclohexylmethylthio-1-(4-(N'-benzyl-N'-trifluoroacetylamino)piperidin-1-ylcarbonyl)ethyl)-3-t-butoxycarbonylthiazolidin-4-ylcarboxamide

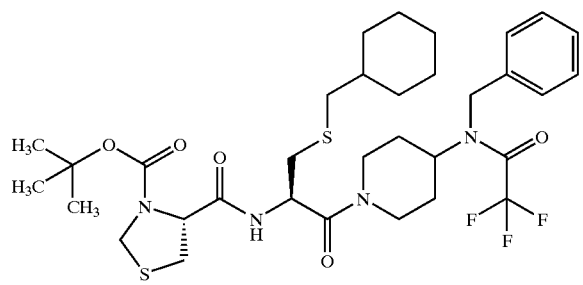

TLC: Rf 0.26 (ethyl acetate:hexane=1:2);

NMR (CDCl$_3$): δ7.50–6.80 (m, 6H), 5.05–4.94 (m, 1H), 4.77–4.56 (m, 5H), 4.38–4.35 (m, 1 H), 4.25–3.96 (m, 2H), 3.39–2.96 (m, 3H), 2.91–2.35 (m, 5H), 1.94–0.80 (m, 24H).

EXAMPLE 3 (33)

(2R)-N-(1-benzylpiperidin-4-yl)-3-cyclohexylmethylthio-2-((2RS, 4R)-3-t-butoxycarbonyl-2-methylthiazolidin-4-ylcarbonylamino)propanamide

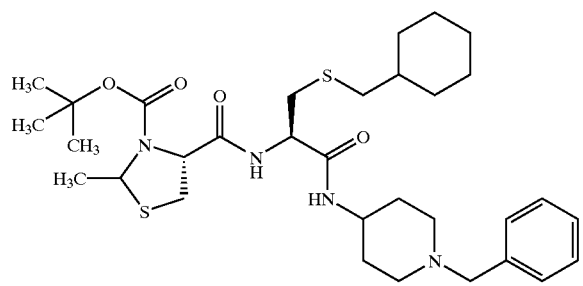

TLC: Rf 0.42 (methylene chloride:methanol 9:1);

NMR (CDCl$_3$): δ7.35–7.20 (m, 6H), 6.93–6.78 (b, 1H), 5.19 (q, J=6 Hz, 1H), 4.68 (t, J=6 Hz, 1H), 4.54–4.42 (m, 1H), 3.83–3.68 (m, 1H), 3.50 (s, 2H), 3.41–3.10 (m, 3H), 2.85–2.68 (m, 3H), 2.50–2.32 (m, 2H), 2.18–2.07 (m, 2H), 1.93–1.33 (m, 22H), 1.33–1.03 (m, 3H), 0.98–0.80 (m, 2H).

EXAMPLE 3 (34)

(4R)-N-((1R)-2-cyclohexylmethylthio-1-(4-(N'-benzyl-N'-methylamino)piperidin-1-ylcarbonyl)ethyl)-3-t-butoxycarbonylthiazolidin-4-ylcarboxamide

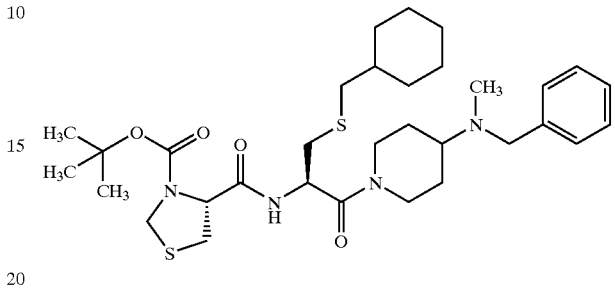

TLC: Rf 0.76 (methanol:chloroform=1:9);

NMR (CD$_3$OD): δ7.58–7.46 (m, 5H), 5.08–4.95 (m, 1H), 4.78–4.04 (m, 7H), 3.74–3.57 (m, 1 H), 3.45–3.06 (m, 3H), 3.01–2.86 (m, 1 H), 2.82–2.64 (m, 5H), 2.50–2.43 (m, 2H), 2.30–2.10 (m, 2H), 2.06–0.86 (m, 24H).

EXAMPLE 3 (35)

(2R)-N-(1-benzylpiperidin-4-yl)-3-cyclohexylmethylthio-2-((2RS)-3-t-butoxycarbonylthiazolidin-2-ylcarbonylamino)propanamide

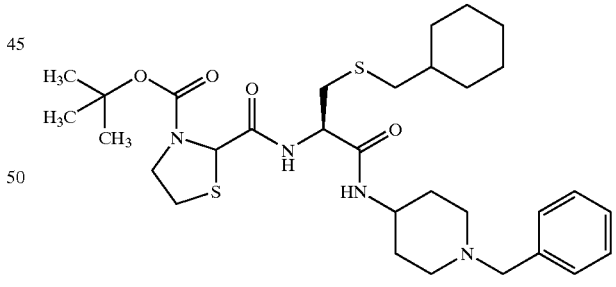

TLC: Rf 0.36 (methylene chloride:methanol=19:1);

NMR (CDCl$_3$): δ7.37–7.20 (m, 5H), 6.93–6.73 (b, 1H), 6.73–6.35 (b, 1H), 5.24 (b) and 5.19 (s) (1H), 4.48–4.35 (m, 1H), 3.93–3.70 (m, 3H), 3.53–3.47 (m, 2H), 3.33–2.92 (m, 3H), 2.85–2.63 (m, 3H), 2.56–2.38 (m, 2H), 2.21–2.07 (m, 2), 1.95–1.35 (m, 19H), 1.33–1.03 (m, 3H), 1.00–0.83 (m, 2H).

EXAMPLE 3 (36)

(2R)-N-(1-benzylpiperidin-4-yl)-3-cyclohexylmethylthio-2-(3-t-butoxycarbonylthiazolidin-2-ylcarbonylamino)propanamide

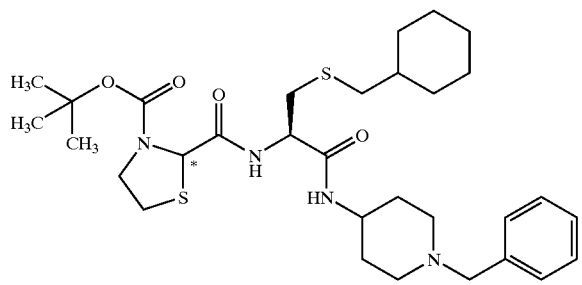

(The determination of the absolute configuration of * is not performed, but the said compound is single optically active isomer.)

[α]$_D$=+27.26 (c 0.50, CHCl$_3$);
TLC: Rf 0.26 (methylene chloride:methanol=19:1);
NMR (CDCl$_3$): δ7.37–7.20 (m, 5H), 6.90–6.76 (b, 1H), 6.67–6.45 (b, 1H), 5.20 (s, 1H), 4.48–4.35 (m, 1H), 3.93–3.70 (m, 3H), 3.49 (s, 2H), 3.34–2.94 (m, 3H), 2.84–2.63 (m, 3H), 2.56–2.41 (m, 2H), 2.20–2.06 (m, 2H), 1.94–1, 36 (m, 19H), 1.31–1.05 (m, 3H), 1.01–0.84 (m, 2H).

EXAMPLE 4

(2R)-N-(1-benzylpiperidin-4-yl)-3-cyclohexylmethylthio-2-(((4R)-3-t-butoxycarbonylthiazolidin-4-ylmethyl)amino)propanamide

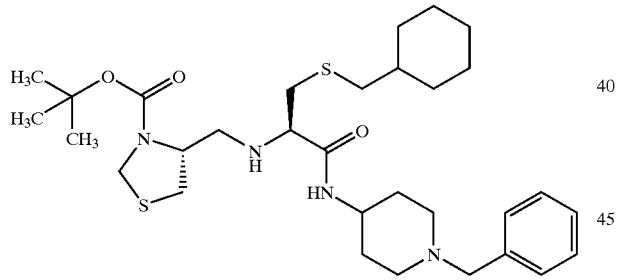

The compound prepared in Reference Example 3 (600 mg) and N-methylmorpholine (131 mg) were dissolved in ethanol (5 ml). Thereto, (4R)-3-t-butoxycarbonyl-4-formylthiazolidine(304 mg) and sodium cyanoborohydride (124 mg) were added successively. The reaction mixture was adjustified to pH5.5 by addition of acetic acid and stirred overnight at room temperature. Thereto, a saturated solution of sodium hydrocarbonate was added. The mixture was extracted with ethyl acetate. The extract was washed by saturated solution of sodium chloride, dried over anhydrous sodium sulfate and concentrated. The residue was purified with column chromatography on silica gel (chloroform methanol 40:1) to obtain the compound (553 mg) of the present invention having the following physical data.

TLC: Rf 0.48 (chloroform:methanol=19:1);
NMR (CD$_3$OD): δ7.33–7.20 (m, 5H), 4.55 (d, J=9.3 Hz, 1H), 4.38–4.22 (m, 1H), 4.20 (d, J=9.3 Hz, 1H), 3.77–3.60 (m, 1H), 3.53 (s, 2H), 3.19 (dd, J=7.5, 5.7 Hz, 1H), 3.12–2.57 (m, 8H), 2.42 (d, J=6.6 Hz, 2H), 2.24–2.08 (m, 2H), 1.93–0.82 (m, 15H), 1.47 (s, 9H).

EXAMPLE 4 (1)

(2R)-N-(1-benzylpiperidin-4-yl)-3-cyclohexylmethylthio-2-((3-t-butoxycarbonylthiazolidin-2-ylmethyl) amino)propanamide

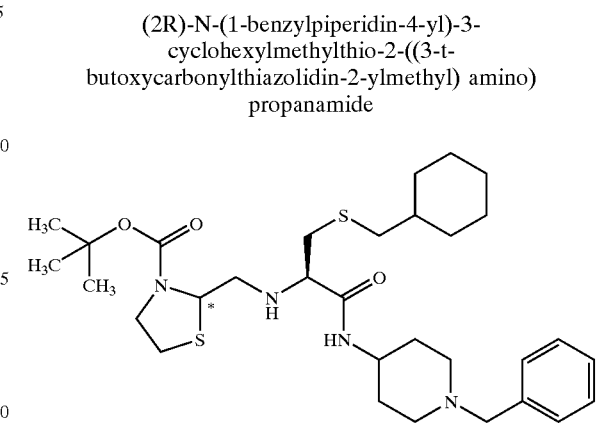

By the same procedure described in Example 4, using (+)-3-t-butoxycarbonyl-2-formylthiazolidine instead of (4R)-3-t-butoxycarbonyl-4-formylthiazolidine in Example 4, the compound of the present invention having the following physical data was obtained.

(The determination of the absolute configuration of * is not performed, but the said compound is single optically active isomer.)

[α]=–13.46 (c 0.50, CHCl$_3$);
TLC: Rf 0.33 (methylene chloride:methanol=19:1);
NMR (CDCl$_3$): δ7.48 (d, J=10 Hz, 1H), 7.35–7.20 (m, 5H), 5.18–5.05 (m, 1H), 4.10–3.88 (m, 1H), 3.88–3.65 (m, 1H), 3.61–3.47 (m, 3H), 3.19–2.71 (m, 8H), 2.58 (dd, J=14, 9 Hz, 1H), 2.41 (dd, J=12.6 Hz, 1H), 2.39 (dd, J=12.6 Hz, 1H), 2.23–2.05 (m, 2H), 1.98–1.30 (m, 19H), 1.30–1.05 (m, 3H), 1.05–0.80 (m, 2H).

EXAMPLE 5

(2R)-N-(1-benzylpiperidin-4-yl)-3-cyclohexylmethylthio-2-((4R)-thiazolidin-4-ylcarbonylamino)propanamide 2hydrochloride

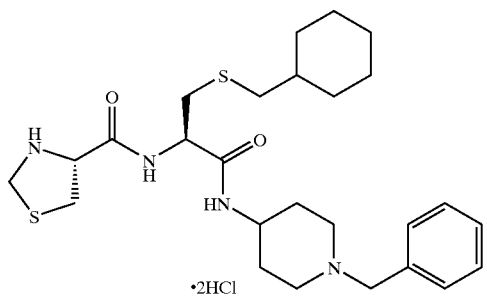

To a soltion of the compound prepared in Example 2 (615 mg) in dioxane (5 ml), 4N-HCl-dioxane (6 ml) was added. The mixture was stirred for 30 minutes at room temperature. The reaction mixture was concentrated to obtain the compound (590 mg) of the present invention having the following physical data.

TLC: Rf 0.49 (methanol:chloroform=1:9);
NMR (CD$_3$OD): δ8.49–8.43 (1H, m), 7.58–7.46 (5H, m), 4.64–4.52 (1H, m), 4.48–4.38 (3H, m), 4.11–3.84 (1H, m), 3.62–3.49 (4H, m), 3.40–3.22 (2H, m), 3.16–3.06 (2H, m), 2.98–2.74 (2H, m), 2.52–2.45 (2H, m), 2.18–2.03 (2H, m), 1.92–1.61 (7H, m), 1.52–1.37 (1H, m), 1.32–1.08 (3H, m), 1.04–0.90 (2H, m).

EXAMPLE 5 (1)~Example 5 (11)

By the same procedure described in Example 5, using the compounds prepared in Example 3 (2)~Example 3 (6), Example 3 (8)~Example 3 (10), Example 3 (19), Example 3 (29) and Example 3 (31), the following compounds of the present invention were obtained.

EXAMPLE 5 (1)

(2R)-N-(1-benzylpiperidin-4-ymethyl)-3-cyclohexylmethylthio-2-((4R)-thiazolidin-4-ylcarbonylamino)propanamide.2hydrochloride

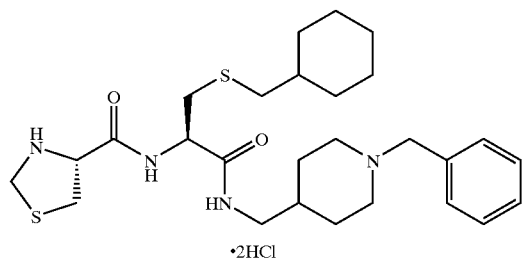

TLC: Rf 0.27 (methanol:chloroform=1:9);

NMR (CD₃OD): δ8.39 (1H, t, J=12.0 Hz), 7.57–7.46 (5H, m), 4.60 (1H, t, J=6.9 Hz), 4.47–4.38 (4H, m), 4.30 (2H, s), 3.76–3.46 (6H, m), 3.28–2.88 (6H, m), 2.79 (1H, dd, J=13.8, 7.8 Hz), 2.47 (2H, d, J=6.9 Hz), 2.06–1.60 (8H, m), 1.55–1.38 (3H, m), 1.33–1.09 (3H, m), 1.03–0.88 (2H, m).

EXAMPLE 5 (2)

(2R)-N-(1-(4-methoxybenzyl)piperidin-4-ylmethyl)-3-cyclohexylmethylthio-2-((4R)-thiazolidin-4-ylcarbonylamino)propanamide 2hydrochloride

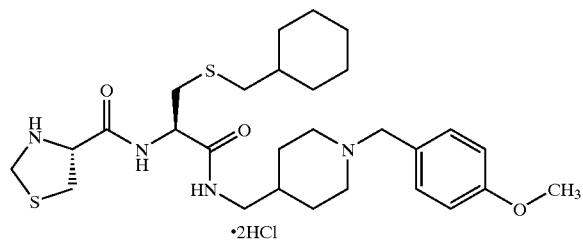

TLC: Rf 0.31 (methanol:chloroform=1:9);

NMR (CD₃OD): δ8.39 (1H. t, J=6.0 Hz), 7.46–7.42 (2H, m), 7.02–6.98 (2H, m), 4.62–4.57 (1 H, m), 4.47–4.38 (3H, m), 4.23 (2H, s), 3.82 (3H, s), 3.62–3.55 (2H, m), 3.49–3.45 (2H, m), 3.28–3.04 (4H, m), 2.98–2.77 (4H, m), 2.49–2.46 (2H, m), 2.06–0.86 (18H, m).

EXAMPLE 5 (3)

(2R)-N-(1-(4-methoxybenzyl)piperidin-4-yl)-3-cyclohexylmethylthio-2-((4R)-thiazolidin-4-ylcarbonylamino)propanamide.2hydrochloride

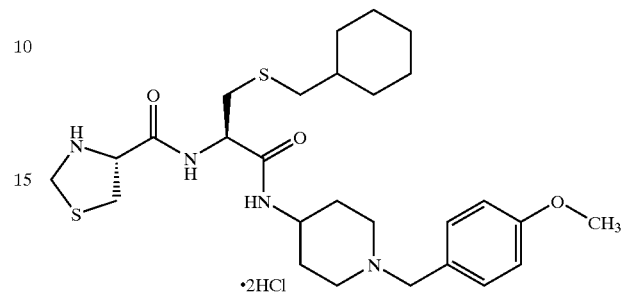

TLC: Rf 0.25 (methanol:chloroform=1:9);

NMR (CD₃OD): δ8.44 (d, J=6.9 Hz, 1H), 7.48–7.43 (m, 2H), 7.04–6.99 (m, 2H), 4.64–4.54 (m,1H), 4.48–4.38 (m, 3H), 4.24 (s, 2H), 4.10–3.84 (m,1H), 3.82 (s, 3h), 3.68–3.47 (m, 3H), 3.36–3.22 (m, 1H), 3.12–3.02 (m, 2H), 2.98–2.74 (m, 2H), 2.51–2.45 (m, 2H), 2.18–2.01 (m, 2H), 1.90–1.60 (m, 7H), 1.52–1.37 (m, 1H), 1.34–1.08 (m, 3H), 1.05–0.87 (m, 2H).

EXAMPLE 5 (4)

(2R)-N-(3-hydroxy-4-methoxybenzyl)-3-cyclohexylmethylthio-2-((4R)-thiazolidin-4-ylcarbonylamino)propanamide.hydrochloride

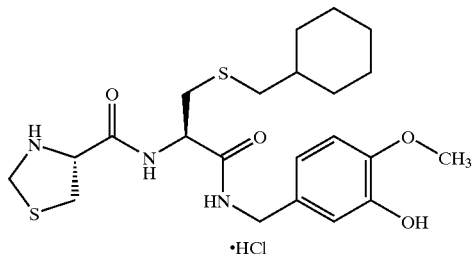

TLC: Rf 0.21 (hexane:ethyl acetate=1:1);

NMR (CD₃OD): δ6.86–6.70 (m, 3H), 4.62–4.49 (m, 2H), 4.43 (d, J=10.0 Hz, 1H), 4.40 (d, J=10.0 Hz, 1H), 4.26 (s, 2H), 3.82 (s, 3H), 3.57 (dd, J=12.0, 7.2 Hz, 1H), 3.22 (dd, J=12.0, 7.2 Hz, 1H), 2.92 (dd, J=14.0, 6.6Hz, 1H), 2.78 (dd, J=14.0, 8.2 Hz, 1H), 2.43 (d, J=6.8 Hz, 2H), 1.87–1.56 (m, 5H), 1.54–0.80 (m, 6H).

EXAMPLE 5 (5)

(2R)-N-methyl-N-(1-benzylpyrrolidin-3-yl)-3-cyclohexylmethylthio-2-((4R)-thiazolidin-4-ylcarbonylamino)propanamide.2hydrochloride

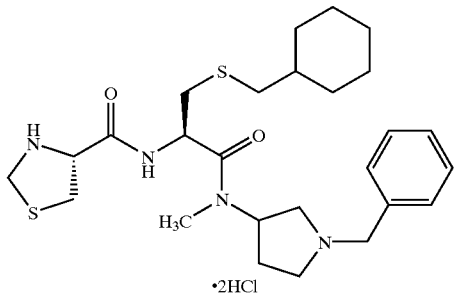

TLC: Rf 0.44 (chloroform:methanol:ammonia 9:1:0.1);

NMR (CD$_3$OD): δ7.58–7.43 (m, 5H), 4.65–4.12 (m, 6H), 3.95–3.19 (m, 9H), 3.03–2.12 (m, 7H), 1.90–1.59 (m, 5H), 1.57–0.80 (m, 6H).

EXAMPLE 5 (6)

(2S)-N-(1-benzylpiperidin-4-yl)-3-cyclohexylmethoxy-2-((4R)-thiazolidin-4-ylcarbonylamino)propanamide.2hydrochloride

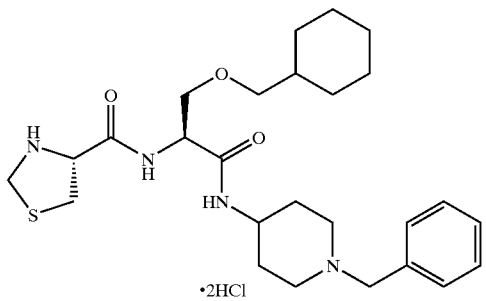

TLC: Rf 0.46 (methanol:methylene chloride=1:9);

NMR (CD$_3$OD): δ7.60–7.47 (m, 5H), 4.67–4.29 (m, 6H), 4.13–3.86 (m, 1H), 3.79–3.45 (m, 6H), 3.40–3.20 (m, 2H), 3.18–3.04 (m, 2H), 2.18–2.00 (m, 2H), 1.93–1.47 (m, 8H), 1.36–1.07 (m, 3H), 1.03–0.84 (m, 2H).

EXAMPLE 5 (7)

(2R)-N-(2-benzylaminoethyl)-3-cyclohexylmethylthio-2-((4R)-thiazolidin-4-ylcarbonylamino)propanamide.2hydrochloride

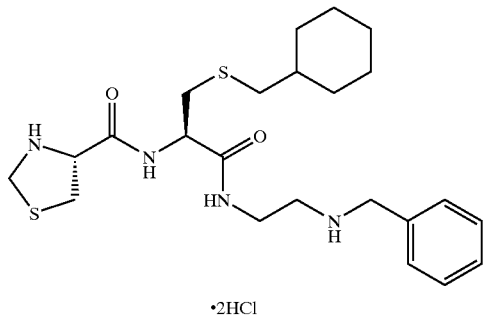

TLC: Rf 0.21 (chloroform:methanol:ammonia 9:1:0.1);

NMR (CD$_3$OD): δ7.55–7.43 (m, 5H), 4.62 (dd, J=7.5, 6.9 Hz, 1H), 4.47 (dd, J=8.1, 6.0 Hz, 1H), 4.41 (s, 2H), 4.27 (s, 2H), 3.67–3.48 (m, 3H), 3.31 (dd, J=12.0, 6.9 Hz, 1H), 3.22 (t, J=6.0 Hz, 2H), 2.97 (dd, J=13.8, 6.0 Hz, 1H), 2.83 (dd, J=13.8, 8.1 Hz, 1H), 2.47 (d, J=6.6 Hz, 2H), 1.85–1.62 (m, 5H), 1.54–1.38 (m, 1H), 1.33–1.08 (m, 3H), 1.02–0.89 (m, 2H).

EXAMPLE 5 (8)

(4R)-N-((1R)-2-cyclohexylmethylthio-1-(4-benzylpiperazin-1-ylcarbonyl)ethyl) thiazolidin-4-ylcarboxamide 2hydrochloride

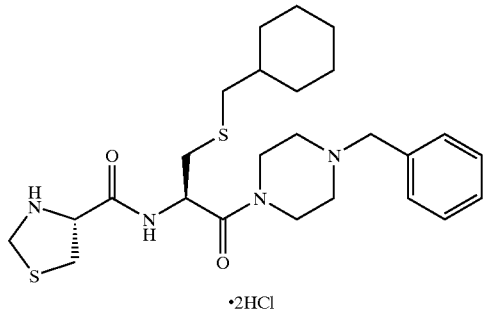

TLC: Rf 0.32 (chloroform:methanol=9:1);

NMR (DMSO-d$_6$): δ12.20–11.56 (br, 1H), 10.82–9.58 (br, 1H), 9.37–9.14 (br, 1H), 7.65–7.62 (m, 2H), 7.44–7.42 (m, 3H), 4.78 (dd, J=14.1, 6.9 Hz, 1H), 4.51–4.22 (m, 5H), 4.15–3.04 (m, 10H), 2.83 (dd, J=13.5, 6.9 Hz, 1H), 2.65 (dd, J=13.5, 6.9 Hz, 1H), 2.40 (d, J=6.6 Hz, 2H), 1.75–1.57 (m, 5H), 1.44–1.29 (m,1H), 1.23–1.00 (m, 3H), 0.92–0.80 (m, 2H).

EXAMPLE 5 (9)

(4R)-N-((1R)-2-cyclohexylmethylthio-1-(4-phenylaminopiperidin-1-ylcarbonyl)ethyl)thiazolidin-4-ylcarboxamide.2hydrochloride

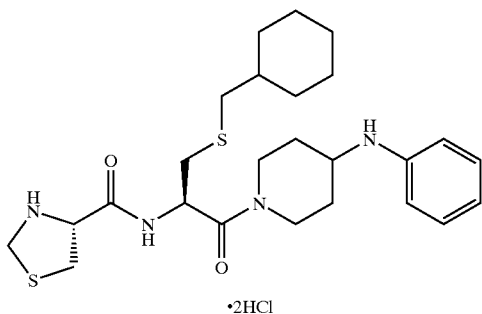

·2HCl

TLC: Rf 0.54 (chloroform:methanol 9:1);

NMR (CD$_3$OD): δ7.63–7.52 (m, 5H), 5.02 (t, J=7.2 Hz, 1H), 4.65–4.38 (m, 4H), 4.27–4.14 (br, 1H), 3.92–3.82 (m, 1H), 3.67–3.53 (m, 1H), 3.35–3.17 (m, 2H), 2.99–2.90 (m, 1H), 2.79–2.69 (m, 2H), 2.50–2.43 (m, 2H), 2.14–2.00 (m, 2H), 1.93–1.59 (m, 7H), 1.53–1.08 (m, 4H), 1.02–0.87 (m, 2H).

EXAMPLE 5 (10)

(2R)-N-(1-benzylpiperidin-4-yl)-3-cyclohexylmethylthio-2-((4R)-5,5-dimethylthiazolidin-4-ylcarbonylamino)propanamide.2hydrochloride

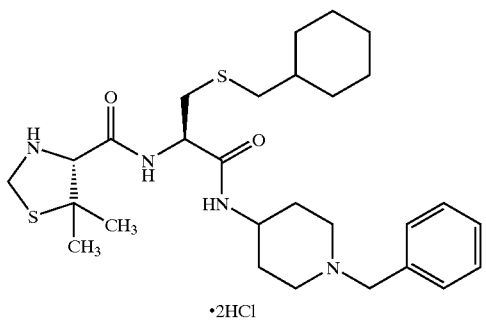

·2HCl

TLC: Rf 0.43 (methylene chloride:methanol 9:1);

NMR (CD$_3$OD): δ7.60–7.45 (m, 5H), 4.55–4.46 (m, 3H), 4.40 and 4.31 (s, 2H), 4.20 and 4.18 (s, 1H), 4.10–4.05 and 3.98–3.84 (m, 1H), 3.56–3.45 and 3.41–3.33 (m, 2H), 3.41–3.33 and 3.18–3.05 (m, 2H), 3.00–2.76 (m, 2H), 2.52 and 2.48 (d, J=7 Hz, 2H), 2.19–2.00 (m, 2H), 1.95–1.56 (m, 10H), 1.54–1.09 (m, 7H), 1.06–0.88 (m, 2H).

EXAMPLE 5 (11)

(2R)-N-(1-benzylpiperidin-4-yl)-3-cyclohexylmethylthio-3-methyl-2-((4R)-thiazolidin-4-ylcarbonylamino)butanamide.2hydrochloride

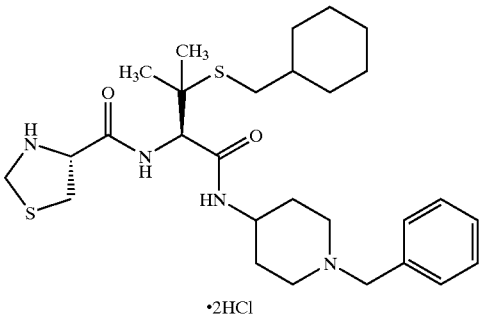

·2HCl

TLC: Rf 0.48 (methylene chloride:methanol=9:1);

NMR (CD$_3$OD): δ7.60–7.45 (m, 5H), 4.66–4.58 (m, 1H), 4.51 and 4.31 (s, 2H), 4.48–4.37 (m, 2H), 4.13–4.06 and 3.98–3.85 (m, 1H), 3.75–3.45 and 3.44–3.32 (m, 4H), 3.44–3.32 and 3.25–3.04 (m, 4H), 2.53 and 2.48 (d, J=7 Hz, 2H), 2.20–2.05 (m, 2H), 1.93–1.60 (m, 7H), 1.50–1.08 (m, 10H), 1.08–0.89 (m, 2H).

EXAMPLE 6

(4R)-N-((1R)-2-cyclohexylmethylthio-1-(4-benzylpiperazin-1-ylcarbonyl)ethyl) thiazolidin-4-ylcarboxamide

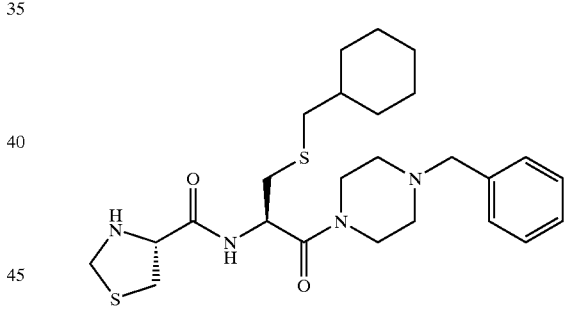

The compound prepared in Example 5 (8) (566 mg) was dispersed in ethyl acetate (20 ml). Thereto, a saturated solution of sodium hydrocarbonate (20 ml) was added. The mixture was stirred for 5 minutes at room temperature. The reaction mixture was extracted with ethyl acetate. The extract was washed by saturated solution of sodium chloride, dried over anhydrous sodium sulfate and concentrated. The residue was dried under reduced pressure to obtain the compound (378 mg) of the present invention having the following physical data.

TLC: Rf 0.32 (chloroform:methanol=9:1);

NMR (CD$_3$OD): δ7.34–7.22 (m, 5H), 4.97 (t, J=6.6 Hz, 1H), 4.18 (d, J=9.3 Hz, 1H), 4.13 (d, J=9.3 Hz, 1H), 4.05 (dd, J=7.5, 4.8 Hz, 1H), 3.69–3.53 (m, 6H), 3.15 (dd, J=10.5, 4.8 Hz, 1H), 3.03 (dd, J=10.5, 7.5 Hz, 1H), 2.90 (dd, J=13.5, 6.6 Hz, 1H), 2.71 (dd, J=13.5, 6.6 Hz, 1H), 2.57–2.40 (m, 6H), 1.84–1.63 (m, 5H), 1.49–1.09 (m, 4H), 1.00–0.87 (m, 2H).

EXAMPLE 6 (1)

(2R)-N-(2-benzylaminoethyl)-3-cyclohexylmethylthio-2-((4R)-thiazolidin-4-ylcarbonylamino)propanamide

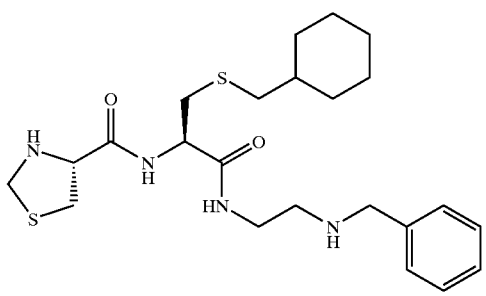

By the same procedure described in Example 6 using the compound prepared in Example 5 (7), the compound of the present invention having the following physical data was obtained.

TLC: Rf 0.26 (chloroform:methanol:ammonia=9:1:0.1);

NMR (CD$_3$OD): δ7.36–7.21 (m, 5H), 4.40 (dd, J=7.2, 6.0 Hz, 1H), 4.21–4.40 (m, 3H), 3.76 (s, 2H), 3.39–3.34 (m, 2H), 3.21 (dd, J=10.5, 4.5 Hz, 1H), 3.01 (dd, J=10.5, 7.2 Hz, 1H), 2.90 (dd, J=13.5, 6.0 Hz, 1H), 2.79 (dd, J=13.5, 7.2 Hz, 1H), 2.74 (t, J=6.3 Hz, 2H), 2.40 (d, J=6.9 Hz, 2H), 1.83–1.62 (m, 5H), 1.48–1.08 (m, 4H), 0.98–0.85 (m, 2H).

EXAMPLE 7~Example 7 (11)

By the same procedure described in Example 5→Example 6 using the compounds prepared in Example 3 (7), Example 3 (11)~Example 3 (16), Example 3 (18) ~Example 3 (19), Example 3 (21), Example 3 (23) and Example 4, the following compounds of the present invention were obtained.

EXAMPLE 7

(2R)-N-(1-(4-methoxybenzoyl)piperidin-4-yl)-3-cyclohexylmethylthio-2-((4R)-thiazolidin-4-ylcarbonylamino)propanamide

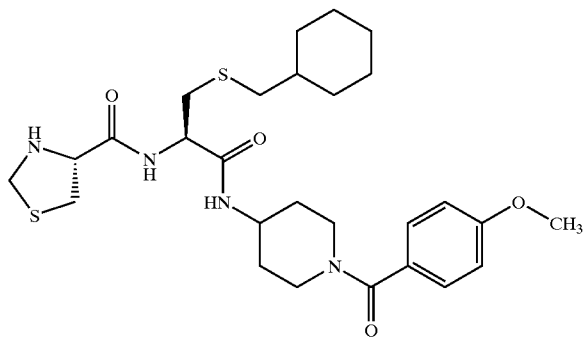

TLC: Rf 0.54 (methanol:chloroform=1:9);

NMR (CDCl$_3$): δ7.86 (d, J=7.5 Hz, 1H), 7.39–7.35 (m, 2H), 6.93–6.89 (m, 2H), 6.65 (d, J=7.5 Hz, 1H), 4.41–4.33 (m, 1H), 4.27 (d, J=9.9 Hz, 1H), 4.21–4.17 (m, 1H), 4.06–3.95 (m, 2H), 3.83 (s, 3H), 3.43 (dd, J=11.1, 4.2 Hz, 1H), 3.15–3.02 (m, 3H), 2.90 (dd, J=13.5, 6.6 Hz, 1H), 2.79 (dd, J=13.5, 7.2 Hz, 1H), 2.46 (d, J=6.9 Hz, 2H), 2.06–1.60 (m, 7H), 1.53–1.38 (m, 3H), 1.31–1.05 (m, 3H), 0.99–0.86 (m, 2H).

EXAMPLE 7 (1)

(4R)-N-((1R)-2-cyclohexylmethylthio-1-(4-diphenylmethylpiperazin-1-ylcarbonyl)ethyl)thiazolidin-4-ylcarboxamide

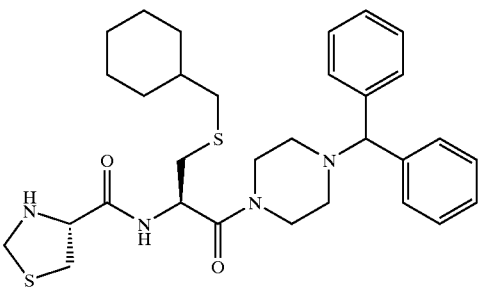

TLC: Rf 0.58 (methanol:chloroform=1:19);

NMR (CDCl$_3$): δ7.82 (d, J=8.7 Hz, 1H), 7.42–7.37 (m, 4H), 7.31–7.26 (m, 4H), 7.22–7.17 (m, 2H), 5.03–4.95 (m, 1H), 4.27–4.21 (m, 2H), 4.14–4.10 (m, 1H), 4.06 (d, J=9.9 Hz 1H), 3.67–3.59 (m, 4H), 3.41 (dd, J=10.8, 4.5 Hz, 1H), 3.11 (dd, J=10.8, 7.8 Hz, 1H), 2.85 (dd, J=13.5, 6.6 Hz, 1H), 2.69 (dd, J=13.5, 6.6 Hz, 1H), 2.48–2.32 (m, 6H), 1.84–1.32 (m, 6H), 1.28–1.04 (m, 3H), 0.96–0.82 (m, 2H).

EXAMPLE 7 (2)

(2R)-N-(1-(4-fluorobenzoyl)piperidin-4-yl)-3-cyclohexylmethylthio-2-((4R)-thiazolidin-4-ylcarbonylamino)propanamide

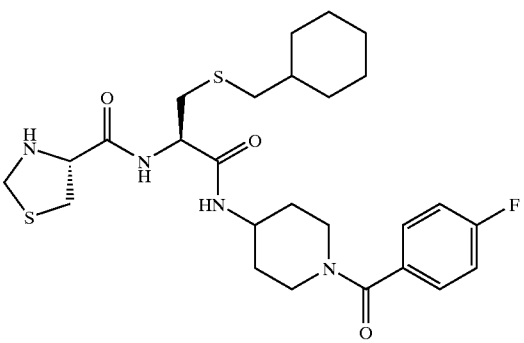

TLC: Rf 0.30 (methanol:chloroform=1:19);

NMR (CDCl$_3$): δ7.87 (d, J=7.5 Hz, 1H), 7.44–7.37 (m, 2H), 7.14–7.06 (m, 2H), 6.63 (d, J=7.2 Hz, 1H), 4.64–4.19 (m, 4H), 4.07–3.96 (m, 2H), 3.44 (dd, J=10.5, 3.9 Hz, 1H), 3.20–3.00 (m, 3H), 2.90 (dd, J=13.8, 6.6 Hz, 1H), 2.79 (dd, J=13.8, 7.5 Hz, 1H), 2.46 (d, J=6.9 Hz, 2H), 2.06–1.62 (m, 5H), 1.52–1.38 (m, 3H), 1.31–1.06 (m, 3H), 1.00–0.85 (m, 2H).

EXAMPLE 7 (3)

(2R)-N-(1-(4-fluorobenzyl)piperidin-4-yl)-3-cyclohexylmethylthio-2-((4R)-thiazolidin-4-ylcarbonylamino)propanamide

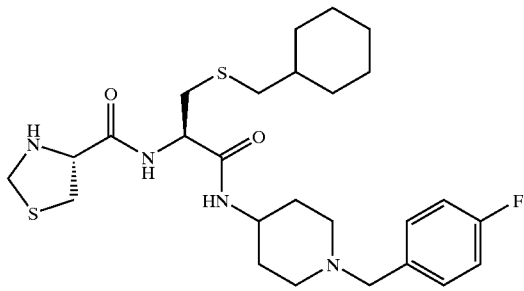

TLC: Rf 0.52 (methanol:chloroform=1:9);

NMR (CDCl$_3$): δ7.85 (d, J=7.2 Hz, 1H), 7.32–7.24 (m, 2H), 7.04–6.97 (m, 2H), 6.44 (d, J=8.1 Hz, 1H), 4.39–4.32 (m, 1H), 4.26 (d, J=9.6 Hz, 1H), 4.17 (dd, J=7.8, 3.9 Hz, 1H), 4.05 (d, J=9.6 Hz, 1H), 3.8 6–3.73 (m, 1H), 3.47 (s, 2H), 3.42 (dd, J=11.1, 4.2 Hz, 1H), 3.12 (dd, J=11.1, 7.8 Hz, 1H), 2.89 (dd, J=13.5, 6.0 Hz, 1H), 2.83–2.72 (m, 3H), 2.47 (d, J=6.6 Hz, 2H), 2.15 (t, J=10.8 Hz, 2H), 1.96–1.37 (m, 10H), 1.32–1.05 (m, 3H), 0.99–0.84 (m, 2H).

EXAMPLE 7 (4)

(4R)-N-((1R)-2-cyclohexylmethylthio-1-(4-(4-methoxyphenyl)piperazin-1-ylcarbonyl)ethyl)thiazolidin-4-ylcarboxamide

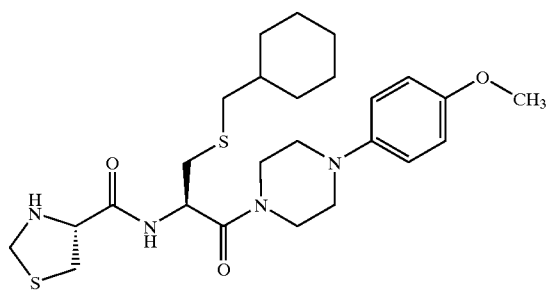

TLC: Rf 0.50 (methanol:chloroform=1:19);

NMR (CDCl$_3$): δ7.85 (d, J=8.7 Hz, 1H), 6.92–6.83 (m, 4H), 5.11–5.04 (m, 1H), 4.27 (d, J=9.9 Hz, 1H), 4.15 (dd, J=7.5, 4.2 Hz, 1H), 4.07 (d, J=9.9 Hz, 1H), 3.89–3.70 (m, 7H), 3.44 (dd, J=10.8, 4.2 Hz, 1H), 3.18–3.01 (m, 5H), 2.90 (dd, J=13.5, 6.9 Hz, 1H), 2.76 (dd, J=13.5, 6.0 Hz, 1H), 2.42 (d, J=6.9 Hz, 2H), 1.85–1.58 (m, 5H), 1.49–1.35 (m, 1H), 1.29–1.05 (m, 3H), 0.98–0.83 (m, 2H).

EXAMPLE 7 (5)

(4R)-N-((1R)-2-cyclohexylmethylthio-1-(4-(pyridin-2-yl)piperazin-1-ylcarbonyl)ethyl)thiazolidin-4-ylcarboxamide

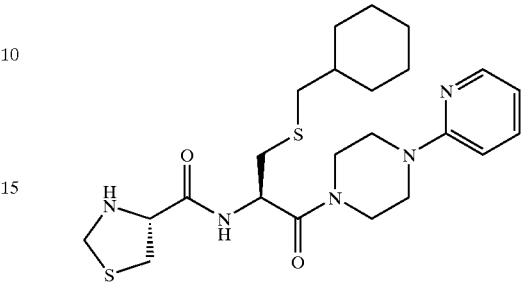

TLC: Rf 0.38 (methanol:chloroform=1:19);

NMR (CDCl$_3$): δ8.22–8.19 (m, 1H), 7.85 (d, J=8.4 Hz, 1H), 7.55–7.49 (m, 1H), 6.71–6.64 (m, 2H), 5.12–5.04 (m, 1H), 4.27 (d, J=9.9 Hz, 1H), 4.15 (dd, J=7.5, 4.2 Hz, 1H), 4.07 (d, J=9.9 Hz, 1H), 3.85–3.54 (m, 8H), 3.44 (dd, J=10.8, 4.2 Hz, 1H), 3.12 (dd, J=10.8, 7.5 Hz, 1H), 2.91 (dd, J=13.2, 6.9 Hz, 1H), 2.76 (dd, J=13.2, 6.3 Hz, 1H), 2.42 (d, J=6.9 Hz, 2H), 1.86–1.59 (m, 6H), 1.50–1.35 (m, 1H), 1.30–1.04 (m, 3H), 0.99–0.84 (m, 2H).

EXAMPLE 7 (6)

(4R)-N-((1R)-2-cyclohexylmethylthio-1-(4-(pyridin-4-yl)piperazin-1-ylcarbonyl)ethyl)thiazolidin-4-ylcarboxamide

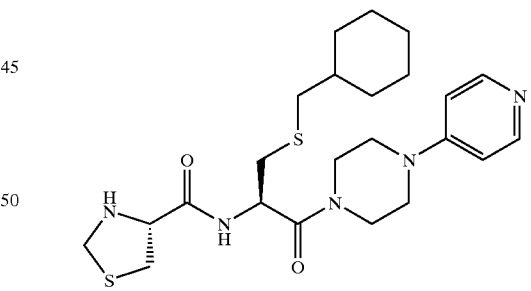

TLC: Rf 0.51 (methanol:chloroform=2:8);

NMR (CDCl$_3$): δ8.32 (dd, J=5.1, 1.8 Hz, 2H), 7.83 (d, J=8.7 Hz, 1H), 6.67 (dd, J=5.1, 1.8 Hz, 2H), 5.09–5.01 (m, 1H), 4.27 (d, J=9.9 Hz, 1H), 4.19–4.14 (m, 1H), 4.05 (d, J=9.9 Hz, 1H), 3.90–3.74 (m, 4H), 3.52–3.32 (m, 5H), 3.12 (dd, J=10.8, 7.8 Hz, 1H), 2.90 (dd, J=13.2, 7.5 Hz, 1H), 2.77 (dd, J=13.2, 6.3 Hz, 1H), 2.42 (d, J=6.9 Hz, 2H), 2.02–1.60 (m, 6H), 1.50–1.34 (m, 1H), 1.30–1.04 (m, 3H), 1.00–0.84 (m, 2H).

EXAMPLE 7 (7)

(2R)-N-(4-(morpholin-4-ylmethyl)phenyl)-3-cyclohexylmethylthio-2-((4R)-thiazolidin-4-ylcarbonylamino)propanamide

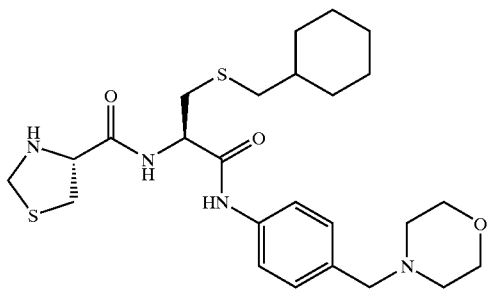

TLC: Rf 0.24 (methanol:chloroform=1:19);

NMR (CDCl₃): δ8.70 (br.s, 1H), 7.99 (d, J=7.8 Hz, 1H), 7.50–7.45 (m, 2H), 7.27 (d, J=8.4 Hz, 2H), 4.58 (dd, J=14.4, 7.2 Hz, 1H), 4.31–4.23 (m, 2H), 4.08 (d, J=9.9 Hz, 1H), 3.71–3.68 (m, 4H), 3.50–3.46 (m, 3H), 3.14 (dd, J=10.8, 7.8 Hz, 1H), 3.00 (dd, J=13.8, 6.6 Hz, 1H), 2.91 (dd, J=13.8, 6.9 Hz, 1H), 2.49 (d, J=6.9, 2H), 2.44–2.41 (m, 4H), 1.87–1.59 (m, 5H), 1.54–1.38 (m, 1H), 1.30–1.04 (m, 3H), 1.00–0.84 (m, 2H).

EXAMPLE 7 (8)

(4R)-N-((1R)-2-cyclohexylmethylthio-1-(4-phenylaminopiperidin-1-ylcarbonyl)ethyl)thiazolidin-4-ylcarboxamide

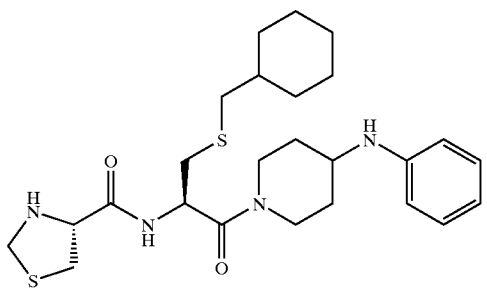

TLC: Rf 0.51 (chloroform:methanol=9:1);

NMR (CDCl₃): δ7.85 (t, J=7.5 Hz, 1H), 7.21–7.16 (m, 2H), 6.73 (t, J=7.2 Hz, 1H), 6.61 (d, J=7.5 Hz, 2H), 5.11–5.02 (m, 1H), 4.51–4.43 (m, 1H), 4.27 (d, J=9.9 Hz, 1H), 4.18–4.01 (m, 3H), 3.60–3.51 (m, 1H), 3.46–3.40 (m, 1H), 3.33–3.23 (m, 1H), 3.13 (dd, J=10.8, 7.5 Hz, 1H), 3.01–2.85 (m, 2H), 2.78–2.69 (m, 1H), 2.44–2.40 (m, 2H), 2.22–2.07 (br, 2H), 1.82–1.06 (m, 11H), 0.98–0.86 (m, 2H).

EXAMPLE 7 (9)

(2R)-N-(4-(N'-methyl-N'-phenylamino)benzyl)-3-cyclohexylmethylthio-2-((4R)-thiazolidin-4-ylcarbonylamino)propanamide

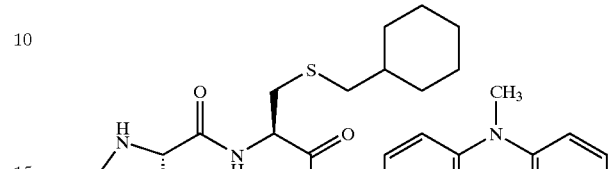

TLC: Rf 0.56 (methanol:chloroform=1:9);

NMR (CDCl₃): δ7.88 (d, J=7.6 Hz, 1H), 7.32–7.25 (m, 2H), 7.19–7.14 (m, 2H), 7.05–6.92 (m, 5H), 6.76 (t, J=5.7 Hz, 1H), 4.46 (dd, J=14.7, 7.2 Hz, 1H), 4.39–4.37 (m, 2H), 4.26 (d, J=9.9 Hz, 1H), 4.15 (dd, J=7.2, 3.9 Hz, 1H), 4.05 (d, J=9.9 Hz, 1H), 3.40 (dd, J=10.8, 3.9 Hz, 1H), 3.30 (s, 3H), 3.09 (dd, J=10.8, 7.8 Hz, 1H), 2.92 (dd, J=13.8, 6.3 Hz, 1H), 2.83 (dd, J=13.8, 7.2 Hz, 1H), 2.54–2.37 (m, 3H), 1.86–1.58 (m, 5H), 1.51–1.36 (m, 1H), 1.30–1.04 (m, 3H), 0.99–0.83 (m, 2H).

EXAMPLE 7 (10)

(2R)-N-amino-N-benzyl-3-cyclohexylmethylthio-2-((4R)-thiazolidin-4-ylcarbonylamino)propanamide

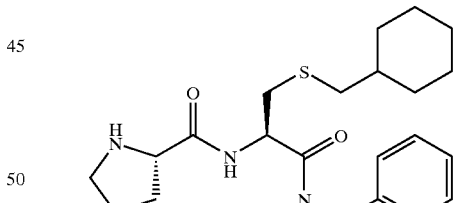

TLC: Rf 0.22 (methylene chloride:methanol=19:1);

NMR (CDCl₃): δ7.88 (bs, 1H), 7.78 (d, J=8 Hz, 1H), 7.39–7.25 (m, 5H), 5.00–4.65 (b, 1H), 4.37 (q, J=8 Hz, 1H), 4.25 (d, J=11 Hz, 1H), 4.12 (dd, J=7, 4 Hz, 1H), 4.02 (d, J=11 Hz, 1H), 3.98 (s, 2H), 3.41 (dd, J=11, 4 Hz, 1H), 3.09 (dd, J=11, 8 Hz, 1H), 2.85 (dd, J=14, 6 Hz, 1 Hz), 2.80 (dd, J=14, 6 Hz, 1H), 2.53–2.25 (b, 1H), 2.42 (d, J=7 Hz, 2H), 1.85–1.50 (m, 5H), 1.50–1.34 (m, 1H), 1.30–1.03 (m, 3H), 1.00–0.83 (m, 2H).

EXAMPLE 7 (11)

(2R)-N-(1-benzylpiperidin-4-yl)-3-cyclohexylmethylthio-2-(((4R)-thiazolidin-4-ylmethyl)amino)propanamide

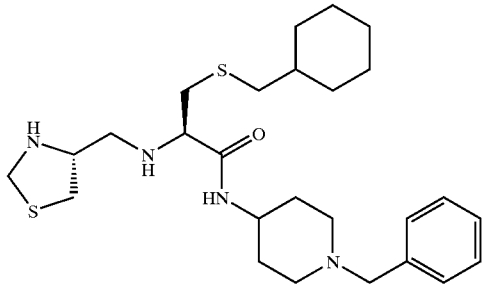

TLC: Rf 0.47 (chloroform:methanol=9:1);

NMR (CD₃OD): δ7.33–7.20 (m, 5H), 4.14 (d, J=9.4 Hz, 1H), 4.05 (d, J=9.4 Hz, 1H), 3.77–3.52 (m, 2H), 3.52 (s, 2H), 3.18 (dd, J=7.5, 5.7 Hz, 1H), 2.97 (dd, J=10.2, 6.2 Hz, 1H), 2.92–2.50 (m, 7H), 2.42 (d, J=6.6 Hz, 2H), 2.23–2.07 (m, 2H), 1.90–0.80 (m, 15H).

EXAMPLE 8

(2R)-N-(1-benzylpiperidin-4-yl)-3-cyclohexylmethylthiG-2-((4R)-3-t-butoxycarbonylthiazolidin-4-ylcarbonylamino)propanamide.hydrochloride

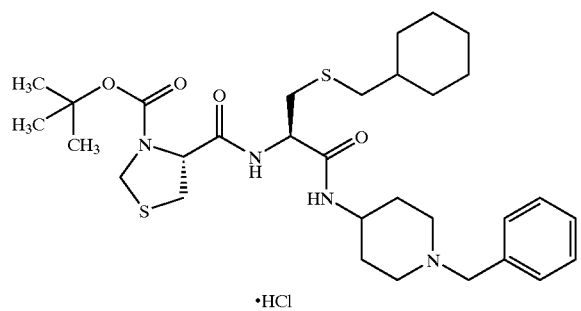

·HCl

To a solution of the compound prepared in Example 2 (1.241 g) in ethyl acetate (10 ml), 0.1N—HCl-ethyl acetate (20.6 ml) was added. The mixture was concentrated. The residue was recrystallized from ethyl acetate-hexane to obtain the compound (1.11 g) of the present invention having the following physical data.

TLC: Rf 0.60 (methanol:chloroform=1:9);

NMR (DMSO-d₆): δ10.74 (br.s, 1H), 8.39–8.14 (m, 2H), 7.60–7.57 (m, 2H), 7.45–7.43 (m, 3H), 4.59–4.21 (m, 6H), 3.80–3.66 (m, 1H), 3.42–3.12 (m, 3H), 3.06–2.91 (m, 3H) 2.75–2.56 (m, 2H), 2.40 (d, J=6.6 Hz, 2H), 1.94–1.52 (m, 9H), 1.45–1.00 (m, 13H), 0.95–0.79 (m, 2H).

EXAMPLE 9~EXAMPLE 9 (4)

By the same procedure described in Example 2→Example 8, using the compound prepared in Reference Example 3 or the compounds prepared by the same procedure described in Reference Example 3 using the compound prepared in Example 1 (26), the following compounds of the present invention were obtained.

EXAMPLE 9

(2R)-N-(1-benzylpiperidin-4-yl)-3-cyclohexylmethylthio-2-((4R)-3-isopropyloxycarbonylthiazolidin-4-ylcarbonylamino)propanamide.hydrochloride

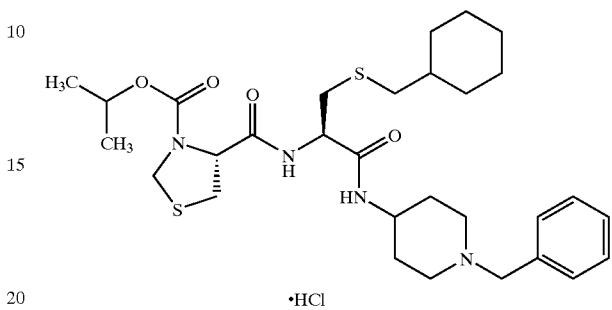

·HCl

TLC: Rf 0.50 (methanol:chloroform=1:9);

NMR (CD₃OD): δ7.35–7.24 (m, 5H), 4.98–4.82 (m, 1H), 4.66 (d, J=9.0 Hz, 1H), 4.62 (dd, J=7.2, 4.8 Hz, 1H), 4.51 (d, J=9.0 Hz, 1H), 4.44 (dd, J=7.5, 6.3 Hz, 1H), 3.74–3.58 (m, 3H), 3.38 (dd, J=12.0, 7.5 H z, 1H), 3.15 (dd, J=12.0, 4.5 Hz, 1H), 2.98–2.69 (m, 4H), 2.44 (d, J=6.9 Hz, 2H), 2.30–2.20 (m, 2H), 1.93–1.78 (m, 4H), 1.76–1.36 (m, 6H), 1.34–1.08 (m, 9H), 1.02–0.86 (m, 2H).

EXAMPLE 9 (1)

(2R)-N-(1-benzylpiperidin-4-yl)-N-methyl-3-cyclohexylmethylthio-2-((4R)-3-t-butoxycarbonylthiazolidin-4-ylcarbonylamino)propanamide.hydrochloride

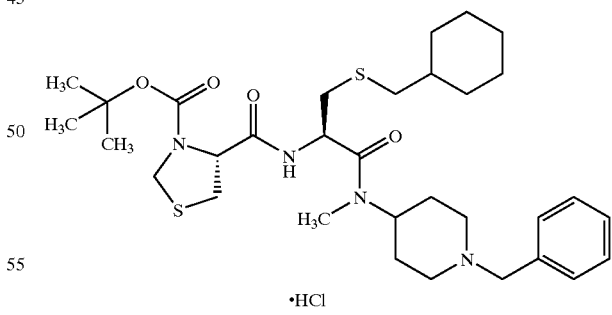

·HCl

TLC: Rf 0.38 (methanol:chloroform=1:19);

NMR (CD₃OD): δ7.59–7.46 (m, 5H), 5.10–4.89 (m, 1H), 4.63–4.42 (m, 4H), 4.35 and 4.32 (s, 2H), 3.64–3.50 (m, 2H), 3.42–3.28 (m, 1H), 3.26–2.68 (m, 8H), 2.47–2.42 (m, 2H), 2.28–1.60 (m, 8H), 1.54–0.84 (m, 16H).

EXAMPLE 9 (2)

(2R)-N-(1-benzylpiperidin-4-yl)-3-cyclohexylmethylthio-2-((4R)-2,2-dimethylthiazolidin-4-ylcarbonylamino)propanamide.2hydrochloride

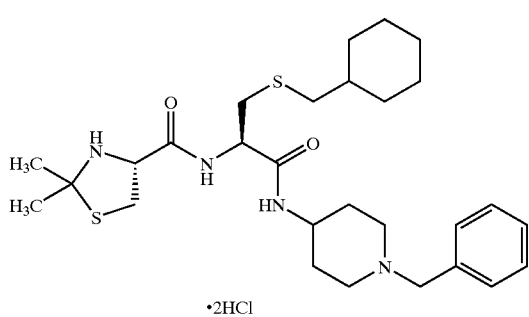

TLC: Rf 0.30 (methylene chloride:methanol=93:7);

NMR (CD$_3$OD): δ7.60–7.45 (m, 5H), 4.80–4.72 (m, 1H), 4.63–4.57 and 4.50–4.43 (m,1H), 4.41 and 4.31 (s, 2H), 4.13–4.06 and 3.99–3.86 (m, 1H), 3.80–3.68 (m, 1H), 3.56–3.33 (m, 3H), 3.19–3.05 (m, 2H), 3.00–2.74 (m, 2H), 2.51 and 2.47 (d, J=7 Hz, 2H), 2.18–2.02 (m, 2H), 1.95–1.60 (m, 13H), 1.52–1.37 (m, 1H), 1.37–1.08 (m, 3H), 1.05–0.88 (m, 2H).

EXAMPLE 9 (3)

(2R)-N-(1-benzylpiperidin-4-yl)-3-cyclohexylmethylthio-2-((2S, 4S)-1-t-butoxycarbonyl-4-fluoropyrrolidin-2-ylcarbonylamino)propanamide.hydrochloride

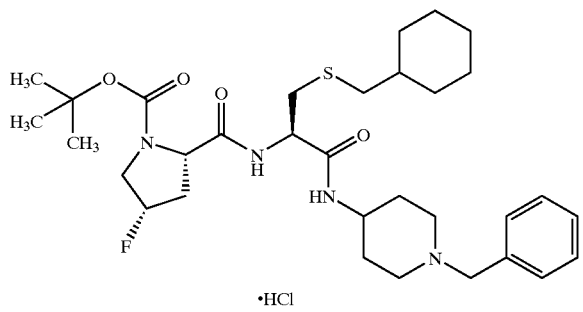

TLC: Rf 0.72 (methanol:chloroform=1:9);

NMR (CD$_3$OD): δ8.27–7.82 (m, 2H), 7.54–7.48 (m, 5H), 5.24 (d, J=52.5 Hz, 1H), 4.46–4.23 (m, 4H), 4.05–3.67 (m, 2H), 3.60–3.03 (m, 5H), 2.99–2.68 (m, 2H), 2.63–2.30 (m, 4H), 2.22–0.86 (m, 24H).

EXAMPLE 9 (4)

(2R)-N-(1-benzylpiperidin-4-yl)-3-cyclohexylmethylthio-2-((2S)-1-t-butoxycarbonyl-4,4-difluoropyrrolidin-2-ylcarbonylamino)propanamide.hydrochloride

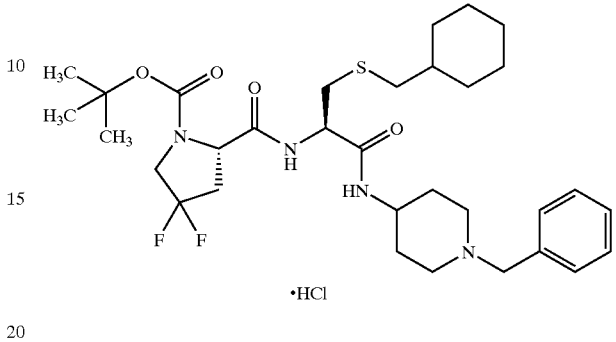

TLC: Rf 0.32 (methanol:chloroform=3:97);

NMR (CD$_3$OD): δ8.46–8.02 (m, 2H), 7.58–7.46 (m, 5H), 4.47–4.31 (m, 4H), 3.98–3.64 (m, 3H), 3.56–3.46 (m, 2H), 3.44–3.04 (m, 5H), 2.94–2.64 (m, 3H), 2.54–2.30 (m, 3H), 2.18–2.00 (m, 2H), 1.90–0.86 (m, 24H).

EXAMPLE 10

(2R)-N-(1-benzylpiperidin-4-yl)-3-cyclohexylmethylthio-2-((4R)-3-(2-methylpropoxycarbonyl)thiazolidin-4-ylcarbonylamino)propanamide

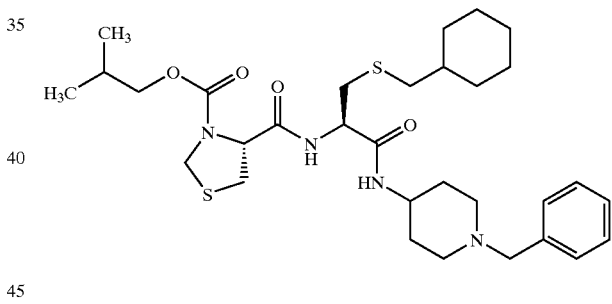

To a solution of the compound prepared in Example 5 (352 mg) in methylene chloride (6 ml), under cooling with ice, N-methylmorpholine (0.14 ml) and isobutyl chloroformate (0.85 ml) were added successively. The mixture was stirred overnight at room temperature. To the reaction mixture, saturated solution of sodium hydrocarbonate (10 ml) was added. The mixture was extracted with methylene chloride (10 ml). The extract was washed by saturated solution of sodium chloride (15 ml), dried over anhydrous sodium sulfate and concentrated. The residue was purified with column chromatography on silica gel (methylene chloride:methanol=19:1) to obtain the compound (304 mg) of the present invention having the following physical data.

TLC: Rf 0.46 (chloroform:methanol=9:1);

NMR (CD$_3$OD): δ7.33–7.22 (m, 5H), 4.69 (d, J=9.0 Hz, 1H), 4.64 (dd, J=7.2, 4.8 Hz, 1H), 4.53 (d, J=9.0 Hz, 1H), 4.44 (dd, J=7.8, 6.3 Hz, 1H), 3.99–3.78 (br, 2H), 3.69–3.58 (m, 1H), 3.52 (s, 2H), 3.42–3.36 (m, 1H), 3.16 (dd, J=11.7, 4.8 Hz, 1H), 2.99–2.69 (br, 4H), 2.44 (d, J=6.9 Hz, 2H), 2.17–2.09 (m, 2H), 2.03–1.36 (m, 11H), 1.33–1.09 (m, 3H), 1.01–0.88 (m, 8H).

EXAMPLE 10 (1)

(2R)-N-(1-benzylpiperidin-4-yl)-3-cyclohexylmethylthio-2-((4R)-3-methoxycarbonylthiazolidin-4-ylcarbonylamino)propanamide

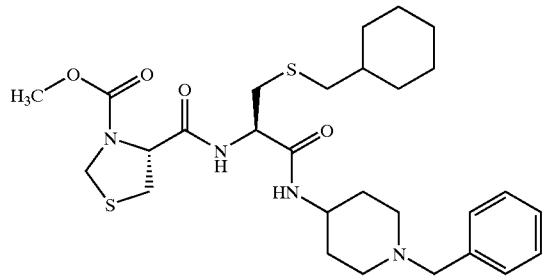

By the same procedure described in Example 10 using the compound prepared in Example 5, the compound of the present invention having the following physical data was obtained TLC: Rf 0.36 (methanol:chloroform=1:19);

NMR (CDCl$_3$): δ7.34–7.22 (m, 5H), 7.10 (d, J=7.8 Hz, 1H), 6.65 (br.s, 1H), 4.76–4.62 (m, 2H), 4.52–4.40 (m, 2H), 3.83–3.72 (m, 4H), 3.50 (s, 2H), 3.33 (dd, J=12.0, 3.9 Hz, 1H), 3.27 (dd, J=12.0, 6.9 Hz, 1H), 3.16–3.02 (m,1H), 2.86–2.72 (m, 3H), 2.48 (dd, J=12.3, 6.6 Hz, 1H), 2.43 (dd, J=12.3, 6.9 Hz, 1H), 2.17–2.08 (m, 2H), 1.94–1.36 (m, 10H), 1.32–1.05 (m, 3H), 1.00–0.84 (m, 2H).

EXAMPLE 11~EXAMPLE 11 (2)

By the same procedure described in Example 10→Example 8 using the compound prepared in Example 5, the following compounds of the present invention were obtained.

EXAMPLE 11

(2R)-N-(1-benzylpiperidin-4-yl)-3-cyclohexylmethylthio-2-((4R)-3-pivaloylthiazolidin-4-ylcarbonylamino)propanamide.hydrochloride

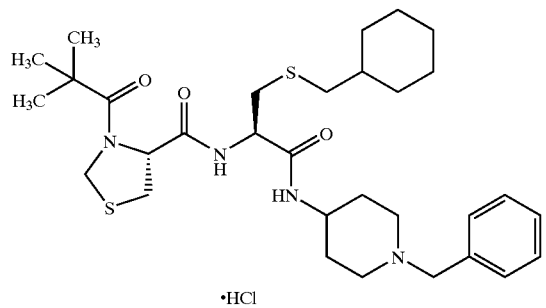

TLC: Rf 0.49 (chloroform:methanol=9:1);

NMR (DMSO-d$_6$, 100° C.): δ10.94–10.63 (br, 1H), 8.05–7.74 (br, 2H), 7.67–7.57 (m, 2H), 7.45–7.43 (m, 3H), 5.01 (dd, J=7.5, 4.5 Hz, 1H), 4.98 (d, J=9.0 Hz, 1H), 4.53 (d, J=9.0 Hz, 1H), 4.44–4.33 (br, 1H), 4.30–4.15 (br, 2H), 3.83–3.66 (br, 1H), 3.38–3.20 (m, 3H), 3.09 (dd, J=11.5, 4.5 Hz, 1H), 3.06–2.92 (br, 2H), 2.85–2.72 (br, 2H), 2.43 (d, J=6.5 Hz, 2H), 2.12–1.84 (br, 4H), 1.77–1.58 (m, 5H), 1.46–1.38 (m, 1H), 1.27–1.09 (m, 12H), 0.99–0.91 (m, 2H).

EXAMPLE 11 (1)

(2R)-N-(1-benzylpiperidin-4-yl)-3-cyclohexylmethylthio-2-((4R)-3-(3-methylbutyryl)thiazolidin-4-ylcarbonylamino)propanamide.hydrochloride

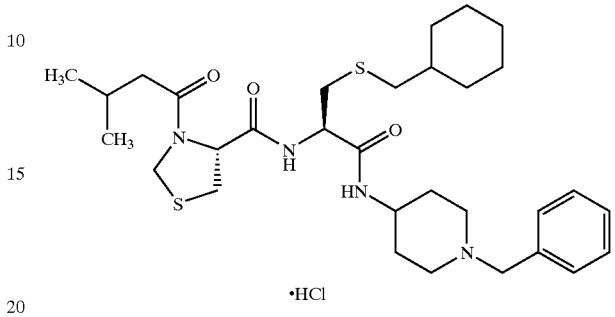

TLC: Rf 0.51 (chloroform:methanol=9:1);

NMR (DMSO-d$_6$, 100° C.): δ10.89–10.60 (br, 1H), 8.14–7.74 (br, 2H), 7.62–7.60 (m, 2H), 7.48–7.43 (m, 3H), 4.85 (dd, J=7.0, 4.5 Hz, 1H), 4.80 (d, J=9.5 Hz, 1H), 4.58–4.33 (br, 2H), 4.32–4.16 (br, 2H), 3.82–3.66 (br, 1H), 3.39–3.24 (br, 3H), 3.14–3.11 (m, 1H), 3.09–2.92 (br, 2H), 2.87–2.69 (br, 2H), 2.43 (d, J=7.0 Hz, 2H), 2.32–2.14 (br, 2H), 2.09–1.83 (m, 5H), 1.77–1.57 (m, 5H), 1.47–1.38 (m, 1H), 1.26–1.10 (m, 3H), 0.99–0.92 (m, 8H).

EXAMPLE 11 (2)

(2R)-N-(1-benzylpiperidin-4-yl)-3-cyclohexylmethylthio-2-((4R)-3-(2-methylpropionyl)thiazolidin-4-ylcarbonylamino)propanamide.hydrochloride

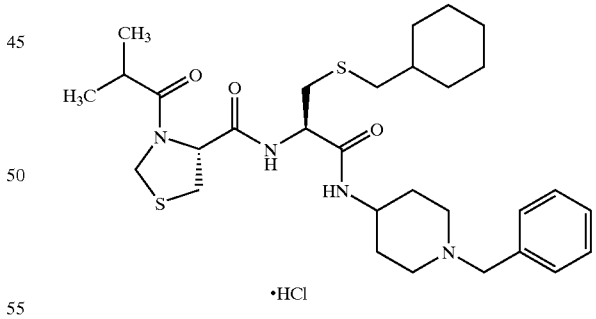

TLC: Rf 0.52 (chloroform:methanol=9:1);

NMR (DMSO-d$_6$, 100° C.): δ10.92–10.65 (br, 1H), 8.06–7.71 (br, 2H), 7.62–7.60 (m, 2H), 7.45–7.43 (m, 3H), 4.88–4.82 (m, 2H), 4.56–4.46 (m, 1H), 4.44–4.33 (br, 1H), 4.31–4.14 (br, 2H), 3.83–3.72 (br, 1H), 3.40–3.26 (br, 3H), 3.16–3.12 (m, 1H), 3.10–2.92 (br, 2H), 2.87–2.69 (br, 2H), 2.51–2.48 (m, 1H), 2.43 (d, J=6.5 Hz, 2H), 2.00–1.83 (m, 9H), 1.46–1.38 (m, 1H), 1.26–0.91 (m, 11H).

EXAMPLE 12

(2R)-N-(2-hydroxyethyl)-N-(1-benzylpiperidin-4-yl)-3-cyclohexylmethylthio-2-((4R)-3-t-butoxycarbonylthiazolidin-4-ylcarbonylamino)propanamide.hydrochloride

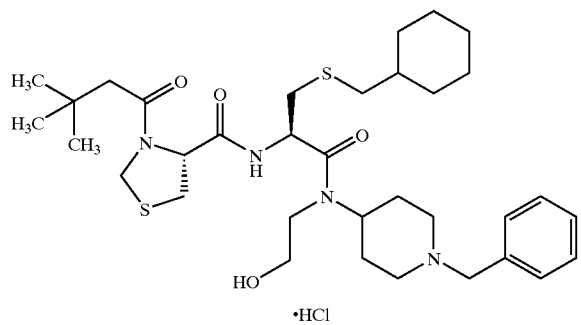

To a solution of the prepared in Example 3 (30) (160 mg) in methanol (4 ml), potassium carbonate (64 mg) was added. The mixture was stirred for 30 minutes at room temperature. To the reaction mixture, water was added. The mixture was extracted with ethyl acetate. The extract was washed by water and saturated solution of sodium chloride successively, dried over anhydrous sodium sulfate and concentrated. The residue was purified with column chromatography on silica gel (methanol:chloroform=1:40). By the same procedure described in Example 8 using the purified compound, the compound (120 mg) of the present invention having the following physical data was obtained.

TLC: Rf 0.34 (methanol:chloroform=1:19);

NMR (CD$_3$OD): δ7.49 (s, 5H), 5.19–4.93 (m, 1H), 4.66–4.54 (m, 2H), 4.49–4.43 (m, 1H), 4.34–3.98 (m, 3H), 3.84–3.27 (m, 8H), 3.22–2.87 (m, 4H), 2.78–2.64 (m, 1H), 2.47–2.28 (m, 3H), 2.13–1.60 (m, 8H), 1.53–1.09 (m, 12H), 1.01–0.85 (m, 3H).

EXAMPLE 12 (1)

(4R)-N-((1R)-2-cyclohexylmethylthio-1-(4-benzylaminopiperidin-1-ylcarbonyl)ethyl)-3-t-butoxycarbonylthiazolidin-4-ylcarboxamide.hydrochloride

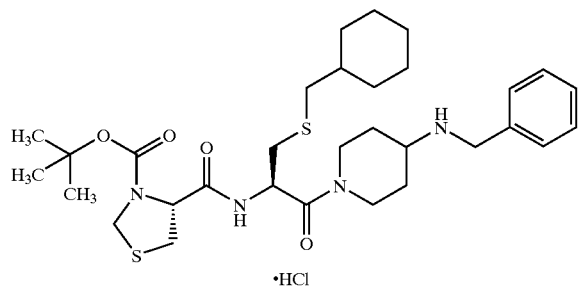

By the same procedure described in Example 12 using the compound prepared in Example 3 (32), the compound of the present invention having the following physical data was obtained.

TLC: Rf 0.47 (methanol:chloroform=1:9);

NMR (CD$_3$OD): δ7.54–7.44 (m, 5H), 5.04–4.94 (m, 1H), 4.70–4.52 (m, 3H), 4.48–4.43 (m, 1H), 4.38–4.16 (m, 3H), 3.56–3.32 (m, 2H), 3.26–3.18 (m, 1H), 3.17–3.07 (m, 1H), 2.99–2.88 (m, 1H), 2.80–2.67 (m, 2H), 2.49–2.44 (m, 2H), 2.36–2.18 (m, 2H) 1.90–0.85 (m, 22H).

EXAMPLE 13

(2R)-N-(1-benzylpiperidin-4-yl)-3-cyclohexylmethylthio-2-(((4R)-3-(3-methylbutyryl)thiazolidin-4-ylmethyl)amino)propanamide.2hydrochloride

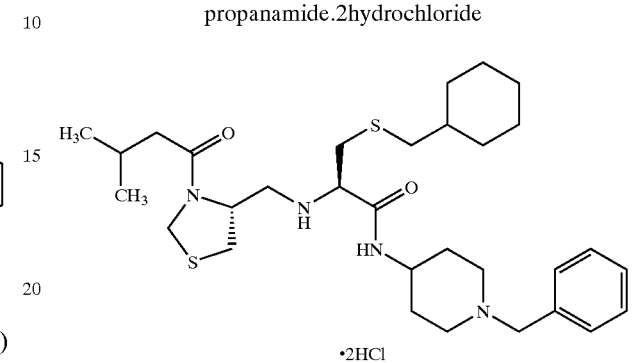

By the same procedure described in Example 4→Example 8 using the compound prepared in Reference Example 3, the compounds of the present invention having the following physical data was obtained.

TLC: Rf 0.49 (methylene chloride:methanol=93:7);

NMR (CD$_3$OD): δ7.60–7.45 (m, 5H), 4.77–4.66 (m, 2H), 4.63–4.55 (m, 1H), 4.42 and 4.32 (s, 2H), 4.24–4.18 and 4.09–3.94 (m, 2H), 3.58–3.48 (m, 2H), 3.42–3.22 (m, 4H), 3.20–2.73 (m, 4H), 2.62–2.50 (m, 2H), 2.38–2.32 (m, 2H), 2.25–2.03 (m, 3H), 1.98–1.62 (m, 7H), 1.58–1.42 (m, 1H), 1.38–1, 10 (m, 3H), 1.08–0.90 (m, 8H).

EXAMPLE 14~EXAMPLE 4 (1)

By the same procedure described in Example 1 to react the compound prepared in Reference Example 1 or the corresponding compounds with 4-amino-1-benzylpiperidine or the corresponding amine derivatives in Example 1, the following compounds of the present invention were obtained.

EXAMPLE 14

(2R)-N-(1-(4-methyl benzyl)piperidin-4-yl)-2-t-butoxycarbonylamino-3-cyclohexylmethylthiopropanamide

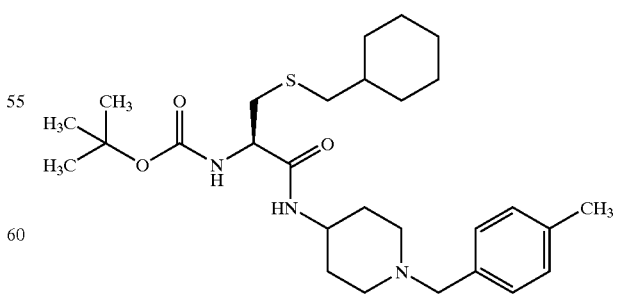

TLC: Rf 0.26 (methanol:chloroform=1:19);

NMR (CD$_3$OD): δ7.21–7.10 (m, 4H), 4.16–4.09 (m, 1H), 3.73–3.58 (m, 1H), 3.47 (s, 2H), 2.89–2.77 (m, 3H), 2.66

(dd, J=13.6, 7.8 Hz, 1H), 2.43 (d, J=6.8 Hz, 2H), 2.31 (s, 3H), 2.17–2.05 (m, 2H), 1.86–1.12 (m, 22H), 1.03–0.84 (m, 2H).

EXAMPLE 14 (1)

(2 RS)-N-(1-benzylpiperidin-4-yl)-2-t-butoxycarbonylamino-4-cyclohexylthiobutanamide

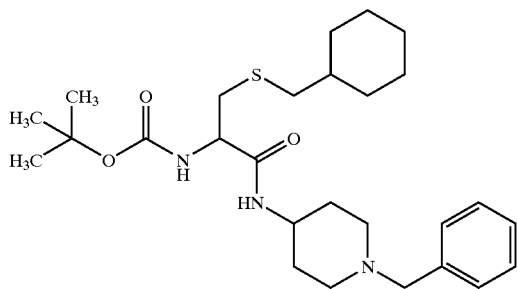

TLC: Rf 0.74 (methanol:chloroform=1:9);

NMR (CDCl$_3$): δ7.40–7.20 (m, 5H), 6.20–6.05 (br, 1H), 5.25–5.10 (br, 1H), 4.25–4.10 (m, 1H), 3.90–3.68 (m, 1H), 3.49 (s, 2H), 2.86–2.46 (m, 5H), 2.21–1.15 (m, 18H), 1.44 (s, 9H).

EXAMPLE 15

(2R)-N-(1-benzylpiperidin-4-yl)-2-t-butoxycarbonylamino-3-cyclohexylmethylsulfinylpropanamide

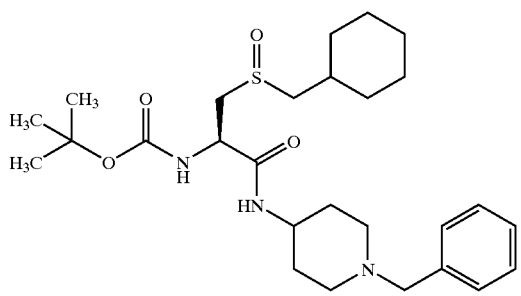

The compound prepared in Example 1 (900 mg) was dissolved into methylene chloride (20 ml). After cooling to the solution to −70° C., m-chloroperbenzoic acid (344 mg) was added thereto. The reaction mixture was stirred for 3 and half hours with warming from −70° C. to −50° C. Thereto, saturated solution of sodium thiosulfate was added. After stirring the mixture, saturated solution of sodium hydrocarbonate was added thereto. After separating organic layer, the residue was washed by saturated solution of sodium chloride, dried over anhydrous sodium sulfate. The solvent was distilled off from the mixture. The residue was purified with column chromatography on silica gel (methanol:chloroform=1:30→1:10) to obtain the compound (714 mg) of the present invention having the following physical data.

TLC: Rf 0.58 (methanol:chloroform=1:9);

NMR (CD$_3$OD): d 7.33–7.22 (m, 5H), 4.49–4.39 (m, 1H), 3.73–3.60 (m, 1H), 3.51 (s, 2H), 3.28–3.20 (m, 1H), 3.06–2.73 (m, 4H), 2.63 (dd, J=12.9, 9.0 Hz, 1H), 2.20–2.08 (m, 2H), 2.00–1.02 (m, 15H), 1.44 (s, 9H).

EXAMPLE 16~EXAMPLE 16 (20)

By the same procedure described in Reference Example 3→Example 2 (in Example 2, (4R)-3-t-butoxycarbonylthiazolidin-4-ylcarboxylic acid or the corresponding derivatives were used) using the compound prepared in Example 1, Example 1 (1), Example 1 (2), Example 1 (12), Example 14, Example 14 (1) or Example 15 and then, if necessary, by the same procedure described in Example 8, the following compounds of the present invention were obtained.

EXAMPLE 16

(2R)-N-(1-benzylpiperidin-4-yl)-3-cyclohexylmethylthio-2-((2S)-1-t-butoxycarbonyl-1,2,3,6-tetrahydropyridin-2-ylcarbonylamino)propanamide.hydrochloride

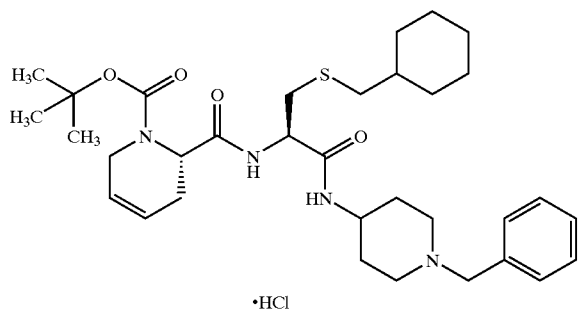

TLC: Rf 0.29 (methanol:chloroform=1:19);

NMR (CD$_3$OD): δ8.33–8.16 (m, 1H), 7.90–7.86 (m, 1H), 7.55–7.44 (m, 5H), 5.80–5.60 (m, 2H), 4.46–4.23 (m, 3H), 4.16–3.76 (m, 3H), 3.58–3.00 (m, 4H), 2.91–2.35 (m, 6H), 2.18–1.96 (m, 2H), 1.88–1.08 (m, 20H), 1.02–0.85 (m, 2H).

EXAMPLE 16 (1)

(2R)-N-(1-benzylpiperidin-4-yl)-3-cyclohexylmethylthio-2-((2S)-1-t-butoxycarbonylpiperidin-2-ylcarbonylamino)propanamide.hydrochloride

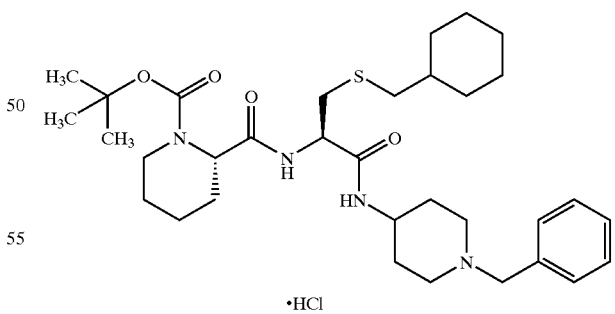

TLC: Rf 0.34 (methanol:chloroform=1:9);

NMR (CD$_3$OD): δ8.29 (br. s, 1H), 7.79 (br. s, 1H), 7.56–7.45 (m, 5H), 4.68 (d, J=3.0 Hz, 1H), 4.44 (dd, J=14.4, 7.5 Hz, 1H), 4.31 (s, 2H), 3.98–3.83 (m, 2H), 3.60–3.00 (m, 5H), 2.89 (dd, J=13.2, 6.0 Hz, 1H), 2.80–2.72 (m, 1H), 2.44 (d, J=6.9 Hz, 2H), 2.20–1.95 (m, 3H), 1.88–1.08 (m, 24H), 1.02–0.85 (m, 2H).

EXAMPLE 16 (2)

(2R)-N-(1-benzylpiperidin-4-yl)-3-cyclohexylmethylthio-2-((4S)-3-t-butoxycarbonyloxazolidin-4-ylcarbonylamino)propanamide

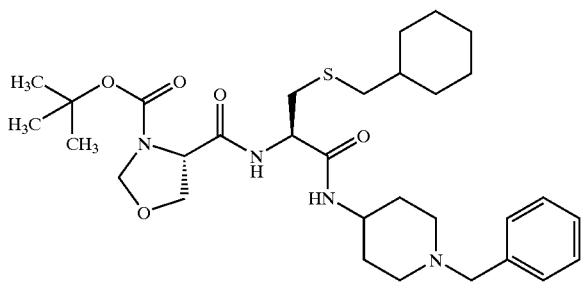

TLC: Rf 0.14 (methanol:chloroform=1:19);

NMR (CDCl$_3$): δ7.33–7.20 (m, 6H), 6.73 (br. s, 1H), 4.96 (br. s, 1H), 4.87 (d, J=4.2 Hz, 1H), 4.49 (br. s, 1H), 4.36 (t, J=6.0 Hz, 1H), 4.20 (d, J=6.0 Hz, 2H), 3.83–3.70 (m, 1H), 3.50 (s, 2H), 3.13 (br. s, 1H), 2.86–2.70 (m, 3H), 2.49–2.37 (m, 2H), 2.17–2.09 (m, 2H), 1.94–1.36 (m, 19H), 1.31–1.04 (m, 3H), 0.98–0.82 (m, 2H).

EXAMPLE 16 (3)

(2R)-N-(1-benzylpiperidin-4-yl)-3-cyclohexylmethylthio-2-((2S)-1-t-butoxycarbonylpyrrolidin-2-ylcarbonylamino)propanamide.hydrochloride

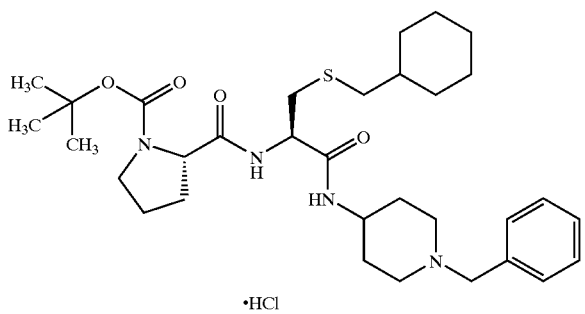

·HCl

TLC: Rf 0.56 (methanol:chloroform=1:9);

NMR (CD$_3$OD): δ8.44–7.89 (m, 2H), 7.54–7.46 (m, 5H), 4.46–4.30 (m, 3H), 4.24–4.12 (m, 1H), 4.04–3.82 (m, 1H), 3.60–3.02 (m, 6H), 2.94–2.66 (m, 2H), 2.48–2.38 (m, 2H), 2.32–0.82 (m, 28H).

EXAMPLE 16 (4)

(2R)-N-(1-benzylpiperidin-4-yl)-3-cyclohexylmethylthio-2-((2S, 4RS)-1-t-butoxycarbonyl-4-methylthiopyrrolidin-2-ylcarbonylamino)propanamide

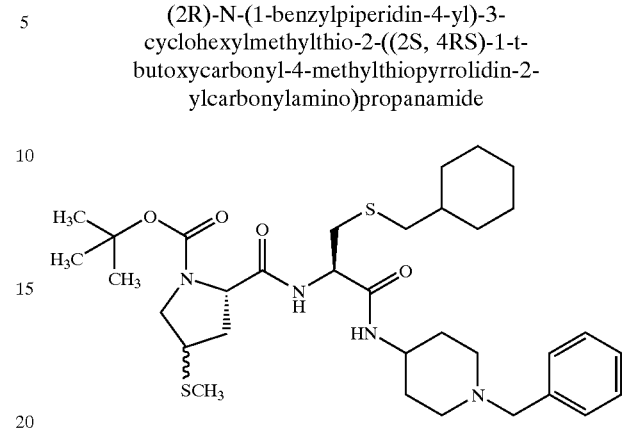

TLC: Rf 0.57 (methanol:chloroform=1:9);

NMR (CDCl$_3$): δ7.34–7.02 (m, 7H), 4.62–4.52 (m, 1H), 4.34–4.25 (m, 1H), 3.90–3.66 (m, 2H), 3.49 (s, 2H), 3.45–3.24 (m, 3H), 2.86–2.68 (m, 3H), 2.65–2.55 (m, 1H), 2.48–2.32 (m, 2H), 2.24–2.06 (m, 6H), 1.94–1.34 (m, 19H), 1.30–1.04 (m, 3H), 1.00–0.82 (m, 2H).

EXAMPLE 16 (5)

(2R)-N-(1-benzylpiperidin-4-yl)-3-cyclohexylmethylthio-2-((3S)-4-t-butoxycarbonylmorpholin-3-ylcarbonylamino)propanamide

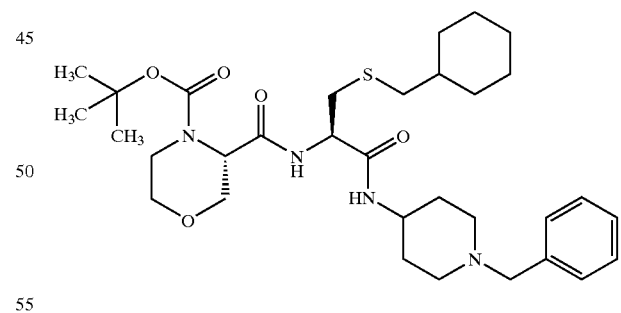

TLC: Rf 0.71 (methanol:chloroform=1:9);

NMR (CDCl$_3$): δ7.32–7.22 (m, 5H), 6.96 (d, J=7.2 Hz, 1H), 6.47 (d, J=5.4 Hz, 1H), 4.48–4.42 (m, 3H), 3.88–3.72 (m, 3H), 3.58 (dd, J=12.0, 3.9 Hz, 1H), 3.53–3.44 (m, 3H), 3.30–3.16 (m, 1H), 3.10–2.96 (m, 1H), 2.84–2.69 (m, 3H), 2.54–2.42 (m, 2H), 2.19–2.09 (m, 2H), 1.94–1.38 (m, 19H), 1.32–1.06 (m, 3H), 1.01–0.85 (m, 2H).

EXAMPLE 16 (6)

(2R)-N-(1-benzylpiperidin-4-yl)-3-cyclohexylmethylthio-2-(2-phenoxybenzoylamino)propanamide

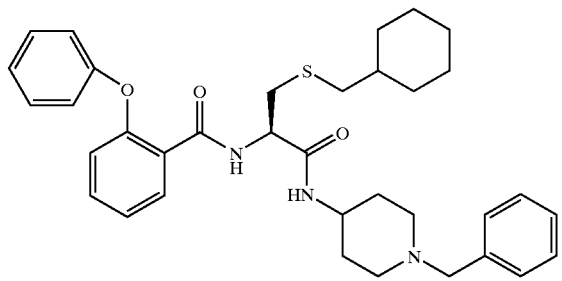

TLC: Rf 0.43 (methanol:chloroform=1:9);

NMR (CDCl$_3$): δ8.53 (d, J=7.2 Hz, 1H), 8.18 (dd, J=7.8, 1.8 Hz, 1H), 7.44–7.16 (m, 10H), 7.10–7.07 (m, 2H), 6.88 (d, J=8.4 Hz, 1H), 6.44 (d, J=8.1 Hz, 1H), 4.73–4.66 (m, 1H), 3.82–3.68 (m, 1H), 3.46 (s, 2H), 3.06 (dd, J=13.5, 4.8 Hz, 1H), 2.77–2.70 (m, 3H), 2.46 (dd, J=12.3, 6.6 Hz, 1H), 2.40 (dd, J=12.3, 6.9 Hz, 1H), 2.16–2.05 (m, 2H), 1.90–1.58 (m, 7H), 1.50–1.30 (m, 3H), 1.26–1.03 (m, 3H), 0.94–0.78 (m, 2H).

EXAMPLE 16 (7)

(2R)-N-(1-benzylpiperidin-4-yl)-3-cyclohexylmethylthio-2-(3-phenoxybenzoylamino)propanamide

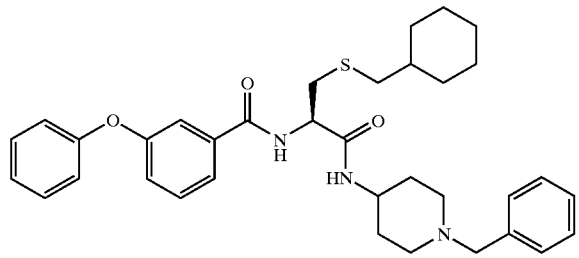

TLC: Rf 0.46 (methanol:chloroform=1:9);

NMR (CDCl$_3$): δ7.51–7.10 (m, 13H), 7.04–6.98 (m, 2H), 6.55 (d, J=7.8 Hz, 1H), 4.59–4.52 (m, 1H), 3.88–3.75 (m, 1H), 3.49 (s, 2H), 3.05 (dd, J=13.8, 4.2 Hz, 1H), 2.80–2.72 (m, 3H), 2.58 (dd, J=12.6, 6.9 Hz, 1H), 2.53 (dd, J=12.6, 6.9 Hz, 1H), 2.21–2.11 (m, 2H), 1.98–1.40 (m, 10H), 1.31–1.05 (m, 3H), 1.01–0.86 (m, 2H).

EXAMPLE 16 (8)

(2R)-N-(1-benzylpiperidin-4-yl)-3-cyclohexylmethylthio-2-(4-phenoxybenzoylamino)propanamide

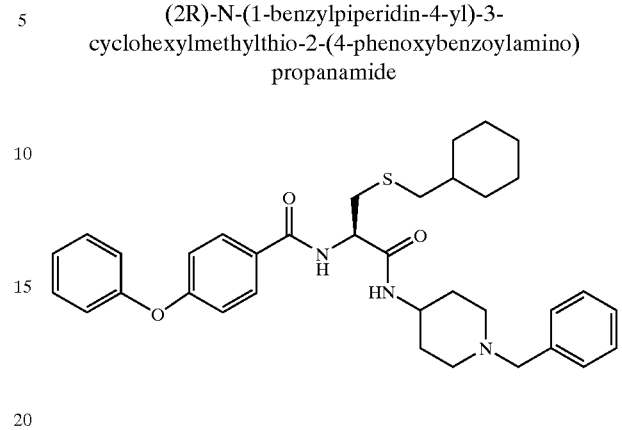

TLC: Rf 0.37 (methanol:chloroform=1:19);

NMR (CDCl$_3$): δ7.83–7.76 (m, 2H), 7.44–7.14 (m, 9H), 7.08–6.97 (m, 4H), 6.60 (d, J=7.8 Hz, 1H), 4.64–4.54 (m, 1H), 3.92–3.74 (m, 1H), 3.49 (s, 2H), 3.07 (dd, J=13.6, 4.4 Hz, 1H), 2.84–2.72 (m, 3H), 2.60 (dd, J=12.8, 6.6 Hz, 1H), 2.53 (dd, J=12.8, 7.0 Hz, 1H), 2.23–2.08 (m, 2H), 2.00–0.83 (m, 15H).

EXAMPLE 16 (9)

(2R)-N-(1-benzylpiperidin-4-yl)-3-cyclohexylmethylthio-2-(3-t-butoxycarbonylthiophn-4-ylcarbonylamino)propanamide

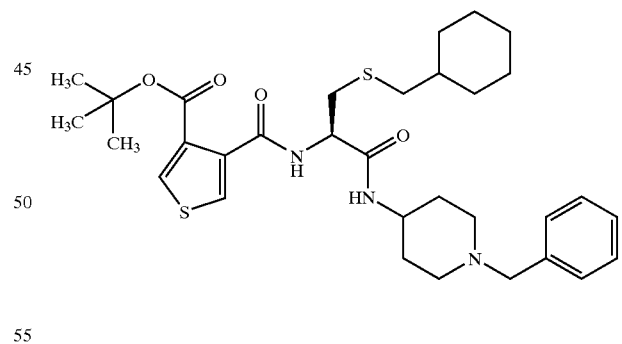

TLC: Rf 0.47 (methanol:chloroform=1:19);

NMR (CDCl$_3$): δ8.87 (d, J=7.8 Hz, 1H), 8.11 (d, J=3.6 Hz, 1H), 8.06 (d, J=3.6 Hz, 1H), 7.30–7.20 (m, 5H), 7.01 (d, J=8.1 Hz, 1H), 4.76–4.69 (m, 1H), 3.88–3.76 (m, 1H), 3.48 (s, 2H), 3.12 (dd, J=13.8, 6.0 Hz, 1H), 2.95 (dd, J=13.8, 6.3 Hz, 1H), 2.81–2.76 (m, 2H), 2.49 (dd, J=12.6, 6.9 Hz, 1H), 2.44 (dd, J=12.6, 6.6 Hz, 1H), 2.18–2.08 (m, 2H), 1.96–1.36 (m, 19H), 1.28–1.03 (m, 3H), 0.98–0.8 2 (m, 2H).

EXAMPLE 16 (10)

(2R)-N-(1-benzylpiperidin-4-yl)-3-cyclohexylmethylthio-2-(2-t-butoxycarbonylbenzoylamino)propanamide

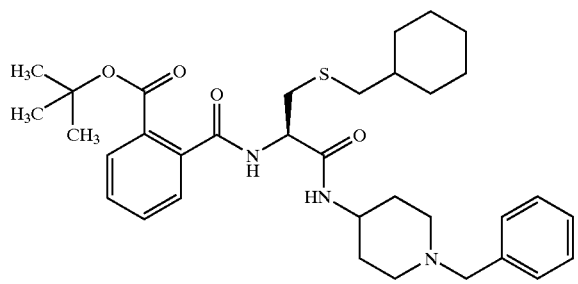

TLC: Rf 0.46 (methanol:chloroform=1:19);

NMR (CDCl₃): δ7.93–7.90 (m, 1H), 7.58–7.41 (m, 4H), 7.33–7.20 (m, 5H), 6.53 (d, J=7.8 Hz, 1H), 4.73 (dt, J=7.8, 5.7 Hz, 1H), 3.90–3.76 (m, 1H), 3.54–3.45 (m, 2H), 3.27 (dd, J=13.8, 5.7 Hz, 1H), 2.93 (dd, J=13.8, 6.0 Hz, 1H), 2.86–2.81 (m, 2H), 2.54–2.41 (m, 2H), 2.16–2.05 (m, 2H), 1.99–1.38 (m, 19H), 1.30–1.04 (m, 3H), 0.99–0.84 (m, 2H).

EXAMPLE 16 (11)

(2R)-N-(1-benzylpiperidin-4-yl)-3-cyclohexylmethylthio-2-(4-t-butoxycarbonylbenzoylamino)propanamide

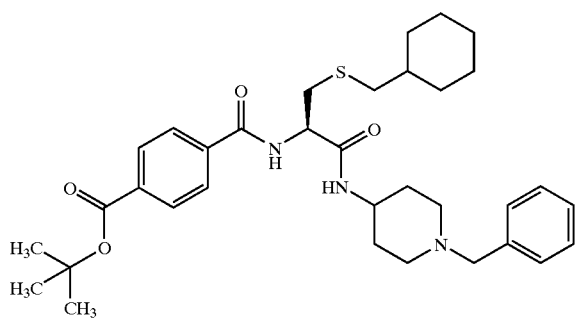

TLC: Rf 0.40 (methanol:chloroform=1:19);

NMR (CDCl₃): δ8.06–8.03 (m, 2H), 7.86–7.83 (m, 2H), 7.34–7.22 (m, 5H), 6.57 (d, J=7.8 Hz, 1H), 4.61–4.54 (m, 1H), 3.90–3.78 (m, 1H), 3.50 (s, 2H), 3.08 (dd, J=14.1, 4.5 Hz, 2H), 2.81–2.73 (m, 3H), 2.65–2.53 (m, 2H), 2.23–2.11 (m, 2H), 1.99–1.43 (m, 19H), 1.33–1.08 (m, 3H), 1.05–0.89 (m, 2H).

EXAMPLE 16 (12)

(2R)-N-(1-benzylpiperidin-4-yl)-3-cyclohexylmethylthio-2-(3-t-butoxycarbonylbenzoylamino)propanamide

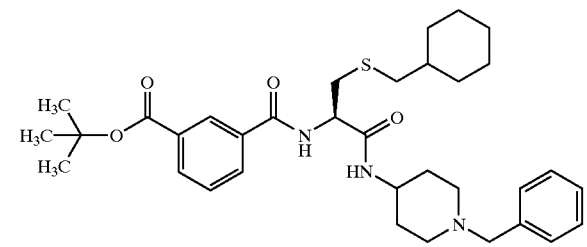

TLC: Rf 0.39 (methanol:chloroform=1:19);

NMR (CDCl₃): δ8.39 (t, J=1.8 Hz, 1H), 8.17–8.12 (m, 1H), 8.01–7.97 (m, 1H), 7.51 (t, J=7.4 Hz, 1H), 7.34–7.24 (m, 5H), 6.56 (d, J=8.4 Hz, 1H), 4.65–4.55 (m, 1H), 3.93–3.75 (m, 1H), 3.49 (s, 2H), 3.08 (dd, J=14.0, 4.8 Hz, 1H), 2.85–2.72 (m, 3H), 2.66–2.49 (m, 2H), 2.25–2.09 (m, 2H), 2.03–1.40 (m, 19H), 1.35–0.85 (m, 5H).

EXAMPLE 16 (13)

(2R)-N-(1-benzylpiperidin-4-yl)-3-cyclohexylmethylthio-2-(1-phenylcyclohexylcarbonylamino)propanamide

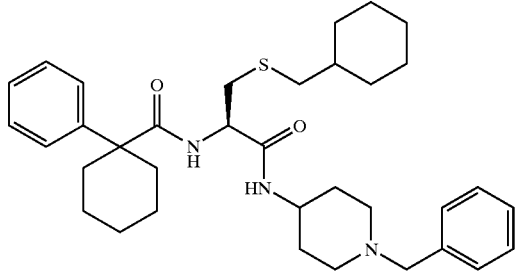

TLC: Rf 0.67 (methanol:chloroform=1:9);

NMR (CDCl₃): δ7.45–7.22 (m, 10H), 6.29 (d, J=7.0 Hz, 1H), 6.18 (d, J=8.0 Hz, 1H), 4.41–4.31 (m, 1H), 3.78–3.57 (m, 1H), 3.48 (s, 2H), 2.88 (dd, J=14.0, 5.4 Hz, 1H), 2.76–2.69 (m, 2H), 2.60 (dd, J=14.0, 7.2 Hz, 1H), 2.42–2.22 (m, 4H), 2.18–0.79 (m, 25H).

EXAMPLE 16 (14)

(2R)-N-(1-(4-methylbenzyl)piperidin-4-yl)-3-cyclohexylmethylthio-2-((4R)-3-t-butoxycarbonylthiazolidin-4-ylcarbonylamino)propanamide

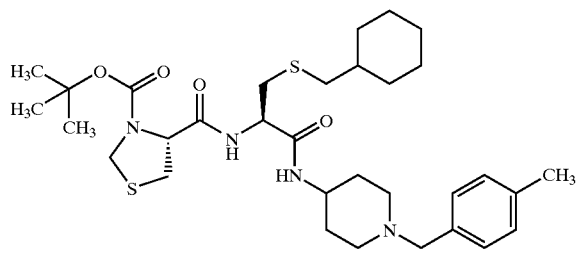

TLC: Rf 0.49 (methanol:chloroform=1:9);

NMR (CD$_3$OD): δ7.18 (d, J=8.1 Hz, 2H), 7.12 (d, J=8.1 Hz, 2H), 4.64–4.53 (m, 2H), 4.48–4.42 (m, 2H), 3.69–3.59 (m, 1H), 3.47 (s, 2H), 3.39–3.33 (m, 1H), 3.13 (dd, J=12.0, 4.8 Hz, 1H), 2.91–2.68 (br, 4H), 2.44 (d, J=6.9 Hz, 2H), 2.31 (s, 3H), 2.15–2.07 (m, 2H), 1.88–1.77 (br, 4H), 1.76–1.36 (m, 15H), 1.33–1.09 (m, 3H), 1.00–0.87 (m, 2H).

EXAMPLE 16 (15)

(2RS)-N-(1-benzylpiperidin-4-yl)-4-cyclohexylthio-2-((4R)-3-t-butoxycarbonylthiazolidin-4-ylcarbonylamino)butanamide

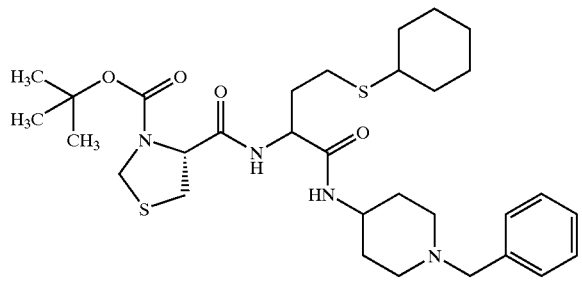

TLC: Rf 0.50 (methanol:chloroform=1:9);

NMR (CD$_3$OD): δ7.40–7.20 (m, 5H), 4.65–4.40 (m, 4H), 3.75–3.55 (m, 1H), 3.55 and 3.54 (s, 2H), 3.45–3.28 (m, 1H), 3.11 (dd, J=12.0, 4.6 Hz, 1H), 2.95–2.80 (m, 2H), 2.73–2.40 (m, 3H), 2.25–1.20 (m, 27H).

EXAMPLE 16 (16)

(2R)-N-(1-benzylpiperidin-4-yl)-3-cyclohexylmethylsulfinyl-2-((4R)-3-t-butoxycarbonylthiazolidin-4-ylcarbonylamino)propanamide

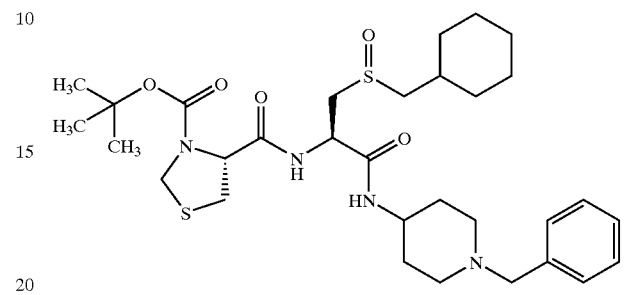

TLC: Rf 0.55 (methanol:chloroform=1:9);

NMR (CD$_3$OD): δ7.34–7.20 (m, 5H), 4.84–4.70 (m, 1H), 4.65–4.45 (m, 3H), 3.74–3.56 (m,1H), 3.51 (s, 2H), 3.44–3.00 (m, 4H), 2.92–2.59 (m, 4H), 2.20–1.00 (m, 17H), 1.49 (s, 9H).

EXAMPLE 16 (17)

(2S)-N-(1-benzylpiperidin-4-yl)-3-cyclohexylmethoxy-2-((4S)-3-t-butoxycarbonyloxazolidin-4-ylcarbonylamino)propanamide

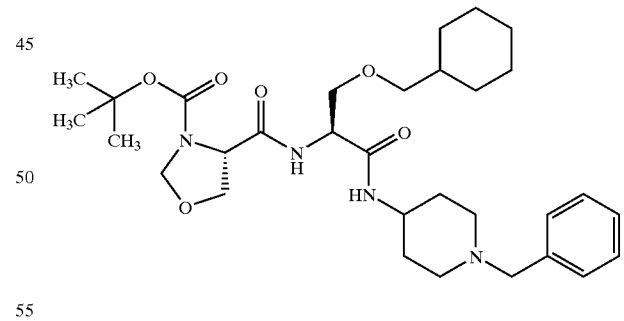

TLC: Rf 0.29 (methanol:chloroform=1:19);

NMR (CD$_3$OD): δ7.32–7.22 (m, 5H), 4.90–4.86 (m, 2H), 4.51–4.43 (br, 1H), 4.33 (dd, J=7.5, 4.5 Hz, 1H), 4.22 (t, J=7.5 Hz, 1H), 4.07–3.96 (br, 1H), 3.71–3.56 (m, 3H), 3.51 (s, 2H), 3.25 (dd, J=9.0, 6.3 Hz, 1H), 3.23 (dd, J=9.0, 6.6 Hz, 1H), 2.89–2.80 (br, 2H), 2.13 (dt, J=11.7, 2.4 Hz, 2H), 1.84–1.39 (m, 19H), 1.31–1.09 (m, 3H), 0.99–0.86 (m, 2H).

EXAMPLE 16 (18)

(2R)-N-(2-benzylaminoethyl)-3-cyclohexylmethylthio-2-((4R)-3-isopropyloxycarbonylthiazolidin-4-ylcarbonylamino)propanamide.hydrochloride

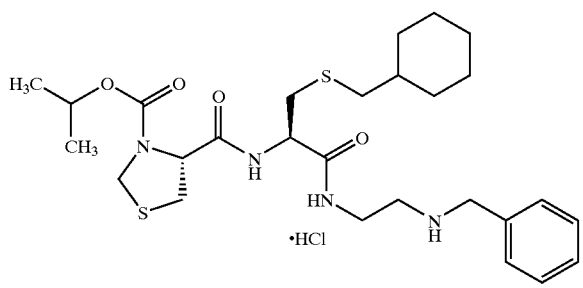

TLC: Rf 0.50 (methanol:chloroform=1:9);

NMR (CD$_3$OD): δ7.52–7.40 (m, 5H), 4.94–4.82 (m, 1H), 4.67–4.64 (m, 2H), 4.48 (d, J=9.0 Hz, 1H), 4.53–4.28 (br, 1H), 4.22 (d, J=13.2 Hz, 1H), 4.19 (d, J=13.2 Hz, 1H), 3.67–3.34 (m, 3H), 3.23–3.09 (m, 3H), 3.01–2.77 (m, 2H), 2.45 (d, J=7.2 Hz, 2H), 1.86–1.63 (m, 5H), 1.52–1.09 (m, 10H), 1.01–0.88 (m, 2H).

EXAMPLE 16 (19)

(2R)-N-(2-benzylaminoethyl)-3-cyclohexylmethylthio-2-((4R)-3-(3-methylbutyryl)thiazolidin-4-ylcarbonylamino)propanamide.hydrochloride

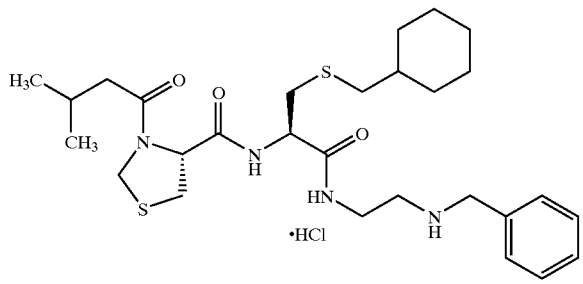

TLC: Rf 0.46 (methanol:chloroform=1:9);

NMR (DMSO-d$_6$): δ9.40–9.00 (br, 2H), 8.25–7.90 (br, 2H), 7.56–7.55 (m, 2H), 7.43–7.40 (m, 3H), 4.88–4.80 (m, 2H), 4.47–4.36 (m, 2H), 4.16 (s, 2H), 3.53–3.41 (m, 2H), 3.37–3.27 (br, 1H), 3.20–3.14 (m, 1H), 3.05–2.94 (m, 2H), 2.91 (dd, J=13.5, 6.0 Hz, 1H), 2.78 (dd, J=13.5, 7.5 Hz, 1H), 2.44 (d, J=7.0 Hz, 2H), 2.30–2.15 (br, 2H), 2.09–2.01 (m, 1H), 1.78–1.58 (m, 5H), 1.47–1.39 (m, 1H), 1.26–1.09 (m, 3H), 0.99–0.90 (m, 8H).

EXAMPLE 16 (20)

(2R)-N-(1-(4-hydroxybenzyl)piperidin-4-yl)-3-cyclohexylmethylthio-2-((4R)-3-t-butoxycarbonylthiazolidin-4-ylcarbonylamino)propanamide

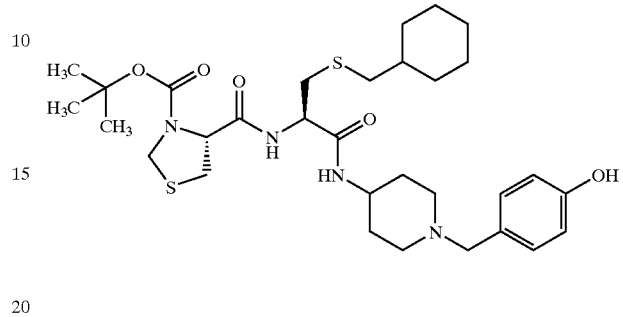

TLC: Rf 0.31 (methanol:chloroform=1:9);

NMR (CD$_3$OD): δ7.12 (d, J=8.4 Hz, 2H), 6.73 (d, J=8.4 Hz, 2H), 4.64–4.53 (m, 2H), 4.48–4.42 (m, 2H), 3.69–3.61 (m, 1H), 3.43–3.33 (m, 3H), 3.14 (dd, J=12.0 4.8 Hz, 1H), 2.90–2.71 (br, 4H), 2.44 (d, J=6.9 Hz, 2H), 2.15–2.08 (m, 2H), 1.89–1.77 (br, 4H), 1.75–1.37 (m, 15H), 1.33–1.09 (m, 3H), 1.00–0.88 (m, 2H).

EXAMPLE 17

(4R)-N-((1R)-2-cyclohexylmethylthio-1-(4-benzylaminopiperidin-1-ylcarbonyl)ethyl)-3-(3-methylbutyryl)thiazolidin-4-ylcarboxamide.hydrochloride

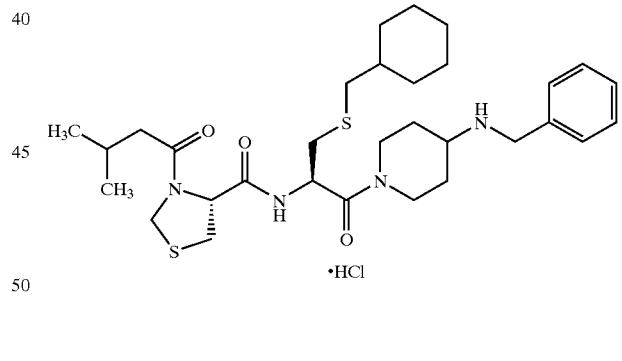

By the same procedure described in Example 5→Example 10 (in Example 10, isovaleryl chloride was used instead of isobutyl chloroformate)→Example 12 using the compound prepared in Example 3 (32), the compound of the present invention having the following physical data was obtained.

TLC: Rf 0.32 (methanol:methylene chloride=7:93);

NMR (CD$_3$OD): δ7.55–7.43 (m, 5H), 5.07–4.93 (m, 1H), 4.90–4.72 (m, 2H), 4.70–4.50 (m, 2H), 4.42–4.10 (m, 3H), 3.56–3.08 (m, 4H), 3.00–2.87 (m, 1H), 2.82–2.66 (m, 2H), 2.50–2.00 (m, 7H), 1.90–1.60 (m, 6H), 1.60–1.36 (m, 2H), 1.36–1.09 (m, 3H), 1.04–0.88 (m, 8H).

EXAMPLE 18

(4R)-N-((1R)-2-cyclohexylmethylthio-1-(4-benzylaminopiperidin-1-ylcarbonyl)ethyl)-3-isopropyloxycarbonylthiazolidin-4-ylcarboxamide.hydrochloride

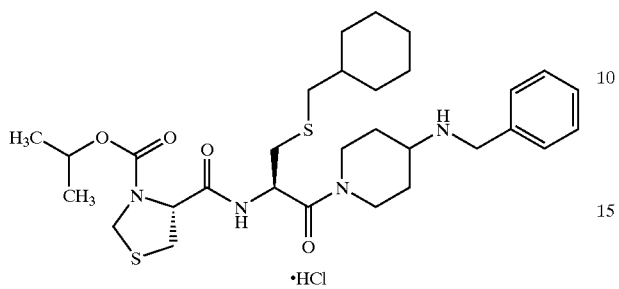

By the same procedure described in Reference Example 3→Example 2 (in Example 2, (4R)-3-isopropyloxycarbonylthiazolidin-4-ylcarboxylic acid was used instead of (4R)-3-t-butoxycarbonylthiazolidin-4-ylcarboxylic acid)→Example 12 using the compound prepared in Example 1 (29), the compound of the present invention having the following physical data was obtained.

TLC: Rf 0.38 (methanol:methylene chloride=7:93);

NMR (CD$_3$OD): δ7.58–7.40 (m, 5H), 5.05–4.94 (m, 1H), 4.93–4.80 (m, 1H), 4.73–4.57 (m, 3H), 4.48 (d, J=9 Hz, 1H), 4.36–4.16 (m, 3H), 3.56–3.05 (m, 4H), 3.01–2.87 (m, 1H), 2.80–2.66 (m, 2H), 2.50–2.42 (m, 2H), 2.34–2.17 (m, 2H), 1.90–1.61 (m, 6H), 1.61–1.37 (m, 2H), 1.36–1.10 (m, 9H), 1.03–0.88 (m, 2H).

EXAMPLE 19

(2R)-N-(1-benzylpiperidin-4-yl)-3-cyclohexylmethylthio-2-((4R)-2,2-dimethyl-3-(3-methylbutyryl)thiazolidin-4-yl carbonylamino)propanamide.hydrochloride

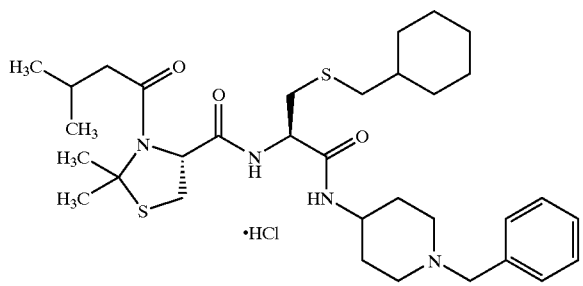

By the same procedure described in Example 2 (in Example 2, (4R)-2,2-dimethylthiazolidin-4-ylcarboxylic acid.hydrochloride was used instead of (4R)-3-t-butoxycarbonylthiazolidin-4-ylcarboxylic acid)→Example 10 (in Example 10, isovaleryl chloride was used instead of isobutyl chloroformate)→Example 8 using the compound prepared in Reference Example 3, the compound of the present invention having the following physical data was obtained TLC: Rf 0.26 (methanol:methylene chloride=7:93);

NMR (CD$_3$OD): δ7.58–7.43 (m, 5H), 4.95–4.88 and 4.50–4.28 (m, 1H), 4.50–4.28 (m, 3H), 4.10–3.83 (m, 1H), 3.56–3.33 (m, 3H), 3.20–3.05 (m, 3H), 2.95–2.70 (m, 2H), 2.50–2.38 (m, 2H), 2.27–1.98 (m, 5H), 1.90–1.60 (m, 10H), 1.53–1.35 (m, 1H), 1.35–1.08 (m, 3H), 1.05–0.85 (m, 11H).

EXAMPLE 20~EXAMPLE 20 (2)

By the same procedure described in Example 8 using the compound prepared in Example 3 (8), Example 3 (9) or Example 3 (27), the following compounds of the present invention were obtained.

EXAMPLE 20

(2S)-N-(1-benzylpiperidin-4-yl)-3-cyclohexylmethoxy-2-((4R)-3-t-butoxycarbonylthiazolidin-4-ylcarbonylamino)propanamide.hydrochloride

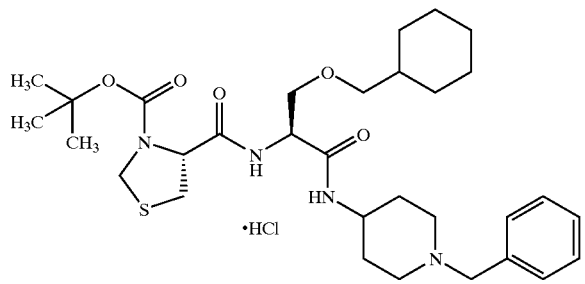

TLC: Rf 0.39 (methanol:methylene chloride=1:19);

NMR (CD$_3$OD): δ7.60–7.43 (m, 5H), 4.65–4.52 (m, 2H), 4.52–4.37 (m, 2H), 4.31 (s, 2H), 4.02–3.85 (m, 1H), 3.79–3.05 (m, 10H), 2.18–2.03 (m, 2H), 1.96–1.62 (m, 7H), 1.60–1.36 (m, 10H), 1.33–1.10 (m, 3H), 1.02–0.83 (m, 2H).

EXAMPLE 20 (1)

(2R)-N-(2-benzylamin oethyl)-3-cyclohexylmethylthio-2-((4R)-3-t-butoxycarbonylthiazolidin-4-ylcarbonylamino)propanamide.hydrochloride

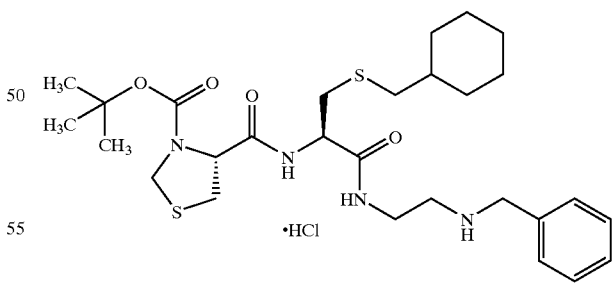

TLC: Rf 0.50 (methanol:chloroform=1:9);

NMR (CD$_3$OD): δ7.53–7.43 (m, 5H), 4.63–4.59 (m, 2H), 4.45 (d, J=9.3 Hz, 1H), 4.39–4.28 (br, 1H), 4.27 (d, J=12.9 Hz, 1H), 4.23 (d, J=12.9 Hz, 1H), 3.74–3.32 (br, 3H), 3.25–3.11 (m, 3H), 2.99–2.74 (br, 2H), 2.45 (d, J=6.9 Hz, 2H), 1.85–1.63 (m, 5H), 1.47–1.37 (m, 10H), 1.34–1.09 (m, 3H), 1.02–0.89 (m, 2H).

EXAMPLE 20 (2)

(2R)-N-(1-benzylpiperidin-4-yl)-3-cyclopentylmethylthio-2-((4R)-3-t-butoxycarbonylthiazolidin-4-ylcarbonylamino)propanamide.hydrochloride

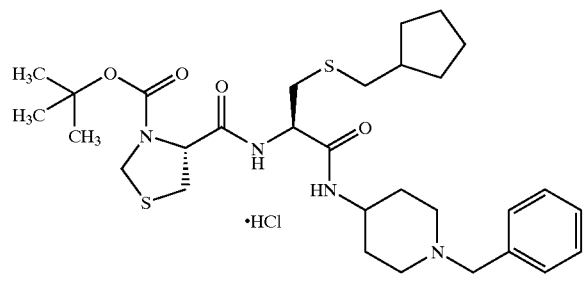

TLC: Rf 0.39 (methanol:methylene chloride=1:19);

NMR (CD$_3$OD): δ7.60–7.43 (m, 5H), 4.66–4.55 (m, 2H), 4.51–4.39 (m, 2H), 4.31 (s, 2H), 4.02–3.84 (m, 1H), 3.58–3.02 (m, 6H), 2.98–2.72 (m, 2H), 2.57 (d, J=8 Hz, 2H), 2.20–1.95 (m, 3H), 1.90–1.71 (m, 3H), 1.71–1.35 (m, 14H), 1.33–1.13 (m, 2H).

EXAMPLE 21~EXAMPLE 21 (5)

By converting the compounds prepared in Example 2, Example 3 (8) or Example 3 (9) into the corresponding salts according to a known method, the following compounds of the present invention were obtained.

EXAMPLE 21

(2R)-N-(1-benzylpiperidin-4-yl)-3-cyclohexylmethylthio-2-((4R)-3-t-butoxycarbonylthiazolidin-4-ylcarbonylamino)propanamide.hydrobromide

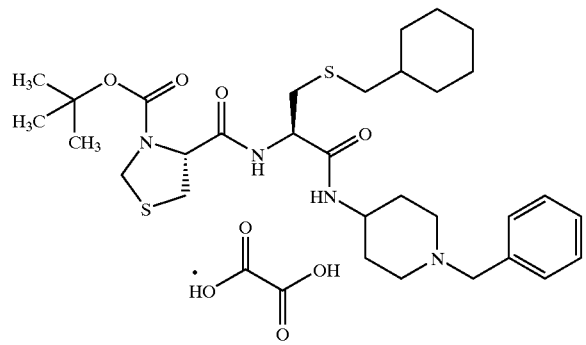

TLC: Rf 0.69 (methanol:chloroform=1:14);

NMR (CD$_3$OD): δ7.53–7.43 (m, 5H), 4.62 (d, J=9.2 Hz, 1H), 4.57 (dd, J=7.2, 4.5 Hz, 1H), 4.47 (d, J=9.2 Hz, 1H), 4.40–4.39 (m, 1H), 4.30 (s, 2H), 3.98–3.85 (m, 1H), 3.52–3.30 (m, 3H), 3.20–3.05 (m, 3H), 2.92–2.71 (m, 2H), 2.44 (d, J=6.9 Hz, 2H), 2.15–2.03 (m, 2H), 1.93–1.60 (m, 7H), 1.52–1.08 (m, 4H), 1.46 (s, 9H), 1.02–0.86 (m, 2H).

EXAMPLE 21 (1)

(2S)-N-(1-benzylpiperidin-4-yl)-3-cyclohexylmethoxy-2-((4R)-3-t-butoxycarbonylthiazolidin-4-ylcarbonylamino)propanamide.hydrobromide

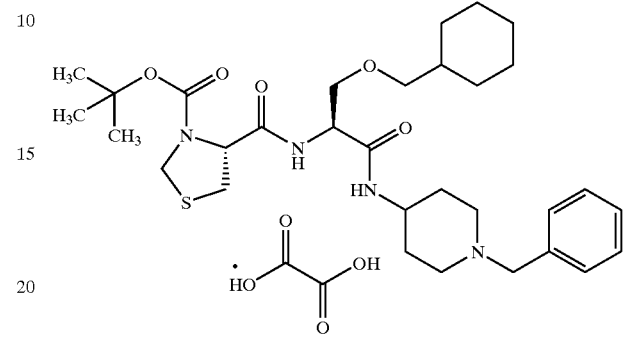

TLC: Rf 0.44 (methanol:chloroform=1:19);

NMR (CD$_3$OD): δ7.48 (S, 5H), 4.64–4.36 (m, 4H), 4.29 (s, 2H), 4.01–3.84 (m, 1H), 3.80–3.04 (m, 10H), 2.18–0.80 (m, 24H).

EXAMPLE 21 (2)

(2R)-N-(2-benzylaminoethyl)-3-cyclohexylmethylthio-2-((4R)-3-t-butoxycarbonylthiazolidin-4-ylcarbonylamino)propanamide.hydrobromide

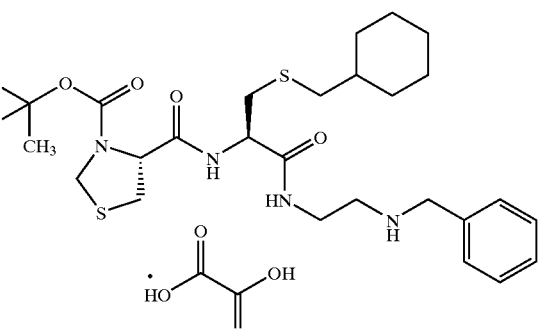

TLC: Rf 0.45 (methanol:chloroform=1:9);

NMR (DMSO-d$_6$): δ8.51–8.14 (br, 2H), 7.48–7.38 (m, 5H), 4.59–4.45 (m, 2H), 4.36–4.30 (m, 2H), 4.13 (s, 2H), 3.41–3.24 (m, 3H), 3.03–2.86 (m, 3H), 2.79–2.55 (m, 2H), 2.38 (d, J=6.9 Hz, 2H), 1.75–1.56 (m, 5H), 1.41–1.24 (m, 10H), 1.23–1.03 (m, 3H), 0.92–0.80 (m, 2H).

EXAMPLE 21 (3)

(2R)-N-(1-benzylpiperidin-4-yl)-3-cyclohexylmethylthio-2-((4R)-3-t-butoxycarbonylthiazolidin-4-ylcarbonylamino)propanamide.fumaric acid salt

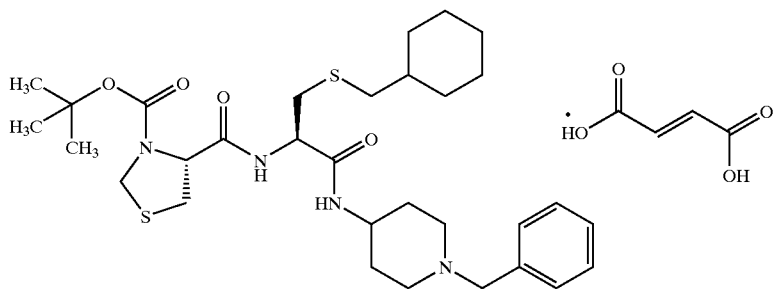

TLC: Rf 0.69 (methanol:chloroform=1:14);
NMR (CD$_3$OD): δ7.50–7.42 (m, 5H), 6.70 (s, 2H), 4.62 (d, J=9.2 Hz, 1H), 4.57 (dd, J=7.1, 4.7 Hz, 1H), 4.47 (d, J=9.2 Hz, 1H), 4.40–4.39 (m, 1H), 4.15 (s, 2H), 3.92–3.81 (m, 1H), 3.42–3.30 (m, 3H), 3.15–3.10 (m, 1H), 3.01–2.73 (m, 4H), 2.44 (d, J=6.9 Hz, 2H), 2.10–2.00 (m, 2H), 1.88–1.60 (m, 7H), 1.55–1.08 (m, 4H), 1.46 (s, 9H), 1.02–0.87 (m, 2H).

EXAMPLE 21 (4)

(2S)-N-(1-benzylpiperidin-4-yl)-3-cyclohexylmethoxy-2-((4R)-3-t-butoxycarbonylthiazolidin-4-ylcarbonylamino)propanamide.fumaric acid salt

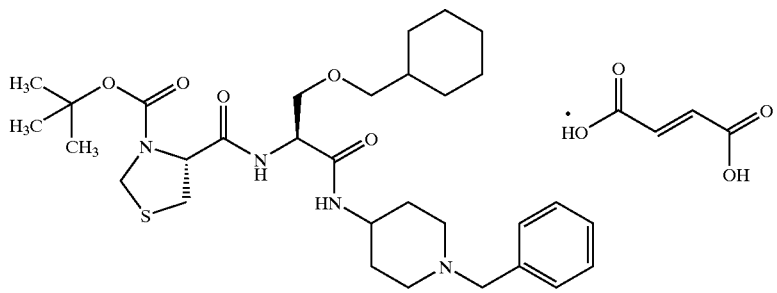

TLC: Rf 0.46 (methanol:chloroform=1:19);
NMR (CD$_3$OD): δ7.45 (S, 5H), 6.70 (s, 2H), 4.64–4.36 (m, 4H), 4.15 (s, 2H), 3.97–3.79 (m, 1H), 3.76–3.54 (m, 2H), 3.43–3.22 (m, 5H), 3.13 (dd, J=12.0, 4.6 Hz, 1H), 3.03–2.86 (m, 2H), 2.13–1.96 (m, 2H), 1.90–1.10 (m, 20H), 1.04–0.80 (m, 2H).

EXAMPLE 21 (5)

(2R)-N-(2-benzylaminoethyl)-3-cyclohexylmethylthio-2-((4R)-3-t-butoxycarbonylthiazolidin-4-ylcarbonylamino)propanamide.malonic acid salt

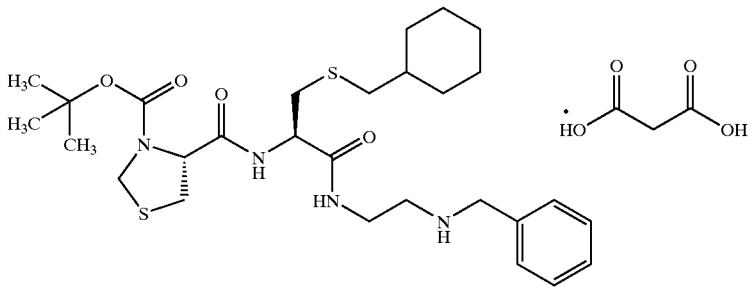

TLC: Rf 0.46 (methanol:chloroform=1:9);

NMR (CDCl₃): δ8.39–8.00 (br, 1H), 7.62–7.32 (m, 6H), 4.64 (t, J=5.0 Hz, 1H), 4.55 (d, J=9.2 Hz, 1H), 4.39 (d, J=9.2 Hz, 1H), 4.32–4.26 (m, 1H), 4.19 (d, J=13.2 Hz, 1H), 4.13 (d, J=13.2 Hz, 1H), 3.71–3.38 (br, 2H), 3.30–3.10 (m, 6H), 2.98–2.86 (m, 2H), 2.38 (d, J=6.9 Hz, 2H), 1.82–1.60 (m, 5H), 1.54–1.35 (m, 10H), 1.28–1.05 (m, 3H), 0.94–0.83 (m, 2H).

Reference Example 4

(4R)-thiazolidin-4-ylcarboxylic acid

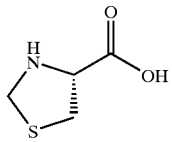

To a solution of L-cystein (100.22 g) in water (180 ml), 35% solution of formic acid (85.0 ml) was added at a dropwise under cooling with ice. The mixture was stirred for 1 hour. The precipitated crystal was collected. The obtained crystal was washed by ethanol and dried under reduced pressure to obtain the title compound (105.4 g) having the following physical data.

TLC:Rf 0.30 (ethyl acetate:acetic acid:water=3:1:1);

NMR (D₂O): δ4.32 (1H, d, J=10.2 Hz), 4.30 (1H, dd, J=7.5, 5.7 Hz), 4.20 (1H, d, J=10.2 Hz), 3.28 (1H, dd, J=12.0, 7.5 Hz), 3.18 (1H, dd, J=12.0, 5.7 Hz).

Reference Example 5

(4R)-3-t-butoxycarbonylthiazolidin-4-ylcarboxylic acid

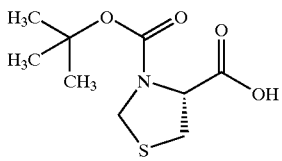

To a solution of the compound prepared in Reference Example 4 (122 g) in ethanol (500 ml), an aqueous solution of 2N—NaOH (460 ml) was added at room temperature. To the obtained solution, di-t-butyl dicarbonate (230 ml) was added at a dropwise under cooling with ice. The reaction mixture was stirred for 1 hour, concentrated under reduced pressure and centurified by 2N—HCl. The mixture was extracted with ethyl acetate. The organic layer was washed by saturated solution of sodium chloride, dried over anhydrous sodium sulfate and concentrated under reduced pressure to obtain the title compound (214 g) having the following physical data.

TLC:Rf 0.29 (methanol:chloroform=1:9);

NMR (CD₃OD) :δ4.80–4.62 (1H, m), 4.56 (1H, d, J=8.7 Hz), 4.43–4.38 (1H, m), 3.44–3.32 (1 H, m), 3.25–3.14 (1 H, m), 1.47 and 1.43 (9H, s).

Reference Example 6

(2R)-2-t-butoxycarbonylamino-3-cyclohexylmethylthiopropanoic acid

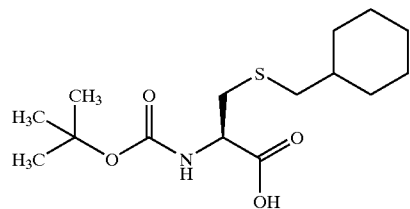

To a solution of L-cystein (4.24 g) in ethanol (35 ml), an aqueous solution of 2N—NaOH (35 ml) was added. After refluxing the solution, (bromomethyl)cyclohexane (5.4 ml) was added thereto. The reaction mixture was stirred for 4 hours. Thereto, di-t-butyl dicarbonate (8.8 ml) was added at a dropwise. The mixture was stirred for 2 hours. Ethanol was distilled off from solution. The mixture was acidfied by addition of 2N—HCl under cooling with ice. The reaction mixture was extracted with ethyl acetate. The organic layer was washed by saturated solution of sodium chloride, dried over anhydrous sodium sulfate and concentrated under reduced pressure to obtain the title compound (10.5 g) having the following physical data. Thus obtained title compound was the same one, which was prepared in Reference Example 1.

EXAMPLE 22

(2 R)-N-(1-benzylpiperidin-4-yl)-2-t-butoxycarbonylamino-3-cyclohexylmethylthiopropanamide

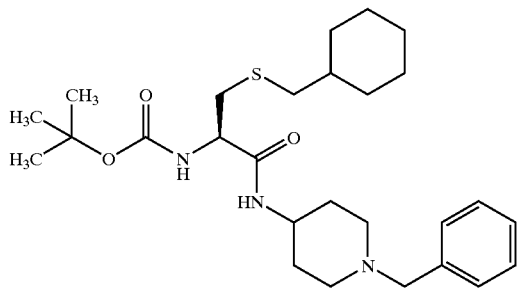

To a solution of the compound prepared in Reference Example 6 (316 g) in dimethylformamide (950 ml), under cooling with ice, 1-hydroxybenzotriazole (153 g), 4-amino-1-benzylpiperidine (204 ml) and 1-ethyl-3-(3-dimethylaminopropyl)-carbodiimide.hydrochloride (230 g) were added successively. The mixture was stirred for 2 and half hours. The reaction mixture was poured into ice-water and extracted with ethyl acetate. The organic layer was washed by saturated solution of sodium hydrogen carbonate and saturated solution of sodium chloride successively, dried over anhydrous magnesium sulfate and concentrated under reduced pressure. The residue was purified with column chromatography on silica gel (methanol:methylene chloride=1:19) to obtain the compound (425 g) of the present invention. Thus obtained compound of the present invention was the same one, which was prepared in Example 1.

Reference Example 7

(2R)-N-(1-benzylpiperidin-4-yl)-2-amino-3-cyclohexylmethylthiopropanamide.2hydrochloride

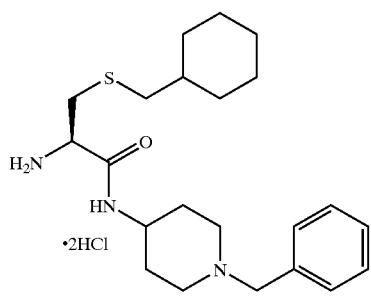

To the compound prepared in Example 22 (423 g), a solution of 4N—HCl-dioxane (1600 ml) was added at room temperature. The mixture was stirred for 3 hours and concentrated under reduced pressure. The obtained solid was washed by ether to obtain the title compound (427 g) having the following physical data. Thus obtained title compound was the same one, which was prepared in Reference Example 3.

TLC:Rf 0.49 (methanol chloroform=1:9);

NMR (CD$_3$OD): δ7.61–7.47 (m, 5H), 4.42 and 4.30 (s, 2H), 4.25–4.14 and 4.02–3.91 (m, 2H), 3.57–3.46 (m, 2H), 3.38–3.32 and 3.12–2.84 (m, 4H), 2.65–245 (m, 2H), 2.19–1.83 (m, 6H), 1.74–1.63 (m, 3H), 1.58–1.41 (m, 1H), 1.36–1.09(m, 3H), 1.05–0.90 (m, 2H).

EXAMPLE 23

(2R)-N-(1-benzylpiperidin-4-yl)-3-cyclohexylmethylthio-2-((4R)-3-t-butoxycarbonylthiazolidin-4-ylcarbonylamino)propanamide

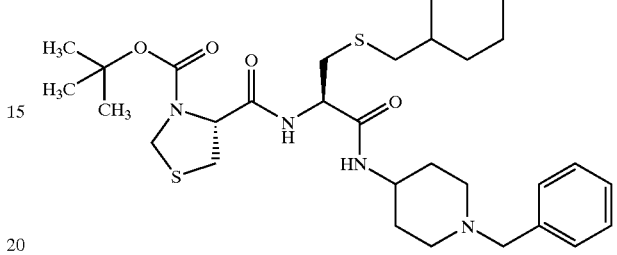

To a solution of the compound prepared in Reference Example 7 (426 g) in dimethylformamide (1000 ml), under cooling with ice, N-methylmorpholine (190 ml), 1-hydroxybenzotriazole (132 g), the compound prepared in Reference Example 5 (202 g) and 1-ethyl-3-(3-dimethylaminopropyl)-carbodiimide hydrochloride (199 g) were added successively. The reaction mixture was stirred for 3 hours and poured into ice-water (4000 ml) and ethyl acetate (1000 ml). The mixture was extracted with ethyl acetate. The organic layer was washed by saturated solution of sodium hydrogen carbonate and saturated solution of sodium chloride successively, dried over anhydrous magnesium sulfate and concentrated under reduced pressure. The obtained solid was recrystqallized from ethanol and water to obtain the compound (420 g) of the present invention. Thus obtained compound of the present invention was the same one, which was prepared in Example 2.

Reference Example 8

(4R)-3-t-butoxycarbonylthiazolidin-4-ylcarboxylic acid.2,5-dioxopyrrolidin-1-yl ester

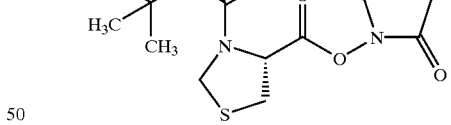

To a solution of the compound prepared in Reference Example 5 (233 g) and N-hydroxysuccinimide (126.5 g) in dimethylformamide (1000 ml), 1-ethyl-3-(3-dimethylaminopropyl)-carbodiimide.hydrochloride(210.9 g) was added under cooling with ice. The reaction mixture was stirred for 3 hours and poured into ice-water (3000 ml). The precipitated crystal was filtered under reduced pressure. The precipitate was washed by ice-water and dried under reduced pressure. The residue was recrystallized from isopropyl alcohol to obtain the title compound (322.2 g) having the following physical data.

TLC:Rf 0.70 (ethyl acetate);

NMR: (CDCl$_3$): δ5.25–5.10 and 5.00–4.85 (m, 1H), 4.75–4.40 (m, 2H), 3.60–3.35 (m, 2H), 2.85 (s, 4H), 1.49 (s, 9H).

Reference Example 9

(2R)-2-((4R)-3-t-butoxycarbonylthiazolidin-4-ylcarbonylamino)-3-cyclohexylmethylthiopropanoic acid

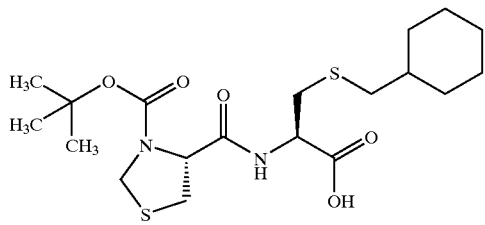

To a suspension of L-cystein (30.3 g) in ethanol (500 ml), an aqueous solution of 2N—NaOH (250 ml) was added. To this solution, (bromomethyl)cyclohexane (40.1 ml) was added. The reaction mixture was refluxed for 2 hours. After cooling the mixture to room temperature, the compound prepared in Reference Example 8 (82.6 g) and dimethylformamide (50 ml) were added thereto. The reaction mixture was stirred for 3 hours and then concentrated. The residue was acidified by addition of ice and 2N—HCl and extracted with ethyl acetate. The organic layer was washed by water and saturated solution of sodium chloride successively, dried over anhydrous magnesium sulfate and concentrated under reduced pressure to obtain the title compound (109.2 g) having the following physical data.

TLC:Rf 0.37 (methanol:chloroform=1:10);

NMR (CDCl$_3$): δ4.83–4.57 (m, 3H), 4.48–4.37 (m, 1H), 3.47–3.14 (m, 2H), 2.99 (d, J=6 Hz, 2H), 2.43 (d, J=7 Hz, 2H), 1.86–1.56 (m, 5H), 1.56–1.370(m, 10H), 1.34–1.05 (m, 3H), 1.05–0.80 (m, 2H).

EXAMPLE 24

(2R)-N-(1-benzylpiperidin-4-yl)-3-cyclohexylmethylthio-2-((4R)-3-t-butoxycarbonylthiazolidin-4-ylcarbonylamino)propanamide

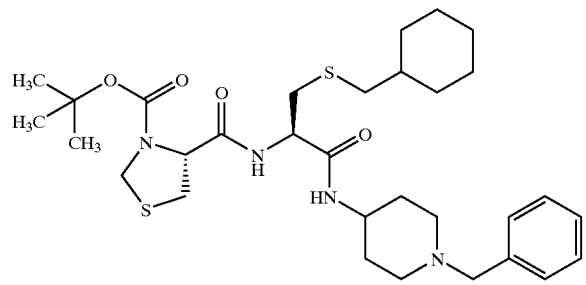

To a solution of the compound prepared in Reference Example 9 (108.2 g) in acetonitrile (1200 ml), under cooling with ice, N-methylmorpholine (27.5 ml) and isobutyl chloroformate (32.4 ml) were added at a dropwise successively. The reaction mixture was stirred for 30 minutes under cooling with ice. Thereto, a solution of 4-amino-1-benzylpiperidine(47.6 g) in acetonitrile (500 ml) was added at a dropwise. The reaction mixture was stirred for 30 minutes and poured into water (7000 ml). The precipitate was collected. The collected precipitate was washed by water. The residue was recrystallized by addition of isopropyl alcohol (1000 ml) to obtain the compound (98.3 g) of the present invention. Thus obtained compound of the present invention was the same one, which was prepared in Example 2 and Example 23.

Formulation Example 1

The following compounds were admixed in conventional method and punched out to obtain 100 tablets each containing 50 mg of active ingredient.

| | |
|---|---|
| (2R)-N-(1-benzylpiperidin-4-yl)-3-cyclohexylmethylthio-2-((4R)-3-t-butoxycarbonylthiazolidin-4-ylcarbonylamino)propanamide | 5.0 g |
| Carboxymethylcellulose calcium (disintegrating agent) | 0.2 g |
| Magnesium stearate (lubricating agent) | 0.1 g |
| Micro crystalline cellulose | 4.7 g |

Formulation Example 2

The following components were admixed in a conventional method, and the solution was sterilized in a conventional method, placed 5 ml portions into ampoules and freeze-dried in a conventional method to obtain 100 ampoules each containing 20 mg of active ingredient.

| | |
|---|---|
| (2R)-N-(1-benzylpiperidin-4-yl)-3-cyclohexylmethylthio-2-((4R)-3-t-butoxycarbonylthiazolidin-4-ylcarbonylamino)propanamide | 2.00 g |
| Mannitol | 20 g |
| Distilled water | 500 ml |

What is claimed is:

1. An amino acid compound of formula (I)

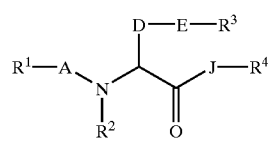

(I)

wherein, $R^1$ is a heterocyclic ring, wherein said heterocyclic ring may be substituted with 1–3 of substituent(s) selected from the group consisting of the following (i)–(xi):
  (i) C1–4 alkyl,
  (ii) C1–alkoxy,
  (iii) phenyl,
  (iv) phenoxy,
  (v) benzyloxy,
  (vi) —SR$^5$ (in which R$^5$ is hydrogen or C1–4 alkyl),
  (vii) C2–5 acyl,
  (viii) halogen,
  (ix) C2–4 alkoxycarbonyl,
  (x) nitro and
  (xi)-NR$^6$R$^7$ (in which R$^6$ and R$^7$ are independently, hydrogen, C1–4 alkyl or C1–4 alkoxycarbonyl, or R$^6$ and R$^7$ taken together with nitrogen atom to which they are attached represents 5–7-membered saturated heterocyclic ring necessarily containing one nitrogen atom and optionally further containing one nitrogen atom or one oxygen atom), A is single bond, —CO— or —SO$_2$—, $R^2$ is hydrogen or C1–4 alkyl which may be substituted with one phenyl, D is C1–4 alkylene or C2–4 alkenylene, E is
1) —COO—,
2) —OCO—,
3) —CONR$^8$— (in which R$^8$ is hydrogen or C1–4 alkyl),
4) —NR$^9$CO— (in which R$^9$ is hydrogen or C1–4 alkyl),
5) —O—,
6) —S—,
7) —SO—,
8) —SO$_2$—,
9) —NR$^{10}$O— (in which R$^{10}$ is hydrogen or C1–4 alkyl),
10) —CO—,
11) —SO$_2$NR$^{11}$— (in which R$^{11}$ is hydrogen or C1–4 alkyl) or
12) —NR$^{12}$SO$_2$— (in which R$^{12}$ is hydrogen or C1–4 alkyl), R$^3$ is
1) carbocyclic ring,
2) heterocyclic ring or
3) C1–4 alkyl substituted with carbocyclic ring or heterocyclic ring, wherein all the said carbocyclic ring and heterocyclic ring in R$^3$ may be substituted with 1–3 of substituent(s) selected from the group consisting of the following (i)–(xi):
(i) C1–4 alkyl,
(ii) C1–4 alkoxy,
(iii) phenyl,
(iv) phenoxy,
(v) benzyloxy,
(vi) —SR-$^{13}$ (in which R$^{13}$ is hydrogen or C1–4 alkyl),
(vii) C2–5 acyl,
(viii) halogen,
(ix) C1–4 alkoxycarbonyl,
(x) nitro and
(xi) —NR$^{14}$R$^{15}$ (in which R$^{14}$ and R$^{15}$ are independently, hydrogen, C1–4 alkyl or C1–4 alkoxycarbonyl, or R$^{14}$ and R$^{15}$ taken together with nitrogen atom to which they are attached represents 5–7-membered saturated heterocyclic ring necessarily containing one nitrogen atom and optionally further containing one nitrogen atom or one oxygen atom), J is
1) —O— or
2) —NR$^{16}$— (in which R$^{16}$ is hydrogen or C1–4 alkyl), R$^4$ is R$^{4-2}$ or R$^{4-3}$, R$^{4-2}$ is
1) carbocyclic ring,
2) heterocyclic ring or
3) C1–8 alkyl substituted with 1–3 of substituent(s) selected from the group consisting of the following (i)–(v):
(i) carbocyclic ring,
(ii) heterocyclic ring,
(iii) COOR$^{32}$ (in which R$^{32}$ is hydrogen or C1–4 alkyl substituted with one phenyl (in which the said phenyl may be substituted with C1–4 alkoxy),
(iv) SR$^{33}$ (in which R$^{33}$ is hydrogen or C1–4 alkyl) and
(v) OR$^{34}$ (in which R$^{34}$ is hydrogen or C1–4 alkyl), provided that when J is —NR$^{16}$—, R$^{4-2}$ and R$^{16}$, taken together with nitrogen atom to which they are attached, may represent heterocyclic ring, wherein at least one ring of all the said carbocyclic ring and heterocyclic ring in R$^{4-2}$ and the said heterocyclic ring represented by R$^{4-2}$ and R$^6$, taken together with nitrogen atom to which they are attached, is substituted with one hydroxy or one —O—(C1–4 alkylene)-O—(C1–4 alkyl) and may be substituted with further 1–2 of substituent(s) selected from the group consisting of the following (i)–(xiii):
(i) C1–4 alkyl,
(ii) C1–4 alkoxy,
(iii) phenyl,
(iv) phenoxy,
(v) benzyloxy,
(vi) —SR$^{35}$ (in which R$^{35}$ is hydrogen or C1–4 alkyl),
(vii) C2–5 acyl,
(viii) halogen,
(ix) C1–4 alkoxycarbonyl,
(x) nitro,
(xi) —NR$^{36}$R$^{37}$ (in which R$^{36}$ and R$^{37}$ are independently, hydrogen, C1–4 alkyl or C1–4 alkoxycarbonyl, or R$^{36}$ and R$^{37}$ taken together with nitrogen atom to which they are attached represents 5–7-membered saturated heterocyclic ring necessarily containing one nitrogen atom and optionally further containing one nitrogen atom or one oxygen atom),
(xii) hydroxy and
(xiii) —O—(C1–4 alkylene)-O—(C1–4 alkyl),
with the proviso that
when R$^{4-2}$ is a carbocyclic ring, the carbocyclic ring is substituted with at least one —NR$^{36}$R$^{37}$ in which R$^{36}$ and R$^{37}$ taken together with the nitrogen atom to which they are attached represents a 5–7 membered saturated heterocyclic ring necessarily containing one nitrogen atom and optionally further containing one nitrogen atom or one oxygen atom, and
when R$^{4-2}$ is a C1–8 alkyl substituted with 1–3 substituents, then at least one of the substituents is an optionally-substituted heterocyclic ring, or a carbocyclic ring substituted with at least one —NR$^{36}$R$^{37}$ in which R$^{36}$ and R$^{37}$ taken together with the nitrogen atom to which they are attached represents a 5–7 membered saturated heterocyclic ring necessarily containing one nitrogen atom and optionally further containing one nitrogen atom or one oxygen atom, R$^{4-3}$ is —L—M, —L— is
1) -(carbocyclic ring which may be substituted with 1–3 substituent(s))-,
2) -(heterocyclic ring which may be substituted with 1–3 substituent(s))- or
3) -(C1–4 alkylene)-(carbocyclic ring which may be substituted with 1–3 substituent(s) or heterocyclic ring which may be substituted with 1–3 substituent (s))-, provided that when J is —NR$^{16}$—, L and R$^{16}$, taken together with nitrogen atom to which they are attached, may represent -(heterocyclic ring which may be substituted with 1–3 of substituent(s))-, M is
1) carbocyclic ring or heterocyclic ring which may be substituted with 1–3 substituent(s) (with the proviso that when the carbocyclic ring is phenyl, said ring is substituted with at least one substituent(s), and that when the said heterocyclic ring is 5–7-membered saturated heterocyclic ring in which the nitrogen atom in the said heterocyclic ring is bonded to group L shown as

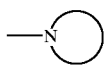

and which may contain further one nitrogen atom or one oxygen atom, then such a ring is substituted with at least one substituent(s)),
2) C1–4 alkyl substituted with 1–2 of substituent(s) selected from the group consisting of the following (i)–(ii):
  (i) carbocyclic ring which may be substituted with 1–3 substituent(s),
  (ii) heterocyclic ring which may be substituted with 1–3 substituent(s),
3) —O-(carbocyclic ring or heterocyclic ring which may be substituted with 1–3 of substituent(s)) (with the proviso that when the carbocyclic ring is phenyl, said ring is substituted with at least one substituent (s)),
4) —S-(carbocyclic ring or heterocyclic ring which may be substituted with 1–3 of substituent(s)),
5) —NR$^{38}$-(carbocyclic ring or heterocyclic ring which may be substituted with 1–3 of substituent(s)) in which R$^{38}$ is hydrogen or C1–4 alkyl which may be substituted with one phenyl,
6) —O—CH2-(carbocyclic ring which may be substituted with 1–3 of substituent(s)) (with the proviso that when the carbocyclic ring is phenyl, said ring is substituted with at least one substituent(s)),
7) —O—(C2–4 alkylene)-(carbocyclic ring which may be substituted with 1–3 of substituent(s)),
8) —O—(C1–4 alkylene)-(heterocyclic ring which may be substituted with 1–3 of substituent(s)),
9) —S—(C1–4 alkylene)-(carbocyclic ring or heterocyclic ring which may be substituted with 1–3 of substituent(s)),
10) —NR$^{39}$—(C1–4 alkylene)-(carbocyclic ring or heterocyclic ring which may be substituted with 1–3 of substituent(s)) (in which R$^{39}$ is hydrogen, C1–4 alkyl which may be substituted with one phenyl or C2–5 acyl which may be substituted with 1–3 of halogen) or
11) —CO-(carbocyclic ring or heterocyclic ring which may be substituted with 1–3 of substituent(s)),
wherein the substituent(s) of the said carbocyclic ring and heterocyclic ring in L and M and the said heterocyclic ring represented by each L and R$^{16}$, L and R$^{17}$, L and R$^{21}$, and L and R$^{23}$ taken together with nitrogen atom to which they are attached is selected from the following (i)–(xiv):
  (i) C1–4 alkyl,
  (ii) C2–4 alkenyl,
  (iii) hydroxy,
  (iv) C1–4 alkoxy,
  (v) —(C1–4 alkylene)-OH,
  (vi) —O—(C14 alkylene)-O—(C1–4 alkyl),
  (vii) halogen,
  (viii) NR$^{40}$R$^{41}$ (in which R$^{40}$ and R$^{41}$ are independently, hydrogen, C1–4 alkyl or C1–4 alkoxycarbonyl, or R$^{40}$ and R$^{41}$ taken together with nitrogen atom to which they are attached represents 5–7-membered saturated heterocyclic ring necessarily containing one nitrogen atom and optionally further containing one nitrogen atom or one oxygen atom),
  (ix) SR$^{42}$ (in which R$^{42}$ is hydrogen or C1–4 alkyl),
  (x) nitro,
  (xi) trifluoromethyl,
  (xii) C1–4 alkoxycarbonyl,
  (xiii) oxo and
  (xiv) C2–5 acyl,
with the proviso that
  at least one optionally substituted heterocyclic ring, or carbocyclic ring substituted with at least one —NR$^{40}$R$^{41}$, in which R$^{40}$ and R$^{41}$ taken together with the nitrogen atom to which they are attached represents a 5–7 membered saturated heterocyclic ring necessarily containing one nitrogen atom and optionally further containing one nitrogen atom or one oxygen atom, is present in —L—M, or a non-toxic salt thereof or a hydrate thereof.

2. A compound according to claim 1, in which R$^1$ is a 5–15-membered mono- or bi-heterocyclic ring containing 1–2 nitrogen atom(s) and 1–2 oxygen atom(s) or one sulfur atom, wherein each heterocyclic ring may be substituted with 1–3 substituents selected from the group consisting of the following (i)–(xi):
  (i) C1–4 alkyl,
  (ii) C1–4 alkoxy,
  (iii) phenyl,
  (iv) phenoxy,
  (v) benzyloxy,
  (vi) —SR$^5$ (in which R$^5$ is hydrogen or C1–4 alkyl),
  (vii) C2–5 acyl,
  (viii) halogen,
  (ix) C1–4 alkoxycarbonyl,
  (x) nitro and
  (xi) —NR$^6$R$^7$ (in which R$^6$ and R$^7$ are independently, hydrogen, C1–4 alkyl or C1–4 alkoxycarbonyl, or R$^6$ and R$^7$ taken together with a nitrogen atom to which they are attached represents 5–7 membered saturated heterocyclic ring necessarily containing one nitrogen atom and optionally further containing one nitrogen atom or one oxygen atom).

3. A compound according to claim 1, in which E is —COO—, —O—, —S—, —SO— or —SO$^2$—.

4. A compound according to claim 1, in which E is —O— or —S—.

5. A compound according to claim 1, in which R$^3$ is a C1–4 alkyl substituted with carbocyclic ring or a carbocyclic ring, wherein each carbocyclic ring may be substituted with 1–3 substituents selected from the group consisting of the following (i)–(xi):
  (i) C1–4 alkyl,
  (ii) C1–4 alkoxy,
  (iii) phenyl,
  (iv) phenoxy,
  (v) benzyloxy,
  (vi) —SR$^{13}$ (in which R$^{13}$ is hydrogen or C1–4 alkyl),
  (vii) C2–5 acyl,
  (viii) halogen,
  (ix) C1–4 alkoxycarbonyl,
  (x) nitro and
  (xi)-NR$^{14}$R$^{15}$ (in which R$^{14}$ and R$^{15}$ are independently, hydrogen, C1–4 alkyl or C1–4 alkoxycarbonyl, or R$^{14}$ and R$^{15}$ taken together with a nitrogen atom to which they are attached represents 5–7 membered saturated heterocyclic ring necessarily containing one nitrogen atom and optionally further containing one nitrogen atom or one oxygen atom).

6. A compound according to claim 1, in which R$^3$ is a C3–10 cycloalkyl or a C1–4 alkyl substituted with C3–10 cycloalkyl, wherein each cycloalkyl may be substituted with 1–3 substituents selected from the group consisting of the following (i)–(xi):
  (i) C1–4 alkyl,
  (ii) C1–4 alkoxy,
  (iii) phenyl,
  (iv) phenoxy,
  (v) benzyloxy,
  (vi) —SR$^{13}$ (in which R$^{13}$ is hydrogen or C1–4 alkyl),
  (vii) C2–5 acyl,
  (viii) halogen,
  (ix) C1–4 alkoxycarbonyl,
  (x) nitro and
  (xi) —NR$^{14}$R$^{15}$ (in which R$^{14}$ and R$^{15}$ are independently, hydrogen, C1–4 alkyl or C1–4 alkoxycarbonyl, or R$^{14}$ and R$^{15}$ taken together with a nitrogen atom to which they are attached represents 5–7 membered saturated heterocyclic ring necessarily containing one nitrogen atom and optionally further containing one nitrogen atom or one oxygen atom).

7. A compound according to claim 1, in which R$^3$ is a heterocyclic ring or a C1–4 alkyl substituted with heterocyclic ring, wherein each heterocyclic ring may be substituted with 1–3 substituents selected from the group consisting of the following (i)–(xi):
  (i) C1–4 alkyl,
  (ii) C1–4 alkoxy,
  (iii) phenyl,
  (iv) phenoxy,
  (v) benzyloxy,
  (vi) —SR$^{13}$ (in which R$^{13}$ is hydrogen or C1–4 alkyl),
  (vii) C2–5 acyl,
  (viii) halogen,
  (ix) C1–4 alkoxycarbonyl,
  (x) nitro and
  (xi) —NR$^{14}$R$^{15}$ (in which R$^{14}$ and R$^{15}$ are independently, hydrogen, C1–4 alkyl or C1–4 alkoxycarbonyl, or R$^{14}$ and R$^{15}$ taken together with a nitrogen atom to which they are attached represents 5–7 membered saturated heterocyclic ring necessarily containing one nitrogen atom and optionally further containing one nitrogen atom or one oxygen atom).

8. The amino acid compound according to claim 1, wherein R$^4$ is a piperidinyl.

9. A compound according to claim 1 which is (1) (2R)-N-(1-benzylpiperidin-4-yl)-3-cyclohexylmethylthio-2-((4R)-3-t-butoxycarbonylthiazolidin-4-ylcarbonylamino)propanamide,
(2) (2R)-N-(1-benzylpiperidin-4-ylmethyl)-3-cyclohexylmethylthio-2-((4R)-3-t-butoxycarbonylthiazolidin-4-ylcarbonylamino)propanamide,
(3) (2R)-N-(1-(4-methoxybenzyl)piperidin-4-ylmethyl)-3-cyclohexylmethylthio-2-((4R)-3-t-butoxycarbonylthiazolidin-4-ylcarbonylamino)propanamide,
(4) (2R)-N-methyl-N-(1-benzylpyrrolidin-3-yl)-3-cyclohexylmethylthio-2-((4R)-3-t-butoxycarbonylthiazolidin-4-ylcarbonylamino)propanamide,
(5) (2R)-N-(1-(4-methoxybenzyl)piperidin-4-yl)-3-cyclohexylmethylthio-2-((4R)-3-t-butoxycarbonylthiazolidin-4-ylcarbonylamino)propanamide,
(6) (2R)-N-(1-(4-methoxybenzoyl)piperidin-4-yl)-3-cyclohexylmethylthio-2-((4R)-3-t-butoxycarbonylthiazolidin4-ylcarbonylamino)propanamide,
(7) (2S)-N-(1-benzylpiperidin-4-yl)-3-cyclohexylmethoxy-2-((4R)-3-t-butoxycarbonylthiazolidin4-ylcarbonylamino)propanamide,
(8) (4R)-N-((1R)-2-cyclohexylmethylthio-1-(4-benzylpiperazin-1-ylcarbonyl)ethyl)-3-t-butoxycarbonylthiazolidin-4-ylcarboxamide,
(9) (4R)-N-((1R)-2-cyclohexylmethylthio-1-(4-diphenylmethylpiperazin-1-ylcarbonyl)ethyl)-3-t-butoxycarbonylthiazolidin-4-ylcarboxamide,
(10) (4R)-N-((1R)-2-cyclohexylmethylthio-1-(4-(4-ethoxyphenyl)piperazin-1-ylcarbonyl)ethyl)-3-t-butoxycarbonylthiazolidin-4-ylcarboxamide,
(11) (2R)-N-(1-(4-fluorobenzyl)piperidin-4-yl)-3-cyclohexylmethylthio-2-((4R)-3-t-butoxycarbonylthiazolidin-4-ylcarbonylamino)propanamide,
(12) (2R)-N-(1-(4-fluorobenzoyl)piperidin4-yl)-3-cyclohexylmethylthio-2-((4R)-3-butoxycarbonylthiazolidin-4-ylcarbonylamino)propanamide,
(13) (4R)-N-((1R)-2-cyclohexylmethylthio-1-(4-(pyridin-2-yl)piperazin-1-ylcarbonyl)ethyl)-3-t-butoxycarbonylthiazolidin-4-ylcarboxamide,
(14) (4R)-N-((1R)-2-cyclohexylmethylthio-1-(4-(pyridin-4-yl)piperazin-1-ylcarbonyl)ethyl)-3-t-butoxycarbonylthiazolidin-4-ylcarboxamide,
(15) (2R)-N-(1-benzylpiperidin-4-yl)-3-cyclohexylmethylthio-2-((3RS)-4-t-butoxycarbonylthiomorpholin-3-ylcarbonylamino)propanamide,
(16) (2R)-N-(4-(morpholin-4-ylmethyl)phenyl)-3-cyclohexylmethylthio-2-((4R)-3-t-butoxycarbonylthiazolidin-4-ylcarbonylamino)propanamide,
(17) (4R)-N-((1R)-2-cyclohexylmethylthio-1-(4-phenylaminopiperidin-1-ylcarbonyl)ethyl)-3-t-butoxycarbonylthiazolidin-4-ylcarboxamide,
(18) (2R)-N-(1-benzylpiperidin-4-yl)-3-cyclohexylmethylthio-2-((4RS)-3-t-butoxycarbonyl-1,3-perhydrothiazin-4-ylcarbonylamino)propanamide,
(19) (2R)-N-(1-benzylpiperidin-4-yl)-3-cyclohexylmethylthio-2-((4S)-3-t-butoxycarbonylthiazolidin-4-ylcarbonylamino)propanamide,
(20) (2S)-N-(1-benzylpiperidin-4-yl)-3-cyclohexylmethylthio-2-((4R)-3-t-butoxycarbonylthiazolidin-47ylcarbonylamino)propanamide,
(21) (2S)-N-(1-benzylpiperidin-4-yl)-3-cyclohexylmethylthio-2-((4S)-3-t-butoxycarbonylthiazolidin-4-ylcarbonylamino)propanamide,
(22) (2R)-N-(1-benzylpiperidin-4-yl)-3-cyclopentylmethylthio-2-((4R)-3-t-butoxycarbonylthiazolidin-4-ylcarbonylamino)propanamide,

(23) (2R)-N-(1-benzylpiperidin-4-yl)-3-cycloheptylmthylthio-2-((4R)-3-t-butoxycarbonylthiazolidin-4-ylcarbonylamino)propanamide,
(24) (2R)-N-(1-benzylpiperidin-4-yl)-3-cyclohexylmethylthio-2-((4R)-3-t-butoxycarbonyl-5,5-dimethylthiazolidin-4-ylcarbonylamino)propanamide,
(25) (2R)-N-(-benzylpiperidin4-yl)-3-cyclohexylmethylthio-3-methyl-2-((4R)-3-t-butoxycarbonylthiazolidin-4-ylcarbonylamino)butanamide,
(26) (4R)-N-((1R)-2-cyclohexylmethylthio-1-(4-(N'-benzyl-N'-trifluoroacetylamino)piperidin-1-ylcarbonyl)ethyl)-3-t-butoxycarbonylthiazolidin-4-ylcarboxamide,
(27) (2R)-N-(1-benzylpiperidin-4-yl)-3-cyclohexylmethylthio-2-((2RS, 4R)-3-t-butoxycarbonyl-2-methylthiazolidin-4-ylcarbonylamino)propanamide,
(28) (4R)-N-((1R)-2-cyclohexylmethylthio-1-(4-(N'-benzyl-N'-methylamino)piperidin-1-ylcarbonyl)ethyl)-3-t-butoxycarbonylthiazolidin-4-ylcarboxamide,
(29) (2R)-N-(1-benzylpiperidin-4-yl)-3-cyclohexylmethylthio-2-((2RS)-3-t-butoxycarbonylthiazolidin-2-ylcarbonylamino)propanamide,
(30) (2R)-N-(1-benzylpiperidin-4-yl)-3-cyclohexylmethylthio-2-(3-t-butoxycarbonylthiazolidin-2-ylcarbonylamino)propanamide,
(31) (2R)-N-(1-benzylpiperidin-4-yl)-3-cyclohexylmethylthio-2-(((4R)-3-t-butoxycarbonylthiazolidin4-ylmethyl)amino)propanamide,
(32) (2R)-N-(1-benzylpiperidin-4-yl)-3-cyclohexylmethylthio-2-((3-t-butoxycarbonylthiazolidin-2-ylmethyl)amino)propanamide,
(33) (2R)-N-(1-benzylpiperidin-4-yl)-3-cyclohexylmethylthio-2-((4R)-thiazolidin-4-ylcarbonylamino)propanamide,
(34) (2R)-N-(1-benzylpiperidin-4-ylmethyl)-3-cyclohexylmethylthio-2-((4R)-thiazolidin-4-ylcarbonylamino)propanamide,
(35) (2R)-N-(1-(4-methoxybenzyl)piperidin-4-ylmethyl)-3-cyclohexylmethylthio-2-((4R)-thiazolidin-4-ylcarbonylamino)propanamide,
(36) (2R)-N-(1-(4-methoxybenzyl)piperidin-4-yl)-3-cyclohexylmethylthio-2-((4R)-thiazolidin-4-ylcarbonylamino)propanamide,
(37) (2R)-N-methyl-N-(1-benzylpyrrolidin-3-yl)-3-cyclohexylmethylthio-2-((4R)-thiazolidin-4-ylcarbonylamino)propanamide,
(38) (2S)-N-(1-benzylpiperidin-4-yl)-3-cyclohexylmethoxy-2-((4R)-thiazolidin-4-ylcarbonylamino)propanamide,
(39) (4R)-N-((1R)-2-cyclohexylmethylthio-1-(4-benzylpiperazin-1-ylcarbonyl)ethyl)thiazolidin4-ylcarboxamide,
(40) (4R)-N-((1R)-2-cyclohexylmethylthio-1-(4-phenylaminopiperidin-1-ylcarbonyl)ethyl)thiazolidin-4-ylcarboxamide,
(41) (2R)-N-(1-benzylpiperidin-4-yl)-3-cyclohexylmethylthio-2-((4R)-5,5-dimethylthiazolidin-4-ylcarbonylamino)propanamide,
(42) (2R)-N-(1-benzylpiperidin-4-yl)-3-cyclohexylmethylthio-3-methyl-2-((4R)-thiazolidin-4-ylcarbonylamino)butanamide,
(43) (2R)-N-(1-(4-methoxybenzoyl)piperidin4-yl)-3-cyclohexylmethylthio-2-((4R)-thiazolidin-4-ylcarbonylamino)propanamide,
(44) (4R)-N-((1R)-2-cyclohexylmethylthio-1-(4-diphenylmethylpiperazin-1-ylcarbonyl)ethyl)thiazolidin4-ylcarboxamide,
(45) (2R)-N-(1-(4-fluorobenzoyl)piperidin-4-yl)-3-cyclohexylmethylthio-2-((4R)-thiazolidin-4-ylcarbonylamino)propanamide,
(46) (2R)-N-(1-(4-fluorobenzyl)piperidin-4-yl)-3-cyclohexylmethylthio-2-((4R)-thiazolidin-4-ylcarbonylamino)propanamide,
(47) (4R)-N-((1R)-2-cyclohexylmethylthio-1-(4-(4-methoxyphenyl)piperazin-1-ylcarbonyl)ethyl)thiazolidin-4-ylcarboxamide,
(48) (4R)-N-((1R)-2-cyclohexylmethylthio-1-(4-(pyridin-2-yl)piperazin-1-ylcarbonyl)ethyl)thiazolidin-4-ylcarboxamide,
(49) (4R)-N-((1R)-2-cyclohexylmethylthio-1-(4-(pyridin-4-yl)piperazin-1-ylcarbonyl)ethyl)thiazolidin4-ylcarboxamide,
ii(50) (2R)-N-(4-(morpholin-4-ylmethyl)phenyl)-3-cyclohexylmethylthio-2-((4R)-thiazolidin-4-ylcarbonylamino)propanamide,
(51) (2R)-N-(1-benzylpiperidin-4-y)-3-cyclohexylmethylthio-2-(((4R)-thiazolidin-4-ylmethyl)amino)propanamide,
(52) (2R)-N-(1-benzylpiperidin-4-yl)-3-cyclohexylmethylthio-2-((4R)-3-isopropyloxycarbonylthiazolidin-4-ylcarbonylamino)propanamide,
(53) (2R)-N-(1-benzylpiperidin-4-yl)-N-methyl-3-cyclohexylmethylthio-2-((4R)-3-t-butoxycarbonylthiazolidin-4-ylcarbonylamino)propanamide,
(54) (2R)-N-(1-benzylpiperidin-4-yl)-3-cyclohexylmethylthio-2-((4R)-2,2-dimethylthiazolidin-4-ylcarbonylamino)propanamide,
(55) (2R)-N-(1-benzylpiperidin4-yl)-3-cyclohexylmethylthio-2-((2S, 4S)-1-t-butoxycarbonyl-4-fluoropyrrolidin-2-ylcarbonylamino)propanamide,
(56) (2R)-N-(1-benzylpiperidin4-yl)-3-cyclohexylmethylthio-2-((2S)-1-t-butoxycarbonyl-4,4-difluoropyrrolidin-2-ylcarbonylamino)propanamide,
(57) (2R)-N-(1-benzylpiperidin-4-yl)-3-cyclohexylmethylthio-2-((4R)-3-(2-methylpropoxycarbonyl)thiazolidin4-ylcarbonylamino)propanamide,
(58) (2R)-N-(1-benzylpiperidin4-yl)-3-cyclohexylmethylthio-2-((4R)-3-methoxycarbonylthiazolidin-4-ylcarbonylamino)propanamide,
(59) (2R)-N-(1-benzylpiperidin4-yl)-3-cyclohexylmethylthio-2-((4R)-3-pivaloylthiazolidin-4-ylcarbonylamino)propanamide,
(60) (2R)-N-(1-benzylpiperidin-4-yl)-3-cyclohexylmethylthio-2-((4R)-3-(3-methylbutyryl)thiazolidin-4-ylcarbonylamino)propanamide,
(61) (2R)-N-(1-benzylpiperidin-4-yl)-3-cyclohexylmethylthio-2-((4R)-3-(2-methylpropionyl)thiazolidin4-ylcarbonylamino)propanamide,
(62) (2R)-N-(2-hydroxyethyl)-N-(1-benzylpiperidin-4-yl)-3-cyclohexylmethylthio-2-((4R)-3-t-butoxycarbonylthiazolidin-4-ylcarbonylamino)propanamide,
(63) (4R)-N-((1R)-2-cyclohexylmethylthio-1-(4-benzylaminopiperidin-1-ylcarbonyl)ethyl)-3-t-butoxycarbonylthiazolidin-4-ylcarboxamide or
(64) (2R)-N-(1-benzylpiperidin4-yl)-3-cyclohexylmethylthio-2-(((4R)-3-(3-methylbutyryl)thiazolidin-4-ylmethyl)amino)propanamide,
or a non-toxic salt thereof or a hydrate thereof.

10. A compound according to claim 1 which is (1) (2R)-N-(1-benzylpiperidin-4-yl)-3-cyclohexylmethylthio-2-((2S)-1-t-butoxycarbonyl-1,2,3,6-tetrahydropyridin-2-ylcarbonylamino)propanamide,
(2) (2R)-N-(1-benzylpiperidin-4-yl)-3-cyclohexylmethylthio-²-((2S)-1-t-butoxycarbonylpiperidin-2-ylcarbonylamino)propanamide,
(3) (2R)-N-(1-benzylpiperidin-4-yl)-3-cyclohexylmethylthio-2-((4S)-3-t-butoxycarbonyloxazolidin-4-ylcarbonylamino)propanamide,
(4) (2R)-N-(1-benzylpiperidin-4-yl)-3-cyclohexylmethylthio-2-((2S)-1-t-butoxycarbonylpyrrolidin-2-ylcarbonylamino)propanamide,
(5) (2R)-N-(1-benzylpiperidin-4-yl)-3-cyclohexylmethylthio-2-((2S, 4RS)-1-t-butoxycarbonyl-4-methylthiopyrrolidin-2-ylcarbonylamino)propanamide,
(6) (2R)-N-(1-benzylpiperidin-4-yl)-3-cyclohexylmethylthio-2-((3S)-4-t-butoxycarbonylmorpholin-3-ylcarbonylamino)propanamide,
(7) (2R)-N-(1-benzylpiperidin-4-yl)-3-cyclohexylmethylthio-2-(3-t-butoxycarbonylthiophn-4-ylcarbonylamino)propanamide,
(8) (2R)-N-(1-(4-methylbenzyl)piperidin-4-yl)-3-cyclohexylmethylthio-2-((4R)-3-t-butoxycarbonylthiazolidin-4-ylcarbonylamino)propanamide,
(9) (2RS)-N-(1-benzylpiperidin-4-yl)-4-cyclohexylthio-2-((4R)-3-t-butoxycarbonylthiazolidin-4-ylcarbonylamino)butanamide,
(10) (2R)-N-(1-benzylpiperidin-4-yl)-3-cyclohexylmethylsulfinyl-2-((4R)-3-t-butoxycarbonylthiazolidin-4-ylcarbonylamino)propanamide,
(11) (2S)-N-(1-benzylpiperidin-4-yl)-3-cyclohexylmethoxy-2-((4S)-3-t-butoxycarbonyloxazolidin-4-ylcarbonylamino)propanamide,
(12) (2R)-N-(1-(4-hydroxybenzyl)piperidin-4-yl)-3-cyclohexylmethylthio-2-((4R)-3-t-butoxycarbonylthiazolidin-4-ylcarbonylamino)propanamide,
(13) (4R)-N-((1R)-2-cyclohexylmethylthio-1-(4-benzylaminopiperidin-1-ylcarbonyl)ethyl)-3-(3-methylbutyryl)thiazolidin-4-ylcarboxamide,
(14) (4R)-N-((1R)-2-cyclohexylmethylthio-1-(4-benzylaminopiperidin-1-ylcarbonyl)ethyl)-3-isopropyloxycarbonylthiazolidin-4-ylcarboxamide or
(15) (2R)-N-(1-benzylpiperidin-4-y)-3-cyclohexylmethylthio-2-((4R)-2,2-dimethyl-3-(3-methylbutyryl)thiazolidin-4-ylcarbonylamino)propanamide, or a non-toxic salt thereof or a hydrate thereof.

11. A pharmaceutical composition comprising, as an active ingredient, an amino acid compound of formula (I) depicted in claim 1, a non-toxic salt thereof or a hydrate thereof.

12. A method for treating or preventing, or both, a disease induced by an excessive release of neurotransmitters from N-type calcium channels, comprising administering to a host in need of such treatment an effective amount of an amino acid compound of formula (I) depicted in claim 1, a non-toxic salt thereof or a hydrate thereof.

13. The method according to claim 12, wherein the disease induced by an excessive release of neurotransmitters from N-type calcium channels is selected from the group consisting of cerebral infarct, transient ischemic attack, encephalomyelopathy after cardiac operation, spinal angiopathy, hypertension with stress, neurosis, epilepsy, asthma and pollakiuria.

14. A method for the treatment of pain induced by an excessive release of neurotransmitters from N-type calcium channels, comprising administering to a host in need of such treatment an effective amount of an amino acid compound of formula (I) depicted in claim 1, a non-toxic salt thereof or a hydrate thereof.

* * * * *